United States Patent
Bamba et al.

(10) Patent No.: US 8,436,004 B2
(45) Date of Patent: May 7, 2013

(54) BICYCLOANILINE DERIVATIVE

(75) Inventors: Makoto Bamba, Tsukuba (JP); Hidetomo Furuyama, Ashigarakami-gun (JP); Kenji Niiyama, Tsuchiura (JP); Toshihiro Sakamoto, Moriya (JP); Satoshi Sunami, Toride (JP); Keiji Takahashi, Yachiyo (JP); Fuyuki Yamamoto, Tsukuba (JP); Takashi Yoshizumi, Ushiku (JP)

(73) Assignee: MSD K.K., Chiyoda-Ku, Tokyo (JP)

( * ) Notice: Subject to any disclaimer, the term of this patent is extended or adjusted under 35 U.S.C. 154(b) by 306 days.

(21) Appl. No.: 12/663,729

(22) PCT Filed: Jun. 12, 2008

(86) PCT No.: PCT/JP2008/061182
§ 371 (c)(1),
(2), (4) Date: May 6, 2010

(87) PCT Pub. No.: WO2008/153207
PCT Pub. Date: Dec. 18, 2008

(65) Prior Publication Data
US 2011/0135601 A1    Jun. 9, 2011

Related U.S. Application Data

(60) Provisional application No. 60/965,918, filed on Aug. 23, 2007.

(30) Foreign Application Priority Data

Jun. 15, 2007    (JP) .................................. 2007-159217

(51) Int. Cl.
*A01N 43/90*  (2006.01)
*A61K 31/519*  (2006.01)
*C07D 487/00*  (2006.01)

(52) U.S. Cl.
USPC ....................................... 514/262.1; 544/256

(58) Field of Classification Search ........................... None
See application file for complete search history.

(56) References Cited

FOREIGN PATENT DOCUMENTS

| WO | 99/61444 | 12/1999 |
|----|----------|---------|
| WO | 01/70741 | 9/2001 |
| WO | 2004/011465 | 2/2004 |
| WO | 2004/041823 | 5/2004 |
| WO | 2005/066171 | 7/2005 |
| WO | 2006/016067 | 2/2006 |
| WO | 2006/032452 | 3/2006 |
| WO | 2007/095188 | 8/2007 |

OTHER PUBLICATIONS

Wamhoff, et. al., Journal of Organic Chemistry (1993), 58(25), 6976-84.*
Wolff et. al., "Burger's Medicinal Chemistry and Drug Discovery," 5th Ed. Part 1, pp. 975-977 (1995).*
Banker, et. al., (1996), Modern Pharmaceuticals, p. 596.*

* cited by examiner

*Primary Examiner* — Jeffrey Murray
(74) *Attorney, Agent, or Firm* — Joan E. Switzer; David A. Muthard

(57) ABSTRACT

The invention relates to a compound of a general formula (I):

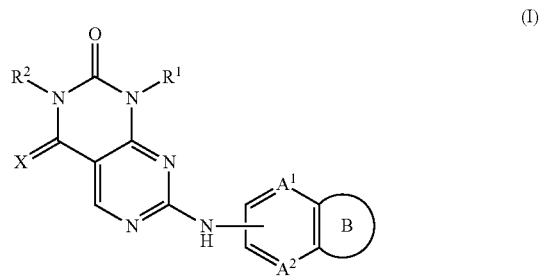

wherein $A^1$ and $A^2$ each mean a nitrogen atom or an optionally-substituted methine group; Ring B means a 5-membered to 7-membered aliphatic ring, or a spiro or bicyclo ring formed from the aliphatic ring and any other 3-membered to 7-membered aliphatic ring; $R^1$ means a hydrogen atom, or an optionally-substituted C1-C6 alkyl group, or an optionally-substituted aryl, aralkyl or heteroaryl group; $R^2$ means an optionally-substituted aryl, aralkyl or heteroaryl group; and X means a group of =NH or =O, etc.

Based on its excellent Wee1 kinase-inhibitory effect, the compound of the invention has cell growth-inhibitory effect and has an additive/synergistic effect with any other anticancer agent, and is therefore useful in the field of medicine.

15 Claims, No Drawings

BICYCLOANILINE DERIVATIVE

PRIORITY CLAIM

This application claims priority from Japanese Provisional Application Serial No. JP2007/159217, filed Jun. 15, 2007, U.S. Provisional Application Ser. No. 60/965,918 filed on Aug. 23, 2007, and PCT Application Serial No. JP2008/061182, filed on Jun. 12, 2008.

TECHNICAL FIELD

The present invention is useful in the field of medicine. More precisely, the bicycloaniline derivatives of the invention are useful in the field of various cancer therapy, as a kinase inhibitor, especially as a Wee1 kinase inhibitor.

BACKGROUND ART

Cells have a checkpoint mechanism of such that, when the DNA therein is damaged, then the cells temporarily stop the cell cycle and repair the damaged DNA (Cell Proliferation, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (The EMBO Journal, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray and gamma ray (Cancer Biology & Therapy, Vol. 3, pp. 305-313; Cancer Research, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known are compounds described in US Application 2005/0250836 (Patent Reference 1), WO2003/091255 (Patent Reference 2), Cancer Research, Vol. 61, pp. 8211-8217 (Non-Patent Reference 1), or Bioorg & Med. Chem. Lett., Vol. 15, pp. 1931-1935 (Non-Patent Reference 2). However, the compounds described in these references quite differ from the compounds of the invention in point of their structures.

On the other hand, WO99/61444 (Patent Reference 3) or WO2004/041823 (Patent Reference 4) discloses various compounds relatively similar to the compounds of the invention in point of their skeletons. However, these references do neither disclose nor suggest the compounds of the invention.

DISCLOSURE OF THE INVENTION

An object of the invention is to provide a novel anticancer agent having a kinase-inhibitory effect, especially a Wee1 kinase-inhibitory effect, or a sensitizer for chemo therapy or radiation therapy of cancers.

As a result of assiduous studies, the present inventors have found that compounds of the following general formula (I) have an excellent kinase-inhibitory effect, especially an excellent Wee1 kinase-inhibitory effect, and have completed the present invention:

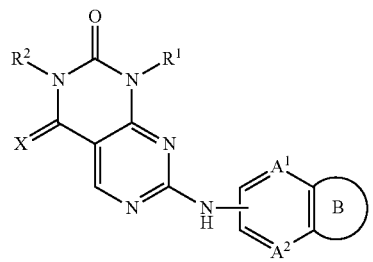

wherein, $A^1$ and $A^2$ each independently mean a nitrogen atom, or mean a methine group optionally substituted with a halogen atom, a hydroxyl group, a cyano group, a C1-C6 alkyl group, a C1-C6 alkoxy group or a hydroxy-C1-C6 alkyl group;

Ring B means a 5-membered to 7-membered aliphatic ring condensed with a ring of formula (a):

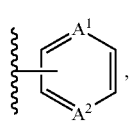

or means a spiro or bicyclo ring formed from the 5-membered to 7-membered aliphatic ring with any other 3-membered to 7-membered aliphatic ring, which is condensed with the ring of formula (a), in which one or two or more methylene groups constituting said Ring B may be independently replaced by an oxygen atom, a sulfur atom, a sulfinyl group, a sulfonyl group, a carbonyl group or a group of —N($R^{1a}$)—, and one or two or more methylene groups constituting said Ring B may be independently substituted with a halogen atom, a hydroxyl group, a C1-C6 alkyl group, a hydroxy-C1-C6 alkyl group or a group of -$Q^{1a}$-N($R^{1b}$)$R^{1c}$;

Cy means an aryl or heterocyclic group optionally substituted with a halogen atom or a C1-C6 alkyl group;

$Q^{1a}$, $Q^{1b}$, $Q^{1d}$ and $Q^{1e}$ each independently mean a single bond or a C1-C6 alkylene group, in which one or two or more methylene groups constituting the C1-C6 alkylene group may be independently replaced by a sulfinyl group, a sulfonyl group or a carbonyl group;

$R^1$ means a hydrogen atom, or means a C1-C6 alkyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

$R^2$ means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

$R^{1a}$ means a hydrogen atom, or means a C1-C6 alkyl, C3-C6 cycloalkyl or C2-C7 alkanoyl group optionally having a substituent selected from a group consisting of a halogen atom, a hydroxyl group, a cyano group, a C1-C6 alkoxy group, a C3-C6 cycloalkyl group and a C2-C7 alkanoyl group, or means a group of $-Q^{1b}-Cy$ or $-Q^{1d}-N(R^{1f})R^{1g}$;

$R^{1b}$ and $R^{1c}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of $-Q^{1e}-N(R^{1h})R^{1i}$;

$R^{1f}$ and $R^{1g}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group;

$R^{1h}$ and $R^{1i}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; and X means a group of =NH or =O.

The compounds (I) of the invention have a kinase-inhibitory effect, especially a Wee1 kinase-inhibitory effect, and they are therefore useful as remedies for various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma, or as sensitizers for chemo therapy or radiation therapy of those cancers.

In particular, the compounds (I) of the invention are useful as remedies, for example, for breast cancer, lung cancer, pancreatic cancer, colon cancer, ovarian cancer, acute leukemia, chronic lymphatic leukemia, chronic myelocytic leukemia, Hodgkin's lymphoma, or as sensitizers for chemo therapy or radiation therapy of those cancers.

The invention relates to the compounds of formula (I), pharmaceutically acceptable salts or N-oxide derivatives thereof, as well as to their production methods and their use.

The meanings of the terms used in this description are described below, and the invention is described in more detail hereinunder.

"Halogen atom" means a fluorine atom, a chlorine atom, a bromine atom and an iodine atom.

"C1-C6 alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isopentyl group, a hexyl group, an isohexyl group.

"Hydroxy-C1-C6 alkyl group" means the above-mentioned C1-C6 alkyl group in which any substitutable position is substituted with one or two or more, preferably 1 or 2 hydroxyl groups, including, for example, a hydroxymethyl group, a 2-hydroxyethyl group, a 1-hydroxy-1-methylethyl group, a 1,2-dihydroxyethyl group, a 3-hydroxypropyl group.

"3-Membered to 7-membered, or 5-membered to 7-membered aliphatic ring" means a structure comprising from 3 to 7, or from 5 to 7 atoms bonding to each other in a ring, and it may be a monocyclic saturated structure by itself, or may be an unsaturated bond-containing ring except an aromatic ring. For example, it includes cyclopropane, cyclopropene, cyclobutane, cyclobutene, cyclopentane, cyclopentene, cyclohexane, cyclohexene, cycloheptane, cyclobutene. The methylene group constituting the aliphatic ring may be "replaced by" or "substituted with" a predetermined atom or group, as described hereinunder.

"5-Membered to 7-membered aliphatic ring condensed with the ring of formula (a)" means a bicyclic condensed ring of the above-mentioned 5-membered to 7-membered aliphatic ring ortho-condensed with the ring of formula (a), forming, for example, groups of the following formula (ab-10):

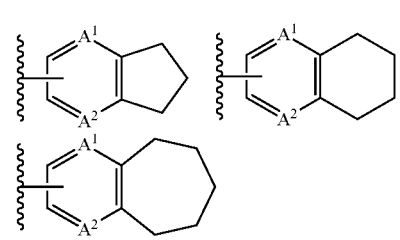

(ab-10)

"Spiro ring formed from the 5-membered to 7-membered aliphatic ring with any other 3-membered to 7-membered aliphatic ring, which is condensed with the ring of formula (a)" means a spiro ring formed by the aliphatic ring moiety of the above-mentioned "5-membered to 7-membered aliphatic ring condensed with the ring of formula (a)" taken together with any other 3-membered to 7-membered aliphatic ring, and this is a ring ortho-condensed with the ring of formula (a), for example, forming a group that contains a tricyclic condensed ring of the following formula (ab-20):

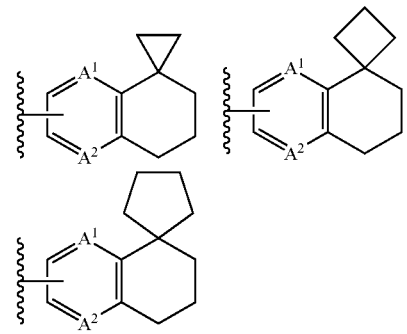

(ab-20)

"Bicyclo ring formed from the 5-membered to 7-membered aliphatic ring with any other 3-membered to 7-membered aliphatic ring, which is condensed with the ring of formula (a)" means a bicyclo ring formed by the aliphatic ring moiety of the above-mentioned "5-membered to 7-membered aliphatic ring condensed with the ring of formula (a)" taken together with any other 3-membered to 7-membered aliphatic ring, and this is a ring ortho-condensed with the ring of formula (a), for example, forming a group that contains a tricyclic condensed ring of the following formula (ab-30):

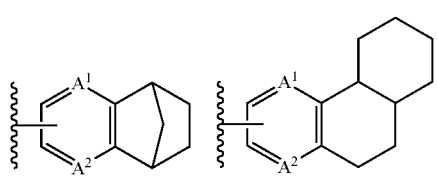
(ab-30)

"C1-C6 alkoxy group" means a linear or branched alkoxy group having from 1 to 6 carbon atoms, including, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy group.

"Halo-C1-C6 alkyl group" means the above-mentioned C1-C6 alkyl group in which any substitutable position is substituted with one or two or more, preferably from 1 to 3, the same or different, above-mentioned halogen atoms, including, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, an iodomethyl group.

"C2-C7 alkanoyl group" means an alkanoyl group having the above-mentioned C1-C6 alkyl group, or that is, an alkanoyl group having from 2 to 7 carbon atoms, including, for example, an acetyl group, a propionyl group, a butyryl group, an isobutyryl group, a valeryl group, an isovaleryl group, a pivaloyl group.

"Aryl group" includes, for example, a phenyl group, a naphthyl group.

"Heteroaryl group" means a 5-membered or 6-membered monocyclic heteroaryl group having one or two or more, preferably from 1 to 3, the same or different hetero atoms selected from a group consisting of an oxygen atom, a nitrogen atom and a sulfur atom; or a condensed cyclic heteroaryl group formed through condensation of that monocyclic heteroaryl group and the above-mentioned aryl group, or through condensation of the same or different such monocyclic heteroaryl groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group.

"Heterocyclic group" means a 3-membered to 7-membered monocyclic heterocyclic group having one or two or more, preferably from 1 to 3, the same or different hetero atoms selected from a group consisting of an oxygen atom, a nitrogen atom and a sulfur atom; or a condensed cyclic heterocyclic group formed through condensation of that monocyclic heterocyclic group and a 3-membered to 7-membered carbocyclic group, or through condensation of the same or different such monocyclic heterocyclic groups; and it includes the above-mentioned heteroaryl group. Its concrete examples are those mentioned hereinabove for the heteroaryl group, and in addition, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group, a thiomorpholinyl group.

"C1-C6 alkylene group" means a linear or branched alkylene group having from 1 to 6 carbon atoms, including, for example, a methylene group, an ethylene group, a trimethylene group, a tetramethylene group, a pentamethylene group, a hexamethylene group.

"C2-C6 alkenyl group" means a linear or branched alkenyl group having from 2 to 6 carbon atoms, including, for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, a 4-pentenyl group.

"C2-C6 alkynyl group" means a linear or branched alkynyl group having from 2 to 6 carbon atoms, including, for example, an ethynyl group, a 1-propynyl group, a 2-propynyl group, a 3-butynyl group, a 2-butynyl group, a 1-butynyl group, a 1-methyl-2-propynyl group, a 1-ethyl-2-propynyl group, a 1-methyl-2-butynyl group, a 4-pentynyl group.

"C3-C6 cycloalkyl group" means a cycloalkyl group having from 3 to 6 carbon atoms, including, for example, a cyclopropyl group, a cyclobutyl group, a cyclopentyl group, a cyclohexyl group.

"Aralkyl group" means the above-mentioned C1-C6 alkyl group in which any substitutable position is substituted with one or two or more, preferably one, above-mentioned aryl groups, including, for example, a benzyl group, a 1-phenylethyl group, a phenethyl group, a 1-naphthylmethyl group, a 2-naphthylmethyl group.

"C1-C6 alkylsulfonyl group" means a linear or branched alkylsulfonyl group having from 1 to 6 carbon atoms, including, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, an isohexylsulfonyl group.

"Pharmaceutically acceptable salts" of the compounds of the invention mean ordinary, pharmaceutically acceptable salts. For example, when the compounds have a hydroxyl group, or an acidic heterocyclic group such as a tetrazolyl group, then they may form base-addition salts at the hydroxyl group or the acidic heterocyclic group; or when the compounds have an amino group or a basic heterocyclic group, then they may form acid-addition salts at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"N-oxide derivatives" of the compounds of the invention are those in which one or two or more arbitrary nitrogen atoms capable of forming N-oxide, existing in the compound, are oxidized to form an N-oxide and which are pharmaceutically acceptable ones. For example, they include compounds of the invention in which the ring-forming nitrogen atom of the dihydropyrimido[4,5-d]pyrimidine skeleton is oxidized, or those in which the ring-forming nitrogen atom of a group of formula (ab-1):

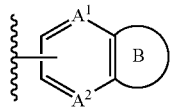

(ab-1)

is oxidized.

For illustrating the compounds of the invention more concretely, preferred examples of the symbols used in this description are described below in more detail.

$A^1$ and $A^2$ each independently mean a nitrogen atom, or mean a methine group optionally substituted with a halogen atom, a hydroxyl group, a cyano group, a C1-C6 alkyl group, a C1-C6 alkoxy group or a hydroxy-C1-C6 alkyl group;

"Methine group optionally substituted with a halogen atom, a hydroxyl group, a cyano group, a C1-C6 alkyl group, a C1-C6 alkoxy group or a hydroxy-C1-C6 alkyl group" means an unsubstituted methine group, or a methine group substituted with a substituent selected from a group consisting of a halogen atom, a hydroxyl group, a cyano group, a C1-C6 alkyl group, a C1-C6 alkoxy group and a hydroxy-C1-C6 alkyl group.

The substituent for the methine group is preferably a halogen atom such as a chlorine atom or a fluorine atom; a hydroxyl group; a C1-C6 alkyl group such as a methyl group or an ethyl group; or a hydroxy-C1-C6 alkyl group such as a hydroxymethyl group or a 2-hydroxyethyl group; more preferably a C1-C6 alkyl group such as a methyl group or an ethyl group.

Preferred embodiments of $A^1$ and $A^2$ are that the two are both unsubstituted methine groups; any one of $A^1$ and $A^2$ is a methine group substituted with a halogen atom, a hydroxyl group, a cyano group, a C1-C6 alkyl group, a C1-C6 alkoxy group or a hydroxy-C1-C6 alkyl group, and the other is an unsubstituted methine group; or any one of $A^1$ and $A^2$ is a nitrogen atom, and the other is a methine group optionally substituted with a halogen atom, a hydroxyl group, a cyano group, a C1-C6 alkyl group, a C1-C6 alkoxy group or a hydroxy-C1-C6 alkyl group, more preferably an unsubstituted methine group. A more preferred embodiment is that $A^1$ and $A^2$ are both unsubstituted methine groups.

In the invention, for example, the expression of a formula (ab-1):

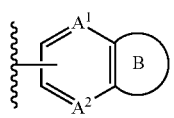

(ab-1)

includes a group of a formula (ab-1'):

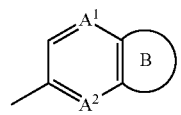

(ab-1')

or a group of a formula (ab-1"):

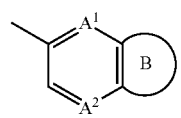

(ab-1")

Ring B means a 5-membered to 7-membered aliphatic ring condensed with a ring of formula (a):

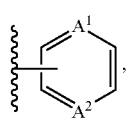

(a)

or means a spiro or bicyclo ring formed from the 5-membered to 7-membered aliphatic ring with any other 3-membered to 7-membered aliphatic ring, which is condensed with the ring of formula (a).

The 5-membered to 7-membered aliphatic ring condensed with the ring of formula (a) includes rings of a formula (b-1):

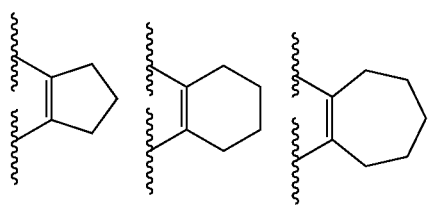

(b-1)

and the spiro ring formed from the aliphatic ring with any other 3-membered to 7-membered aliphatic ring, which is condensed with the ring of formula (a), includes rings of a formula (b-2):

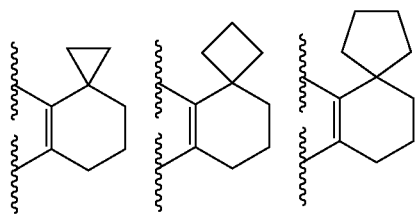

(b-2)

and the bicyclo ring formed from the aliphatic ring with any other 3-membered to 7-membered aliphatic ring, which is condensed with the ring of formula (a), includes rings of a formula (b-3):

(b-3)

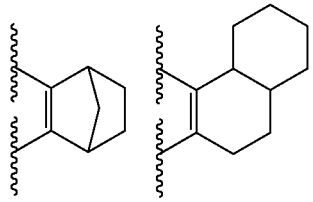

One or two or more methylene groups constituting said Ring B may be independently replaced by an oxygen atom, a sulfur atom, a sulfinyl group, a sulfonyl group, a carbonyl group or a group of —N(R$^{1a}$)—. In this, "said Ring B may be independently replaced by an oxygen atom, a sulfur atom, a sulfinyl group, a sulfonyl group, a carbonyl group or a group of —N(R$^{1a}$)—" means that one or two or more methylene groups constituting said Ring B are by themselves replaced by the same or different, one or two or more, preferably from 1 to 3 groups or atoms selected from a group consisting of an oxygen atom, a sulfur atom, a sulfinyl group, a sulfonyl group, a carbonyl group and a group of —N(R$^{1a}$)—, or they are not replaced; and as a result of the replacement, the group of formula (ab-1):

(ab-1)

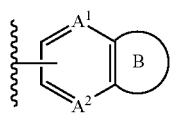

includes a group selected from a group consisting of a formula (b-10):

(b-10)

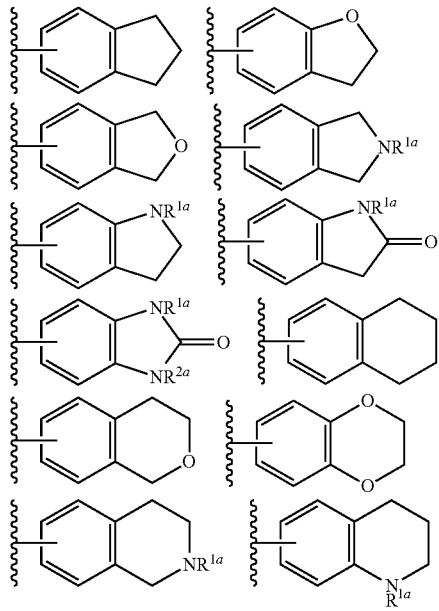

-continued

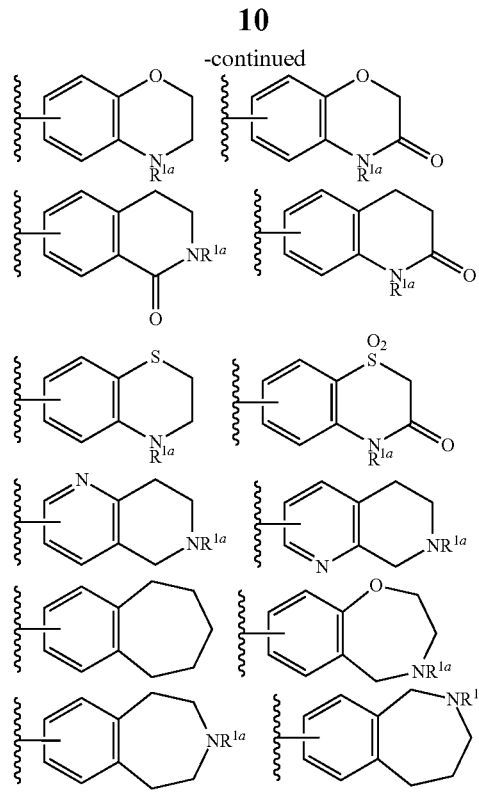

a group selected from a group consisting of a formula (b-20):

(b-20)

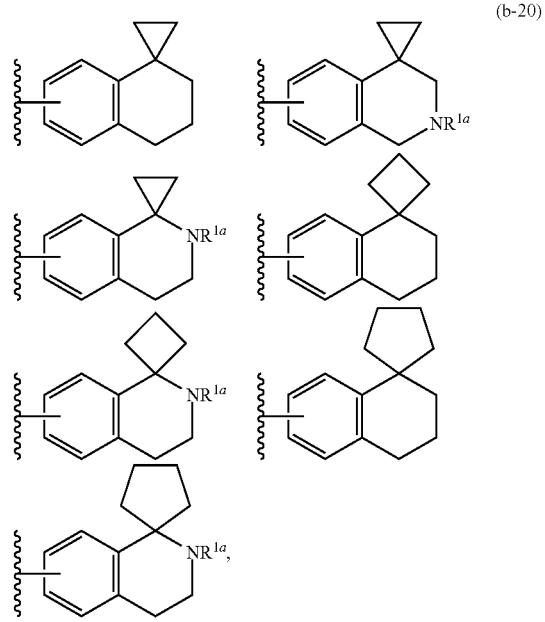

or a group selected from a group consisting of a formula (b-30):

(b-30)

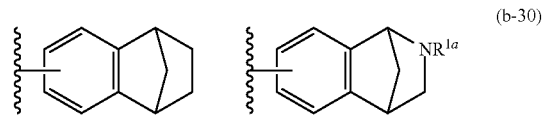

-continued

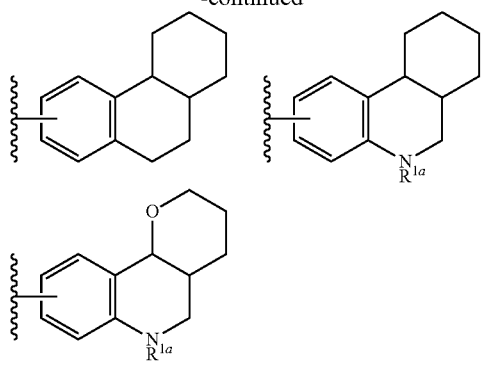

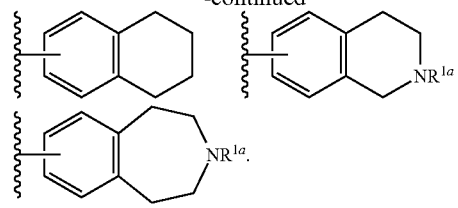

Of the groups of formula (b-20), preferred are those selected from a formula (b-21):

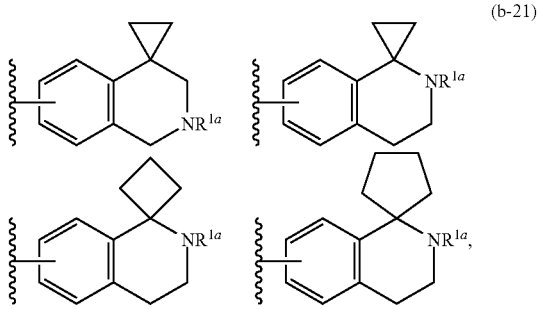
(b-21)

more preferred are those selected from a formula (b-22):

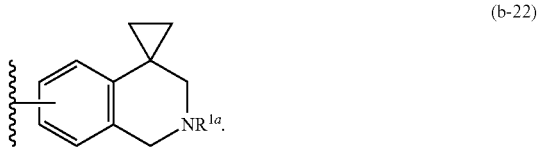
(b-22)

One aspect of the invention provides compounds where X is a group of =NH, and the group of formula (ab-1) is a group selected from those of formula (b-10).

Another aspect of the invention provides compounds where X is a group of =NH, and the group of formula (ab-1) is a group selected from those of formula (b-20).

Still another aspect of the invention provides compounds where X is a group of =NH, and the group of formula (ab-1) is a group selected from those of formula (b-30).

One aspect of the invention provides compounds where X is a group of =O, and the group of formula (ab-1) is a group selected from those of formula (b-10).

Another aspect of the invention provides compounds where X is a group of =O, and the group of formula (ab-1) is a group selected from those of formula (b-20).

Still another aspect of the invention provides compounds where X is a group of =O, and the group of formula (ab-1) is a group selected from those of formula (b-30).

Of the groups of formula (b-10), preferred are those selected from a formula (b-11):

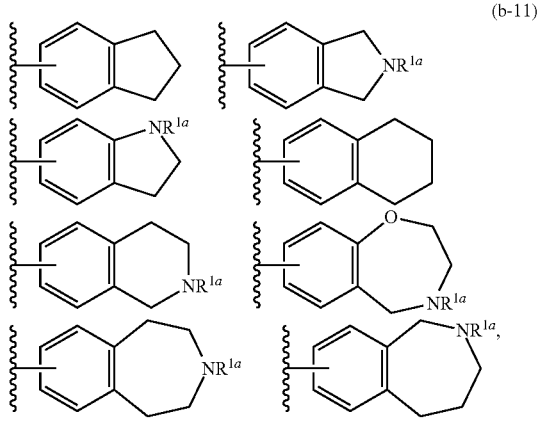
(b-11)

more preferred are those selected from a formula (b-12):

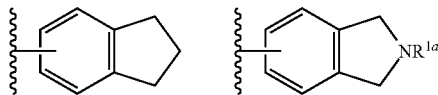
(b-12)

In the above formulae, $R^{1a}$ and $R^{2a}$ each independently mean a hydrogen atom, or mean a C1-C6 alkyl, C3-C6 cycloalkyl or C2-C7 alkanoyl group optionally having a substituent selected from a group consisting of a halogen atom, a hydroxyl group, a cyano group, a C1-C6 alkoxy group, a C3-C6 cycloalkyl group and a C2-C7 alkanoyl group, or mean a group of $-Q^{1b}$-Cy or $-Q^{1d}$-N($R^{1f}$)$R^{1g}$.

"C1-C6 alkyl, C3-C6 cycloalkyl or C2-C7 alkanoyl group optionally having a substituent selected from a group consisting of a halogen atom, a hydroxyl group, a cyano group, a C1-C6 alkoxy group, a C3-C6 cycloalkyl group and a C2-C7 alkanoyl group" means the above-mentioned, unsubstituted C1-C6 alkyl, C3-C6 cycloalkyl or C2-C7 alkanoyl group, or means the above-mentioned C1-C6 alkyl, C3-C6 cycloalkyl or C2-C7 alkanoyl group having a substituent at any substitutable position, in which the substituent may be the same or different, one or two or more, preferably one or two substituents selected from a group consisting of a halogen atom, a hydroxyl group, a cyano group, a C1-C6 alkoxy group, a C3-C6 cycloalkyl group and a C2-C7 alkanoyl group.

The substituent is preferably a halogen atom such as a chlorine atom or a fluorine atom; a hydroxyl group; a C1-C6 alkoxy group such as a methoxy group or an ethoxy group; a C3-C6 cycloalkyl group such as a cyclopropyl group; or a C2-C7 alkanoyl group such as an acetyl group; more preferably a halogen atom such as a fluorine atom; a hydroxyl group; or a C1-C6 alkoxy group such as a methoxy group.

"C1-C6 alkyl group" itself of the above-mentioned, optionally-substituted C1-C6 alkyl group for $R^{1a}$ or $R^{2a}$ is preferably a methyl group, an ethyl group, a propyl group, an isopropyl group or a 2-methylpropyl group, more preferably a methyl group or an ethyl group.

Preferred embodiments of the above-mentioned, optionally-substituted C1-C6 alkyl group for $R^{1a}$ or $R^{2a}$ include a methyl group, an ethyl group, an isopropyl group, a 2,2-difluoroethyl group, a 2-hydroxyethyl group, a 2-hydroxypropyl group, a 2-hydroxy-2-methylpropyl group, or a 2-methoxyethyl group; and more preferred is a methyl group, an ethyl group, or a 2-hydroxyethyl group.

The above-mentioned, optionally-substituted C3-C6 cycloalkyl group for $R^{1a}$ or $R^{2a}$ is preferably a cyclopropyl group.

The above-mentioned, optionally-substituted C2-C7 alkanoyl group for $R^{1a}$ or $R^{2a}$ is preferably an acetyl group.

In the group of -$Q^{1b}$-Cy, Cy means an aryl or heterocyclic group optionally substituted with a halogen atom or a C1-C6 alkyl group; $Q^{1b}$ means a single bond or a C1-C6 alkylene group. One or two or more methylene groups constituting the C1-C6 alkylene group may be independently replaced by a sulfinyl group, a sulfonyl group or a carbonyl group.

"Aryl or heterocyclic group optionally substituted with a halogen atom or a C1-C6 alkyl group" means the above-mentioned unsubstituted aryl or heterocyclic group, or the above-mentioned aryl or heterocyclic group having a substituent at any substitutable position. The substituent may be the same or different, one or two or more, preferably 1 or 2 substituents selected from a halogen atom and a C1-C6 alkyl group.

The substituent is preferably a halogen atom such as a chlorine atom or a fluorine atom; or a C1-C6 alkyl group such as a methyl group or an ethyl group.

The aryl group for Cy is preferably a phenyl group; and the heterocyclic group is preferably a pyridyl group, a tetrahydrofuryl group or a pyrrolidinyl group, more preferably a pyridyl group.

The C1-C6 alkylene group for $Q^{1b}$ is preferably a methylene group or an ethylene group.

Preferred embodiments of the group of -$Q^{1b}$-Cy are an aralkyl group, preferably benzyl, a 2-pyridyl group, a tetrahydrofuran-3-ylmethyl group, a 1-methyl-2-pyrrolidinylmethyl group, a 2-(1-pyrrolidinyl)ethyl group; and more preferred is a 2-pyridyl group.

In the group of -$Q^{1d}$-N($R^{1f}$)$R^{1g}$, $R^{1f}$ and $R^{1g}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; $Q^{1d}$ means a single bond or a C1-C6 alkylene group, in which one or two or more methylene groups constituting the C1-C6 alkylene group may be independently replaced by a sulfinyl group, a sulfonyl group or a carbonyl group.

"C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" means the above-mentioned, unsubstituted C1-C6 alkyl, C2-C7 alkanoyl or C1-C6 alkylsulfonyl group, or means the above-mentioned C1-C6 alkyl, C2-C7 alkanoyl or C1-C6 alkylsulfonyl group having a substituent at any substitutable position, in which the substituent may be the same or different, one or two or more, preferably one or two substituents selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group.

The substituent is preferably a halogen atom such as a chlorine atom or a fluorine atom; a hydroxyl group; a C1-C6 alkoxy group such as a methoxy group or an ethoxy group; a C3-C6 cycloalkyl group such as a cyclopropyl group; or a C2-C7 alkanoyl group such as an acetyl group; or a C1-C6 alkylsulfonyl group such as a methylsulfonyl group; more preferably a halogen atom such as a fluorine atom or a hydroxyl group.

"C1-C6 alkyl group" itself of the above-mentioned, optionally-substituted C1-C6 alkyl group for $R^{1f}$ or $R^{1g}$ is preferably a methyl group, an ethyl group or a propyl group, more preferably a methyl group or an ethyl group.

The above-mentioned, optionally-substituted C2-C7 alkanoyl group for $R^{1f}$ or $R^{1g}$ is preferably an acetyl group.

The above-mentioned, optionally-substituted C1-C6 alkylsulfonyl group for $R^{1f}$ or $R^{1g}$ is preferably a methylsulfonyl group.

The C1-C6 alkylene group for $Q^{1d}$ is preferably a methylene group or an ethylene group.

Preferred embodiments of the group of -$Q^{1d}$-N($R^{1f}$)$R^{1g}$ are a 2-(dimethylamino)ethyl group, a dimethylaminocarbonylmethyl group, a dimethylaminomethylcarbonyl group, a 2-[methyl(methylsulfonyl)amino]ethyl group, a 2-[acetyl (methyl)amino]ethyl group; and more preferred are a 2-(dimethylamino)ethyl group, a dimethylaminocarbonylmethyl group, or a dimethylaminomethylcarbonyl group.

Preferred embodiments of $R^{1a}$ or $R^{2a}$ are a hydrogen atom, the above-mentioned, optionally-substituted C1-C6 alkyl or C2-C7 alkanoyl group, and a group of -$Q^{1d}$-N($R^{1f}$)$R^{1g}$; and more preferred is the above-mentioned, optionally-substituted C1-C6 alkyl or C2-C7 alkanoyl group.

One or two or more methylene groups constituting the aliphatic ring corresponding to above Ring B may be independently substituted with a halogen atom, a hydroxyl group, a C1-C6 alkyl group, a hydroxy-C1-C6 alkyl group or a group of -$Q^{1a}$-N($R^{1b}$)$R^{1c}$.

The halogen atom for the substituent is preferably a chlorine atom or a fluorine atom.

The C1-C6 alkyl group for the substituent is preferably a methyl group or an ethyl group.

The hydroxy-C1-C6 alkyl group for the substituent is preferably a hydroxymethyl group or a 2-hydroxyethyl group.

In the group of -$Q^{1a}$-N($R^{1b}$)$R^{1e}$, $R^{1b}$ and $R^{1c}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of -$Q^{1e}$-N ($R^{1h}$)$R^{1i}$; $Q^{1a}$ means a single bond or a C1-C6 alkylene group, in which one or two or more methylene groups constituting the C1-C6 alkylene group may be independently replaced by a sulfinyl group, a sulfonyl group or a carbonyl group.

"C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" means the above-mentioned, unsubstituted C1-C6 alkyl, C2-C7 alkanoyl or C1-C6 alkylsulfonyl group, or means the above-mentioned C1-C6 alkyl, C2-C7 alkanoyl or C1-C6 alkylsulfonyl group having a substituent at any substitutable position, in which the substituent may be the same or different, one or two or more, preferably one or two substituents selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group.

The substituent is preferably a halogen atom such as a chlorine atom or a fluorine atom; a hydroxyl group; a C1-C6 alkoxy group such as a methoxy group or an ethoxy group; a C3-C6 cycloalkyl group such as a cyclopropyl group; or a C2-C7 alkanoyl group such as an acetyl group; or a C1-C6 alkylsulfonyl group such as a methylsulfonyl group; more preferably a hydroxyl group.

"C1-C6 alkyl group" itself of the above-mentioned, optionally-substituted C1-C6 alkyl group for $R^{1b}$ or $R^{1c}$ is preferably a methyl group, an ethyl group or a propyl group, more preferably a methyl group or an ethyl group.

Preferred embodiments of the above-mentioned, optionally-substituted C1-C6 alkyl group for $R^{1b}$ or $R^{1c}$ include a methyl group, an ethyl group, an isopropyl group, a 2,2-difluoroethyl group, a 2-hydroxyethyl group, a 2-hydroxypropyl group, a 2-hydroxy-2-methylpropyl group, or a 2-methoxyethyl group; and more preferred is a methyl group, or a 2-hydroxyethyl group.

The above-mentioned, optionally-substituted C2-C7 alkanoyl group for $R^{1b}$ or $R^{1c}$ is preferably an acetyl group.

The above-mentioned, optionally-substituted C1-C6 alkylsulfonyl group for $R^{1b}$ or $R^{1c}$ is preferably a methylsulfonyl group.

In the group of $-Q^{1e}-N(R^{1h})R^{1i}$, $R^{1h}$ and $R^{1i}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; $Q^{1e}$ means a single bond or a C1-C6 alkylene group, in which one or two or more methylene groups constituting the C1-C6 alkylene group may be independently replaced by a sulfinyl group, a sulfonyl group or a carbonyl group.

"C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for $R^{1h}$ or $R^{1i}$ has the same meaning as that of the "C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" for the above-mentioned $R^{1b}$ or $R^{1c}$.

$R^{1h}$ or $R^{1i}$ is preferably a hydrogen atom, or the above-mentioned, optionally substituted C1-C6 alkyl group, such as a methyl group or a 2,2-difluoroethyl group.

$Q^{1e}$ is preferably a methylene group or an ethylene group.

The group of $-Q^{1e}-N(R^{1h})R^{1i}$ is preferably a dimethylaminomethylcarbonyl group.

$Q^{1a}$ is preferably a single bond, or a C1-C6 alkylene group such as a methylene group.

Preferred embodiments of the group of $-Q^{1a}-N(R^{1b})R^{1c}$ are a dimethylamino group, a 2-hydroxyethyl(methyl)amino group, a dimethylaminomethyl group, a 2-(dimethylamino)ethyl group, a (dimethylaminomethylcarbonyl)amino group; and more preferred are a dimethylamino group, a 2-hydroxyethyl(methyl)amino group, a dimethylaminomethyl group; even more preferred are a dimethylamino group, a dimethylaminomethyl group.

The substituent that may be on one or two or more methylene groups constituting the aliphatic ring corresponding to above Ring B is preferably a C1-C6 alkyl group or a group of $-Q^{1a}-N(R^{1b})R^{1c}$.

Preferred embodiments of the group of formula (ab-1):

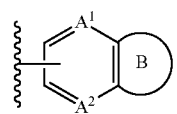

(ab-1)

are mentioned below.

Preferred embodiments of the above-mentioned, optionally-substituted group of

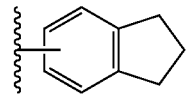

include a 2-(dimethylamino)-2,3-dihydro-1H-inden-5-yl group, a 3-(dimethylamino)-1,1-dimethyl-2,3-dihydro-1H-inden-5-yl group, or a 2-[(2-hydroxyethyl)(methyl)amino]-2,3-dihydro-1H-inden-5-yl group.

Preferred embodiments of the above-mentioned, optionally-substituted group of

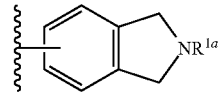

include a 1,1,2-trimethyl-2,3-dihydro-1H-isoindol-5-yl group, a 2,3,3-trimethyl-2,3-dihydro-1H-isoindol-5-yl group, or a 1,1,2,3,3-pentamethyl-2,3-dihydro-1H-isoindol-5-yl group.

Preferred embodiments of the above-mentioned, optionally-substituted group of

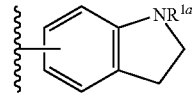

include a 1-[2-(dimethylamino)ethyl]-2,3-dihydro-1H-indol-5-yl group.

Preferred embodiments of the above-mentioned, optionally-substituted group of

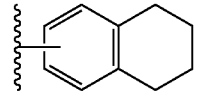

include a 6-(dimethylamino)-5,6,7,8-tetrahydronaphthalen-2-yl group, a 7-(dimethylamino)-5,6,7,8-tetrahydronaphthalen-2-yl group, a 8-(dimethylamino)-5,6,7,8-tetrahydronaphthalen-2-yl group, a 6-[(dimethylamino)methyl]-5,6,7,8-tetrahydronaphthalen-2-yl group, or a 7-[(dimethylamino)methyl]-5,6,7,8-tetrahydronaphthalen-2-yl group.

Preferred embodiments of the above-mentioned, optionally-substituted group of

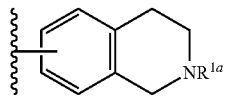

include a 1,2,3,4-tetrahydroisoquinolin-7-yl group, a 1-ethyl-1,2,3,4-tetrahydroisoquinolin-6-yl group, a 2-methyl-1,2,3,4-tetrahydroisoquinolin-6-yl group, a 2-ethyl-1,2,3,4-tetrahydroisoquinolin-6-yl group, a 2-methyl-1,2,3,4-tetrahydroisoquinolin-7-yl group, a 2-isopropyl-1,2,3,4-tetrahydroisoquinolin-7-yl group, a 1,1-dimethyl-1,2,3,4-tetrahydroisoquinolin-6-yl group, a 2,5-dimethyl-1,2,3,4-tetrahydroisoquinolin-7-yl group, a 4,4-dimethyl-1,2,3,4-tetrahydroisoquinolin-7-yl group, a 1,1,2-trimethyl-1,2,3,4-tetrahydroisoquinolin-6-yl group, a 2-ethyl-1,1-dimethyl-1,2,3,4-tetrahydroisoquinolin-6-yl group, a 2-cyclopropyl-1,1-dimethyl-1,2,3,4-tetrahydroisoquinolin-6-yl group, a 1,1,2-trimethyl-1,2,3,4-tetrahydroisoquinolin-7-yl group, a 2,4,4-trimethyl-1,2,3,4-tetrahydroisoquinolin-7-yl group, a 2-(2-hydroxyethyl)-1,2,3,4-tetrahydroisoquinolin-6-yl group, a 2-(2-hydroxypropyl)-1,2,3,4-tetrahydroisoquinolin-6-yl group, a 2-(2-hydroxyethyl)-1,2,3,4-tetrahydroisoquinolin-7-yl group, a 2-(2-hydroxy-2-methylpropyl)-1,2,3,4-tetrahydroisoquinolin-7-yl group, a 2-(2-hydroxyethyl)-1,1-dimethyl-1,2,3,4-tetrahydroisoquinolin-6-yl group, a 2-(2-hydroxyethyl)-1,1-dimethyl-1,2,3,4-tetrahydroisoquinolin-7-yl group, a 2-(2-hydroxyethyl)-4,4-dimethyl-1,2,3,4-tetrahydroisoquinolin-7-yl group, a 2-(2-hydroxy-2-methylpropyl)-1,1-dimethyl-1,2,3,4-tetrahydroisoquinolin-6-yl group, a 2-(2-methoxyethyl)-1,2,3,4-tetrahydroisoquinolin-6-yl group, a 2-(2-methoxyethyl)-1,2,3,4-tetrahydroisoquinolin-7-yl group, a 2-(2-methoxyethyl)-1,1-dimethyl-1,2,3,4-tetrahydroisoquinolin-6-yl group, a 2-(N,N-dimethylglycyl)-1,1-dimethyl-1,2,3,4-tetrahydroisoquinolin-6-yl group, a 2-acetyl-1,1-dimethyl-1,2,3,4-tetrahydroisoquinolin-6-yl group, or a 2-pyridin-2-yl-1,2,3,4-tetrahydroisoquinolin-6-yl group.

Preferred embodiments of the above-mentioned, optionally-substituted group of

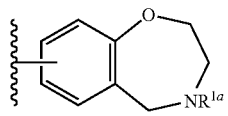

include a 4-methyl-2,3,4,5-tetrahydro-1,4-benzoxazepin-7-yl group.

Preferred embodiments of the above-mentioned, optionally-substituted group of

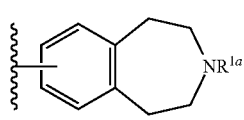

include a 3-methyl-2,3,4,5-tetrahydro-1H-3-benzazepin-7-yl group, a 3-cyclopropyl-2,3,4,5-tetrahydro-1H-3-benzazepin-7-yl group, a 3-(2,2-difluoroethyl)-2,3,4,5-tetrahydro-1H-3-benzazepin-7-yl group, a 3-(2-hydroxyethyl)-2,3,4,5-tetrahydro-1H-3-benzazepin-7-yl group, a 3-(2-methoxyethyl)-2,3,4,5-tetrahydro-1H-3-benzazepin-7-yl group, or a 3-(dimethylaminocarbonylmethyl)-2,3,4,5-tetrahydro-1H-3-benzazepin-7-yl group.

Preferred embodiments of the above-mentioned, optionally-substituted group of

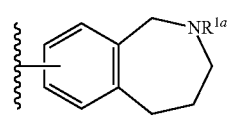

include a 2-methyl-2,3,4,5-tetrahydro-1H-2-benzazepin-7-yl group, or a 2-methyl-2,3,4,5-tetrahydro-1H-2-benzazepin-8-yl group.

Preferred embodiments of the above-mentioned, optionally-substituted group of

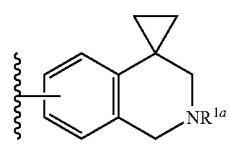

include a 2'-methyl-2',3'-dihydro-1'H-spiro[cyclopropane-1,4'-isoquinolin]-7'-yl group.

Preferred embodiments of the above-mentioned, optionally-substituted group of

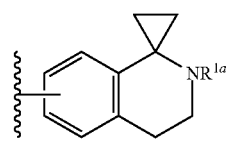

include a 3',4'-dihydro-2'H-spiro[cyclopropane-1,1'-isoquinolin]-6'-yl group, or a 2'-methyl-3',4'-dihydro-2'H-spiro[cyclopropane-1,1'-isoquinolin]-6'-yl group.

Preferred embodiments of the above-mentioned, optionally-substituted group of

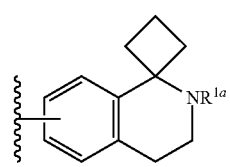

include a 3',4'-dihydro-2'H-spiro[cyclobutane-1,1'-isoquinolin]-6'-yl group, a 2'-methyl-3',4'-dihydro-2'H-spiro[cyclobutane-1,1'-isoquinolin]-6'-yl group, or a 2'-(2-hydroxyethyl)-3',4'-dihydro-2'H-spiro[cyclobutane-1,1'-isoquinolin]-6'-yl group.

Preferred embodiments of the above-mentioned, optionally-substituted group of

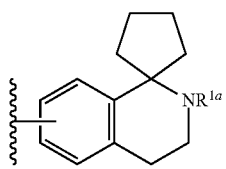

include a 3',4'-dihydro-2'H-spiro[cyclopentane-1,1'-isoquinolin]-6'-yl group, a 2'-methyl-3',4'-dihydro-2'H-spiro[cyclopentane-1,1'-isoquinolin]-6'-yl group.

More preferred embodiments of the group of formula (ab-1):

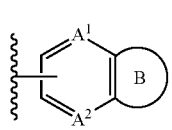

(ab-1)

include a 2-(dimethylamino)-2,3-dihydro-1H-inden-5-yl group, a 3-(dimethylamino)-1,1-dimethyl-2,3-dihydro-1H-inden-5-yl group, a 1,1,2-trimethyl-2,3-dihydro-1H-isoindol-5-yl group, a 7-(dimethylamino)-5,6,7,8-tetrahydronaphthalen-2-yl group, a 6-[(dimethylamino)methyl]-5,6,7,8-tetrahydronaphthalen-2-yl group, a 2-ethyl-1,2,3,4-tetrahydroisoquinolin-6-yl group, a 2-methyl-1,2,3,4-tetrahydroisoquinolin-7-yl group, a 2,5-dimethyl-1,2,3,4-tetrahydroisoquinolin-7-yl group, a 1,1,2-trimethyl-1,2,3,4-tetrahydroisoquinolin-6-yl group, a 2,4,4-trimethyl-1,2,3,4-tetrahydroisoquinolin-7-yl group, a 2-(2-hydroxyethyl)-1,1-dimethyl-1,2,3,4-tetrahydroisoquinolin-6-yl group, a 2-acetyl-1,1-dimethyl-1,2,3,4-tetrahydroisoquinolin-6-yl group, a 3-methyl-2,3,4,5-tetrahydro-1H-3-benzazepin-7-yl group, or a 2'-methyl-2',3'-dihydro-1'H-spiro[cyclopropane-1,4'-isoquinolin]-7'-yl group; and more preferred is a 2'-methyl-2',3'-dihydro-1'H-spiro[cyclopropane-1,4'-isoquinolin]-7'-yl group.

$R^1$ means a hydrogen atom, or means a C1-C6 alkyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

"C1-C6 alkyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group" means the above-mentioned, unsubstituted C1-C6 alkyl group, or the above-mentioned C1-C6 alkyl group having a substituent at any substitutable position, in which the substituent may be the same or different, one or two or more, preferably one or two substituents selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group.

The substituent is preferably a halogen atom such as a chlorine atom or a fluorine atom; a hydroxy group; a C1-C6 alkoxy group such as a methoxy group or an ethoxy group; a C3-C6 cycloalkyl group such as a cyclopropyl group; a C2-C7 alkanoyl group such as an acetyl group; or a C1-C6 alkylsulfonyl group such as a methylsulfonyl group; more preferably a halogen atom such as a fluorine atom, or a hydroxyl group.

The above-mentioned optionally-substituted C1-C6 alkyl group for $R^1$ is preferably a methyl group, an ethyl group, a propyl group, an isopropyl group, or a 2-methylpropyl group, more preferably a methyl group.

"Aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group" for $R^1$ means the above-mentioned, unsubstituted aryl, aralkyl or heteroaryl group, or means the above-mentioned aryl, aralkyl or heteroaryl group having a substituent at any substitutable position, in which the substituent may be the same or different, one or two or more, preferably 1, 2 or 3 substituents selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

The substituent is preferably a halogen atom such as a chlorine atom or a fluorine atom; a cyano group; a C1-C6 alkyl group such as a methyl group; a C1-C6 alkoxy group such as a methoxy group or an ethoxy group; a halo-C1-C6 alkyl group such as a trifluoromethyl group; or a hydroxy-C1-C6 alkyl group such as a hydroxymethyl group; more preferably a halogen atom such as a chlorine atom or a fluorine atom, or a C1-C6 alkyl group such as a methyl group.

"Aryl group" itself of the above-mentioned, optionally-substituted aryl group for $R^1$ is preferably a phenyl group.

"Aralkyl group" itself of the above-mentioned, optionally-substituted aralkyl group for $R^1$ is preferably a benzyl group.

"Heteroaryl group" itself of the above-mentioned, optionally-substituted heteroaryl group for $R^1$ is preferably a pyridyl group.

Preferred embodiments of $R^1$ include a hydrogen atom, or the above-mentioned, optionally-substituted C1-C6 alkyl group, and more preferred is a hydrogen atom or a methyl group.

$R^2$ means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

"Aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group" means the above-mentioned, unsubstituted aryl, aralkyl or heteroaryl group, or means the above-mentioned aryl, aralkyl or heteroaryl group optionally having a substituent at any substitutable position, in which the substituent may be the same or different, one or two or more, preferably 1, 2 or 3 substituents selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

The substituent is preferably a halogen atom such as a chlorine atom or a fluorine atom; a cyano group; a C1-C6 alkyl group such as a methyl group; a C1-C6 alkoxy group such as a methoxy group or an ethoxy group; a halo-C1-C6 alkyl group such as a trifluoromethyl group; or a hydroxy-C1-C6 alkyl group such as a hydroxymethyl group; more preferably a halogen atom such as a chlorine atom or a fluorine atom, or a C1-C6 alkyl group such as a methyl group.

"Aryl group" itself of the above-mentioned, optionally-substituted aryl group for $R^2$ is preferably a phenyl group.

"Aralkyl group" itself of the above-mentioned, optionally-substituted aralkyl group for $R^2$ is preferably a benzyl group.

"Heteroaryl group" itself of the above-mentioned, optionally-substituted heteroaryl group for $R^2$ is preferably a pyridyl group.

Preferred embodiments of $R^2$ include a phenyl group, a 2-chlorophenyl group, a 2-fluorophenyl group, a 2,6-dichlorophenyl group, a 2-chloro-3-fluorophenyl group, a 2-chloro-4-fluorophenyl group, a 2-chloro-5-fluorophenyl group, a 2-chloro-6-fluorophenyl group, a 2,6-dichloro-4-fluorophenyl group, a 2-chloro-4,6-difluorophenyl group, a 2-chloro-4-methylphenyl group, a 2-chloro-6-methylphenyl group, a 2,6-dichloro-4-methylphenyl group, a 2-chloro-5-trifluoromethylphenyl group, a 2,6-dichloro-4-trifluoromethylphenyl group, a 2-cyanophenyl group, a 2-alkoxyphenyl group, a 2,6-dichloro-4-hydroxymethylphenyl group, or a 2,4-dichloro-3-pyridyl group; and more preferred is a 2,6-dichlorophenyl group, a 2-chloro-6-fluorophenyl group, a 2,6-dichloro-4-fluorophenyl group, a 2-chloro-4,6-difluorophenyl group, a 2-chloro-6-methylphenyl group, or a 2,4-dichloro-3-pyridyl group.

X means a group of =NH or =O. In the invention, X is preferably a group of =NH.

The terms "any substitutable position" mean positions having substitutable hydrogen(s) on carbon, nitrogen, oxygen and/or sulfur atom(s) where the substitution of hydrogen is chemically allowed and the substitution results in a stable compound.

In the invention, for example, the "replacing" of the methylene group constituting Ring B and the like, for example, by an oxygen atom, a sulfur atom, a sulfinyl group, a sulfonyl group, a carbonyl group or a group of —N($R^{1a}$)— is allowed only when the "replacing" is chemically allowed and gives a stable compound. The "replacing" of the methylene group constituting a C1-C6 alkylene group, for example, by a sulfinyl group, a sulfonyl group or a carbonyl group is allowed only when the "replacing" is chemically allowed and gives a stable compound.

Depending on the type of the substituent therein and on the salt form thereof, the compound of the invention may include stereoisomers and tautomers such as optical isomers, diastereomers and geometric isomers; and the compound of the invention encompasses all such stereoisomers, tautomers and their mixtures.

The invention includes various crystals, amorphous substances, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of these compounds include active compounds that are produced by putting the compounds of the invention in a biological environment, and are within the scope of the invention.

Examples of the compounds of formula (I) and pharmaceutically acceptable salts and N-oxide derivatives thereof are, for example, the compounds and pharmaceutically acceptable salts and N-oxide derivatives thereof described in Examples; and more preferred are the following compounds and pharmaceutically acceptable salts or N-oxide derivatives thereof:

(1) 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one;

(2) 3-(2,6-dichlorophenyl)-4-imino-7-{[2,4,4-trimethyl-1,2,3,4-tetrahydroisoquinolin-7-yl]amino}-3,4-dihydropyrimido[4,5-d]pyrimidin-2(1H)-one;

(3) 3-(2,6-dichlorophenyl)-4-imino-7-[(1,1,2-trimethyl-1,2,3,4-tetrahydroisoquinolin-6-yl)amino]-3,4-dihydropyrimido[4,5-d]pyrimidin-2(1H)-one;

(4) 3-(2,4-dichloropyridin-3-yl)-4-imino-7-{[1,1,2-trimethyl-1,2,3,4-tetrahydroisoqunolin-6-yl]amino}-3,4-dihydropyrimido[4,5-d]pyrimidin-2(1H)-one;

(5) 3-(2,6-dichlorophenyl)-4-imino-7-[(1,1,2-trimethyl-2,3-dihydro-1H-isoindol-5-yl)amino]-3,4-dihydropyrimido[4,5-d]pyrimidin-2(1H)-one;

(6) 3-(2,6-dichlorophenyl)-7-{[2-(dimethylamino)-2,3-dihydro-1H-inden-5-yl]amino}-4-imino-1-methyl-3,4-dihydropyrimido[4,5-d]pyrimidin-2(1H)-one;

(7) 3-(2,6-dichlorophenyl)-7-{[3-(dimethylamino)-1,1-dimethyl-2,3-dihydro-1H-inden-5-yl]amino}-4-imino-3,4-dihydropyrimido[4,5-d]pyrimidin-2(1H)-one;

(8) 3-(2-chloro-6-methylphenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one;

(9) 3-(2-chloro-6-fluorophenyl)-4-imino-7-{[2-methyl-1,2,3,4-tetrahydroisoquinolin-7-yl]amino}-3,4-dihydropyrimido[4,5-d]pyrimidin-2(1H)-one;

(10) 3-(2-chloro-4,6-difluorophenyl)-4-imino-7-{[2-methyl-1,2,3,4-tetrahydroisoquinolin-7-yl]amino}-3,4-dihydropyrimido[4,5-d]pyrimidin-2(1H)-one;

(11) 3-(2,6-dichloro-4-fluorophenyl)-4-imino-7-{[2-methyl-1,2,3,4-tetrahydroisoquinolin-7-yl]amino}-3,4-dihydropyrimido[4,5-d]pyrimidin-2(1H)-one;

(12) 3-(2,6-dichlorophenyl)-7-{[2,5-dimethyl-1,2,3,4-tetrahydroisoquinolin-7-yl]amino}-4-imino-3,4-dihydropyrimido[4,5-d]pyrimidin-2(1H)-one;

(13) 3-(2,6-dichlorophenyl)-7-{[2-(2-hydroxyethyl)-1,1-dimethyl-1,2,3,4-tetrahydroisoquinolin-6-yl]amino}-4-imino-1-methyl-3,4-dihydropyrimido[4,5-d]pyrimidin-2(1H)-one;

(14) 3-(2,6-dichlorophenyl)-4-imino-7-{[2-ethyl-1,2,3,4-tetrahydroisoquinolin-6-yl]amino}-3,4-dihydropyrimido[4,5-d]pyrimidin-2(1H)-one;

(15) 3-(2,6-dichlorophenyl)-4-imino-7-[(2-methyl-1,2,3,4-tetrahydroisoquinolin-6-yl)amino]-3,4-dihydropyrimido[4,5-d]pyrimidin-2(1H)-one;

(16) 3-(2,6-dichlorophenyl)-7-{[2-(dimethylamino)-2,3-dihydro-1H-inden-5-yl]amino}-4-imino-3,4-dihydropyrimido[4,5-d]pyrimidin-2(1H)-one;

(17) 3-(2,6-dichlorophenyl)-7-{[7-(dimethylamino)-5,6,7,8-tetrahydronaphthalen-2-yl]amino}-4-imino-3,4-dihydropyrimido[4,5-d]pyrimidin-2(1H)-one;

(18) 3-(2,6-dichlorophenyl)-4-imino-7-[(3-methyl-2,3,4,5-tetrahydro-1H-3-benzazepin-7-yl)amino]-3,4-dihydropyrimido[4,5-d]pyrimidin-2(1H)-one;

(19) 3-(2,6-dichlorophenyl)-7-({6-[(dimethylamino)methyl]-5,6,7,8-tetrahydronaphthalen-2-yl}amino)-4-imino-3,4-dihydropyrimido[4,5-d]pyrimidin-2(1H)-one; or

(20) 7-[(2-acetyl-1,1-dimethyl-1,2,3,4-tetrahydroisoquinolin-6-yl)amino]-3-(2,6-dichlorophenyl)-4-imino-3,4-dihydropyrimido[4,5-d]pyrimidin-2(1H)-one.

Methods for producing the compounds of the invention are described below.

Compounds (I) of the invention may be produced, for example, according to the production methods mentioned below or according to the methods shown in Examples and Production Examples. However, the production methods for compounds (I) of the invention should not be limited to those reaction examples.

Production Method 1

A compound of a general formula (II):

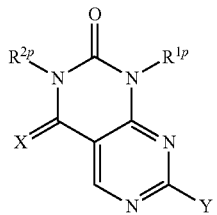

(II)

wherein, $R^{1p}$ means a hydrogen atom, or means a C1-C6 alkyl group optionally having a substituent selected from a group consisting of a halogen atom, a cyano group, an optionally-protected hydroxyl group, a C1-C6 alkoxy group, a C3-C6 cycloalkyl group, a C2-C7 alkanoyl group and a C1-C6 alkylsulfonyl group, or means an aryl, aralkyl or heteroaryl group optionally having a substituent selected from a group consisting of a halogen atom, an optionally-protected hydroxyl group, a cyano group, an optionally-protected amino group, a C1-C6 alkyl group, a C1-C6 alkoxy group, a halo-C1-C6 alkyl group and an optionally-protected hydroxy-C1-C6 alkyl group;

$R^{2p}$ means an aryl, aralkyl or heteroaryl group optionally having a substituent selected from a group consisting of a halogen atom, an optionally-protected hydroxyl group, a cyano group, an optionally-protected amino group, a C1-C6 alkyl group, a C1-C6 alkoxy group, a halo-C1-C6 alkyl group and an optionally-protected hydroxy-C1-C6 alkyl group;

Y means a leaving group; and X has the same meaning as above] is reacted with a compound of the following general formula (III) or a salt thereof:

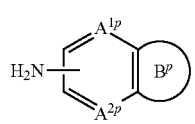

(III)

wherein, $A^{1p}$ and $A^{2p}$ each independently mean a nitrogen atom, or mean a methine group optionally substituted with a halogen atom, an optionally-protected hydroxyl group, a cyano group, a C1-C6 alkyl group or an optionally-protected hydroxy-C1-C6 alkyl group;

Ring $B^p$ means a 5-membered to 7-membered aliphatic ring condensed with a ring of formula (ap):

(ap)

or means a spiro or bicyclo ring formed from the 5-membered to 7-membered aliphatic ring with any other 3-membered to 7-membered aliphatic ring, which is condensed with the ring of formula (ap), in which one or two or more methylene groups constituting said Ring $B^p$ may be independently replaced by an oxygen atom, a sulfur atom, a sulfinyl group, a sulfonyl group, an optionally-protected carbonyl group or a group of —N($R^{1ap}$)—; and one or two or more methylene groups constituting said Ring $B^p$ may be independently substituted with a halogen atom, an optionally-protected hydroxyl group, a C1-C6 alkyl group, an optionally-protected hydroxy-C1-C6 alkyl group or a group of -$Q^{1ap}$-N($R^{1bp}$)$R^{1cp}$;

$Q^{1ap}$, $Q^{1bp}$, $Q^{1dp}$ and $Q^{1ep}$ each independently mean a single bond or a C1-C6 alkylene group, in which one or two or more methylene groups constituting the C1-C6 alkylene group may be independently replaced by a sulfinyl group, a sulfonyl group or an optionally-protected carbonyl group;

$R^{1ap}$ means a hydrogen atom, or means a C1-C6 alkyl, C3-C6 cycloalkyl or C2-C7 alkanoyl group optionally having a substituent selected from a group consisting of a halogen atom, an optionally-protected hydroxyl group, a cyano group, a C1-C6 alkoxy group, a C3-C6 cycloalkyl group and a C2-C7 alkanoyl group, or means a group of -$Q^{1bp}$-Cy or -$Q^{1dp}$-N($R^{1fp}$)$R^{1gp}$;

$R^{1bp}$ and $R^{1cp}$ each independently mean an amino or iminoprotective group, or means a hydrogen atom, or means a C1-C6 alkyl, C2-C7 alkanoyl or C1-C6 alkylsulfonyl group optionally having a substituent selected from a group consisting of a halogen atom, an optionally-protected hydroxyl group, a cyano group, a C1-C6 alkoxy group, a C3-C6 cycloalkyl group, a C2-C7 alkanoyl group and a C1-C6 alkylsulfonyl group, or mean a group of -$Q^{1ep}$-N($R^{1hp}$)$R^{1ip}$;

$R^{1fp}$ and $R^{1gp}$ each independently mean a protective group for the amino or imino group, or mean a hydrogen atom, or mean a C1-C6 alkyl, C2-C7 alkanoyl or C1-C6 alkylsulfonyl group optionally having a substituent selected from a group consisting of a halogen atom, an optionally-substituted hydroxyl group, a cyano group, a C1-C6 alkoxy group, a C3-C6 cycloalkyl group, a C2-C7 alkanoyl group and a C1-C6 alkylsulfonyl group;

$R^{1hp}$ and $R^{1ip}$ each independently mean an amino or iminoprotective group, or mean a hydrogen atom, or mean a C1-C6 alkyl, C2-C7 alkanoyl or C1-C6 alkylsulfonyl group optionally having a substituent selected from a group consisting of a halogen atom, an optionally-protected hydroxyl group, a cyano group, a C1-C6 alkoxy group, a C3-C6 cycloalkyl group, a C2-C7 alkanoyl group and a C1-C6 alkylsulfonyl group, and Cy has the same means as described above], thereby giving a compound of a general formula (IV):

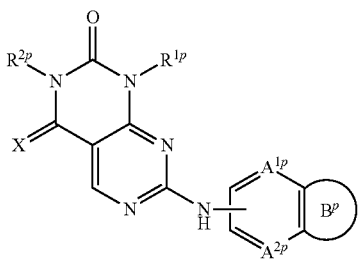

(IV)

wherein $A^{1p}, A^{2p}, B^p, R^{1p}, R^{2p}$ and X have the same meanings as above, and when the compound (IV) has a protective group of the amino, imino, hydroxyl or carbonyl group, then this is processed according to a process suitably selected from the following:

(1) a step of removing the protective group, or (2) a step of oxidizing the nitrogen atom in the compound when the intended compound to be produced is an N-oxide derivative, thereby producing a compound of formula (I) or its N-oxide derivative.

In case where the compound of formula (IV) does not have a protective group of the amino, imino, hydroxyl or carbonyl group, then the compound (IV) signifies a compound of formula (I).

The leaving group for Y includes, for example, a halogen atom such as a fluorine atom, a chlorine atom, a bromine atom or an iodine atom; a methylsulfinyl group; an organic sulfonyl group such as a methylsulfonyl group, an ethylsulfonyl group, a phenylsulfonyl group; and an organic sulfonyloxy group such as a methylsulfonyloxy group, a trifluoromethylsulfonyloxy group, a p-tolylsulfonyloxy group; and of those, preferred are a chlorine atom, a methylsulfinyl group, a methylsulfonyl group.

The above production method is a general production method for the compounds of formula (I).

In the above reaction, when the reactants have an amino group, an imino group, a hydroxyl group, a carbonyl group or the like not participating in the reaction, then the amino group, the imino group, the hydroxyl group and the carbonyl group may be suitably protected with an amino or imino-protective group, a hydroxyl-protective group or a carbonyl-protective group prior to the reaction, and the protective group may be removed after the reaction.

Not specifically defined, "amino or imino-protective group" may be any one having its function. For example, it includes an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as benzenesulfonyl group, a toluenesulfonyl group; and is especially preferably an acetyl group, a benzoyl group, a tert-butoxycarbonyl group, a trimethylsilylethoxymethyl group, a methylsulfonyl group.

Not specifically defined, "hydroxyl-protective group" may be any one having its function. For example, it includes a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group; and is especially preferably a methyl group, a methoxymethyl group, a tetrahydropyranyl group, a trityl group, a trimethylsilylethoxymethyl group, a tert-butyldimethylsilyl group, an acetyl group.

Not specifically defined, "carbonyl-protective group" may be any one having its function. For example, it includes acetals and ketals such as ethylene ketal, trimethylene ketal, dimethyl ketal.

For the reaction of the compound of formula (II) and the compound of formula (III), in general, an equimolar or excessive molar amount, preferably from an equimolar amount to 1.5 mols of the compound (III) is used relative to one mol of the compound (II).

The reaction is attained generally in an inert solvent. The inert solvent is, for example, preferably a non-polar solvent, for example, an aromatic hydrocarbon such as toluene, benzene, xylene; a polar solvent such as methylene chloride, chloroform, tetrahydrofuran, dioxane, dimethylformamide, N-methylpyrrolidone, dimethylsulfoxide; or their mixed solvent.

When X is $=$NH, in general, the reaction is preferably attained in a polar solvent, for example, an alcohol such as methanol, ethanol, butanol, isopropanol.

Preferably, the reaction is attained in the presence of a base or an acid.

The acid includes, for example, inorganic acids such as hydrochloric acid, sulfuric acid, nitric acid, phosphoric acid, perchloric acid; organic acids such as maleic acid, fumaric acid, tartaric acid, citric acid, ascorbic acid, trifluoroacetic acid; sulfonic acids such as methanesulfonic acid, isethionic acid, benzenesulfonic acid, p-toluenesulfonic acid; and Lewis acids such as hafnium trifluoromethanesulfonate, ytterbium trifluoromethanesulfonate, scandium trifluoromethanesulfonate; and preferred are p-toluenesulfonic acid, hafnium trifluoromethanesulfonate.

The amount of the acid to be used may be generally from 0.01 to excessive molar amount, preferably from 0.02 to 1.5 mols relative to one mol of the compound of formula (II).

The base includes, for example, organic bases such as triethylamine, diisopropylethylamine, pyridine, 4-dimethylaminopyridine; and inorganic bases such as sodium hydrogencarbonate, sodium carbonate, potassium carbonate, cesium carbonate, sodium hydroxide, potassium hydroxide.

The amount of the base to be used may be generally from an equimolar amount to an excessive molar amount, preferably from 1 to 3 mols relative to one mol of the compound of formula (II).

The reaction temperature may be generally from 0° C. to 200° C., preferably from 20° C. to 150° C.

The reaction time may be generally from 5 minutes to 7 days, preferably from 30 minutes to 24 hours.

After the reaction, the system may be processed in an ordinary manner to obtain a crude product of the compound of formula (IV). Thus obtained, the compound of formula (IV) is purified in an ordinary manner, or not purified, optionally it is processed for removing the protective group of the amino group, the imino group, the hydroxyl group or the carbonyl group, if any, in the compound (IV), according to a process suitably selected from the following:

(1) a step of removing the protective group, or
(2) a step of oxidizing the nitrogen atom in the compound when the intended compound to be produced is an N-oxide derivative, thereby producing a compound of formula (I) or its N-oxide derivative.

The method of removing the protective group varies, depending on the type of the protective group and on the stability of the intended compound (I), and may be attained by suitably combining reactions of removing the protective group of the amino group, the hydroxyl group and the carbonyl group. For example, the deprotection may be attained according to methods described in references [see Protective Groups in Organic Synthesis, 3rd. Ed., by T. W. Greene, John Wiley & Sons (1999)] or according to methods similar thereto. For example, herein employable are a method of solvolysis with an acid or a base, which comprises processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; and a method of chemical reduction with a metal hydride complex, or catalytic reduction with a palladium-carbon catalyst or a Raney nickel catalyst.

The process of oxidizing the nitrogen atom to produce an N-oxide derivative may be attained, for example, by the use of an oxidizing agent such as m-chloroperbenzoic acid, dioxirane, sodium periodate, hydrogen peroxide.

The amount of the oxidizing agent to be used may be generally from 0.5 mols to an excessive molar amount, preferably from 1 to 5 mols relative to one mol of the compound of formula (IV).

The reaction may be attained in a solvent suitably selected in accordance with the oxidizing agent to be used for the reaction. For example, when m-chloroperbenzoic acid is used as the oxidizing agent, then the solvent is preferably methylene chloride or chloroform; and when dioxirane is used as the oxidizing agent, then the solvent is preferably acetone or water.

The reaction temperature may be generally from −50° C. to 100° C., preferably from −20° C. to 50° C.

The reaction time may be generally from 15 minutes to 7 days, preferably from 30 minutes to 24 hours.

The compound of formula (I) or its N-oxide derivative may be readily isolated and purified in any ordinary separation method. Examples of the method are, for example, solvent extraction, recrystallization, column chromatography, partitioning thin-layer chromatography.

The compounds may be converted into pharmaceutically acceptable salts thereof in an ordinary manner; and on the contrary, their salts may also be converted into free compounds in an ordinary manner.

"Salts" of the compound of formula (III) mean ordinary salts used in the field of organic chemistry. For example, when the compound has an amino group or a basic heterocyclic group, then its salts are acid-addition salts at the amino group or the basic heterocyclic group.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; sulfonates such as methanesulfonates, isethionates, benzenesulfonates, p-toluenesulfonates.

The compounds of formulae (II) and (III) may be commercially available, or may be produced according to known methods or according to methods similar to them, or according to the methods described below, or according to the methods described in Examples and Production Examples, optionally as suitably combined.

Production Method A

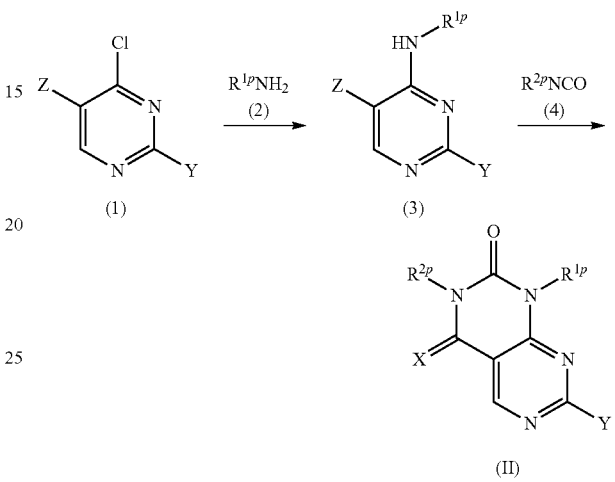

wherein Z means a cyano group or a group of —COOR$^{p1}$; R$^{p1}$ means an ester residue; and R$^{1p}$, R$^{2p}$, X and Y have the same meanings as above.

This production method is a method for producing a compound of formula (II).

The ester residue for R$^{p1}$ is one used in condensation in the field of organic chemistry. Not specifically defined, this may be any one not having any adverse effect on the reaction. For example, it includes a lower alkyl group such as a methyl group, an ethyl group, a propyl group, an isopropyl group, a butyl group, a sec-butyl group, a tert-butyl group; an aryl group such as a phenyl group, a tolyl group; and an aralkyl group such as a benzyl group.

According to the production method, the compound of formula (II) may be produced by reacting a compound of formula (1) and an amine of formula (2) to give a compound of formula (3) and then reacting the compound (3) and an isocyanate of formula (4).

The step of reacting a compound of formula (1) and an amine of formula (2) to give a compound (3) may be attained, generally using from 0.5 mols to an excessive molar amount, preferably from an equimolar amount to 3.0 mols of the amine (2) relative to one mol of the compound (1).

In general, the reaction is attained in an inert solvent. The inert solvent is, for example, preferably methylene chloride, chloroform, tetrahydrofuran, ethyl ether, benzene, toluene, dimethylformamide, or their mixed solvents.

Preferably, the reaction is attained in the presence of a base. The base includes, for example, organic bases such as triethylamine, diisopropylethylamine, pyridine, 4-dimethylaminopyridine; inorganic bases such as sodium hydroxide, potassium hydroxide, sodium carbonate, potassium carbonate, sodium hydrogencarbonate.

In general, the amount of the base to be used is preferably from an equimolar amount to an excessive molar amount relative to one mol of the compound (1). When the base is liquid, then the base may serve also as a solvent.

The reaction temperature may be generally from −78° C. to 100° C., preferably from 20° C. to 80° C.

The reaction time may be generally from 5 minutes to 7 days, preferably from 30 minutes to 24 hours.

In the step of reacting the compound (3) and an isocyanate of formula (4) to give a compound of formula (II), in general, from 0.5 mols to an excessive molar amount, preferably from an equimolar amount to 3.0 mols of the isocyanate (4) is used relative to one mol of the compound (3).

In general, the reaction may be attained in an inert solvent. The inert solvent is, for example, preferably methylene chloride, chloroform, tetrahydrofuran, ethyl ether, benzene, toluene, dimethylformamide, or their mixed solvents, more preferably dimethylformamide.

In general, the reaction may be attained in the presence of a base. The base includes, for example, organic bases such as triethylamine, diisopropylethylamine, pyridine, 4-dimethylaminopyridine; inorganic bases such as sodium hydride, potassium tert-butoxide, sodium tert-butoxide.

In general, the amount of the base to be used is preferably from an equimolar amount to an excessive molar amount relative to one mol of the compound (3). When the base is liquid, then the base may serve also as a solvent.

The reaction temperature may be generally from −78° C. to 100° C., preferably from 20° C. to 80° C.

The reaction time may be generally from 5 minutes to 7 days, preferably from 30 minutes to 24 hours.

The compounds of formulae (1), (2) and (4) may be commercial products, or may be produced according to known methods, or according to the methods described in Examples or according to methods similar to them, as suitably combined.

(Alternative Method)

The compounds of formula (I) may be produced by reacting a compound of formula (3) and a compound of formula (III) or its salt to give a compound of a general formula (V-1):

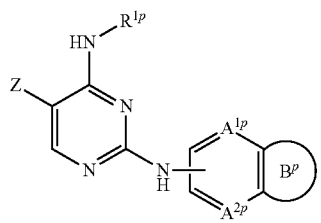

(V-1)

wherein $A^{1p}$, $A^{2p}$, $B^p$, $R^{1p}$ and Z have the same meanings as above, and then reacting the compound (V-1) and an isocyanate of formula (4) to give a compound of a general formula (IV):

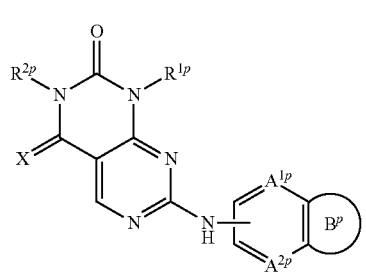

(IV)

wherein $A^{1p}$, $A^{2p}$, $B^p$, $R^{1p}$, $R^{2p}$ and X have the same meanings as above, and when the compound has a protective group of the amino, imino, hydroxyl or carbonyl group, then this is processed according to a process suitably selected from the following:

(1) a step of removing the protective group, or (2) a step of oxidizing the nitrogen atom in the compound when the intended compound to be produced is an N-oxide derivative, thereby producing a compound of formula (I) or its N-oxide derivative.

The step of reacting a compound of formula (3) and a compound of formula (III) or its salt to give a compound of formula (V-1) is similar to the step of reacting a compound of formula (II) and a compound of formula (III) or its salt to give a compound of formula (IV) in the above-mentioned production method 1.

Salts of the compound of formula (III) usable in this step may be the salts of the compound of formula (III) shown in the production method 1.

The step of reacting a compound (V-1) with an isocyanate of formula (4) to give a compound of formula (IV) may be similar to the step of reacting the compound (3) and an isocyanate of formula (4) to give a compound of formula (II) in the above-mentioned production method A.

The optional step of removing the protective group and/or forming an N-oxide derivative may be similar to that in the above-mentioned production method 1.

Pharmacological Test Examples of the compounds of the invention are shown below.

Pharmacological Test 1 (Wee1 Kinase-Inhibitory Effect)

(1) Purification of Wee1 Kinase:

A cDNA of Wee1 kinase with glutathion-5-transferase (GST) fused at the amino terminal thereof was inserted into a baculovirus expression vector to construct a recombinant baculovirus, with which cells of an insect cell line Sf9 were infected for high expression therein. The infected cells were recovered and solubilized, and then the GST-tagged Wee1 kinase protein was adsorbed by a glutathion column, and eluted from the column with glutathion, and the active fraction was desalted in a desalting column to give a purified enzyme.

(2) Determination of Wee1 Kinase Activity:

In determination of the Wee1 kinase activity, a synthetic peptide, Poly(Lys,Tyr) Hydrobromide (Lys:Tyr (4:1)) bought from Sigma was used as the substrate.

The amount of the reaction liquid was 21.1 μL; and the composition of the reaction buffer was 50 mM Tris-HCl buffer (pH 7.4)/10 mM magnesium chloride/1 mM dithiothreitol. The purified Wee1 kinase, 2.5 μg of the substrate peptide, 10 μM of non-labeled adenosine triphosphate (ATP) and 1 μCi of [γ-$^{33}$P]-labeled ATP (2500 Ci/mmol or more) were added to it, and reacted at 30° C. for 30 minutes. Next, 10 μL of 350 mM phosphate buffer was added to the reaction system to stop the reaction. The substrate peptide was adsorbed by a P81 paper filter 96-well plate, then washed a few times with 130 mM phosphate buffer, and its radioactivity was counted with a liquid scintillation counter. The [γ-$^{33}$P]-labeled ATP was bought from Amersham Bioscience.

To add the test compound to the reaction system, the compound was diluted with dimethylsulfoxide (DMSO) to prepare a series of dilutions. 1.1 μL of each dilution was added to the reaction system. As a control, 1.1 μL of DMSO was added to the reaction system.

As in Table 1, the compounds of the invention exhibit an excellent Wee1-inhibitory activity.

TABLE 1

| Compound | Wee1-Inhibitory Effect (IC50, nM) |
| --- | --- |
| Example 1 | 5 |
| Example 2 | 5.6 |
| Example 4 | 8.3 |
| Example 5 | 9.6 |
| Example 7 | 4.3 |
| Example 9 | 6.6 |
| Example 10 | 13.1 |
| Example 14 | 10.4 |
| Example 16 | 6.8 |
| Example 17 | 9.2 |
| Example 18 | 8.9 |
| Example 21 | 4.8 |
| Example 22 | 5.2 |
| Example 30 | 7.1 |
| Example 39 | 6.5 |
| Example 43 | 5.1 |
| Example 48 | 8.6 |
| Example 53 | 6.5 |
| Example 79 | 6.3 |
| Example 82 | 3.3 |

The Cdc2 tyrosine 15-phosphorylation-inhibitory effect of the compounds of formula (I) of the invention is described below.

Pharmacological Test 2 (Method of Determining Drug Potency with Cells (Cdc2 (Cdk1) Tyrosine 15-Phosphorylation-Inhibitory Effect))

a) Reagents:

Fetal bovine serum (FBS) was obtained from Morgate; media RPMI1640 and DMEM were from Invitrogen; camptothecin was from Sigma; gemcitabine was from Nippon Eli Lilly; nocodazole and protease inhibitor cocktail were from Sigma; rabbit anti-Cdc2 antibody and mouse anti-Cdc2 antibody were from Santa Cruz Biotechnology; rabbit anti-tyrosine 15-phosphorylated Cdc2 antibody and horseradish peroxidase-labeled anti-mouse IgG antibody were from Cell Signaling Technology; sure blue reserve TMB peroxidase substrate was from Kirkegaard and Perry Laboratories.

b) Cells:

Human non-small cell lung cancer cells (NCI-H1299) and human colon cancer cells (WiDr) were obtained from American Type Culture Collection (ATCC).

c) Method of Effect Determination:

In the method of using NCI-H1299 cells, the cells were suspended in a medium of 10% FBS-added RPMI1640, and the cell suspension was applied to a 96-well Nunclondelta-processed plastic plate (bought from Nunc), in an amount of 2000 cells/100 µL/well, in which the cells were incubated overnight in 5% $CO_2$-95% air at 37° C. Camptothecin was dissolved in dimethylsulfoxide (DMSO), and diluted with a medium of 10% FBS-added RPMI1640, and then this was applied to the plate on which the cells had been previously sowed, in an amount of 50 µL/well in such a manner that the final concentration of camptothecin could be 200 nM. Then, the cells were incubated for 16 hours at 37° C. in 5% $CO_2$-95% air. The test compound was stepwise diluted with DMSO, then diluted with 4000 nM nocodazole-containing, 10% FBS-added RPMI1640, and applied to the plate on which the camptothecin-treated cells had been sowed, in an amount of 50 µL/well. The cells were incubated for 8 hours at 37° C. in 5% $CO_2$-95% air, then the culture was removed, and a cytolytic buffer was added to the plate in an amount of 100 µL/well, shaken at 4° C. for 2 hours, then frozen at −80° C., and thawed to give a cell solution. Cdc2 and tyrosine 15-phosphorylated Cdc2 in the cell solution were determined through enzyme-linked immunosorbent assay (ELISA), and the ratio of tyrosine 15-phosphorylated Cdc2 to Cdc2 was calculated to obtain the 50% phosphorylation-inhibitory concentration of the test compound to the cells (EC50, nM). The cytolytic buffer used herein is an aqueous solution containing 20 mM Hepes (pH 7.5), 150 mM sodium chloride, 1 mM disodium ethylenediaminetetraacetate, 0.1% polyoxyethylene (10) octylphenyl ether, 1% protease inhibitor cocktail, 1 mM dithiothreitol, 2 mM sodium orthovanadate, 10 mM sodium fluoride and 10 mM glycerol diphosphate. Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorpimmuno plate (bought from Nunc), in an amount of 50 µL/well, and statically kept overnight at 4° C. so as to fix the antibody on the plate. Next, this was washed three times with phosphate-buffered physiological saline (PBS), and 5% bovine serum albumin-containing PBS (5% BSA/PBS) was added thereto in an amount of 300 µL/well, and statically kept at room temperature for 2 hours, and then again washed three times with PBS. A mouse anti-Cdc2 antibody solution that had been diluted 100-fold with 0.05% polyoxyethylene sorbitan monolaurate and 1% BSA-containing Tris-HCl-buffered physiological saline (1% BSA/TBS-T) was added to it in an amount of 50 µL/well, and the cell solution was added thereto in an amount of 5 µL/well and statically kept overnight at 4° C. Next, this was washed three times with 0.05% polyoxyethylene sorbitan monolaurate and 0.1% BSA-containing Tris-HCl-buffered physiological saline (0.1% BSA/TBS-T), and then a horseradish peroxidase-labeled anti-mouse IgG antibody solution that had been diluted 2000-fold with 1% BSA/TBS-T was added thereto in an amount of 70 µL/well, and statically kept at room temperature for 3 hours. Finally, this was washed five times with 0.1% BSA/TBS-T, then a substrate of sure blue reserve TMB peroxidase was added to it in an amount of 100 µL/well, and left for coloration in a dark place at room temperature for 15 minutes. Then, 1 M hydrochloric acid was added to it in an amount of 100 µL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorpimmuno plate in an amount of 50 µL/well, and statically kept overnight at 4° C. so as to fix the antibody on the plate. Next, this was washed three times with PBS, and 5% BSA/PBS was added thereto in an amount of 300 µL/well, and statically kept at room temperature for 2 hours, and then again washed three times with PBS. A mouse anti-Cdc2 antibody solution that had been diluted 100-fold with 1% BSA/TBS-T was added to it in an amount of 50 µL/well, and the cell solution was added thereto in an amount of 5 µL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 µL/well, and statically kept at room temperature for 3 hours. Finally, this was washed five times with 0.1% BSA/TBS-T, then a substrate of sure blue reserve TMB peroxidase was added to it in an amount of 100 µL/well, and left for coloration in a dark place at room temperature for 5 minutes. Then, 1 M hydrochloric acid was added to it in an amount of 100 µL/well to stop the reaction, and this was analyzed through colorimetry.

In the method of using WiDr cells, the cells were suspended in a medium of 10% FBS-added DMEM, and the cell suspension was applied to a 96-well Nunclondelta-processed plastic plate in an amount of 2000 cells/100 µL/well, in which the cells were incubated overnight in 5% $CO_2$-95% air at 37° C. Gemcitabine was dissolved in PBS, and diluted with a medium of 10% FBS-added DMEM, and then this was applied to the plate on which the cells had been previously sowed, in an amount of 50 µL/well in such a manner that the final concentration of gemcitabine could be 100 nM. Then, the cells were incubated for 24 hours at 37° C. in 5% $CO_2$-95% air. The test compound was stepwise diluted with DMSO, then diluted with 1200 nM nocodazole-containing, 10% FBS-added DMEM, and applied to the plate on which the gemcitabine-treated cells had been sowed, in an amount of 50 µL/well. The cells were incubated for 8 hours at 37° C. in 5% $CO_2$-95% air, then the culture was removed, and a cytolytic buffer was added to the plate in an amount of 100 µL/well, shaken at 4° C. for 2 hours, then frozen at −80° C., and thawed to give a cell solution. Cdc2 and tyrosine 15-phosphorylated Cdc2 in the cell solution were determined through ELISA, and the ratio of tyrosine 15-phosphorylated Cdc2 to Cdc2 was calculated to obtain the 50% phosphorylation-inhibitory concentration of the test compound to the cells (EC50, nM). Cdc2 was determined through ELISA as follows: A rabbit anti-Cdc2 antibody solution, which had been diluted 200-fold with 50 mM carbonate-bicarbonate buffer (pH 9.6), was applied to a 96-well maxisorp plastic plate in an amount of 50 µL/well, and statically kept overnight at 4° C. so as to fix the antibody on the plate. Next, this was washed three times with PBS, and 5% BSA/PBS was added thereto in an amount of 300 µL/well, and statically kept at room temperature for 2 hours, and then again washed three times with PBS. A mouse anti-Cdc2 antibody solution that had been diluted 100-fold with 1% BSA/TBS-T was added to it in an amount of 50 µL/well, and the cell solution was added thereto in an amount of 10 µL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 µL/well, and statically kept at room temperature for 3 hours. Finally, this was washed five times with 0.1% BSA/TBS-T, then a substrate of sure blue reserve TMB peroxidase was added to it in an amount of 100 µL/well, and left for coloration in a dark place at room temperature for 15 minutes. Then, 1 M hydrochloric acid was added to it in an amount of 100 µL/well to stop the reaction, and this was analyzed through colorimetry. Tyrosine 15-phosphorylated Cdc2 was determined through ELISA as follows: A rabbit anti-tyrosine 15-phosphorylated Cdc2 antibody solution, which had been diluted 100-fold with 50 mM carbonate-bicarbonate buffer (pH 9.6), was applied to a 96-well maxisorp plastic plate in an amount of 50 µL/well, and statically kept overnight at 4° C. so as to fix the antibody on the plate. Next, this was washed three times with PBS, and 5% BSA/PBS was added thereto in an amount of 300 µL/well, and statically kept at room temperature for 2 hours, and then again washed three times with PBS. A mouse anti-Cdc2 antibody solution that had been diluted 100-fold with 1% BSA/TBS-T was added to it in an amount of 50 µL/well, and the cell solution was added thereto in an amount of 10 µL/well and statically kept overnight at 4° C. Next, this was washed three times with 0.1% BSA/TBS-T, and then a horseradish peroxidase-labeled anti-mouse IgG antibody solution that had been diluted 2000-fold with 1% BSA/TBS-T was added thereto in an amount of 70 µL/well, and statically kept at room temperature for 3 hours. Finally, this was washed five times with 0.1% BSA/TBS-T, then a substrate of sure blue reserve TMB peroxidase was added to it in an amount of 100 µL/well, and left for coloration in a dark place at room temperature for 10 minutes. Then, 1 M hydrochloric acid was added to it in an amount of 100 µL/well to stop the reaction, and this was analyzed through colorimetry.

As in Table 2 and Table 3, the compounds of the invention exhibit an excellent Cdc2-tyrosine 15 phosphorylation-inhibitory effect to human-derived cancer cells (NCI-H1299 and WiDr).

TABLE 2

| Compound | Cdc2-Y15 Phosphorylation-Inhibitory Effect (H1299, + camptothecin) (EC50, nM) |
|---|---|
| Example 1 | 19 |
| Example 2 | 27 |
| Example 4 | 28 |
| Example 5 | 70 |
| Example 7 | 17 |
| Example 9 | 24 |
| Example 10 | 61 |
| Example 14 | 77 |
| Example 16 | 50 |
| Example 17 | 47 |
| Example 18 | 35 |
| Example 21 | 11 |
| Example 22 | 16 |
| Example 30 | 25 |
| Example 39 | 37 |
| Example 43 | 45 |
| Example 48 | 54 |
| Example 53 | 59 |
| Example 82 | 30 |

TABLE 3

| Compound | Cdc2-Y15 Phosphorylation-Inhibitory Effect (WiDr, + gemcitabine) (EC50, nM) |
|---|---|
| Example 1 | 21 |
| Example 2 | 46 |
| Example 7 | 24 |

The checkpoint-escape effect in cells of the compounds of formula (I) of the invention is described below.
Pharmacological Test 3 (Method of Determining Drug Potency with Cells (Checkpoint-Escape Effect))
a) Reagents:
Fetal bovine serum (FBS) was obtained from Morgate; a medium of DMEM was from Invitrogen; gemcitabine was from Nippon Eli Lilly; nocodazole and 4',6-diamidino-2-phenylindole were from Sigma; rabbit anti-phosphorylated histone H3 antibody was from Upstate; and fluorescence-labeled (Alexa Fluor 488) anti-rabbit IgG antibody was from Molecular Probe.
b) Cells:
Human colon cancer cells (WiDr) were obtained from American Type Culture Collection (ATCC).
c) Method of Effect Determination:
The cells were suspended in a medium of 10% FBS-added DMEM, and the cell suspension was applied to a poly-D-lysine-coated 96-well plastic plate (bought from Becton Dickinson) in an amount of 2000 cells/100 µL/well, in which the cells were incubated overnight in 5% $CO_2$-95% air at 37° C. Gemcitabine was dissolved in phosphate-buffered saline (PBS), and diluted with a medium of 10% FBS-added DMEM, and then this was applied to the plate on which the cells had been previously sowed, in an amount of 50 µL/well in such a manner that the final concentration of gemcitabine could be 100 nM. Then, the cells were incubated for 24 hours at 37° C. in 5% $CO_2$-95% air. The test compound was stepwise diluted with dimethylsulfoxide, then diluted with 1200 nM nocodazole-containing, 10% FBS-added DMEM, and applied to the plate on which the gemcitabine-treated cells had been sowed, in an amount of 50 μL/well. The cells were incubated for 8 hours at 37° C. in 5% $CO_2$-95% air, then the culture was removed, and methanol that had been cooled to −20° C. was added to it in an amount of 100 μL/well. Then, the plate was kept overnight at −20° C. so as to fix the cells thereon. Next, the methanol-fixed cells were washed with PBS, and 1% bovine serum albumin-containing PBS (1% BSA/BPS) was added to it in an amount of 50 μL/well, and statically kept at room temperature for 30 minutes, and then rabbit anti-phosphorylated histone H3 antibody that had been diluted 250-fold with 1% BSA/PBS was added thereto in an amount of 50 μL/well, and statically kept at room temperature for 90 minutes. Next, this was washed with PBS, and a solution containing 4',6-diamidino-2-phenylindole that had been diluted with 1% BSA/PBS to have a concentration 10 μg/mL and a fluorescence-labeled (Alexa Fluor 488) anti-rabbit IgG antibody that had been diluted 250-fold was added to it in an amount 50 μL/well, and reacted in a dark place at room temperature for 60 minutes. Finally, this was washed with PBS, and its fluorescence intensity was determined to calculate the ratio of the phosphorylated histone H3-positive cells (cells that had been in a cell division cycle through removal of checkpoint). From this, obtained was the 50% checkpoint removal concentration to the cells of the test compound (EC50, nM).

As in Table 4, the compound of the invention exhibits an excellent checkpoint escape effect to human-derived cancer cells (WiDr).

TABLE 4

| Compound | Checkpoint Escape Effect (WiDr + gemcitabine) (EC50, nM) |
|---|---|
| Example 1 | 37 |

Pharmacological Test 4 (Tumor Growth Inhibitory Effect)

Human colon cancer cells WiDr (obtained from ATCC) were implanted into the subcutaneous area of the back of F344/N Jcl-rnu nude rats. 12 days after the implantation, 5 mg/kg of gemcitabine (Gemzar, from Eli Lily) was intravenously administered to them; and after 24 hours, a test compound suspended in a solvent (0.5% methyl cellulose) was orally administered thereto. This was repeated once a week for 3 weeks. The tumor volume (0.5×major diameter×(minor diameter)$^2$) was measured on days 0, 3, 6, 10, 13, 17, 20, 24 and 27 (the first gemcitabine administration is on day 0). The relative tumor volume was calculated, based on the tumor volume on day 0, as 1. The tumor growth rate (% T/C) was obtained according to the formulae mentioned below.

In case where the tumor volume change from day 0 in the test compound administration group is more than 0 (>0):

% T/C=(tumor volume change in the test compound group on days 3, 6, 10, 13, 17, 20, 24 and 27/tumor volume change in the control group on days 3, 6, 10, 13, 17, 20, 24 and 27)×100.

In case where the tumor volume change from day 0 in the test compound administration group is less than 0 (<0):

% T/C=(tumor volume change in the test compound group on days 3, 6, 10, 13, 17, 20, 24 and 27/tumor volume change in the test compound group on day 0)×100.

The data of the tumor growth inhibitory effect are shown in Table 5.

TABLE 5

| | | % T/C | | | | | | | |
|---|---|---|---|---|---|---|---|---|---|
| Compound | n | day 3 | day 6 | day 10 | day 13 | day 17 | day 20 | day 24 | day 27 |
| Control | 5 | 100 | 100 | 100 | 100 | 100 | 100 | 100 | 100 |
| Gemcitabine 5 mg/kg | 5 | 62 | 67 | 66 | 64 | 57 | 49 | 52 | 54 |
| Gemcitabine + compound of Example 1 15 mg/kg | 5 | −16 | −6 | −17 | −13 | −17 | −5 | 7 | 13 |
| compound of Example 1 15 mg/kg | 5 | 107 | 100 | 87 | 91 | 88 | 85 | 83 | 88 |

Gemcitabine was administered on days 0, 7 and 14.

The compound of Example 1 was administered on days 1, 8 and 15.

The gemcitabine administration reduced the tumor growth rate; and, the combined administration of the compound of the invention and gemcitabine further reduced the tumor growth rate. In the group given high-dose combined administration, tumor involution was observed.

As mentioned above, when combined with any other anticancer agent, the compound of the invention enhanced the anticancer effect of the other anticancer agent.

Pharmacological Test 5 (Method of Determining Drug Potency with Cells (Radiation (X Ray)-Sensitizing Effect))

a) Reagents:

Fetal bovine serum (FBS) is obtained from Morgate; RPMI1640 medium and 0.25% trypsin EDTA are from Invitrogen; cycle test plus DNA reagent kit is from Becton Dickinson); and nylon net filter is from Millipore.

b) Cells:

Human non-small cell lung cancer cells (NCI-H1299) are obtained from ATCC.

c) Method of Effect Determination:

NCI-H1299 cells are suspended in a medium of 10% FBS-added RPMI1640, and the cell suspension is applied to a 6-well Nunclondelta-processed plastic plate (bought from Nunc), in an amount of 100000 cells/2 mL/well, in which the cells are incubated overnight in 5% $CO_2$-95% air at 37° C. Using Softex's M-150WE, the cells are irradiated with 5000 R X-ray, and then incubated in 5% $CO_2$-95% air at 37° C. for 16 hours. The test compound is stepwise diluted with DMSO, and applied to the plate on which the X-ray-treated cells have been sowed, in an amount of 2 μL/well. The cells are incubated for 8 hours at 37° C. in 5% $CO_2$-95% air, then the culture is sampled. The cells having remained on the plate are mixed with 0.25% trypsin added thereto in an amount of 600

µL/well, and then statically kept at room temperature to be a cell suspension. The cell suspension and the previously-sampled culture are mixed, then centrifuged, and the supernatant is removed thereby finishing the sampling operation. The sample is suspended in 1 mL of a buffer of the cycle test plus DNA reagent kit, and frozen and stored at −80° C. The stored sample is thawed on a test day, then centrifuged to remove the supernatant, this is suspended in 250 µL of the solution A of the cycle test plus kit, then statically left at room temperature for further 10 minutes, and then 150 µL of the solution B of the kit is added thereto, then statically left at room temperature for further 10 minutes. Next, 150 µL of the solution C of the kit is added to it, statically kept at 4° C. for 10 minutes, and then filtered through the nylon net filter, thereby finish the DNA coloration. Using Becton Dickinson's FACS Calibur, the DNA amount of the cell is quantified according to a FACS method, and the ratio of the cells with DNA fragmentation is determined.

As in the above, the excellent DNA fragmentation-inducing effect of the compound of the invention to the human-derived cancer cells (NCI-H1299) can be determined, and the X-ray-sensitizing effect of the compound of the invention can be thereby determined.

The compounds of formula (I) can be administered orally or parenterally, and after formulated into preparations suitable to such administration modes, the compounds can be used as pharmaceutical compositions and anticancer agents.

The term "cancer" as referred to in this description includes various sarcoma and carcinoma and includes solid cancer and hematopoietic cancer. The solid cancer as referred to herein includes, for example, brain tumor, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The compounds of the invention are expected to be effective especially to human solid cancer. The human solid cancer includes, for example, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

The pharmaceutical composition and anticancer agent of the invention may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

With regard to each preparation of the pharmaceutical composition and anticancer agent of the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

The preparation can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The compounds of the invention may be used, optionally as combined with any other agent useful for treatment of various cancers or with radiotherapy. The individual ingredients for such combination may be administered at different times or at the same time as divided preparations or one preparation during the term of treatment. Accordingly, the invention should be so interpreted that it includes all modes of administration at the same time or at different times, and the administration in this invention should be interpreted so. The scope of the combination of the compound of the invention and any other agent useful for the above-mentioned diseases should include, in principle, any and every combination thereof with any and every pharmaceutical agent useful for the treatment of the above-mentioned diseases.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The compounds of the invention may be combined with radiation therapy to enhance the therapeutical effect in radiation therapy; and the compounds may be therefore useful as a radiation sensitizer in the field of treatment of cancer.

Another aspect of the compounds of the invention is that the compounds are also useful as a sensitizer for any other anticancer agents in the field of treatment of cancer.

The compounds of the invention may be combined with radiation therapy and/or combined with any other anticancer agents described below in their use for treatment of cancer.

"Sensitizer" for radiation therapy or anticancer agent as referred to herein is meant to indicate a medical agent which, when used as combined with radiation therapy and/or chemotherapy with an anticancer agent, may additively or synergistically augment the therapeutical effect of that radiation therapy and/or chemotherapy.

The agents to be in the combined preparations in the invention may have any forms selected in any manner, and they may be produced in the same manner as that for the above-mentioned preparations. The combined agent comprising the compound of the invention and some other anticancer agent may be readily produced by anyone skilled in the art according to ordinary methods or conventional techniques.

The above-mentioned combination includes not only the compositions of the invention that contain one other active substance but also those containing two or more other active substances. There are a lot of examples of the combination of the composition of the invention and one or two or more active substances selected from the remedies for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., Gan to Kagaku Ryoho, 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine Examples of "interferon" include interferon α, interferon α-2a, interferon α-2b, interferon β, interferon γ-1a and interferon γ-nl.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon $\alpha$ from Sumitomo Pharmaceutical Co., Ltd. as Sumiferon (tradename); interferon $\alpha$-2a from Takeda Pharmaceutical Co., Ltd. as Canferon-A (tradename); interferon $\alpha$-2b from Schering-Plough Corp. as Intron A (tradename); interferon $\beta$ from Mochida Pharmaceutical Co., Ltd. as IFN$\beta$ (tradename); interferon $\gamma$-1a from Shionogi & Co., Ltd. as Immunomax-$\gamma$ (tradename); and interferon $\gamma$-nl from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the compound of the invention or a pharmaceutically acceptable salt or ester thereof.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 $m^2$; 50 mg in one administration for an area of 1.25 $m^2$ to less than 1.5 $m^2$; 60 mg in one administration for an area of 1.5 $m^2$ or more. This dose is appropriately increased or decreased depending on the condition of the patient.

The therapeutic unit for gemcitabine is, for example, 1 g as gemcitabine/$m^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/$m^2$ (body surface area) or less, and it may be appropriately increased or decreased within the range.

The therapeutic unit for etoposide is such that, for example, in the case of intravenous injection, 60 to 100 mg/$m^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/$m^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/$m^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/$m^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/$m^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/$m^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/$m^2$ is administered once a day by intravenous drip infusion for 3 or 4 times at an interval of one week, followed by withdrawal from medication for at least two weeks.

The therapeutic unit for topotecan is such that, for example, 1.5 mg/$m^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/$m^2$ is administered on the first day by intravenous drip infusion, and then 250 mg/$m^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/$m^2$ of 5-FU and 200 mg/$m^2$ of leucovorin are administered from the first day to the fifth day by intravenous drip infusion, and this course is repeated at an interval of 4 weeks.

The invention is described more concretely with reference to the following Examples and Production Examples, which, however, are not intended to restrict the scope of the invention.

In thin-layer chromatography in Examples and Production Examples, Silica gel$_{60}$F$_{254}$ (Merck) was used for the plate, and a UV detector was used for detection. Wakogel™ C-300 or C-200 (Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethylsulfoxide was used as the internal standard in a heavy dimethylsulfoxide solution; a spectrometer of Gemini-300 (300 MHz; Varian), VXR-300 (300 MHz; Varian), Mercury 400 (400 MHz; Varian) or Inova 400 (400 MHz; Varian) was used; and all δ values are by ppm.

The meanings of the abbreviations in Production Examples and Examples are mentioned below.

| s: | singlet |
| d: | doublet |
| dd: | double doublet |
| t: | triplet |
| dt: | double triplet |
| q: | quartet |
| m: | multiplet |
| br: | broad |
| J: | coupling constant |
| Hz: | hertz |
| DMSO-$d_6$: | heavy dimethylsulfoxide |
| CDCl$_3$: | heavy chloroform |
| CD$_3$OD: | heavy methanol |
| BH$_3$-DMS: | borane-dimethyl sulfide complex |
| Bu$_4$NHSO$_4$: | tetrabutylammonium hydrogensulfate |
| Boc: | tert-butoxycarbonyl |
| Hf(OTf)$_4$: | hafnium trifluoromethanesulfonate |
| MTBE: | tent-butyl methyl ether |
| Tf: | trifluoromethanesulfonyl |
| pTs: | p-toluenesulfonyl |
| TBS: | tert-butyldimethylsilyl |

PRODUCTION EXAMPLE 1

Production of 7-chloro-3-(2,6-dichlorophenyl)-4-imino-3,4-dihydropyrimido[4,5-d]pyrimidin-2(1H)-one

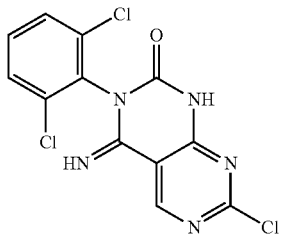

1.12 g of sodium hydride was added to an N,N-dimethylformamide (35 mL) solution of 3.0 g of 4-amino-2-chloropyrimidine-5-carbonitrile, and stirred at room temperature for 5 minutes. 4.38 g of 2,6-dichlorophenyl isocyanate was added to the reaction liquid, and stirred at room temperature for 1 hour. Ethyl acetate and aqueous 1 N hydrochloric acid solution were added to the reaction solution, and the organic layer was separated. This was washed with saturated saline water, dried with anhydrous magnesium sulfate, and the solvent was evaporated away. The precipitated solid was solidified with a mixed solvent of methanol/ethyl acetate and taken out through filtration to obtain 3.8 g of the entitled compound as a white solid.

$^1$H-NMR (400 MHz, DMSO-$d_6$) δ: 9.33 (1H, s), 7.66 (2H, d, J=8.2 Hz), 7.53 (1H, t, J=8.2 Hz) ESI-MS Found: m/z [M+H] 342

PRODUCTION EXAMPLE 2

Production of 7-chloro-3-(2-chloro-6-methylphenyl)-4-imino-3,4-dihydropyrimido[4,5-d]pyrimidin-2(1H)-one

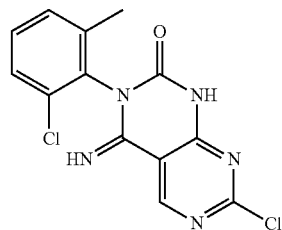

110 mg of the entitled compound was obtained as a pale yellow solid according to the same method as in Production Example 1, for which, however, 298 mg of 2-chloro-6-methylphenyl isocyanate was used in place of 2,6-dichlorophenyl isocyanate used in Production Example 1.

ESI-MS Found: m/z [M+H] 322

PRODUCTION EXAMPLE 3

Production of 7-chloro-3-(2-chloro-6-fluorophenyl)-4-imino-3,4-dihydropyrimido[4,5-d]pyrimidin-2(1H)-one

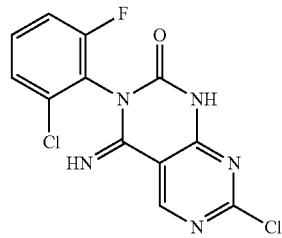 [SMILES: N=c1c2cnc(Cl)nc2[nH]c(=O)n1-c1c(Cl)cccc1Cl]

520 mg of the entitled compound was obtained as a pale yellow solid according to the same method as in Production Example 1, for which, however, 589 mg of 2-chloro-6-fluorophenyl isocyanate, which had been prepared from 2-chloro-6-fluoroaniline and triphosgene, was used in place of 2,6-dichlorophenyl isocyanate used in Production Example 1.

ESI-MS Found: m/z [M+H] 326

PRODUCTION EXAMPLE 4

Production of 7-chloro-3-(2,6-dichloro-4-fluorophenyl)-4-imino-3,4-dihydropyrimido[4,5-d]pyrimidin-2(1H)-one

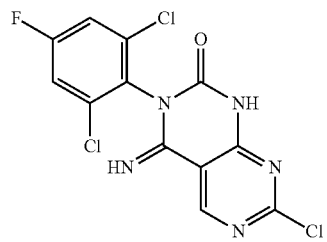 [SMILES: N=c1c2cnc(Cl)nc2[nH]c(=O)n1-c1c(Cl)cc(F)cc1Cl]

350 mg of the entitled compound was obtained as a pale yellow solid according to the same method as in Production Example 1, for which, however, 570 mg of 2,6-dichloro-4-fluorophenyl isocyanate, which had been prepared from 2,6-dichloro-4-fluoroaniline and triphosgene, was used in place of 2,6-dichlorophenyl isocyanate used in Production Example 1.

ESI-MS Found: m/z [M+H] 359

PRODUCTION EXAMPLE 5

Production of 7-chloro-3-(2-chloro-4,6-difluorophenyl)-4-imino-3,4-dihydropyrimido[4,5-d]pyrimidin-2(1H)-one

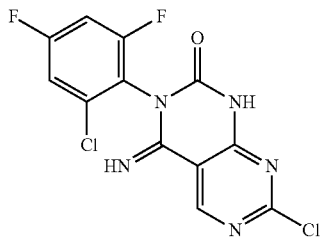 [SMILES: N=c1c2cnc(Cl)nc2[nH]c(=O)n1-c1c(F)cc(F)cc1Cl]

170 mg of the entitled compound was obtained as a pale yellow solid according to the same method as in Production Example 1, for which, however, 613 mg of 2-chloro-4,6-difluorophenyl isocyanate, which had been prepared from 2-chloro-4,6-difluoroaniline and triphosgene, was used in place of 2,6-dichlorophenyl isocyanate used in Production Example 1.

ESI-MS Found: m/z [M+H] 344

PRODUCTION EXAMPLE 6

Production of 7-chloro-3-(2,4-dichloropyridin-3-yl)-4-imino-3,4-dihydropyrimido[4,5-d]pyrimidin-2(1H)-one

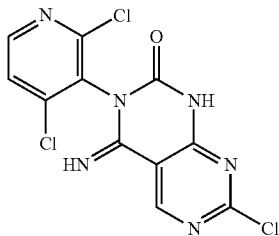 [SMILES: N=c1c2cnc(Cl)nc2[nH]c(=O)n1-c1c(Cl)ccnc1Cl]

230 mg of the entitled compound was obtained as a pale yellow solid according to the same method as in Production Example 1, for which, however, 611 mg of 2,4-dichloro-3-isocyanatopyridine, which had been prepared from 3-amino-2,4-dichloropyridine and triphosgene, was used in place of 2,6-dichlorophenyl isocyanate used in Production Example 1.

ESI-MS Found: m/z [M+H] 343

PRODUCTION EXAMPLE 7

Production of 7-chloro-3-(2,6-dichlorophenyl)-4-imino-1-methyl-3,4-dihydropyrimido[4,5-d]pyrimidin-2(1H)-one

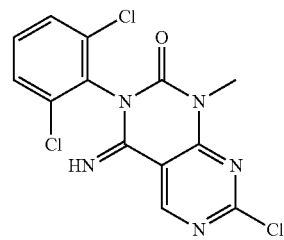 [SMILES: Cn1c(=O)n(-c2c(Cl)cccc2Cl)c(=N)c2cnc(Cl)nc21]

484 mg of potassium carbonate and 456 mg of methyl iodide were added to an N,N-dimethylformamide (5 mL) solution of 1.00 g of 7-chloro-3-(2,6-dichlorophenyl)-4-imino-3,4-dihydropyrimido[4,5-d]pyrimidin-2(1H)-one obtained in Production Example 1, and stirred at room temperature for 1 hour. The reaction solution was added to ethyl acetate and aqueous 0.5 N hydrochloric acid solution with stirring, and the organic layer was separated. This was washed with saturated saline water, dried with anhydrous sodium sulfate, and the solvent was evaporated away. The crude product was solidified from chloroform/methanol/hexane to obtain 700 mg of the entitled compound as a yellow solid.

$^1$H-NMR (400 MHz, DMSO-$d_6$) δ: 9.78 (1H, s), 9.44 (1H, s), 7.67 (2H, d, J=8.0 Hz), 7.54 (1H, t, J=8.0 Hz), 3.48 (1H, s)

ESI-MS Found: m/z [M+H]$^+$ 356

PRODUCTION EXAMPLE 8

Production of 7-chloro-3-(2-chloro-6-methylphenyl)-4-imino-1-methyl-3,4-dihydropyrimido[4,5-d]pyrimidin-2(1H)-one

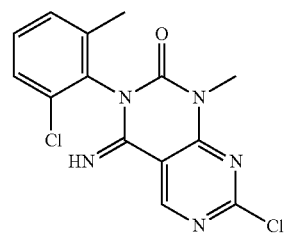 [SMILES: Cc1cccc(Cl)c1-n1c(=N)c2cnc(Cl)nc2n(C)c1=O]

156 mg of the entitled compound was obtained as a pale yellow solid according to the same method as in Production Example 7, for which, however, 200 mg of 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one used in Production Example 7.

$^1$H-NMR (400 MHz, DMSO-$d_6$) δ: 9.28 (1H, s), 7.52-7.35 (3H, m), 6.82 (1H, brs), 3.64 (3H, s), 2.34 (3H, s)

ESI-MS Found: m/z [M+H]$^+$ 336

PRODUCTION EXAMPLE 9

Production of 7-chloro-3-(2,4-dichloropyridin-3-yl)-4-imino-1-methyl-3,4-dihydropyrimido[4,5-d]pyrimidin-2(1H)-one

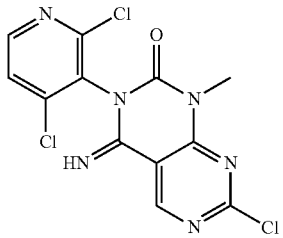 [SMILES: Cn1c(=O)n(-c2c(Cl)ccnc2Cl)c(=N)c2cnc(Cl)nc21]

38 mg of the entitled compound was obtained as a pale yellow solid according to the same method as in Production Example 7, for which, however, 7-chloro-3-(2,4-dichloropyridin-3-yl)-4-imino-3,4-dihydropyrimido[4,5-d]pyrimidin-2(1H)-one obtained in Production Example 6 was used in place of 7-chloro-3-(2,6-dichlorophenyl)-4-imino-3,4-dihydropyrimido[4,5-d]pyrimidin-2(1H)-one used in Production Example 7.

ESI-MS Found: m/z [M+H]$^+$ 357

PRODUCTION EXAMPLE 10

Production of 2'-methyl-2',3'-dihydro-1'H-spiro[cyclopropane-1,4'-isoquinolin]-7'-amine

1) Production of methyl 1-(2-cyanophenyl)cyclopropanecarboxylate

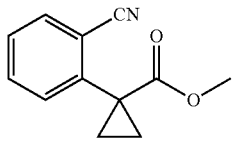

1.5 g of tetra-n-butylammonium bromide, 6.5 g of 1,2-dibromoethane and 20 mL of aqueous 50% sodium hydroxide solution were added to a toluene (40 mL) solution of 4.0 g of methyl 2-cyanophenylacetate, and stirred at room temperature for 1 hour. Water was added to the reaction liquid, and extracted with ethyl acetate. The organic layer was washed with saturated saline water, dried with anhydrous magnesium sulfate, and the solvent was evaporated away under reduced pressure. The crude product was purified through silica gel column chromatography (hexane/ethyl acetate) to obtain 3.0 g of the entitled compound as a colorless compound.

$^1$H-NMR (400 MHz, CDCl$_3$) δ: 7.66 (1H, dd, J=7.6, 1.2 Hz), 7.55 (1H, td, J=7.6, 1.2 Hz), 7.43-7.36 (2H, m), 3.66 (3H, s), 1.82 (2H, q, J=3.7 Hz), 1.30 (2H, q, J=3.7 Hz)

ESI-MS Found: m/z [M+H] 202

2) Production of methyl 1-[2-(aminomethyl)phenyl]cyclopropanecarboxylate monohydrochloride

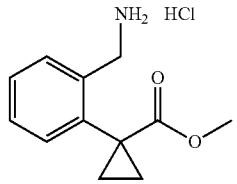

1.6 g of 10% palladium-carbon was added to an ethanol (50 mL) solution of 2.95 g of the compound obtained in the above reaction 1), and stirred in a hydrogen atmosphere under 2 atmospheric pressure at room temperature for 3 hours. The palladium-carbon was removed through filtration, the filtrate was concentrated under reduced pressure, and the crude product was washed with diethyl ether to obtain 3.2 g of the entitled compound as a colorless solid.

$^1$H-NMR (DMSO-d$_6$) δ: 8.47 (2H, s), 7.55 (1H, d, J=6.8 Hz), 7.38 (3H, td, J=7.2, 2.1 Hz), 7.36-7.29 (2H, m), 4.04 (2H, d, J=4.9 Hz), 3.54 (3H, s), 1.61-1.56 (2H, m), 1.33-1.29 (2H, m)

ESI-MS Found: m/z [M+H] 206

3) Production of 1',2'-dihydro-3'H-spiro[cyclopropane-1,4'-isoquinolin]-3'-one

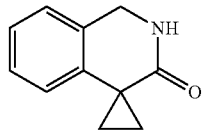 [SMILES: O=C1NCc2ccccc2C12CC2]

4 mL of aqueous 5 N sodium hydroxide solution was added to a methanol (50 mL) solution of 3.2 g of the compound obtained in the above reaction 2), and stirred at room temperature for 30 minutes. This was neutralized with aqueous 1 N hydrochloric acid added thereto, and methanol was evaporated away under reduced pressure. The residue was diluted with water, and extracted three times with ethyl acetate. The organic layer was washed with saturated saline water, dried with anhydrous magnesium sulfate, and the solvent was evaporated away under reduced pressure to obtain 2.1 g of the entitled compound as a colorless solid.

$^1$H-NMR (CDCl$_3$) δ: 7.23 (1H, td, J=7.8, 1.1 Hz), 7.18 (1H, td, J=7.3, 1.1 Hz), 7.10 (1H, dd, J=7.3, 1.0 Hz), 6.73 (1H, dd, J=7.8, 1.0 Hz), 4.69 (2H, d, J=1.5 Hz), 1.85 (2H, q, J=3.7 Hz), 1.24 (2H, q, J=3.7 Hz)

ESI-MS Found: m/z [M+H] 174

4) Production of 7'-nitro-1',2'-dihydro-3'H-spiro[cyclopropane-1,4'-isoquinolin]-3'-one

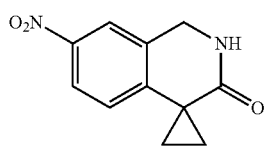 [SMILES: O=C1NCc2cc([N+](=O)[O-])ccc2C12CC2]

1.3 g of potassium nitrate was gradually added to a sulfuric acid (60 mL) solution of 2.1 g of the compound obtained in the above reaction 3), taking 5 minutes, and further stirred at room temperature for 10 minutes. The reaction liquid was poured into ice water, the precipitated crystal was taken out through filtration, and washed with water to obtain 2.4 g of the entitled compound as a yellow solid.

$^1$H-NMR (CDCl$_3$) δ: 8.09 (1H, dd, J=8.8, 2.4 Hz), 8.01 (1H, t, J=2.4 Hz), 6.86 (1H, d, J=8.8 Hz), 6.30 (1H, s), 4.78 (2H, d, J=1.5 Hz), 2.01 (2H, q, J=4.1 Hz), 1.35 (2H, q, J=4.1 Hz)

ESI-MS Found: m/z [M+H] 219

5) Production of 7'-nitro-1',2'-dihydro-3'H-spiro[cyclopropane-1,4'-isoquinoline]

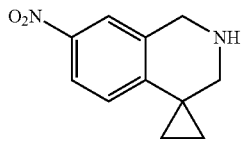 [SMILES: O=[N+]([O-])c1ccc2c(c1)CNCC21CC1]

With cooling with ice, 6.3 g of boron trifluoride-diethyl ether complex was added to a tetrahydrofuran suspension of 1.3 g of sodium borohydride, and stirred for 1 hour. A tetrahydrofuran (100 ml) solution of 2.4 g of the compound obtained in the above reaction 4) was added to the reaction liquid, and heated under reflux for 2 hours. The reaction liquid was cooled, and then neutralized with aqueous saturated sodium bicarbonate solution. The solvent was evaporated away under reduced pressure, the residue was dissolved in ethanol, 5 N hydrochloric acid was added to it, and heated under reflux for 1 hour. The reaction liquid was cooled, then the solvent was evaporated away under reduced pressure, and the residue was neutralized with aqueous potassium carbonate solution. The aqueous layer was extracted with chloroform, the organic layer was dried with anhydrous magnesium sulfate, and the solvent was evaporated away under reduced pressure to obtain the entitled compound.

ESI-MS Found: m/z [M+H] 205

6) Production of 2'-methyl-7'-nitro-2',3'-dihydro-1'H-spiro[cyclopropane-1,4'-isoquinoline]

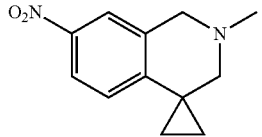

1.5 g of sodium cyanoborohydride was added to a methanol (50 mL) solution of the compound (2.3 g) obtained in the above reaction 5), 2.7 mL of aqueous 37% formaldehyde solution and 0.7 mL of acetic acid, and stirred at room temperature for 15 hours. The reaction liquid was neutralized with aqueous saturated sodium bicarbonate solution, and methanol was evaporated away under reduced pressure. The residue was diluted with water and extracted three times with chloroform. The organic layer was dried with anhydrous magnesium sulfate, the solvent was evaporated away under reduced pressure, and the crude product was purified through silica gel column chromatography (hexane/ethyl acetate) to obtain 1.7 g of the entitled compound as a colorless solid.

$^1$H-NMR (CDCl$_3$) δ: 7.97 (1H, dd, J=8.8, 2.4 Hz), 7.91 (1H, d, J=2.4 Hz), 6.78 (1H, d, J=8.8 Hz), 3.77 (2H, s), 2.57 (2H, s), 2.48 (3H, s), 1.16-1.12 (2H, m), 1.10-1.06 (2H, m)

ESI-MS Found: m/z [M+H] 219

7) Production of 2'-methyl-2',3'-dihydro-1'H-spiro[cyclopropane-1,4'-isoquinolin]-7'-amine

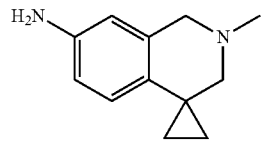

800 mg of 10% palladium-carbon was added to an ethanol (20 mL) solution of 1.7 g of the compound obtained in the above reaction 6), and stirred in a hydrogen atmosphere under 1 atmospheric pressure at room temperature for 15 hours. Palladium-carbon was removed through filtration, the filtrate was concentrated under reduced pressure, and the crude product was purified through basic silica gel column chromatography (hexane/ethyl acetate) to obtain 1.1 g of the entitled compound as a colorless solid.

$^1$H-NMR (CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz)

ESI-MS Found: m/z [M+H] 189

PRODUCTION EXAMPLE 11

Production of 3-methyl-2,3,4,5-tetrahydro-1H-3-benzazepin-7-amine

1) Production of 7-nitro-2,3,4,5-tetrahydro-1H-3-benzazepine monohydrochloride

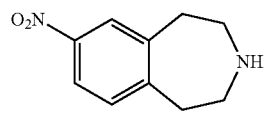 [SMILES: O=[N+]([O-])c1ccc2c(c1)CCNCC2]

With cooling with ice, 7.2 g of potassium nitrate was added to a sulfuric acid (30 mL) solution of 10 g of 2,3,4,5-tetrahydro-1H-3-benzazepine, and stirred for 1 hour. The reaction liquid was poured into ice water, neutralized with aqueous 5 N sodium hydroxide solution, and extracted with a mixed solvent of 20% isopropanol/chloroform. The organic layer was dried with anhydrous magnesium sulfate, and the solvent was evaporated away under reduced pressure. The residue was dissolved in ethyl acetate, and 4 N hydrochloric acid/ethyl acetate was added thereto. The precipitated solid was taken out through filtration, and washed with ethyl acetate to obtain 9.1 g of the entitled compound as a yellow solid.

$^1$H-NMR (DMSO-d$_6$) δ: 9.42 (2H, s), 8.12 (1H, d, J=2.4 Hz), 8.06 (1H, dd, J=8.3, 2.4 Hz), 7.50 (1H, d, J=8.3 Hz), 3.28-3.16 (8H, m)

ESI-MS Found: m/z [M+H] 193

2) Production of 3-methyl-7-nitro-2,3,4,5-tetrahydro-1H-3-benzazepine

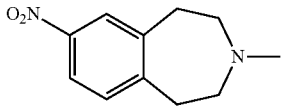

1.8 g of the entitled compound was obtained as a yellow oil according to the same method as in Production Example 10-6), for which, however, the compound obtained in the above reaction 1) was used in place of 7'-nitro-2',3'-dihydro-1'H-spiro[cyclopropane-1,4'-isoquinoline] used in Production Example 10-6).

$^1$H-NMR (CDCl$_3$) δ: 8.00 (1H, d, J=2.0 Hz), 7.98 (1H, s), 7.24 (1H, d, J=8.8 Hz), 3.03 (8H, t, J=5.1 Hz), 2.39 (3H, s)

ESI-MS Found: m/z [M+H] 207

3) Production of 3-methyl-2,3,4,5-tetrahydro-1H-3-benzazepin-7-amine

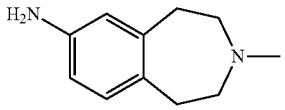

850 mg of the entitled compound was obtained as a yellow oil according to the same method as in Production Example 10-7), for which, however, the compound obtained in the above reaction 2) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.88 (1H, d, J=7.8 Hz), 6.48-6.44 (2H, m), 3.53 (2H, s), 2.83 (4H, s), 2.59-2.47 (4H, m), 2.36 (3H, s)

ESI-MS Found: m/z [M+H] 177

PRODUCTION EXAMPLE 12

Production of 3-cyclopropyl-2,3,4,5-tetrahydro-1H-3-benzazepin-7-amine

1) Production of 3-cyclopropyl-7-nitro-2,3,4,5-tetrahydro-1H-3-benzazepine

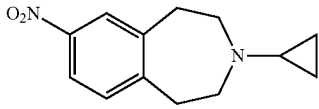 [SMILES: O=[N+]([O-])c1ccc2c(c1)CCN(C1CC1)CC2]

0.55 g of sodium cyanoborohydride was added to a methanol (40 mL) solution of 1 g of the compound obtained in Production Example 11-1), 1.5 g of (1-ethoxycyclopropoxy) trimethylsilane and 0.25 mL of acetic acid, and stirred at 50° C. for 15 hours. The reaction liquid was neutralized with aqueous saturated sodium bicarbonate solution, and methanol was evaporated away under reduced pressure. The residue was diluted with water, and extracted three times with chloroform. The organic layer was dried with anhydrous magnesium sulfate, the solvent was evaporated away under reduced pressure, and the crude product was purified through basic silica gel column chromatography (hexane/ethyl acetate) to obtain 860 mg of the entitled compound as a yellow oil.

$^1$H-NMR (CDCl$_3$) δ: 7.99-7.96 (2H, m), 7.24 (1H, t, J=4.6 Hz), 2.97 (4H, dd, J=5.9, 4.4 Hz), 2.82 (4H, s), 1.79 (1H, dq, J=10.9, 3.0 Hz), 0.54-0.47 (4H, m)

ESI-MS Found: m/z [M+H] 233

2) Production of 3-cyclopropyl-2,3,4,5-tetrahydro-1H-3-benzazepin-7-amine

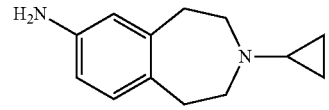

680 mg of the entitled compound was obtained as a yellow solid according to the same method as in Production Example 10-7), for which, however, 860 mg of the compound obtained in Production Example 12-1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.89 (1H, d, J=7.3 Hz), 6.46 (2H, td, J=7.3, 2.4 Hz), 3.53 (2H, s), 2.78 (8H, d, J=4.4 Hz), 1.76 (1H, tt, J=5.9, 3.1 Hz), 0.51-0.46 (4H, m)

ESI-MS Found: m/z [M+H] 203

PRODUCTION EXAMPLE 13

Production of 3-(2-methoxyethyl)-2,3,4,5-tetrahydro-1H-3-benzazepin-7-amine

1) Production of 3-(2-methoxyethyl)-7-nitro-2,3,4,5-tetrahydro-1H-3-benzazepine

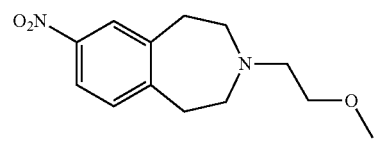 [SMILES: COCCN1CCc2ccc([N+](=O)[O-])cc2CC1]

A 1,4-dioxane (10 mL) solution of 1 g of the compound obtained in Production Example 11-1), 830 mg of 2-chloroethyl methyl ether, 660 mg of triethylamine and 1.8 g of potassium carbonate was stirred at 100° C. for 15 hours. The reaction liquid was cooled, diluted with ethyl acetate, and washed with aqueous saturated sodium bicarbonate solution and saturated saline water in that order. The organic layer was dried with anhydrous magnesium sulfate, the solvent was evaporated away under reduced pressure, and the crude product was purified through silica gel column chromatography (hexane/ethyl acetate) to obtain 620 mg of the entitled compound as a yellow oil.

$^1$H-NMR (CDCl$_3$) δ: 7.99-7.96 (2H, m), 7.25-7.21 (1H, m), 3.53 (2H, t, J=5.6 Hz), 3.37 (3H, s), 3.03 (4H, dd, J=6.6, 3.7 Hz), 2.76-2.71 (6H, m)

ESI-MS Found: m/z [M+H] 251

2) Production of 3-(2-methoxyethyl)-2,3,4,5-tetrahydro-1H-3-benzazepin-7-amine

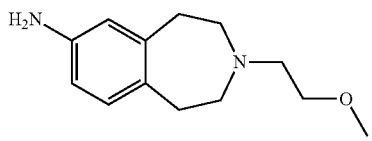

400 mg of the entitled compound was obtained as a yellow solid according to the same method as in Production Example 10-7), for which, however, 620 mg of the compound obtained in Production Example 6-1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.87 (1H, d, J=7.8 Hz), 6.48-6.43 (2H, m), 3.53 (4H, t, J=5.9 Hz), 3.36 (3H, s), 2.84-2.80 (4H, m), 2.75-2.65 (6H, m)

ESI-MS Found: m/z [M+H] 221

PRODUCTION EXAMPLE 14

Production of 2-(7-amino-1,2,4,5-tetrahydro-3H-3-benzazepin-3-yl)ethanol

1) Production of 2-(7-nitro-1,2,4,5-tetrahydro-3H-3-benzazepin-3-yl)ethanol

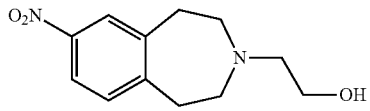 [SMILES: O=[N+]([O-])c1ccc2c(c1)CCN(CCO)CC2]

1.6 g of sodium cyanoborohydride was added to a methanol (100 mL) solution of 3 g of the compound obtained in Production Example 11-1) and 4.6 g of (tert-butyldimethylsiloxy)acetaldehyde, and stirred at room temperature for 3 hours. The reaction liquid was neutralized with aqueous saturated sodium bicarbonate solution, and methanol was evaporated away under reduced pressure. The residue was diluted with water and extracted three times with chloroform. The organic layer was dried with anhydrous magnesium sulfate, and the solvent was evaporated away under reduced pressure. The residue was dissolved in tetrahydrofuran, hydrochloric acid/methanol solution was added to it, and stirred at room temperature for 30 minutes. The solvent was evaporated away under reduced pressure, and the residue was dissolved in chloroform, and washed with aqueous saturated sodium bicarbonate solution and saturated saline water in that order. The organic layer was dried with anhydrous magnesium sulfate, the solvent was evaporated away under reduced pressure, and the crude product was purified through basic silica gel column chromatography (hexane/ethyl acetate) to obtain 3.1 g of the entitled compound as a yellow oil.

$^1$H-NMR (CDCl$_3$) δ: 8.01-7.97 (1H, m), 7.98 (1H, s), 7.24 (1H, s), 3.64 (2H, t, J=5.1 Hz), 3.03 (2H, dd, J=6.3, 3.4 Hz), 2.76-2.70 (4H, m), 2.68 (4H, dd, J=6.3, 4.4 Hz)

ESI-MS Found: m/z [M+H] 237

2) Production of 2-(7-amino-1,2,4,5-tetrahydro-3H-3-benzazepin-3-yl)ethanol

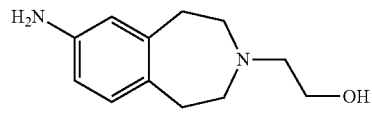

710 mg of the entitled compound was obtained as a yellow solid according to the same method as in Production Example 10-7), for which, however, 1.1 g of the compound obtained in Production Example 7-1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.88 (1H, d, J=7.3 Hz), 6.48-6.44 (2H, m), 3.61 (2H, t, J=5.4 Hz), 3.54 (2H, s), 2.84-2.79 (4H, m), 2.71-2.62 (4H, m), 2.64 (2H, t, J=5.4 Hz)

ESI-MS Found: m/z [M+H] 207

PRODUCTION EXAMPLE 15

Production of 3-(2,2-difluoroethyl)-2,3,4,5-tetrahydro-1H-3-benzazepin-7-amine

1) Production of 2,2-difluoroethyl trifluoromethanesulfonate

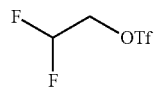

With cooling with ice, 2.7 ml of trifluoromethanesulfonic acid anhydride was added to a chloroform (100 mL) solution of 1 mL of 2,2-difluoroethanol and 2.2 mL of triethylamine, and stirred for 30 minutes. The reaction liquid was diluted with chloroform, and washed with aqueous saturated sodium bicarbonate solution and saturated saline water in that order. The organic layer was dried with anhydrous magnesium sulfate, and the solvent was evaporated away under reduced pressure to obtain the entitled compound.

2) Production of 3-(2,2-difluoroethyl)-7-nitro-2,3,4,5-tetrahydro-1H-3-benzazepine

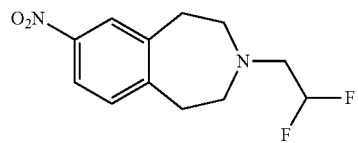 [SMILES: Nc1ccc2c(c1)CCN(CC(F)F)CC2]

An acetonitrile (100 mL) solution of 1 g of the compound obtained in Production Example 11-1), 3.2 g of the compound obtained in Production Example 15-1) and 1.2 g of potassium carbonate was stirred at 60° C. for 5 hours. The reaction liquid was cooled, then diluted with chloroform, and washed with aqueous saturated sodium bicarbonate solution and saturated saline water in that order. The organic layer was dried with anhydrous magnesium sulfate, the solvent was evaporated away under reduced pressure, and the crude product was purified through silica gel column chromatography (hexane/ethyl acetate) to obtain 430 mg of the entitled compound as a yellow oil.

$^1$H-NMR (CDCl$_3$) δ: 8.00-7.96 (2H, m), 7.24 (1H, d, J=7.8 Hz), 5.90 (1H, tt, J=56.1, 4.3 Hz), 3.07-3.00 (4H, m), 2.97-2.88 (2H, m), 2.86-2.81 (4H, m)

ESI-MS Found: m/z [M+H] 257

3) Production of 3-(2,2-difluoroethyl)-2,3,4,5-tetrahydro-1H-3-benzazepin-7-amine

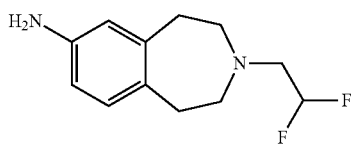

330 mg of the entitled compound was obtained as a yellow solid according to the same method as in Production Example 10-7), for which, however, 430 mg of the compound obtained in Production Example 15-2) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.87 (1H, d, J=8.3 Hz), 6.46 (1H, s), 6.45-6.44 (1H, m), 5.90 (1H, tt, J=56.1, 4.1 Hz), 3.54 (2H, s), 2.90 (2H, td, J=14.9, 4.4 Hz), 2.80 (8H, dd, J=11.0, 8.5 Hz)

ESI-MS Found: m/z [M+H] 227

PRODUCTION EXAMPLE 16

Production of 2-(7-amino-1,2,4,5-tetrahydro-3H-3-benzazepin-3-yl)-N,N-dimethylacetamide 1) Production of ethyl(7-nitro-1,2,4,5-tetrahydro-3H-3-benzazepin-3-yl)acetate

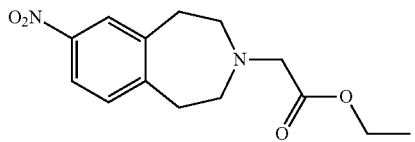 [SMILES: CCOC(=O)CN1CCc2ccc([N+](=O)[O-])cc2CC1]

730 mL of ethyl bromoacetate was added to a tetrahydrofuran (40 mL) suspension of 1 g of the compound obtained in Production Example 11-1), 1.2 g of potassium carbonate and 0.6 mL of triethylamine, and heated under reflux for 15 hours. The reaction liquid was cooled, diluted with ethyl acetate, and washed with aqueous saturated sodium bicarbonate solution and saturated saline water in that order. The organic layer was dried with anhydrous magnesium sulfate, the solvent was evaporated away under reduced pressure, and the crude product was purified through silica gel column chromatography (hexane/ethyl acetate) to obtain 1.1 g of the entitled compound as a yellow oil.

$^1$H-NMR (CDCl$_3$) δ: 8.01-7.97 (1H, m), 7.98 (1H, s), 7.24 (1H, d, J=8.3 Hz), 4.18 (2H, q, J=7.2 Hz), 3.39 (2H, s), 3.05 (4H, t, J=5.1 Hz), 2.81 (4H, td, J=5.1, 3.1 Hz), 1.27 (3H, t, J=7.2 Hz)

ESI-MS Found: m/z [M+H] 279

2) Production of N,N-dimethyl-2-(7-nitro-1,2,4,5-tetrahydro-3H-3-benzazepin-3-yl)acetamide

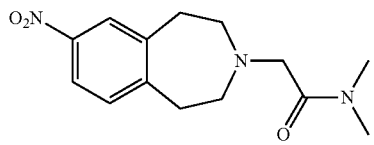 [SMILES: CN(C)C(=O)CN1CCc2ccc([N+](=O)[O-])cc2CC1]

5 mL of aqueous 5 N sodium hydroxide solution was added to 20 ml of a solution of 1.1 g of the compound obtained in the above reaction 1) in a mixed solvent of tetrahydrofuran/methanol (1/1), and stirred at room temperature for 20 minutes. The reaction liquid was neutralized with aqueous hydrochloric acid solution, and the solvent was evaporated away under reduced pressure. The residue was dissolved in 40 mL of N,N-dimethylformamide, and 770 mg of dimethylamine hydrochloride, 1.6 g of 1-(3-dimethylaminopropyl)-3-ethyl-carbodiimide hydrochloride, 630 mg of 1-hydroxybenzotriazole and 2.8 mL of triethylamine were added to it, and stirred at room temperature for 15 hours. The reaction liquid was diluted with chloroform, and washed with aqueous saturated sodium bicarbonate solution and saturated saline water in that order. The organic layer was dried with anhydrous magnesium sulfate, then the solvent was evaporated away under reduced pressure, and the crude product was purified through silica gel column chromatography (hexane/ethyl acetate) to obtain 1.1 g of the entitled compound as a yellow oil.

ESI-MS Found: m/z [M+H] 278

3) Production of 2-(7-amino-1,2,4,5-tetrahydro-3H-3-benzazepin-3-yl)-N,N-dimethylacetamide

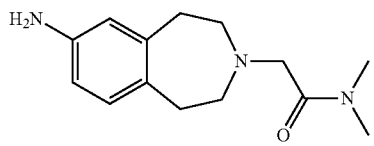

600 mg of the entitled compound was obtained as a yellow solid according to the same method as in Production Example 10-7), for which, however, the compound obtained in Production Example 9-2) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.87 (1H, d, J=7.8 Hz), 6.47-6.43 (2H, m), 3.53 (2H, s), 3.26 (2H, s), 3.14 (3H, s), 2.96 (3H, s), 2.84-2.80 (4H, m), 2.69-2.62 (4H, m)

ESI-MS Found: m/z [M+H] 248

PRODUCTION EXAMPLE 17

Production of (2S*)—N$^2$,N$^2$-dimethylindan-2,5-diamine, and (2R*)—N$^2$,N$^2$-dimethylindan-2,5-diamine

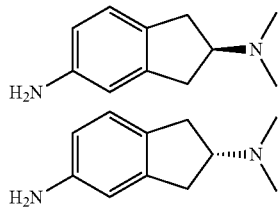

1) Production of N,N-dimethyl-5-nitroindan-2-amine 3.29 g of the entitled compound was obtained as an orange oily compound according to the same method as in Production Example 10-6), for which, however, 5-nitro-2-aminoindan monosulfate, which had been produced according to the method described in Advanced Synthesis & Catalysis, Vol. 343, pp. 461-472, in place of the starting compound used in Production Example 10-6).

ESI-MS Found: m/z [M+H] 207

2) Production of (2S*)—$N^2,N^2$-dimethylindan-2,5-diamine, and (2R*)—$N^2,N^2$-dimethylindan-2,5-diamine 1.58 g of a racemic mixture of the entitled compounds was obtained as a pale yellow solid compound according to the same method as in Production Example 10-7), for which, however, the compound obtained in the above 1) was used in place of 2'-methyl-7'-nitro-2',3'-dihydro-1'H-spiro[cyclopropane-1,4'-isoquinoline] used in Production Example 10-7).

The racemic mixture of the compounds was optically resolved with CHIRALPAK OD-H (20 mm×250 mm) (hexane/isopropanol/diethylamine=75/25/0.1) to obtain 582 mg of (2S*)—$N^2,N^2$-dimethylindan-2,5-diamine as a white solid and 550 mg of (2R*)—$N^2,N^2$-dimethylindan-2,5-diamine as a white solid.

$^1$H-NMR (CDCl$_3$) δ: 7.34-7.32 (1H, m), 6.98-6.94 (1H, m), 6.60-6.50 (2H, m), 3.17-3.11 (1H, m), 3.04-2.97 (2H, m), 2.86-2.77 (2H, m), 2.34 (6H, s)

PRODUCTION EXAMPLE 18

Production of 2-[[(2S*)-5-amino-2,3-dihydro-1H-inden-2-yl](methyl)amino]ethanol, and 2-[[(2R*)-5-amino-2,3-dihydro-1H-inden-2-yl](methyl)amino]ethanol

1) Production of N-(2-{[tert-butyl(dimethyl)silyl]oxy}ethyl)-5-nitroindan-2-amine

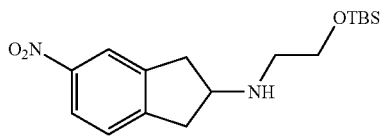 [SMILES: CC(C)(C)[Si](C)(C)OCCNC1Cc2ccc([N+](=O)[O-])cc2C1]

0.91 g of sodium cyanoborohydride was added to a methanol (100 mL) solution of 2 g of 5-nitroindan-2-amine sulfate and 1.9 g of (tert-butyldimethylsiloxy)acetaldehyde, and stirred at room temperature for 2 days. The reaction liquid was neutralized with aqueous saturated sodium bicarbonate solution, and methanol was evaporated away under reduced pressure. The residue was diluted with water, and extracted three times with chloroform. The organic layer was dried with anhydrous magnesium sulfate, the solvent was evaporated away under reduced pressure, and the crude product was purified through silica gel column chromatography (hexane/ethyl acetate) to obtain 1.56 g of the entitled compound as a yellow oil.

$^1$H-NMR (CDCl$_3$) δ: 8.06-8.02 (1H, m), 8.05 (1H, s), 7.32 (1H, d, J=8.8 Hz), 3.74 (3H, t, J=5.4 Hz), 3.26 (1H, dd, J=7.3, 2.9 Hz), 3.22 (1H, dd, J=7.3, 3.4 Hz), 2.86 (1H, dd, J=5.9, 2.9 Hz), 2.82 (2H, t, J=4.6 Hz), 2.78 (2H, t, J=5.4 Hz), 0.88 (9H, s), 0.06 (6H, s)

ESI-MS Found: m/z [M+H] 337

2) Production of tert-butyl (2-hydroxyethyl)-(5-nitro-2,3-dihydro-1H-inden-2-yl)carbamate

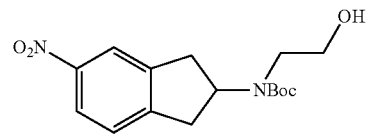 [SMILES: CC(C)(C)OC(=O)N(CCO)C1Cc2ccc([N+](=O)[O-])cc2C1]

1.4 mL of di-tert-butyl dicarboxylic anhydride and 1.3 mL of triethylamine were added to a chloroform (100 mL) solution of 1.56 g of the compound obtained in the above reaction 1), and stirred at room temperature for 5 hours. The reaction liquid was concentrated under reduced pressure, and the residue was dissolved in tetrahydrofuran. 7 mL of 1 M tetrabutylammonium fluoride/tetrahydrofuran solution was added to it, and stirred at room temperature for 1 hour. The reaction liquid was diluted with ethyl acetate, and washed with aqueous 0.5 N hydrochloric acid solution, aqueous saturated sodium bicarbonate solution and saturated saline water in that order. The organic layer was dried with anhydrous magnesium sulfate, the solvent was evaporated away under reduced pressure, and the crude product was purified through silica gel column chromatography (chloroform/methanol) to obtain 1.5 g of the entitled compound as a yellow oil.

$^1$H-NMR (CDCl$_3$) δ: 8.07-8.03 (1H, m), 8.04 (1H, s), 7.32 (1H, d, J=8.3 Hz), 4.75 (1H, s), 3.76 (2H, q, J=5.2 Hz), 3.41 (2H, s), 3.32-3.15 (4H, m), 1.41 (9H, s)

ESI-MS Found: m/z [M+H] 323

3) Production of 2-[[(2S*)-5-amino-2,3-dihydro-1H-inden-2-yl](methyl)amino]ethanol, and 2-[[(2R*)-5-amino-2,3-dihydro-1H-inden-2-yl](methyl)amino]ethanol

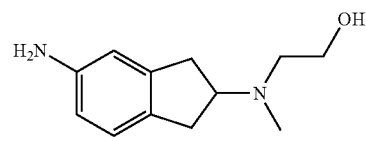

1 mL of trifluoroacetic acid was added to a chloroform (5 mL) solution of 300 mg of the compound obtained in the above reaction 2), and stirred at room temperature for 30 minutes. The reaction liquid was neutralized with aqueous saturated sodium bicarbonate solution, and extracted with chloroform. The organic layer was washed with saturated saline water, then dried with anhydrous magnesium sulfate, and the solvent was evaporated away under reduced pressure. 0.12 g of sodium cyanoborohydride was added to a methanol (10 mL) solution of the residue, 0.2 mL of aqueous 37% formaldehyde solution and 0.05 mL of acetic acid, and stirred at room temperature for 2 hours. The reaction liquid was neutralized with aqueous saturated sodium bicarbonate solution, and methanol was evaporated away under reduced pressure. The residue was diluted with water, and extracted three times with chloroform. The organic layer was dried with anhydrous magnesium sulfate, and the solvent was evaporated away under reduced pressure. 100 mg of 10% palladium-carbon was added to an ethanol (10 mL) solution of the resulting residue, and stirred in a hydrogen atmosphere under 1 atmospheric pressure at room temperature for 2 hours. Palladium-carbon was removed through filtration, the filtrate was concentrated under reduced pressure, and the crude product was purified through basic silica gel column chromatography (hexane/ethyl acetate) to obtain a racemic mixture of the entitled compounds. The mixture was optically resolved with CHIRALPAK AD-H (20 mm×250 mm) (hexane/isopropanol/diethylamine=85/15/0.1) to obtain 2-[[(2S*)-5-amino-2,3-dihydro-1H-inden-2-yl](methyl)amino]ethanol, and 2-[[(2R*)-5-amino-2,3-dihydro-1H-inden-2-yl](methyl)amino]ethanol, 33.6 mg and 31.9 mg, respectively, both as a white solid.

$^1$H-NMR (CDCl$_3$) δ: 6.96 (1H, d, J=7.8 Hz), 6.55 (1H, s), 6.50 (1H, dd, J=7.8, 2.4 Hz), 3.60 (2H, t, J=5.4 Hz), 3.48-3.40 (1H, m), 2.97 (2H, dt, J=16.9, 5.9 Hz), 2.79 (2H, td, J=14.5, 8.3 Hz), 2.59 (2H, t, J=5.4 Hz), 2.26 (3H, s)

ESI-MS Found: m/z [M+H] 237

PRODUCTION EXAMPLE 19

Production of tert-butyl 6'-amino-3',4'-dihydro-2'H-spiro[cyclopropane-1,1'-isoquinoline]-2'-carboxylate 1) Production of 2'H-spiro[cyclopropane-1,1'-isoquinolin]-3'(4'H)-one:

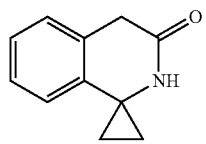 [SMILES: O=C1Cc2ccccc2C2(CC2)N1]

38 mL of 2 Methylmagnesium bromide/diethyl ether solution was dropwise added to a diethyl ether (200 mL) solution of 10 g of methyl 2-cyanophenylacetate and 17.9 g of titanium tetraisopropoxide at room temperature, and further stirred for 1 hour. Aqueous 1 N hydrochloric acid solution was added to the reaction liquid, and the organic layer was separated. Further, the aqueous layer was extracted with chloroform, and the organic layer was washed with saturated saline water, and dried with anhydrous magnesium sulfate. The solvent was evaporated away under reduced pressure, and the crude product was purified through basic silica gel column chromatography (hexane/ethyl acetate) to obtain 1.8 g of the entitled compound as a colorless solid.

$^1$H-NMR (CDCl$_3$) δ: 7.39 (1H, s), 7.19-7.11 (2H, m), 6.80-6.76 (1H, m), 3.66 (2H, s), 1.24 (2H, t, J=2.2 Hz), 1.22 (2H, t, J=2.2 Hz)

ESI-MS Found: m/z [M+H] 174

2) Production of 6'-nitro-2'H-spiro[cyclopropane-1,1'-isoquinolin]-3'(4'H)-one

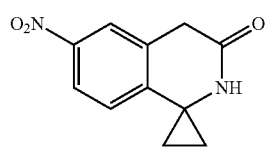 [SMILES: O=C1Cc2cc([N+](=O)[O-])ccc2C2(CC2)N1]

With cooling with ice, 1.1 g of potassium nitrate was gradually added to a sulfuric acid (20 mL) solution of 1.8 g of the compound obtained in the above reaction 1), and further stirred at room temperature for 15 hours. The reaction liquid was neutralized with aqueous 28% ammonia solution, and extracted two times with chloroform. The organic layer was dried with anhydrous magnesium sulfate, and the solvent was evaporated away under reduced pressure. The resulting solid was washed with ethyl acetate to obtain 1.3 g of the entitled compound as a yellow solid.

$^1$H-NMR (DMSO-d$_6$) δ: 8.26 (1H, s), 8.11 (1H, d, J=2.4 Hz), 8.02 (1H, dd, J=8.8, 2.4 Hz), 7.21 (1H, d, J=8.3 Hz), 3.73 (2H, s), 1.32 (2H, t, J=1.7 Hz), 1.31 (2H, t, J=1.7 Hz)

ESI-MS Found: m/z [M+H] 219

3) Production of 6'-nitro-3',4'-dihydro-2'H-spiro[cyclopropane-1,1'-isoquinoline]

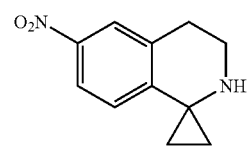 [SMILES: O=[N+]([O-])c1ccc2c(c1)CCNC21CC1]

940 mg of the entitled compound was obtained as a yellow oil according to the same method as in Production Example 10-5), for which, however, the compound obtained in the above reaction 2) was used in place of 7'-nitro-1',2'-dihydro-3'H-spiro[cyclopropane-1,4'-isoquinolin]-3'-one used in Production Example 10-5).

$^1$H-NMR (CDCl$_3$) δ: 7.98-7.93 (2H, m), 6.73 (1H, d, J=8.4 Hz), 3.23 (2H, t, J=6.0 Hz), 2.98 (2H, t, J=6.0 Hz), 1.28-1.24 (2H, m), 1.18-1.15 (2H, m)

ESI-MS Found: m/z [M+H] 205

4) Production of tert-butyl 6'-nitro-3',4'-dihydro-2'H-spiro[cyclopropane-1,1'-isoquinoline]-2'-carboxylate

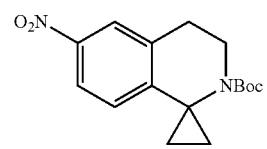 [SMILES: CC(C)(C)OC(=O)N1CCc2cc([N+](=O)[O-])ccc2C12CC2]

0.06 mL of di-tert-butyl dicarboxylic anhydride and 0.05 mL of triethylamine were added to a chloroform (2 mL) solution of 38 mg of the compound obtained in the above reaction 3), and stirred at room temperature for 18 hours. The reaction liquid was concentrated under reduced pressure, and the crude product was purified through silica gel column chromatography (hexane/ethyl acetate) to obtain 35 mg of the entitled compound as a yellow oil.

ESI-MS Found: m/z [M+H] 305

5) Production of tert-butyl 6'-amino-3',4'-dihydro-2'H-spiro[cyclopropane-1,1'-isoquinoline]-2'-carboxylate

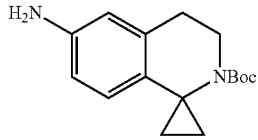

27 mg of the entitled compound was obtained as a yellow solid according to the same method as in Production Example 10-7), for which, however, 35 mg of the compound obtained in the above reaction 4) was used in place of 2'-methyl-7'-nitro-2',3'-dihydro-1'H-spiro[cyclopropane-1,4'-isoquinoline] used in Production Example 10-7).
$^1$H-NMR (CDCl$_3$) δ: 6.52 (1H, d, J=8.2 Hz), 6.43-6.39 (2H, m), 3.72 (2H, t, J=6.3 Hz), 2.84 (2H, t, J=6.3 Hz), 1.37 (9H, s), 1.31-1.26 (2H, m), 1.14-1.10 (2H, m)
ESI-MS Found: m/z [M+H] 275

PRODUCTION EXAMPLE 20

Production of 2'-methyl-3',4'-dihydro-2'H-spiro[cyclopropane-1,1'-isoquinolin]-6'-amine 1) Production of 2'-methyl-6'-nitro-3',4'-dihydro-2'H-spiro[cyclopropane-1,1'-isoquinoline]

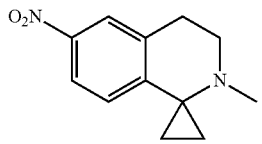 [SMILES: CN1CCc2cc([N+](=O)[O-])ccc2C12CC2]

100 mg of the entitled compound was obtained as a colorless solid according to the same method as in Production Example 10-6), for which, however, the compound obtained in Production Example 19-3) was used in place of 7'-nitro-1',2'-dihydro-3'H-spiro[cyclopropane-1,4'-isoquinoline] used in Production Example 10-6).

2) Production of 2'-methyl-3',4'-dihydro-2'H-spiro[cyclopropane-1,1'-isoquinolin]-6'-amine

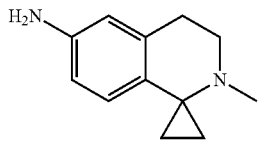

40 mg of the entitled compound was obtained as a yellow solid according to the same method as in Production Example 10-7), for which, however, 100 mg of the compound obtained in the above reaction 1) was used in place of 2'-methyl-7'-nitro-2',3'-dihydro-1'H-spiro[cyclopropane-1,4'-isoquinoline] used in Production Example 10-7).
$^1$H-NMR (CDCl$_3$) δ: 6.49 (2H, d, J=1.2 Hz), 6.46 (1H, s), 3.52 (2H, brs), 3.22 (2H, t, J=6.3 Hz), 2.83 (2H, t, J=6.3 Hz), 2.40 (3H, s), 1.00 (2H, t, J=2.5 Hz), 0.95 (2H, t, J=2.5 Hz)
ESI-MS Found: m/z [M+H] 189

PRODUCTION EXAMPLE 21

Production of 2-methyl-2,3,4,5-tetrahydro-1H-2-benzazepin-8-amine

1) Production of 2,3,4,5-tetrahydro-1H-2-benzazepin-1-one

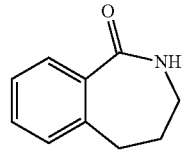 [SMILES: O=C1NCCCc2ccccc21]

With cooling with ice, 2.6 g of sodium azide was added to a concentrated hydrochloric acid (60 mL) solution of 5 mL of alpha-tetralone, and stirred at room temperature for 15 hours. The reaction liquid was poured into ice water, and neutralized with potassium carbonate. This was extracted with chloroform, and the organic layer was washed with saturated saline water and dried with anhydrous magnesium sulfate. The solvent was evaporated away under reduced pressure, and the crude product was purified through silica gel column chromatography (chloroform/methanol) to obtain 2.3 g of the entitled compound as a yellow solid.
$^1$H-NMR (CDCl$_3$) δ: 7.71 (1H, dd, J=7.3, 1.5 Hz), 7.41 (1H, td, J=7.6, 1.6 Hz), 7.34 (1H, td, J=7.6, 1.5 Hz), 7.19 (1H, d, J=7.8 Hz), 6.42 (1H, s), 3.13 (2H, q, J=6.5 Hz), 2.87 (2H, t, J=7.1 Hz), 2.06-1.99 (2H, m)
ESI-MS Found: m/z [M+H]162

2) Production of 2,3,4,5-tetrahydro-1H-2-benzazepine

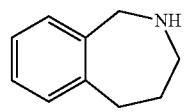 [SMILES: c1ccc2c(c1)CCCNC2]

710 mg of lithiumaluminium hydride was added to a tetrahydrofuran (50 mL) solution of 1 g of the compound obtained in the above reaction 1), and stirred at 50° C. for 15 hours. With cooling with ice, 0.7 mL of water and 0.7 mL of aqueous 5 N sodium hydroxide solution were added to the reaction liquid, and stirred for 2 hours. The insoluble matter was removed through filtration through Celite, and further this was washed with diethyl ether. The filtrate was evaporated under reduced pressure to obtain the entitled compound.

3) Production of 2-methyl-2,3,4,5-tetrahydro-1H-2-benzazepine

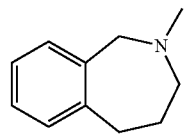

600 mg of the entitled compound was obtained as a colorless solid according to the same method as in Production Example 10-6), for which, however, the compound obtained in the above 1) was used in place of 7'-nitro-1',2'-dihydro-3'H-spiro[cyclopropane-1,4'-isoquinoline] used in Production Example 10-6).

¹H-NMR (CDCl₃) δ: 7.15-7.10 (4H, m), 3.79 (2H, s), 3.01 (2H, t, J=5.4 Hz), 2.87 (2H, t, J=5.6 Hz), 2.31 (3H, s), 1.79-1.73 (2H, m)

ESI-MS Found: m/z [M+H] 162

4) Production of 2-methyl-8-nitro-2,3,4,5-tetrahydro-1H-2-benzazepine

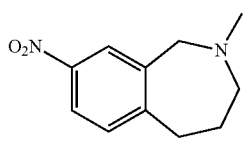

510 mg of the entitled compound was obtained as a yellow solid according to the same method as in Production Example 19-2), for which, however, the compound obtained in the above reaction 3) was used in place of 2'H-spiro[cyclopropane-1,1'-isoquinolin]-3'(4'H)-one used in Production Example 19-2).

¹H-NMR (CDCl₃) δ: 8.01 (2H, td, J=4.4, 2.4 Hz), 7.29-7.26 (1H, m), 3.87 (2H, s), 3.04 (2H, t, J=5.6 Hz), 2.98 (2H, t, J=5.6 Hz), 2.34 (3H, s), 1.82-1.77 (2H, m)

ESI-MS Found: m/z [M+H] 207

5) Production of 2-methyl-2,3,4,5-tetrahydro-1H-2-benzazepin-8-amine

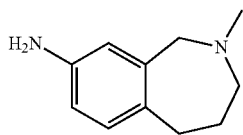

280 mg of the entitled compound was obtained as a yellow solid according to the same method as in Production Example 10-7), for which, however, 520 mg of the compound obtained in the above reaction 4) was used in place of 2'-methyl-7'-nitro-2',3'-dihydro-1'H-spiro[cyclopropane-1,4'-isoquinoline] used in Production Example 10-7).

¹H-NMR (DMSO-d₆) δ: 6.73 (1H, d, J=7.8 Hz), 6.33 (1H, d, J=2.4 Hz), 6.28 (1H, dd, J=7.8, 2.4 Hz), 4.75 (2H, s), 3.53 (2H, s), 2.84 (2H, t, J=5.6 Hz), 2.62 (2H, t, J=5.6 Hz), 2.13 (3H, s), 1.57-1.51 (2H, m)

ESI-MS Found: m/z [M+H] 177

PRODUCTION EXAMPLE 22

Production of 2-methyl-1,2,3,4-tetrahydroisoquinolin-7-amine

1) Production of 7-nitro-1,2,3,4-tetrahydroisoquinoline monohydrochloride

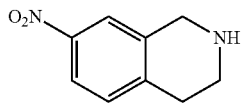 [SMILES: O=[N+]([O-])c1ccc2c(c1)CNCC2]

7-Nitro-1,2,3,4-tetrahydroisoquinoline was obtained according to the same method as in Production Example 19-2), for which, however, 1,2,3,4-tetrahydroisoquinoline was used in place of 2'H-spiro[cyclopropane-1,1'-isoquinolin]-3'(4'H)-one used in Production Example 19-2). This was dissolved in ethyl acetate, and 4 N hydrochloric acid/ethyl acetate was added to it, and the precipitated solid was taken out through filtration, and washed with ethyl acetate. Further, this was recrystallized from methanol to obtain 5.6 g of the entitled compound as a yellow solid.

¹H-NMR (DMSO-d₆) δ: 9.48 (2H, s), 8.21 (1H, d, J=2.0 Hz), 8.11 (1H, dd, J=8.3, 2.0 Hz), 7.52 (1H, d, J=8.3 Hz), 3.42-3.33 (4H, m), 3.14-3.10 (2H, m)

ESI-MS Found: m/z [M+H] 180

2) Production of 2-methyl-7-nitro-1,2,3,4-tetrahydroisoquinoline

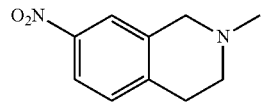

5.9 g of sodium cyanoborohydride was added to a methanol (450 mL) solution of 10 g of the compound obtained in the above reaction 1), 10.4 mL of aqueous 37% formaldehyde solution and 4 mL of acetic acid, and stirred at 50° C. for 15 hours. The precipitated solid was taken out through filtration and washed with methanol. The resulting crude product was purified through basic silica gel column chromatography (hexane/ethyl acetate) to obtain 8.7 g of the entitled compound as a colorless solid.

¹H-NMR (CDCl₃) δ: 7.99 (1H, dd, J=8.5, 2.0 Hz), 7.92 (1H, d, J=2.0 Hz), 7.26 (1H, d, J=8.5 Hz), 3.65 (2H, s), 3.01 (2H, t, J=5.9 Hz), 2.73 (2H, t, J=5.9 Hz), 2.49 (3H, s)

ESI-MS Found: m/z [M+H] 193

3) Production of 2-methyl-1,2,3,4-tetrahydroisoquinolin-7-amine

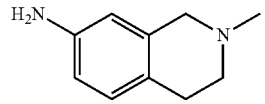

7.3 g of the entitled compound was obtained as a yellow solid according to the same method as in Production Example 10-7), for which, however, 8.7 g of the compound obtained in the above reaction 2) was used in place of 2'-methyl-7'-nitro-2',3'-dihydro-1'H-spiro[cyclopropane-1,4'-isoquinoline] used in Production Example 10-7).

¹H-NMR (CDCl₃) δ: 6.89 (1H, d, J=8.3 Hz), 6.51 (1H, dd, J=8.3, 2.0 Hz), 6.36 (1H, d, J=2.0 Hz), 3.51 (2H, brs), 3.48 (2H, s), 2.80 (2H, t, J=6.1 Hz), 2.64 (2H, t, J=6.1 Hz), 2.43 (3H, s)

ESI-MS Found: m/z [M+H] 164

PRODUCTION EXAMPLE 23

Production of 2-isopropyl-1,2,3,4-tetrahydroisoquinolin-7-amine

1) Production of 2-isopropyl-7-nitro-1,2,3,4-tetrahydroisoquinoline

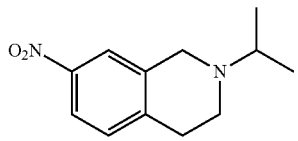

870 mg of the entitled compound was obtained as a colorless solid according to the same method as in Production Example 10-6), for which, however, the compound obtained in Production Example 22-1) was used in place of 7'-nitro-1',2'-dihydro-3'H-spiro[cyclopropane-1,4'-isoquinoline] used in Production Example 10-6), and acetone was used in place of aqueous formaldehyde solution.

$^1$H-NMR (CDCl$_3$) δ: 7.99-7.92 (2H, m), 7.24 (1H, d, J=8.3 Hz), 3.79 (2H, s), 2.98 (2H, t, J=5.6 Hz), 2.98-2.91 (1H, m), 2.81 (2H, t, J=5.6 Hz), 1.15 (6H, d, J=6.3 Hz)

ESI-MS Found: m/z [M+H] 221

2) Production of 2-isopropyl-1,2,3,4-tetrahydroisoquinolin-7-amine

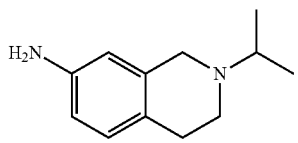 [SMILES: CC(C)N1CCc2ccc([N+](=O)[O-])cc2C1]

500 mg of the entitled compound was obtained as a yellow solid according to the same method as in Production Example 10-7), for which, however, 870 mg of the compound obtained in the above reaction 1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.88 (1H, d, J=8.3 Hz), 6.49 (1H, dd, J=8.3, 2.4 Hz), 6.38 (1H, d, J=2.4 Hz), 3.63 (2H, s), 3.49 (2H, s), 2.91-2.84 (1H, m), 2.79-2.71 (4H, m), 1.12 (6H, d, J=6.3 Hz)

ESI-MS Found: m/z [M+H] 191

PRODUCTION EXAMPLE 25

Production of 2-(2-methoxyethyl)-1,2,3,4-tetrahydroisoquinolin-7-amine

1) Production of 2-(2-methoxyethyl)-7-nitro-1,2,3,4-tetrahydroisoquinoline

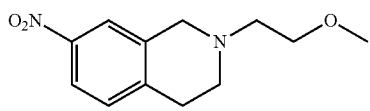 [SMILES: COCCN1CCc2ccc([N+](=O)[O-])cc2C1]

720 mg of the entitled compound was obtained as a yellow solid according to the same method as in Production Example 13-1), for which, however, 1 g of the compound obtained in Production Example 22-1) was used in place of 7-nitro-2,3,4,5-tetrahydro-1H-3-benzazepine used in Production Example 13-1) and acetonitrile was used in place of 1,4-dioxane.

$^1$H-NMR (CDCl$_3$) δ: 7.98 (1H, dd, J=8.3, 2.4 Hz), 7.92 (1H, d, J=2.4 Hz), 7.24 (1H, d, J=8.3 Hz), 3.78 (2H, s), 3.61 (2H, t, J=5.9 Hz), 3.40 (3H, s), 3.01 (2H, t, J=5.4 Hz), 2.84 (2H, t, J=5.9 Hz), 2.79 (2H, t, J=5.4 Hz)

ESI-MS Found: m/z [M+H] 237

2) Production of 2-(2-methoxyethyl)-1,2,3,4-tetrahydroisoquinolin-7-amine

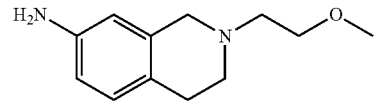

590 mg of the entitled compound was obtained as a yellow solid according to the same method as in Production Example 10-7), for which, however, the compound obtained in the above reaction 1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.87 (1H, d, J=8.3 Hz), 6.50 (1H, dd, J=8.3, 2.4 Hz), 6.36 (1H, d, J=2.4 Hz), 3.66-3.57 (4H, m), 3.50 (2H, s), 3.38 (3H, s), 2.88-2.71 (6H, m)

ESI-MS Found: m/z [M+H] 207

PRODUCTION EXAMPLE 26

Production of 2-(7-amino-3,4-dihydroisoquinolin-2(1H)-yl)ethanol

1) Production of 2-(7-nitro-3,4-dihydroisoquinolin-2(1H)-yl)ethanol

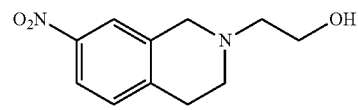 [SMILES: O=[N+]([O-])c1ccc2c(c1)CN(CCO)CC2]

An acetonitrile solution (30 mL) of 3 g of the compound obtained in Production Example 22-1), 2.3 g of 2-chloroethanol and 3.9 g of potassium carbonate was stirred at 100° C. for 15 hours. The reaction liquid was cooled, diluted with chloroform and washed with saturated saline water. The organic layer was washed with saturated saline water, dried with anhydrous magnesium sulfate, and the solvent was evaporated away under reduced pressure. The resulting crude product was purified through basic silica gel column chromatography (hexane/ethyl acetate) and further through silica gel column chromatography (hexane/ethyl acetate) to obtain 1.5 g of the entitled compound as a colorless solid.

$^1$H-NMR (CDCl$_3$) δ: 8.00 (1H, dd, J=8.5, 2.2 Hz), 7.93 (1H, d, J=2.2 Hz), 7.28-7.25 (1H, m), 3.78 (2H, s), 3.74 (2H, t, J=5.5 Hz), 3.00 (2H, t, J=5.9 Hz), 2.86 (2H, t, J=5.9 Hz), 2.76 (2H, t, J=5.5 Hz)

ESI-MS Found: m/z [M+H] 223

2) Production of 2-(7-amino-3,4-dihydroisoquinolin-2(1H)-yl)ethanol

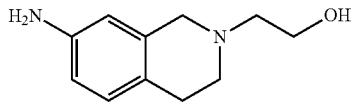

1.1 g of the entitled compound was obtained as a yellow solid according to the same method as in Production Example 10-7), for which, however, the compound obtained in the above reaction 1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.91 (1H, d, J=8.3 Hz), 6.53 (1H, dd, J=8.3, 2.4 Hz), 6.37 (1H, d, J=2.4 Hz), 3.69 (2H, t, J=5.4 Hz), 3.63-3.41 (2H, m), 3.61 (2H, s), 2.79 (4H, s), 2.70 (2H, t, J=5.4 Hz)

ESI-MS Found: m/z [M+H] 193

PRODUCTION EXAMPLE 27

Production of 1,2,3,4-tetrahydroisoquinolin-7-amine

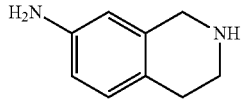

500 mg of the entitled compound was obtained as a yellow oil according to the same method as in Production Example 10-7), for which, however, 1 g of the compound obtained in Production Example 22-1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.88 (1H, d, J=8.3 Hz), 6.51 (1H, dd, J=8.3, 2.4 Hz), 6.36 (1H, d, J=2.4 Hz), 3.92 (2H, s), 3.52 (2H, s), 3.10 (2H, t, J=5.9 Hz), 2.67 (2H, t, J=5.9 Hz)

ESI-MS Found: m/z [M+H] 149

PRODUCTION EXAMPLE 28

Production of 1-[2-(dimethylamino)ethyl]indolin-5-amine

1) Production of N,N-dimethyl-2-(5-nitro-2,3-dihydro-1H-indol-1-yl)ethylamine

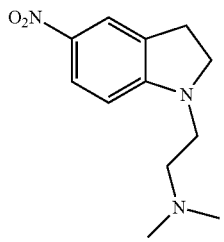 [SMILES: CN(C)CCN1CCc2cc([N+](=O)[O-])ccc21]

730 mg of sodium hydride was added to an N,N-dimethylformamide solution of 1 g of 5-nitroindoline, and stirred at room temperature for 30 minutes. 1.8 g of 2-dimethylaminoethyl chloride hydrochloride was added to the reaction liquid, and stirred at 70° C. for 1 hour. The reaction liquid was cooled, diluted with chloroform, and washed with aqueous saturated sodium bicarbonate solution and saturated saline water in that order. The organic layer was dried with anhydrous magnesium sulfate, and the solvent was evaporated away under reduced pressure. The resulting crude product was purified through basic silica gel column chromatography (chloroform/methanol) to obtain 950 mg of the entitled compound as a yellow oil.

$^1$H-NMR (CDCl$_3$) δ: 8.26 (1H, dd, J=8.8, 2.4 Hz), 8.14 (1H, d, J=2.4 Hz), 6.96 (1H, d, J=8.8 Hz), 3.88 (2H, t, J=6.8 Hz), 3.64 (2H, s), 2.57 (2H, t, J=6.8 Hz), 2.30 (6H, s)

ESI-MS Found: m/z [M+H] 250

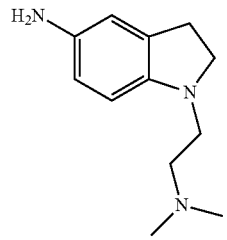

599 mg of the entitled compound was obtained as a yellow oil according to the same method as in Production Example 10-7), for which, however, 940 mg of the compound obtained in the above reaction 1) was used in place of 2'-methyl-7'-nitro-2',3'-dihydro-1'H-spiro[cyclopropane-1,4'-isoquinoline] used in Production Example 10-7).

$^1$H-NMR (CDCl$_3$) δ: 6.67 (1H, d, J=2.0 Hz), 6.66 (1H, d, J=8.3 Hz), 6.60 (1H, dd, J=8.3, 2.0 Hz), 3.78 (2H, t, J=7.3 Hz), 3.51 (2H, brs), 3.45 (2H, s), 2.54 (2H, t, J=7.3 Hz), 2.31 (6H, s)

ESI-MS Found: m/z [M+H] 220

PRODUCTION EXAMPLE 29

Production of 2-(6-amino-1,1-dimethyl-3,4-dihydroisoquinolin-2(1H)-yl)ethanol hydrochloride 1) Production of tert-butyl[2-(3-nitrophenyl)ethyl]carbamate

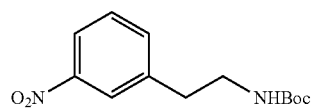

6.44 mL of borane-dimethylsulfide complex was added to a tetrahydrofuran (100 mL) solution of 10 g of 3-nitrophenylacetonitrile, and stirred under reflux for 2 hours. The reaction liquid was cooled to room temperature, then 40 mL of 5% hydrochloric acid/methanol solution was added to it, and heated under reflux for 1 hour. The solvent was evaporated away, and diethyl ether was added to it. To the resulting solid, added were 50 mL of tetrahydrofuran, 27.1 mL of 5 M sodium hydroxide and 16.15 g of di-tert-butyl dicarboxylic anhydride, and stirred overnight at room temperature. Water and ethyl acetate were added to the reaction liquid to separate the organic layer. This was washed with saturated saline water, dried with anhydrous magnesium sulfate, and the solvent was evaporated away to obtain 15.95 g of the entitled compound as a colorless oil.

$^1$H-NMR (CDCl$_3$) δ: 8.11-8.09 (1H, m), 8.07 (1H, s), 7.55 (1H, d, J=7.8 Hz), 7.48 (1H, t, J=7.8 Hz), 4.59 (1H, s), 3.42 (2H, q, J=6.7 Hz), 2.93 (2H, t, J=7.1 Hz), 1.43 (9H, d, J=3.9 Hz)

2) Production of tert-butyl[2-(3-aminophenyl)ethyl]carbamate

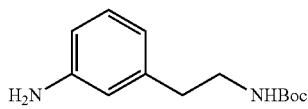

4.21 g of palladium hydroxide-carbon was added to a solution of 15.95 g of the compound obtained in the above 1) in 100 mL of tetrahydrofuran and 50 mL of methanol, and in a hydrogen atmosphere, this was stirred overnight. The catalyst was removed through filtration, and the filtrate was concentrated to obtain 13.75 g of the entitled compound as a white solid.

ESI-MS Found: m/z [M+H] 237

3) Production of 1,1-dimethyl-1,2,3,4-tetrahydroisoquinolin-6-amine

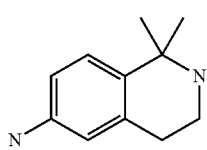

10 mL of trifluoroacetic acid was added to 2.36 g of the compound obtained in the above 2), and stirred at room temperature for 30 minutes. The reaction liquid was concentrated, and 6 mL of 85% phosphoric acid and 1.6 mL of 2,2-dimethoxypropane were added to it and stirred at 70° C. for 3 days. Further, 1 mL of 2,2-dimethoxypropane was added to it, and reacted at 140° C. for 3 hours, using a microwave reactor. The reaction liquid was diluted with water, then potassium carbonate was added thereto and extracted with ethyl acetate. This was washed with saturated saline water, dried with anhydrous magnesium sulfate, and the solvent was evaporated away. The crude product was purified through basic silica gel column chromatography (hexane/ethyl acetate) to obtain 1.24 g of a colorless oil of the entitled compound.

$^1$H-NMR (CDCl$_3$) δ: 7.01 (1H, d, J=8.3 Hz), 6.53 (1H, dd, J=8.3, 2.9 Hz), 6.39 (1H, d, J=2.4 Hz), 3.53 (2H, s), 3.10 (2H, t, J=5.9 Hz), 2.68 (2H, t, J=5.9 Hz), 1.41 (6H, s)

4) Production of tert-butyl(1,1-dimethyl-1,2,3,4-tetrahydroisoquinolin-6-yl)carbamate

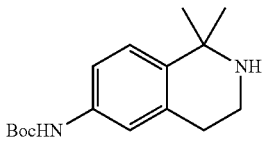 [SMILES: CC(C)(C)OC(=O)Nc1ccc2c(c1)CCNC2(C)C]

3.82 mL of 1 M hydrochloric acid and 1.08 g of di-tert-butyl icarboxylic anhydride were added to an ethanol solution (10 mL) of 673 mg of the compound obtained in the above 3), and stirred overnight at 70° C. The reaction liquid was concentrated, then aqueous saturated sodium hydrogencarbonate solution was added thereto and extracted with ethyl acetate. This was washed with saturated saline water, dried with anhydrous magnesium sulfate, and the solvent was evaporated away. The crude product was purified through basic silica gel column chromatography (hexane/ethyl acetate) to obtain 660 mg of the entitled compound as a colorless oil.

$^1$H-NMR (CDCl$_3$) δ: 7.16 (1H, s), 7.12 (1H, d, J=8.6 Hz), 7.05 (1H, dd, J=8.6, 2.3 Hz), 6.40 (1H, s), 3.11 (2H, t, J=6.1 Hz), 2.75 (2H, t, J=5.9 Hz), 1.51 (9H, s), 1.42 (6H, s)

5) Production of tert-butyl[2-(2-{[tert-butyl(dimethyl)silyl]oxy}ethyl)-1,1-dimethyl-1,2,3,4-tetrahydroisoquinolin-6-yl)carbamate

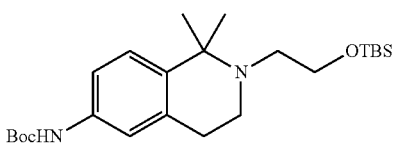 [SMILES: CC(C)(C)OC(=O)Nc1ccc2c(c1)CCN(CCO[Si](C)(C)C(C)(C)C)C2(C)C]

480 mg of the entitled compound was obtained as a white solid according to the same method as in Production Example 18-1), for which, however, the compound obtained in the above 4) was used in place of 5-nitroindan-2-amine monosulfate used in Production Example 18-1).

6) Production of 2-(6-amino-1,1-dimethyl-3,4-dihydroisoquinolin-2(1H)-yl)ethanol hydrochloride

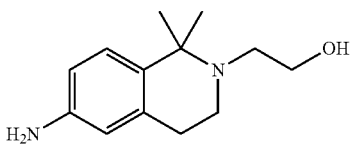

480 mg of the compound obtained in the above 5) was dissolved in 5 mL of 4 N hydrochloric acid/dioxane solution, and stirred at room temperature for 2 hours, and then at 50° C. for 2 hours. This was cooled to room temperature, then the precipitated solid was taken out through filtration, washed with diethyl ether, and dried under reduced pressure to obtain 300 mg of the entitled compound as a white solid.

¹H-NMR (DMSO-d₆) δ: 10.33 (1H, s), 7.48 (1H, d, J=8.5 Hz), 7.13 (1H, dd, J=8.5, 2.1 Hz), 7.02 (1H, d, J=2.1 Hz), 3.96-3.76 (3H, m), 3.63-3.52 (2H, m), 3.49-3.35 (2H, m), 3.01-2.86 (2H, m), 1.78 (3H, s), 1.59 (3H, s)

ESI-MS Found: m/z [M+H]⁺ 221

PRODUCTION EXAMPLE 30

Production of 3',4'-dihydro-2'H-spiro[cyclobutane-1,1'-isoquinolin]-6'-amine

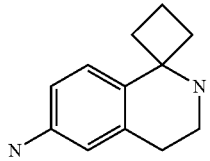 [SMILES: Nc1ccc2c(c1)CCNC21CCC1]

2 mL of 85% phosphoric acid was added to 350 mg of the compound obtained in Production Example 29-2), and stirred at 70° C. for 1 hour. Further, 0.144 mL of cyclobutanone was added to it, and reacted at 140° C. for 3 hours, using a microwave reactor. The reaction liquid was diluted with water, then potassium carbonate was added to it, and extracted with ethyl acetate. This was washed with saturated saline water, dried with anhydrous magnesium sulfate, and the solvent was evaporated away. The crude product was purified through basic silica gel column chromatography (hexane/ethyl acetate) to obtain 157 mg of the entitled compound as a colorless oily compound.

¹H-NMR (CDCl₃) δ: 7.28 (1H, d, J=8.3 Hz), 6.59 (1H, dd, J=8.3, 2.9 Hz), 6.37 (1H, d, J=2.4 Hz), 3.54 (2H, s), 3.03 (2H, t, J=5.9 Hz), 2.68 (2H, t, J=6.1 Hz), 2.47-2.40 (2H, m), 2.18-2.07 (3H, m), 2.02-1.92 (1H, m)

PRODUCTION EXAMPLE 31

Production of 3',4'-dihydro-2'H-spiro[cyclopentane-1,1'-isoquinolin]-6'-amine

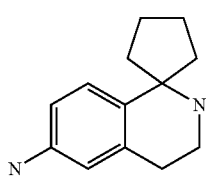 [SMILES: Nc1ccc2c(c1)CCNC21CCCC1]

107 mg of the entitled compound was obtained as a colorless oily compound according to the same method as in Production Example 30, for which, however, cyclopentanone was used in place of cyclobutanone in Production Example 30.

¹H-NMR (CDCl₃) δ: 6.98 (1H, d, J=8.3 Hz), 6.54 (1H, dd, J=8.3, 2.4 Hz), 6.38 (1H, d, J=2.4 Hz), 3.52 (2H, s), 3.05 (2H, t, J=5.9 Hz), 2.67 (2H, t, J=5.9 Hz), 1.89-1.81 (8H, m)

PRODUCTION EXAMPLE 32

Production of 2-acetyl-1,1-dimethyl-1,2,3,4-tetrahydroisoquinolin-6-amine

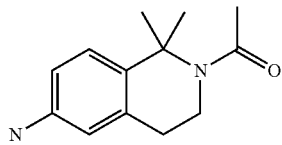 [SMILES: CC(=O)N1CCc2cc(N)ccc2C1(C)C]

0.08 mL of acetic anhydride was added to a pyridine (1 mL) solution of 100 mg of the compound obtained in Production Example 29-4), and stirred at room temperature for 1 hour. The reaction liquid was concentrated, water was added thereto, and extracted with ethyl acetate. The organic layer was washed with aqueous 10% phosphoric acid solution, aqueous saturated sodium hydrogencarbonate solution and saturated saline water, and dried with anhydrous magnesium sulfate, and the solvent was evaporated away. 1 mL of trifluoroacetic acid was added to the crude product, then aqueous saturated sodium hydrogencarbonate solution was added thereto, and extracted with ethyl acetate. This was dried with anhydrous magnesium sulfate, and the solvent was evaporated away to obtain 44.3 mg of the entitled compound as a white solid.

¹H-NMR (CDCl₃) δ: 7.09 (1H, d, J=8.3 Hz), 6.60 (1H, dd, J=8.8, 2.4 Hz), 6.40 (1H, d, J=2.4 Hz), 3.58 (2H, brs), 3.53 (2H, t, J=5.4 Hz), 2.75 (2H, t, J=5.4 Hz), 2.19 (3H, s), 1.78 (6H, s)

PRODUCTION EXAMPLE 33

Production of 1,1,2-trimethyl-1,2,3,4-tetrahydroisoquinolin-7-amine

1) Production of 1,1-dimethyl-1,4-dihydroisoquinolin-3(2H)-one

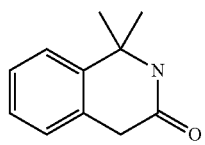

A polyphosphoric acid (200 g) solution of 10 g of phenylacetonitrile was heated at 140° C., and 14.9 g of acetone was dropwise added thereto, taking 1 hour. Further, this was stirred for 1 hour, then cooled, and ice water and diisopropyl ether were added to the reaction liquid. The organic layer was separated, and the aqueous layer was extracted with chloroform. The chloroform layer was washed with aqueous saturated sodium hydrogencarbonate solution, dried with anhydrous magnesium sulfate, and the solvent was evaporated away to obtain 6.22 g of the entitled compound as a brown solid.

2) Production of 1,1-dimethyl-1,2,3,4-tetrahydroisoquinoline hydrochloride

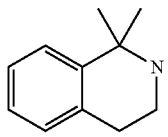

9.06 mL of borane-dimethylsulfide complex was added to a tetrahydrofuran (60 mL) solution of 5.57 g of the compound obtained in the reaction of the above 1), and heated overnight. The reaction liquid was cooled to room temperature, then 30 mL of methanol solution was added to it, and heated under reflux for 30 minutes. The reaction liquid was cooled to room temperature, then 3.13 mL of concentrated hydrochloric acid was added to it, and heated under reflux for 30 minutes. The solvent was evaporated away, then ethanol and diisopropyl ether were added thereto, and the resulting solid was taken out through filtration to obtain 1.56 g of the entitled compound as a white solid.

$^1$H-NMR (DMSO-$d_6$) δ: 7.40-7.37 (1H, m), 7.28-7.16 (3H, m), 3.36 (2H, q, J=6.8 Hz), 3.03 (2H, t, J=6.3 Hz), 1.65 (6H, s)

3) Production of 1,1-dimethyl-7-nitro-1,2,3,4-tetrahydroisoquinoline

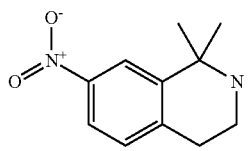

With cooling with ice, 25 mL of concentrated sulfuric acid and fuming nitric acid (d1.52) 1 mL were added to 3.1 g of the compound obtained by the method of the above 2), and stirred for 2 hours with cooling with ice. The reaction liquid was poured into ice water, and made alkaline with aqueous 5 M sodium hydroxide solution added thereto, and then extracted with ethyl acetate. This was washed with saturated saline water, dried with anhydrous magnesium sulfate, and the solvent was evaporated away to obtain 1.3 g of the entitled compound as a brown solid.

$^1$H-NMR (CDCl$_3$) δ: 8.10 (1H, d, J=2.0 Hz), 7.96 (1H, dd, J=8.5, 2.2 Hz), 7.22 (1H, d, J=8.8 Hz), 3.17 (2H, t, J=5.9 Hz), 2.87 (2H, t, J=5.9 Hz), 1.51 (6H, s)

4) Production of 1,1,2-trimethyl-7-nitro-1,2,3,4-tetrahydroisoquinoline

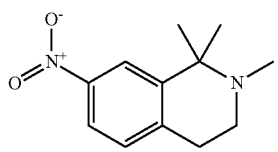 [SMILES: CN1CCc2ccc([N+](=O)[O-])cc2C1(C)C]

90.9 mg of the entitled compound was obtained as a white solid according to the same method as in Production Example 10-6), for which, however, the compound obtained in the above 3) was used in place of 7'-nitro-1',2'-dihydro-3'H-spiro[cyclopropane-1,4'-isoquinoline] used in Production Example 10-6).

$^1$H-NMR (CDCl$_3$) δ: 8.16 (1H, d, J=2.4 Hz), 7.96 (1H, dd, J=8.3, 2.4 Hz), 7.21 (1H, d, J=8.8 Hz), 2.97-2.88 (4H, m), 2.46 (3H, s), 1.45 (6H, s)

5) Production of 1,1,2-trimethyl-1,2,3,4-tetrahydroisoquinolin-7-amine

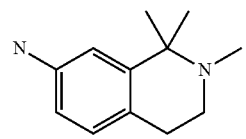

120 mg of palladium hydroxide-carbon was added to 90.9 mg of the compound obtained in the method of the above 4), in 10 mL of ethanol, and in a hydrogen atmosphere, this was stirred overnight. The catalyst was removed through filtration, and the filtrate was concentrated to obtain the entitled compound as a crude product.

$^1$H-NMR (CDCl$_3$) δ: 6.85 (1H, d, J=8.0 Hz), 6.59 (1H, d, J=2.4 Hz), 6.50 (1H, dd, J=8.0, 2.4 Hz), 3.52 (2H, brs), 2.85 (2H, t, J=5.9 Hz), 2.75 (2H, t, J=5.9 Hz), 2.42 (3H, s), 1.38 (6H, s)

PRODUCTION EXAMPLE 34

Production of 2-ethyl-1,2,3,4-tetrahydroisoquinolin-6-amine

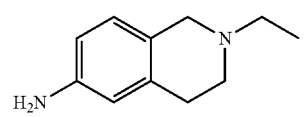

7.65 mL of ethylamine was dropwise added to a chloroform (15 mL) solution of 1.08 g of 2-{2-[(methylsulfonyl)oxyethyl}-4-nitrobenzylmethanesulfonate, which had been produced according to the method described in Journal of Organic Chemistry, Vol. 63, pp. 4116-4119, and stirred for 12 hours. 1 N hydrochloric acid was added to the reaction solution, and stirred, and then the aqueous layer was separated. Aqueous 5 N sodium hydroxide solution was added to the resulting aqueous layer, extracted with chloroform, and the organic layer was dried with anhydrous sodium sulfate, and the solvent was evaporated away. The crude product was purified through silica gel column chromatography (hexane/ethyl acetate) to obtain 210 mg of 2-ethyl-6-nitro-1,2,3,4-tetrahydroisoquinoline as a yellow solid.

In a nitrogen atmosphere, 208 mg of 10% palladium-carbon was added to a solution of 208 mg of the thus-obtained compound in 1 mL of tetrahydrofuran and 1 mL of methanol, and in a hydrogen atmosphere, this was stirred for 12 hours. The reaction system was purged with nitrogen, the catalyst was removed through filtration, the filtrate was concentrated, and the crude product was purified through silica gel column chromatography (hexane/ethyl acetate) to obtain 164 mg of the entitled compound as a yellow solid.
¹H-NMR (400 MHz, CD₃OD) δ: 6.83 (1H, d, J=8.0 Hz), 6.56 (1H, dd, J=8.0, 2.4 Hz), 6.53 (1H, d, J=2.4 Hz), 3.54 (2H, s), 2.85 (2H, m), 2.74 (2H, m), 2.59 (2H, q, J=7.6 Hz), 1.20 (3H, d, J=7.6 Hz)
ESI-MS Found: m/z [M+H]⁺ 177

PRODUCTION EXAMPLE 35

Production of (2S)-1-(6-amino-3,4-dihydroisoquinolin-2(1H)-yl)propan-2-ol

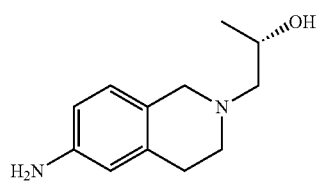

49.7 mg of the entitled compound was obtained as a yellow solid according to the same method as in Production Example 34, for which, however, (2S)-1-aminopropan-2-ol was used in place of ethylamine used in Production Example 34.
¹H-NMR (400 MHz, CD₃OD) δ: 6.82 (1H, d, J=7.6 Hz), 6.56 (1H, d, J=7.6 Hz), 6.53 (1H, d, J=2.4 Hz), 4.07 (1H, m), 3.64 (1H, d, J=14.0 Hz), 3.57 (1H, d, J=14.0 Hz), 3.66-3.55 (5H), 2.45 (1H, m), 1.21 (3H, d, J=6.4 Hz)
ESI-MS Found: m/z [M+H]⁺ 207

PRODUCTION EXAMPLE 36

Production of 2-(2-methoxyethyl)-1,2,3,4-tetrahydroisoquinolin-6-amine 39.1 mg of the entitled compound was obtained as a yellow solid according to the same method as in Production Example 34, for which, however, 2-methoxyethanamine was used in place of ethylamine used in Production Example 34.

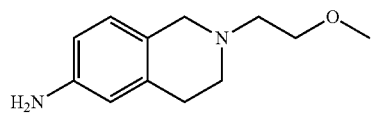

¹H-NMR (400 MHz, CD₃OD) δ: 6.82 (1H, d, J=8.0 Hz), 6.57 (1H, dd, J=8.0, 2.4 Hz), 6.52 (1H, d, J=2.4 Hz), 3.58-3.54 (4H), 3.39 (3H, s), 2.83 (2H, m), 2.72 (2H, m), 2.67 (2H, m)
ESI-MS Found: m/z [M+H]⁺ 207

PRODUCTION EXAMPLE 37

Production of 2-(6-amino-3,4-dihydroisoquinolin-2(1H)-yl)ethanol

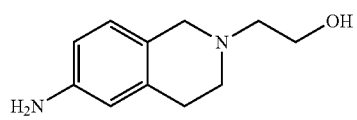 [SMILES: Nc1ccc2c(c1)CCN(CCO)C2]

31.4 mg of the entitled compound was obtained as a yellow solid according to the same method as in Production Example 34, for which, however, 2-aminoethanol was used in place of ethylamine used in Production Example 34.
¹H-NMR (400 MHz, CD₃OD) δ: 6.81 (1H, d, J=8.0 Hz), 6.55 (1H, dd, J=8.0, 2.4 Hz), 6.52 (1H, d, J=2.4 Hz), 3.62-3.58 (4H), 2.83 (2H, m), 2.72 (2H, m), 2.58 (2H, m)
ESI-MS Found: m/z [M+H]⁺ 193

PRODUCTION EXAMPLE 38

Production of (7R*)-7-[(dimethylamino)methyl]-5,6,7,8-tetrahydronaphthalen-2-amine, and (7S*)-7-[(dimethylamino)methyl]-5,6,7,8-tetrahydronaphthalen-2-amine, and (6R*)-6-[(dimethylamino)methyl]-5,6,7,8-tetrahydronaphthalen-2-amine, and (6S*)-6-[(dimethylamino)methyl]-5,6,7,8-tetrahydronaphthalen-2-amine 1) Production of N,N-dimethyl-1,2,3,4-tetrahydronaphthalene-2-carboxamide

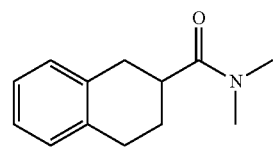

1.94 mL of oxalyl chloride and 0.026 mL of N,N-dimethylformamide were added to a chloroform (20 mL) solution of 3 g of 1,2,3,4-tetrahydronaphthalene-2-carboxylic acid, and stirred at room temperature for 1 hour. The reaction liquid was concentrated, and the residue was dissolved in 20 mL of tetrahydrofuran, and 22.13 mL of 2 M dimethylamine/tetrahydrofuran solution was added thereto. Water was added to the reaction liquid, extracted with ethyl acetate, washed with saturated saline water, dried with anhydrous magnesium sulfate, and the solvent was evaporated away to obtain 3.53 g of the entitled compound as a crude product.
¹H-NMR (CDCl₃) δ: 7.13-7.08 (4H, m), 3.12-3.05 (1H, m), 3.10 (3H, s), 3.00 (3H, s), 2.97-2.79 (4H, m), 2.06-1.86 (2H, m)

2) Production of N,N-dimethyl-1-(1,2,3,4-tetrahydronaphthalen-2-yl)methanamine

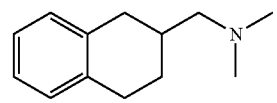

With cooling with ice, a solution of 3.53 g of the compound obtained in the above 1), in 30 ml of tetrahydrofuran was dropwise added to a tetrahydrofuran (30 mL) solution of 1.32 g of lithiumaluminium hydride. The reaction liquid was stirred overnight at 70° C., and then with cooling with ice, 1.5 mL of aqueous 4 M sodium hydroxide solution and 1.5 mL of water were added to it. The insoluble matter was removed through filtration, the filtrate was then concentrated, and the crude product was purified through basic silica gel column chromatography (hexane/ethyl acetate) to obtain 2.97 g of the entitled compound as a colorless oily substance.

¹H-NMR (CDCl₃) δ: 7.12-7.08 (4H, m), 2.94 (1H, ddd, J=16.6, 4.9, 2.0 Hz), 2.83 (2H, dd, J=6.3, 3.9 Hz), 2.43 (1H, dd, J=16.6, 10.2 Hz), 2.28-2.22 (2H, m), 2.25 (6H, s), 2.00-1.89 (2H, m), 1.45-1.35 (1H, m)

3) Production of N,N-dimethyl-1-(7-nitro-1,2,3,4-tetrahydronaphthalen-2-yl)methanamine and N,N-dimethyl-1-(6-nitro-1,2,3,4-tetrahydronaphthalen-2-yl)methanamine

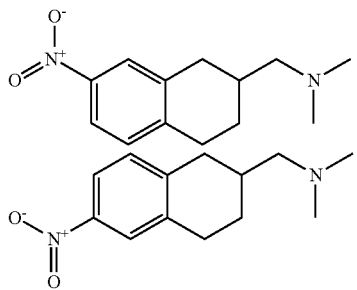

4 mL of nitric acid (specific gravity, 1.41) was added to a trifluoroacetic acid (15 mL) solution of 2.97 g of the compound obtained in the above 2), and stirred overnight at room temperature. The reaction liquid was poured into ice water, then made alkaline with aqueous 5 M sodium hydroxide solution added thereto, and extracted with ethyl acetate. This was washed with saturated saline water, dried with anhydrous sodium sulfate, and the solvent was evaporated away. The crude product was purified through basic silica gel column chromatography (hexane/ethyl acetate) to obtain 2.95 g of a mixture of the entitled compounds.
ESI-MS Found: m/z [M+H]⁺ 235

4) Production of (7R*)-7-[(dimethylamino)methyl]-5,6,7,8-tetrahydronaphthalen-2-amine, (7S*)-7-[(dimethylamino)methyl]-5,6,7,8-tetrahydronaphthalen-2-amine, (6R*)-6-[(dimethylamino)methyl]-5,6,7,8-tetrahydronaphthalen-2-amine, and (6S*)-6-[(dimethylamino)methyl]-5,6,7,8-tetrahydronaphthalen-2-amine

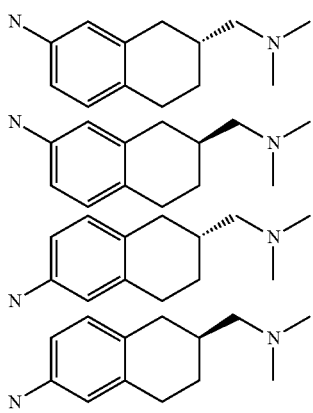

656 mg of a mixture of 6-[(dimethylamino)methyl]-5,6,7,8-tetrahydronaphthalen-2-amine and its position isomer, and 601 mg of 7-[(dimethylamino)methyl]-5,6,7,8-tetrahydronaphthalen-2-amine were obtained according to the same method as in Production Example 33-5), for which, however, the compound obtained in the above 3) was used in place of 1,1,2-trimethyl-7-nitro-1,2,3,4-tetrahydroisoquinoline used in Production Example 33-5).

6-[(Dimethylamino)methyl]-5,6,7,8-tetrahydronaphthalen-2-amine was optically resolved, using CHIRALCEL OD-H (20 mm×250 mm) (hexane/isopropanol/diethylamine=75/25/0.1) to obtain 156 mg of (6R*)-6-[(dimethylamino)methyl]-5,6,7,8-tetrahydronaphthalen-2-amine, and 159 mg of (6S*)-6-[(dimethylamino)methyl]-5,6,7,8-tetrahydronaphthalen-2-amine.

7-[(Dimethylamino)methyl]-5,6,7,8-tetrahydronaphthalen-2-amine was optically resolved, using CHIRALPAK AD-H (20 mm×250 mm) (hexane/isopropanol/diethylamine=85/15/0.1) to obtain 237 mg of (7R*)-7-[(dimethylamino)methyl]-5,6,7,8-tetrahydronaphthalen-2-amine, and 243 mg of (7S*)-7-[(dimethylamino)methyl]-5,6,7,8-tetrahydronaphthalen-2-amine.

(6R*)-6-[(dimethylamino)methyl]-5,6,7,8-tetrahydronaphthalen-2-amine, and (6S*)-6-[(dimethylamino)methyl]-5,6,7,8-tetrahydronaphthalen-2-amine ¹H-NMR (CDCl₃) δ: 6.89 (1H, d, J=7.8 Hz), 6.48 (1H, dd, J=7.8, 2.4 Hz), 6.44 (1H, d, J=2.4 Hz), 3.49 (2H, s), 2.82 (1H, dd, J=16.8, 5.1 Hz), 2.73 (2H, dd, J=8.5, 4.1 Hz), 2.34-2.26 (1H, m), 2.24 (6H, s), 2.23-2.20 (2H, m), 1.95-1.88 (2H, m), 1.41-1.31 (1H, m)

(7R*)-7-[(dimethylamino)methyl]-5,6,7,8-tetrahydronaphthalen-2-amine, and (7S*)-7-[(dimethylamino)methyl]-5,6,7,8-tetrahydronaphthalen-2-amine ¹H-NMR (CDCl₃) δ: 6.88 (1H, d, J=7.8 Hz), 6.48 (1H, dd, J=7.8, 2.4 Hz), 6.45 (1H, s), 3.49 (2H, s), 2.83 (1H, dd, J=17.6, 5.4 Hz), 2.73-2.69 (2H, m), 2.40-2.29 (1H, m), 2.27-2.20 (2H, m), 2.24 (6H, s), 1.95-1.88 (2H, m), 1.41-1.30 (1H, m)

PRODUCTION EXAMPLE 39

Production of (2S*)—N²,N²-dimethyl-1,2,3,4-tetrahydronaphthalene-2,7-diamine, (2R*)—N²,N²-dimethyl-1,2,3,4-tetrahydronaphthalene-2,7-diamine, (2S*)—N²,N²-dimethyl-1,2,3,4-tetrahydronaphthalene-2,6-diamine, and (2R*)—N²,N²-dimethyl-1,2,3,4-tetrahydronaphthalene-2,6-diamine 1) Production of N,N-dimethyl-1,2,3,4-tetrahydronaphthalen-2-amine

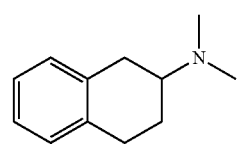

46 ml of a methanol solution of 0.3 M sodium cyanoborohydride-1/2 zinc chloride and 6.9 mL of a tetrahydrofuran solution of 2 M dimethylamine were added to a tetrahydrofuran (10 mL) solution of 2.02 g of β-tetralone, and stirred for a day at room temperature. The reaction liquid was concentrated, and 1 N hydrochloric acid was added thereto. The acidic solution was washed with ethyl acetate, then made alkaline with aqueous 5 M sodium hydroxide solution, and extracted with ethyl acetate. This was washed with saturated saline water, dried with anhydrous magnesium sulfate, and the solvent was evaporated away to obtain 857 mg of the entitled compound as a colorless oily substance.

$^1$H-NMR (CDCl$_3$) δ: 7.12-7.07 (4H, m), 2.98-2.73 (4H, m), 2.60 (1H, tdd, J=10.7, 4.9, 2.9 Hz), 2.37 (6H, s), 2.15-2.08 (1H, m), 1.67-1.57 (1H, m)

2) Production of N,N-dimethyl-6-nitro-1,2,3,4-tetrahydronaphthalen-2-amine, and N,N-dimethyl-7-nitro-1,2,3,4-tetrahydronaphthalen-2-amine

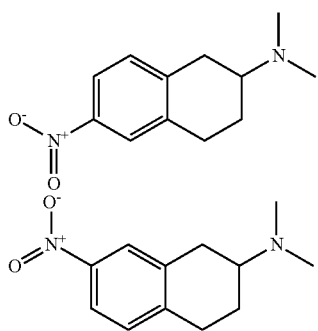

946 mg of the entitled compounds were obtained as a colorless oily mixture thereof according to the same method as in Production Example 38-3), for which, however, N,N-dimethyl-1,2,3,4-tetrahydronaphthalen-2-amine was used in place of N,N-dimethyl-1-(1,2,3,4-tetrahydronaphthalen-2-yl)methanamine used in Production Example 38-3).

ESI-MS Found: m/z [M+H]$^+$ 221

3) Production of (2S*)—N$^2$,N$^2$-dimethyl-1,2,3,4-tetrahydronaphthalene-2,7-diamine, (2R*)—N$^2$,N$^2$-dimethyl-1,2,3,4-tetrahydronaphthalene-2,7-diamine, (2S*)—N$^2$,N$^2$-dimethyl-1,2,3,4-tetrahydronaphthalene-2,6-diamine, and (2R*)—N$^2$,N$^2$-dimethyl-1,2,3, 4-tetrahydronaphthalene-2,6-diamine

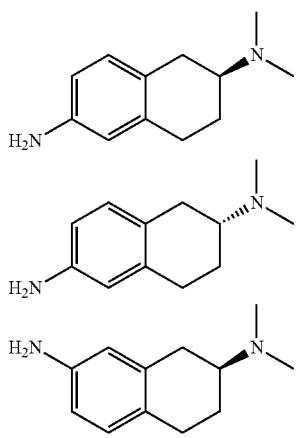

500 mg of palladium hydroxide-carbon (20%) was added to a solution of 946 mg of the compound obtained in the above 2), in 10 mL of ethanol, and stirred in a hydrogen atmosphere for 3 hours. The catalyst was removed through filtration, the filtrate was concentrated, and the crude product was purified through basic silica gel column chromatography (hexane/ethyl acetate) to obtain 119 mg of a racemic mixture of N$^2$,N$^2$-dimethyl-1,2,3,4-tetrahydronaphthalene-2,6-diamine, and 420 mg of a racemic mixture of N$^2$,N$^2$-dimethyl-1,2,3,4-tetrahydronaphthalene-2,7-diamine.

N$^2$,N$^2$-dimethyl-1,2,3,4-tetrahydronaphthalene-2,6-diamine was optically resolved with CHIRALPAK AD-H (20 mm×250 mm) (hexane/isopropanol/diethylamine=80/20/0.1) to obtain 57.4 mg of (2S*)—N$^2$,N$^2$-dimethyl-1,2,3,4-tetrahydronaphthalene-2,6-diamine as a white solid, and 52.9 mg of (2R*)—N$^2$,N$^2$-dimethyl-1,2,3,4-tetrahydronaphthalene-2,6-diamine as a white solid.

N$^2$,N$^2$-dimethyl-1,2,3,4-tetrahydronaphthalene-2,7-diamine was optically resolved with CHIRALPAK AD-H (20 mm×250 mm) (hexane/isopropanol/diethylamine=80/20/0.1) to obtain 144 mg of (2S*)—N$^2$,N$^2$-dimethyl-1,2,3,4-tetrahydronaphthalene-2,7-diamine as a white solid, and 146 mg of (2R*)—N$^2$,N$^2$-dimethyl-1,2,3,4-tetrahydronaphthalene-2,7-diamine as a white solid.

(2S*)—N$^2$,N$^2$-dimethyl-1,2,3,4-tetrahydronaphthalene-2,6-diamine, and (2R*)—N$^2$,N$^2$-dimethyl-1,2,3, 4-tetrahydronaphthalene-2,7-diamine $^1$H-NMR (CDCl$_3$) δ: 6.89 (1H, d, J=8.3 Hz), 6.49 (1H, dd, J=8.0, 2.2 Hz), 6.44 (1H, s), 3.50 (2H, s), 2.86-2.70 (3H, m), 2.64 (1H, dd, J=15.1, 10.7 Hz), 2.55 (1H, tdd, J=10.7, 4.6, 2.6 Hz), 2.35 (6H, s), 2.10-2.03 (1H, m), 1.61-1.52 (1H, m)

(2S*)—N$^2$,N$^2$-dimethyl-1,2,3,4-tetrahydronaphthalene-2,7-diamine, and (2R*)—N$^2$,N$^2$-dimethyl-1,2,3, 4-tetrahydronaphthalene-2,7-diamine $^1$H-NMR (CDCl$_3$) δ: 6.87 (1H, d, J=8.3 Hz), 6.48 (1H, dd, J=7.8, 2.4 Hz), 6.44 (1H, d, J=2.4 Hz), 3.51 (2H, s), 2.85-2.77 (2H, m), 2.74-2.65 (2H, m), 2.57 (1H, tdd, J=10.7, 4.9, 2.9 Hz), 2.35 (6H, s), 2.10-2.04 (1H, m), 1.61-1.51 (1H, m)

PRODUCTION EXAMPLE 40

Production of 2-pyridin-2-yl-1,2,3,4-tetrahydroisoquinolin-6-amine

1) Production of 6-bromo-2-pyridin-2-yl-3,4-dihydroisoquinolin-1(2H)-one

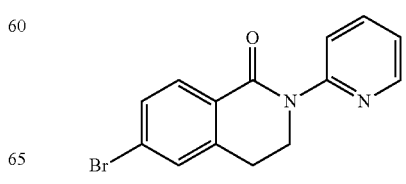

5 mL of 1,4-dioxane was added to 552 mg of 6-bromo-3,4-dihydroisoquinolin-1(2H)-one, 0.521 mL of 2-iodopyridine, 0.077 mL of trans-N,N'-dimethylcyclohexane-1,2-diamine and 622 mg of tripotassium phosphate, and stirred at 100° C. for 2 hours. Ethyl acetate was added to the reaction liquid, washed with aqueous saturated ammonia solution and saturated saline water, and dried with anhydrous magnesium sulfate. The solvent was evaporated away, and the residue was purified through silica gel column chromatography (hexane/ethyl acetate) to obtain 582 mg of a mixture (1/1) of the entitled compound with 6-iodo-2-pyridin-2-yl-3,4-dihydroisoquinolin-1(2H)-one as a white solid.

ESI-MS Found: m/z [M+H]$^+$ 305

2) Production of tert-butyl (1-oxo-2-pyridin-2-yl-1,2,3,4-tetrahydroisoquinolin-6-yl)carbamate

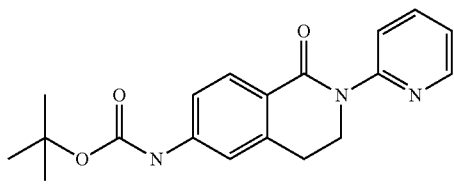 [SMILES: CC(C)(C)OC(=O)Nc1ccc2c(c1)CCN(c1ccccn1)C2=O]

207 mg of XANTPHOS (trade name), 20 mg of palladium acetate, 1.75 g of cesium carbonate, and 251 mg of tert-butyl carbamate were added to a tetrahydrofuran (14 mL) solution of 582 mg of the mixture obtained in the above reaction, and stirred overnight at 70° C. The reaction liquid was filtered, the filtrate was concentrated, and the residue was purified through silica gel column chromatography (hexane/ethyl acetate) to obtain 590 mg of the entitled compound as a white solid.

$^1$H-NMR (CDCl$_3$) δ: 8.43 (1H, dq, J=4.9, 1.0 Hz), 8.09 (1H, d, J=8.3 Hz), 8.00 (1H, d, J=8.3 Hz), 7.71 (1H, ddd, J=8.8, 6.8, 1.5 Hz), 7.57 (1H, s), 7.12-7.06 (2H, m), 6.67 (1H, s), 4.30-4.26 (2H, m), 3.09 (2H, t, J=6.3 Hz), 1.54 (9H, s)

3) Production of 6-amino-2-pyridin-2-yl-3,4-dihydroisoquinolin-1(2H)-one

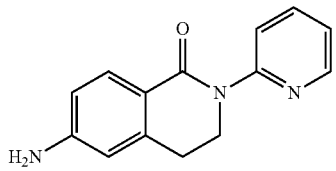 [SMILES: Nc1ccc2c(c1)CCN(c1ccccn1)C2=O]

3 mL of trifluoroacetic acid was added to 686 mg of the compound obtained in the above reaction, and stirred for 30 minutes. The reaction liquid was diluted with tetrahydrofuran, and neutralized with aqueous saturated sodium hydrogencarbonate solution. This was extracted with ethyl acetate, washed with saturated saline water, dried with anhydrous magnesium sulfate, and the solvent was evaporated away. The residue was purified through basic silica gel column chromatography (hexane/ethyl acetate) to obtain 422 mg of the entitled compound as a white solid.

$^1$H-NMR (CDCl$_3$) δ: 8.42 (1H, ddd, J=4.9, 2.0, 1.0 Hz), 8.00 (1H, dd, J=2.0, 1.0 Hz), 7.98 (1H, dd, J=2.0, 1.0 Hz), 7.69 (1H, ddd, J=8.8, 6.8, 1.5 Hz), 7.05 (1H, ddd, J=7.3, 4.9, 1.0 Hz), 6.62 (1H, dd, J=8.5, 2.2 Hz), 6.46 (1H, t, J=1.2 Hz), 4.25 (2H, t, J=6.3 Hz), 4.05 (2H, s), 3.00 (2H, t, J=6.3 Hz)

4) Production of 2-pyridin-2-yl-1,2,3,4-tetrahydroisoquinolin-6-amine

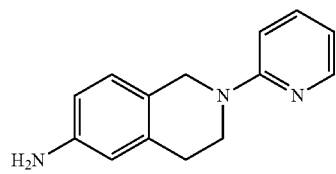 [SMILES: Nc1ccc2c(c1)CCN(c1ccccn1)C2]

With cooling with ice, a tetrahydrofuran (1 mL) solution of 70 mg of the compound obtained in the above reaction was added to a tetrahydrofuran (3 mL) solution of 33.3 mg of lithiumaluminium hydride. The reaction liquid was stirred at 70° C. for 1 hour, then with cooling with ice, 0.05 mL of aqueous 4 M sodium hydroxide solution and 0.05 mL of water were added to it. The insoluble matter was removed through filtration, the filtrate was concentrated, and the crude product was purified through basic silica gel column chromatography (hexane/ethyl acetate) to obtain 52.2 mg of the entitled compound as a colorless oily substance.

$^1$H-NMR (CDCl$_3$) δ: 8.21 (1H, dd, J=4.9, 1.8 Hz), 7.50-7.46 (1H, m), 6.99 (1H, d, J=8.2 Hz), 6.64 (1H, d, J=8.6 Hz), 6.59-6.54 (2H, m), 6.52 (1H, s), 4.58 (2H, s), 3.81 (2H, t, J=5.9 Hz), 3.59 (2H, s), 2.87 (2H, t, J=5.9 Hz)

PRODUCTION EXAMPLE 41

Production of 2-ethyl-1,1-dimethyl-1,2,3,4-tetrahydroisoquinolin-6-amine

1) Production of tert-butyl (2-ethyl-1,1-dimethyl-1,2,3,4-tetrahydroisoquinolin-6-yl)carbamate

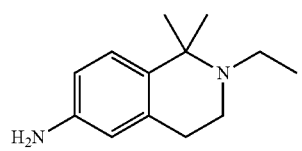

104 mg of the entitled compound was obtained as a white solid according to the same method as in Production Example 10-6), for which, however, the compound obtained in Production Example 29-4) was used in place of 7-nitro-1',2'-dihydro-3'H-spiro[cyclopropane-1,4'-isoquinoline] used in Production Example 10-6) and acetaldehyde was used in place of aqueous 37% formaldehyde solution.

2) Production of 2-ethyl-1,1-dimethyl-1,2,3,4-tetrahydroisoquinolin-6-amine 66 mg of the entitled compound was obtained as a white solid according to the same method as in Production Example 29-6), for which, however, the compound obtained in the above 1) was used in place of tert-butyl[2-(2-{[tert-butyl(dimethyl)silyl]oxy}ethyl)-1,1-dimethyl-1,2,3,4-tetrahydroisoquinolin-6-yl)carbamate used in Production Example 29-6).

$^1$H-NMR (CDCl$_3$) δ: 7.02 (1H, d, J=8.3 Hz), 6.52 (1H, dd, J=8.3, 2.7 Hz), 6.37 (1H, d, J=2.7 Hz), 3.84 (6H, s), 3.50 (2H, brs), 2.82 (2H, t, J=5.6 Hz), 2.74 (2H, t, J=5.6 Hz), 2.55 (2H, q, J=7.0 Hz), 1.13 (3H, t, J=7.0 Hz)

ESI-MS Found: m/z [M+H]$^+$ 205

PRODUCTION EXAMPLE 42

Production of 1-(6-amino-1,1-dimethyl-3,4-dihydroisoquinolin-2(1H)-yl)-2-methylpropan-2-ol 1) Production of tert-butyl[2-(2-hydroxy-2-methylpropyl)-1,1-dimethyl-1,2,3,4-tetrahydroisoquinolin-6-yl]carbamate

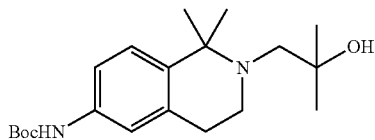 [SMILES: CC(C)(O)CN1CCc2cc(NC(=O)OC(C)(C)C)ccc2C1(C)C]

Isobutylene oxide (117 mg) was added to an ethanol (4 mL) solution of 100 mg of the compound obtained in Production Example 29-4), and overnight heated under reflux. The solvent was evaporated away, and the residue was purified through silica gel column chromatography (hexane/ethyl acetate) to obtain 41 mg of the entitled compound as a white amorphous substance.

$^1$H-NMR (CDCl$_3$) δ: 7.17-7.10 (2H, m), 7.09-7.02 (1H, m), 6.40 (1H, s), 2.95 (2H, t, J=5.6 Hz), 2.81 (2H, t, J=5.6 Hz), 2.51 (2H, s), 1.51 (9H, s), 1.35 (6H, s), 1.22 (6H, s)

2) Production of 1-(6-amino-1,1-dimethyl-3,4-dihydroisoquinolin-2(1H)-yl)-2-methylpropan-2-ol

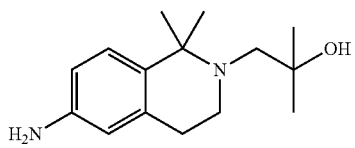

30 mg of the entitled compound was obtained as a white amorphous substance according to the same method as in Production Example 29-6), for which, however, the compound obtained in the above 1) was used in place of tert-butyl[2-(2-{[tert-butyl(dimethyl)silyl]oxy}ethyl)-1,1-dimethyl-1,2,3,4-tetrahydroisoquinolin-6-yl)carbamate used in Production Example 29-6).

ESI-MS Found: m/z [M+H]$^+$ 249

PRODUCTION EXAMPLE 43

Production of 2-cyclopropyl-1,1-dimethyl-1,2,3,4-tetrahydroisoquinolin-6-amine

1) Production of tert-butyl (2-cyclopropyl-1,1-dimethyl-1,2,3,4-tetrahydroisoquinolin-6-yl)carbamate

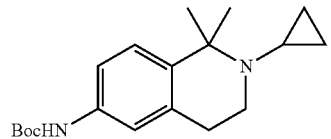 [SMILES: CC(C)(C)OC(=O)Nc1ccc2c(c1)CCN(C1CC1)C2(C)C]

387 mg of the entitled compound was obtained as a colorless oil according to the same method as in Production Example 12-1), for which, however, the compound obtained in Production Example 29-4) was used in place of 7-nitro-2,3,4,5-tetrahydro-1H-3-benzazepine monohydrochloride used in Production Example 12-1).

2) Production of 1-(6-amino-1,1-dimethyl-3,4-dihydroisoquinolin-2(1H)-yl)-2-methylpropan-2-ol

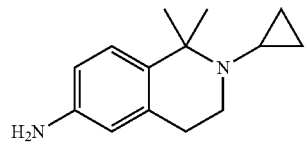

260 mg of the entitled compound was obtained as a white solid according to the same method as in Production Example 29-6), for which, however, the compound obtained in the above 1) was used in place of tert-butyl[2-(2-{[tert-butyl(dimethyl)silyl]oxy}ethyl)-1,1-dimethyl-1,2,3,4-tetrahydroisoquinolin-6-yl)carbamate used in Production Example 29-6.

$^1$H-NMR (CDCl$_3$) δ: 7.06 (1H, d, J=8.6 Hz), 6.52 (1H, dd, J=8.6, 2.3 Hz), 6.39 (1H, d, J=2.3 Hz), 3.51 (2H, brs), 3.07 (2H, t, J=6.1 Hz), 2.73 (2H, t, J=6.1 Hz), 1.97-1.92 (1H, m), 1.47 (6H, s), 0.61-0.48 (4H, m)

ESI-MS Found: m/z [M+H]$^+$ 217

PRODUCTION EXAMPLE 44

Production of 2-[(dimethylamino)acetyl]-1,1-dimethyl-1,2,3,4-tetrahydroisoquinolin-6-amine 1) Production of 1,1-dimethyl-6-nitro-1,4-dihydroisoquinolin-3(2H)-one

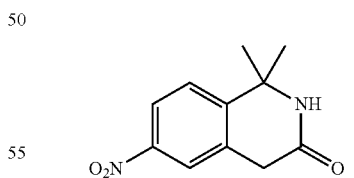

With cooling with ice, 692 mg of potassium nitrate was added to 4 mL of sulfuric acid, and 1 g of 1,1-dimethyl-1,4-dihydroisoquinolin-3(2H)-one obtained in Production Example 33-1 was added thereto, and stirred overnight at room temperature. The reaction solution was processed with ice water, and the precipitated solid was taken out through filtration. This was washed with water, and dried at 50° C. under reduced pressure to obtain 937 mg of a mixture of the entitled compound with its position isomer, as a pale yellow solid.

2) Production of tert-butyl 1,1-dimethyl-6-nitro-3,4-dihydroisoquinolin-2(1H)-carboxylic acid

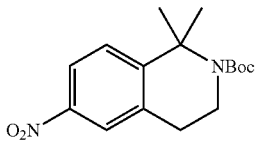 [SMILES: CC(C)(C)OC(=O)N1CCc2cc([N+](=O)[O-])ccc2C1(C)C]

8.17 mL of 1.0 M borane/tetrahydrofuran solution was added to a tetrahydrofuran (30 mL) suspension of 600 mg of the compound obtained in the above 1), and stirred at 70° C. for 1 hour. Aqueous 5 N hydrochloric acid solution was slowly dropwise added to it, and further stirred at 70° C. for 30 minutes. The solvent was evaporated away, and the residue was diluted with ethyl acetate, neutralized with saturated sodium hydrogencarbonate, and extracted with ethyl acetate. The organic layer was washed with saturated saline water, and dried with anhydrous sodium sulfate. The solvent was evaporated away, and the residue was purified through silica gel column chromatography (chloroform/ethanol) to obtain 321 mg of a mixture of 1,1-dimethyl-6-nitro-1,2,3,4-tetrahydroisoquinoline and 1,1-dimethyl-7-nitro-1,2,3,4-tetrahydroisoquinoline as a brown solid. 0.2 mL of triethylamine and 371 mg of tert-butyl dicarbonate were added to a chloroform (1 mL) solution of 270 mg of the mixture, and then overnight heated under reflux. The solvent was evaporated away, and the residue was purified through silica gel column chromatography (hexane/ethyl acetate) to obtain 51 mg of tert-butyl 1,1-dimethyl-6-nitro-3,4-dihydroisoquinolin-2(1H)-carboxylate as a colorless amorphous substance.

3) Production of 1,1-dimethyl-6-nitro-1,2,3,4-tetrahydroisoquinoline

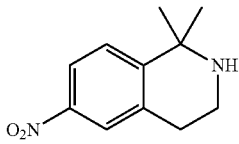

1 mL of trifluoroacetic acid was added to a chloroform (1 mL) solution of 50 mg of the compound obtained in the above 2), and stirred at room temperature for 2 hours. The solvent was evaporated away, and the residue was diluted with ethyl acetate, and neutralized with aqueous saturated sodium hydrogencarbonate solution. The organic layer was washed with saturated saline water, dried with anhydrous sodium sulfate, and the solvent was evaporated away to obtain 30 mg of the entitled compound as a yellow-white amorphous substance.

4) Production of 2-(1,1-dimethyl-6-nitro-3,4-dihydroisoquinolin)-2(1H)-yl)-N,N-dimethyl-2-oxoethanamine

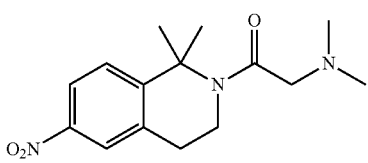 [SMILES: CN(C)CC(=O)N1CCc2cc([N+](=O)[O-])ccc2C1(C)C]

The compound obtained in the above 3) was added to a chloroform (2 mL) solution of 0.024 mL of chloroacetyl chloride, then 0.082 mL of triethylamine was added thereto, and stirred overnight at room temperature. The reaction solution was neutralized with aqueous 1 N hydrochloric acid solution, and diluted with water. The organic layer was washed with water and saturated saline water, then dried with anhydrous sodium sulfate. The solvent was evaporated away to obtain 41 mg of 2-(chloroacetyl)-1,1-dimethyl-6-nitro-1,2,3,4-tetrahydroisoquinoline as a yellow oil. 0.22 mL of 2.0 M dimethylamine/tetrahydrofuran solution was added to an acetonitrile (2 mL) solution of 41 mg of the compound, and stirred at 60° C. for 20 minutes. The solvent was evaporated away, and the residue was dissolved in ethyl acetate, and washed with water and saturated saline water. The organic layer was dried with anhydrous sodium sulfate, then the solvent was evaporated away, and the residue was purified through preparative thin-layer chromatography (chloroform/methanol) to obtain 20 mg of the entitled compound as a white solid.

$^1$H-NMR (CDCl$_3$) δ: 8.08 (1H, dd, J=8.8, 2.4 Hz), 7.98 (1H, d, J=2.4 Hz), 7.47 (1H, d, J=8.8 Hz), 3.72 (2H, t, J=5.4 Hz), 3.18 (2H, s), 2.96 (2H, t, J=5.4 Hz), 2.30 (6H, s), 1.86 (6H, d, J=7.8 Hz)

5) Production of 2-[dimethylamino)acetyl]-1,1-dimethyl-1,2,3,4-tetrahydroisoquinolin-6-amine

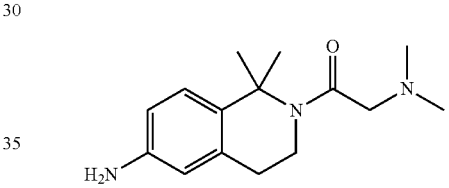

In a nitrogen atmosphere, 20 mg of 10% palladium-carbon was added to a methanol (3 mL) solution of 20 mg of the compound obtained in the above 4), then purged with hydrogen, and stirred at room temperature for 2 hours. After purged with nitrogen, this was filtered through Celite to remove the insoluble matter, and the solvent was evaporated away from the filtrate to obtain 16 mg of the entitled compound as an amorphous substance.

ESI-MS Found: m/z [M+H]$^+$ 262

PRODUCTION EXAMPLE 45

Production of N',N'-dimethyl-1,2,3,4-tetrahydronaphthalene-1,7-diamine

1) Production of N,N-dimethyl-7-nitro-1,2,3,4-tetrahydronaphthalen-1-amine

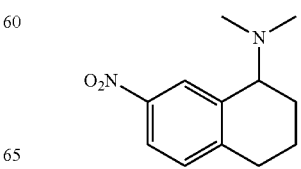

With cooling with ice, 0.16 mL of methanesulfonyl chloride and 0.29 mL of triethylamine were added to a tetrahydrofuran (5 mL) solution of 200 mg of 7-nitro-1,2,3,4-tetrahydronaphthalen-1-ol obtained according to the method described in WO2004/087124, and stirred for 1 hour. The insoluble matter was removed through filtration through Celite, the solvent was evaporated away from the filtrate, the residue was dissolved in 3 mL of N,N-dimethylformamide, then 1.55 mL of 2 M dimethylamine/tetrahydrofuran solution was added to it, and stirred overnight at 60° C. After left cooled, water was added to the reaction solution, and then diluted with ethyl acetate. The organic layer was washed with water and saturated saline water, and dried with anhydrous sodium sulfate. The solvent was evaporated away, and the residue was purified through silica gel column chromatography (hexane/ethyl acetate) to obtain 100 mg of the entitled compound as a yellow oil.

2) Production of N',N'-dimethyl-1,2,3,4-tetrahydronaphthalene-1,7-diamine

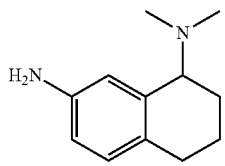 [SMILES: CN(C)C1CCCc2ccc([N+](=O)[O-])cc21]

24 mg of ammonium chloride and 500 mg of iron were added to a methanol (3 mL) solution of 100 mg of the compound obtained in the above 1), and stirred at 70° C. for 2 hours. The insoluble matter was removed through hot filtration, and the solvent was evaporated away from the filtrate. The residue was neutralized with aqueous saturated sodium hydrogencarbonate solution, and extracted with chloroform. The organic layer was washed with saturated saline water, dried with anhydrous sodium sulfate, and the solvent was evaporated away to obtain 80 mg of the entitled compound as a colorless oil.

$^1$H-NMR (CDCl$_3$) δ: 6.96 (1H, d, J=2.3 Hz), 6.82 (1H, d, J=7.8 Hz), 6.48 (1H, dd, J=7.8, 2.3 Hz), 3.74-3.67 (1H, m), 3.49 (2H, brs), 2.64-2.54 (2H, m), 2.24 (6H, s), 1.95-1.83 (2H, m), 1.63-1.56 (2H, m)

ESI-MS Found: m/z [M+H]$^+$ 191

PRODUCTION EXAMPLE 46

Production of 2-(2-methoxyethyl)-1,1-dimethyl-1,2,3,4-tetrahydroisoquinolin-6-amine 1) Production of tert-butyl[2-(2-methoxyethyl)-1,1-dimethyl-1,2,3,4-tetrahydroisoquinolin-6-yl]carbamate

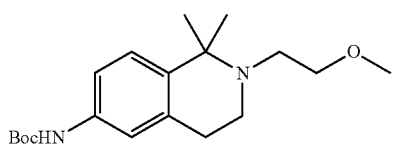 [SMILES: COCCN1CCc2cc(NC(=O)OC(C)(C)C)ccc2C1(C)C]

The entitled compound was obtained according to the same method as in Production Example 13-1), for which, however, tert-butyl (1,1-dimethyl-1,2,3,4-tetrahydroisoquinolin-6-yl)carbamate obtained in Production Example 29-4) was used in place of 7-nitro-2,3,4,5-tetrahydro-1H-3-benzazepine monohydrochloride used in Production Example 13-1).

2) Production of 2-(2-methoxyethyl)-1,1-dimethyl-1,2,3,4-tetrahydroisoquinolin-6-amine

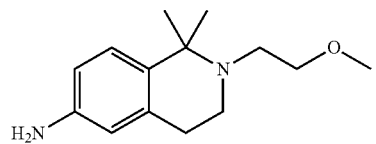 [SMILES: COCCN1CCc2cc(N)ccc2C1(C)C]

The entitled compound was obtained as a pale yellow solid according to the same method as in Production Example 29-6), for which, however, the compound obtained in the above reaction 1) was used in place of tert-butyl[2-(2-{[tert-butyl(dimethyl)silyl]oxy}ethyl)-1,1-dimethyl-1,2,3,4-tetrahydroisoquinolin-6-yl)carbamate used in Production Example 29-6).

ESI-MS Found: m/z [M+H]$^+$ 235

PRODUCTION EXAMPLE 47

Production of 2,3,4,5-tetrahydro-1H-2-benzazepin-7-amine

1) Production of 7-amino-2,3,4,5-tetrahydro-1H-2-benzazepin-1-one

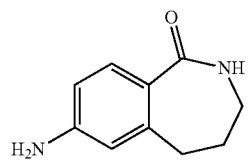

With cooling with ice, 890 mg of sodium azide was added to a concentrated hydrochloric acid (30 mL) solution of 2 g of 6-amino-1,2,3,4-tetrahydronaphthalen-1-one, and stirred at 40° C. for 15 hours. The reaction liquid was poured into ice water, and neutralized with potassium carbonate. This was extracted with chloroform, and the organic layer was washed with saturated saline water, and dried with anhydrous magnesium sulfate. The solvent was evaporated away under reduced pressure, and the crude product was purified through basic silica gel column chromatography (chloroform/methanol) to obtain 1.1 g of the entitled compound as a colorless solid.

$^1$H-NMR (CDCl$_3$) δ: 7.55 (1H, d, J=8.3 Hz), 6.60 (1H, dd, J=8.0, 2.2 Hz), 6.46 (1H, d, J=2.4 Hz), 5.98 (1H, s), 3.89 (2H, s), 3.49 (2H, d, J=5.9 Hz), 3.13 (2H, q, J=6.3 Hz), 2.77 (2H, t, J=7.1 Hz), 2.01-1.94 (2H, m)

ESI-MS Found: m/z [M+H]$^+$ 177

2) Production of
2,3,4,5-tetrahydro-1H-2-benzazepin-7-amine

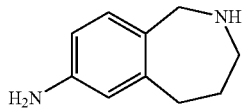

250 mg of the entitled compound was obtained as a colorless solid according to the same method as in Production Example 21-2), for which, however, the compound obtained in the above 1) was used in place of 2,3,4,5-tetrahydro-1H-2-benzazepin-1-one used in Production Example 21-2).

$^1$H-NMR (CDCl$_3$) δ: 6.90 (1H, d, J=7.8 Hz), 6.52 (1H, d, J=2.0 Hz), 6.42 (1H, dd, J=7.8, 2.0 Hz), 3.83 (2H, s), 3.57 (2H, s), 3.17 (2H, t, J=5.6 Hz), 2.84 (2H, t, J=5.6 Hz), 1.73-1.66 (2H, m)

ESI-MS Found: m/z [M+H]$^+$ 163

PRODUCTION EXAMPLE 48

Production of
5-amino-1,1,2,3,3-pentamethylisoindoline

1) Production of 1,1,2,3,3-pentamethylisoindoline

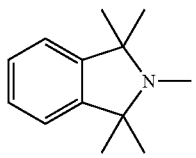

With cooling with ice, 1.40 g of zirconium chloride was added to 6.0 mL of a THF solution of 483 mg of N-methylphthalimide, and stirred for 30 minutes with cooling with ice. 18.7 mL of 0.96 M methylmagnesium chloride/THF solution was added to it, and stirred at room temperature for 18 hours. With cooling with ice, 20 mL of aqueous 5 M sodium hydroxide solution was added to the reaction liquid, and extracted with chloroform. The organic layer was dried with anhydrous sodium sulfate, and the solvent was evaporated away under reduced pressure. The crude product was purified through NH silica gel column chromatography (hexane/ethyl acetate) to obtain 105 mg of the entitled compound as a yellow solid.

$^1$H-NMR (400 MHz, CDCl$_3$) δ: 7.25-7.20 (2H, m), 7.17-7.13 (2H, m), 2.42 (3H, s), 1.33 (12H, s)

ESI-MS Found: m/z [M+H]$^+$ 190

2) Production of
5-nitro-1,1,2,3,3-pentamethylisoindoline

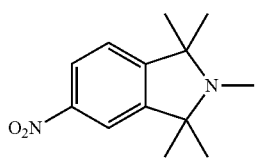 [SMILES: CN1C(C)(C)c2ccc([N+](=O)[O-])cc2C1(C)C]

63 mg of the entitled compound was obtained as a yellow solid according to the same method as in Production Example 19-2), for which, however, the compound obtained in the above 1) was used in place of 2'H-spiro[cyclopropane-1,1'-isoquinolin]-3'(4'H)-one used in Production Example 19-2).

$^1$H-NMR (400 MHz, CDCl$_3$) δ: 8.13 (1H, dd, J=8.3, 2.1 Hz), 8.00 (1H, d, J=2.1 Hz), 7.27 (1H, d, J=8.3 Hz), 2.42 (3H, s), 1.37 (6H, s), 1.36 (6H, s)

3) Production of
5-amino-1,1,2,3,3-pentamethylisoindoline

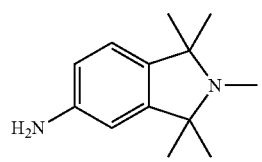

55 mg of the entitled compound was obtained as a pale yellow solid according to the same method as in Production Example 10-7), for which, however, the compound obtained in the above 2) was used in place of 2'-methyl-7'-nitro-2',3'-dihydro-1'H-spiro[cyclopropane-1,4'-isoquinoline] used in Production Example 10-7).

$^1$H-NMR (400 MHz, CDCl$_3$) δ: 6.93 (1H, d, J=8.0 Hz), 6.60 (1H, dd, J=8.0, 2.2 Hz), 6.47 (1H, d, J=2.2 Hz), 3.65 (2H, br. s), 2.45 (3H, br. s), 1.35 (12H, br. s)

ESI-MS Found: m/z [M+H]$^+$ 205

PRODUCTION EXAMPLE 49

Production of 5-amino-1,1,2-trimethylisoindoline

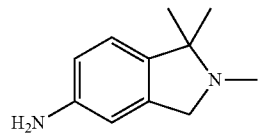

1) Production of
5-methoxy-2,3,3-trimethylisoindolin-1-one

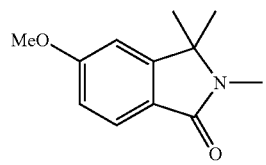

With cooling with ice, 96 mg of 60% sodium hydride was added to 8.0 mL of a DMF solution of 382 mg of 5-methoxy-3,3-dimethylisoindolin-1-one, and stirred for 30 minutes with cooling with ice. 0.19 mL of methyl iodide was added to it, and stirred at room temperature for 7 hours. The solvent was evaporated away under reduced pressure, water was added to the residue and extracted with ethyl acetate. The organic layer was washed with water and aqueous saturated sodium chloride solution, dried with anhydrous sodium sulfate, and the solvent was evaporated away under reduced pressure. The crude product was purified through silica gel column chromatography (hexane/ethyl acetate) to obtain 381 mg of the entitled compound as a colorless solid.

¹H-NMR (400 MHz, CDCl₃) δ: 7.74 (1H, d, J=8.3 Hz), 6.95 (1H, dd, J=8.3, 2.2 Hz), 6.88 (1H, d, J=2.2 Hz), 3.88 (3H, s), 3.01 (3H, s), 1.44 (6H, s)

2) Production of 5-hydroxy-2,3,3-trimethylisoindolin-1-one

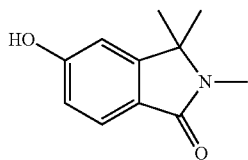

With cooling with ice, 3.66 mL of 1.0 M boron tribromide/dichloromethane solution was added to 5.5 mL of a chloroform solution of 376 mg of the compound obtained in the above 1), and stirred for 8 hours with cooling with ice. 10 mL of water was added to the reaction liquid, and extracted with ethyl acetate. The organic layer was dried with anhydrous sodium sulfate, and the solvent was evaporated away under reduced pressure. The crude product was purified through silica gel column chromatography (chloroform/methanol) to obtain 339 mg of the entitled compound as a colorless solid.

¹H-NMR (400 MHz, CDCl₃) δ: 7.90 (1H, s), 7.64 (1H, d, J=9.0 Hz), 6.93-6.90 (2H, m), 3.02 (3H, s), 1.43 (6H, s)

3) Production of 2,3,3-trimethylisoindolin-1-one

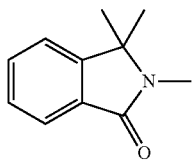

179 mg of potassium carbonate was added to 4.3 mL of a DMF solution of 185 mg of the compound obtained in the above 2) and 187 mg of 5-chloro-1-phenyl-1H-tetrazole, and stirred at room temperature for 13 hours. The solvent was evaporated away under reduced pressure, water was added to the residue, and extracted with ethyl acetate. The organic layer was washed with water and aqueous saturated sodium chloride solution, dried with anhydrous sodium sulfate, and the solvent was evaporated away under reduced pressure. The crude product was purified through silica gel column chromatography (hexane/ethyl acetate), and the resulting colorless oil was dissolved in 9.0 mL of ethanol, then 200 mg of 10% palladium-carbon was added to it, and in a 50-psi hydrogen atmosphere, this was shaken at room temperature for 3 days. The reaction liquid was filtered, the catalyst was washed with methanol, and the filtrate was evaporated under reduced pressure. The residue was purified through silica gel column chromatography (chloroform) to obtain 134 mg of the entitled compound as a colorless oil.

¹H-NMR (400 MHz, CDCl₃) δ: 7.83 (1H, dt, J=7.4, 1.0 Hz), 7.54 (1H, dt, J=1.0, 7.4 Hz), 7.43 (1H, dt, J=1.0, 7.4 Hz), 7.42 (1H, dt, J=7.4, 1.0 Hz), 3.04 (3H, s), 1.46 (6H, s)

4) Production of 2,3,3-trimethyl-6-nitroisoindolin-1-one

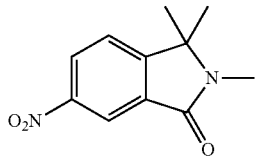 [SMILES: CN1C(=O)c2cc([N+](=O)[O-])ccc2C1(C)C]

158 mg of the entitled compound was obtained as a yellow solid according to the same method as in Production Example 19-2), for which, however, the compound obtained the above 3) was used in place of 2'H-spiro[cyclopropane-1,1'-isoquinolin]-3'(4'H)-one used in Production Example 19-2).

¹H-NMR (400 MHz, CDCl₃) δ: 8.67 (1H, dd, J=2.2, 0.5 Hz), 8.44 (1H, dd, J=8.3, 2.2 Hz), 7.59 (1H, dd, J=8.3, 0.5 Hz), 3.07 (3H, s), 1.52 (6H, s)

5) Production of 1,1,2-trimethyl-5-nitroisoindoline

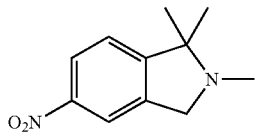

2.40 mL of 1.17 M borane/THF solution was added to 3.5 mL of a THF solution of 155 mg of the compound obtained in the above 4), and heated under reflux for 40 hours. With cooling with ice, 4 mL of 1 M hydrochloric acid was added to the reaction liquid, and then heated under reflux for 1 hour. The reaction liquid was made basic with aqueous 5 M sodium hydroxide solution added thereto, and then extracted with chloroform. The organic layer was washed with aqueous saturated sodium chloride solution, dried with anhydrous sodium sulfate, and the solvent was evaporated away under reduced pressure. The crude product was purified through silica gel column chromatography (hexane/ethyl acetate) to obtain 63 mg of the entitled compound as a yellow solid. This was extracted with ethyl acetate. The organic layer was dried with anhydrous sodium sulfate, and the solvent was evaporated away under reduced pressure. The crude product was purified through silica gel column chromatography (chloroform/methanol) to obtain 120 mg of the entitled compound as a pale yellow oil.

¹H-NMR (400 MHz, CDCl₃) δ: 8.13 (1H, dd, J=8.2, 2.2 Hz), 8.07-8.06 (1H, m), 7.25 (1H, d, J=8.2 Hz), 3.98 (2H, s), 2.48 (3H, s), 1.29 (6H, s)

6) Production of 5-amino-1,1,2-trimethylisoindoline

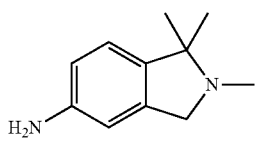

24 mg of 10% palladium-carbon was added to 3.0 mL of a methanol solution of 120 mg of the compound obtained in the above 5), and in a hydrogen atmosphere, this was stirred at room temperature for 1 hour. The reaction liquid was filtered, the catalyst was washed with methanol, and the filtrate was evaporated under reduced pressure to obtain 100 mg of the entitled compound as a yellow oil.

$^1$H-NMR (400 MHz, CDCl$_3$) δ: 6.92-6.88 (1H, m), 6.58-6.53 (2H, m), 3.86 (2H, s), 3.58 (2H, br. s), 2.46 (3H, s), 1.23 (6H, s)

ESI-MS Found: m/z [M+H]$^+$ 177

PRODUCTION EXAMPLE 50

Production of 5-amino-2,3,3-trimethylisoindoline

1) Production of 5-(trifluoromethanesulfonyl)oxy-2,3,3-trimethylisoindolin-1-one

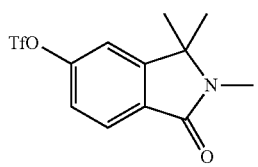 [SMILES: CN1C(=O)c2ccc(OS(=O)(=O)C(F)(F)F)cc2C1(C)C]

With cooling with ice, 0.192 mL of triethylamine and 0.174 mL of trifluoromethanesulfonic acid anhydride were added to 4.3 mL of a chloroform solution of 165 mg of 5-hydroxy-2,3,3-trimethylisoindolin-1-one obtained in Production Example 49-2, and stirred for 1 hour with cooling with ice. 2 mL of aqueous saturated sodium hydrogencarbonate solution was added to the reaction liquid, and extracted with chloroform. The organic layer was dried with anhydrous sodium sulfate, and the solvent was evaporated away under reduced pressure. The crude product was purified through silica gel column chromatography (chloroform) to obtain 257 mg of the entitled compound as a colorless solid.

$^1$H-NMR (400 MHz, CDCl$_3$) δ: 7.91 (1H, dd, J=7.9, 0.9 Hz), 7.37-7.32 (2H, m), 3.05 (3H, s), 1.49 (6H, s)

2) Production of 5-(tert-butoxycarbonyl)amino-2,3,3-trimethylisoindolin-1-one

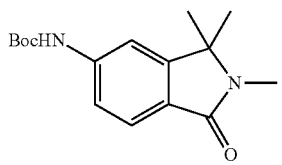 [SMILES: CN1C(=O)c2ccc(NC(=O)OC(C)(C)C)cc2C1(C)C]

A mixture of 255 mg of the compound obtained in the above 1), 111 mg of tert-butyl carbamate, 9 mg of palladium acetate, 91 mg of XANTPHOS (trade name), 514 mg of cesium carbonate and 8.0 mL of THF was stirred at 70° C. for 13 hours. The reaction liquid was diluted with 30 mL of ethyl acetate, the mixture was filtered. The filtrate was washed with water and aqueous saturated sodium chloride solution, dried with anhydrous sodium sulfate, and the solvent was evaporated away under reduced pressure. The crude product was purified through silica gel column chromatography (chloroform/methanol) to obtain 110 mg of the entitled compound as a pale orange solid.

$^1$H-NMR (400 MHz, CDCl$_3$) δ: 7.83 (1H, br. s), 7.71 (1H, d, J=8.3 Hz), 7.06 (1H, dd, J=8.3, 1.8 Hz), 6.72 (1H, br. s), 3.01 (3H, s), 1.45 (6H, s)

3) Production of 5-amino-2,3,3-trimethylisoindolin-1-one

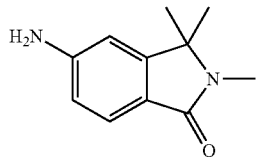

A mixture of 110 mg of the compound obtained in the above 2) and 0.50 mL of trifluoroacetic acid was stirred at room temperature for 30 minutes. The solvent was evaporated away under reduced pressure, aqueous saturated sodium hydrogencarbonate solution was added to the residue, and extracted with chloroform. The organic layer was dried with anhydrous sodium sulfate, and the solvent was evaporated away under reduced pressure. The crude product was purified through basic silica gel column chromatography (chloroform) to obtain 89 mg of the entitled compound as a pale yellow solid.

$^1$H-NMR (400 MHz, CDCl$_3$) δ: 7.60 (1H, d, J=8.2 Hz), 6.67 (1H, dd, J=8.2, 2.1 Hz), 6.63 (1H, d, J=2.1 Hz), 4.00 (2H, br. s), 2.98 (3H, s), 1.41 (6H, s)

ESI-MS Found: m/z [M+H]$^+$ 191

4) Production of 5-amino-2,3,3-trimethylisoindoline

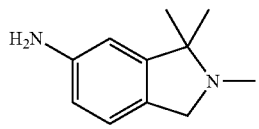

29 mg of lithiumaluminium hydride was added to 3.8 mL of a THF solution of 89 mg of 5-amino-2,3,3,-trimethylisoindolin-1-one, and the mixture was stirred at 70° C. for 3 hours. 0.05 mL of aqueous 5 M sodium hydroxide solution was added to it, and the solvent was evaporated away under reduced pressure. 10% methanol/chloroform was added to the residue, the mixture was filtered, and the filtrate was concentrated under reduced pressure. The residue was purified through basic silica gel column chromatography (hexane/ethyl acetate) to obtain 45 mg of the entitled compound as a pale yellow solid.

$^1$H-NMR (400 MHz, CDCl$_3$) δ: 6.97 (1H, dd, J=8.0, 0.5 Hz), 6.52 (1H, dd, J=8.0, 2.2 Hz), 6.48 (1H, d, J=2.2 Hz), 3.82 (2H, s), 3.60 (2H, br. s), 2.44 (3H, s), 1.22 (6H, s)

ESI-MS Found: m/z [M+H]$^+$ 177

PRODUCTION EXAMPLE 51

Production of 1,1,2-trimethyl-1,2,3,4-tetrahydroisoquinolin-6-amine

1) Production of tert-butyl (1,1,2-trimethyl-1,2,3,4-tetrahydroisoquinolin-6-yl)carbamate

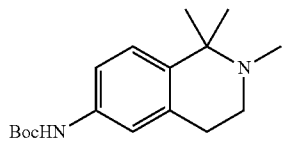 [SMILES: CN1CCc2cc(NC(=O)OC(C)(C)C)ccc2C1(C)C]

10 mL of 0.3 M ½ ZnCl$_2$.NaBH$_3$CN/methanol solution was added to the compound obtained in Production Example 29-4), then 0.57 mL of aqueous 37% formaldehyde solution was added to it, and stirred at room temperature for 2 hours. The solvent was evaporated away, then the residue was dissolved in ethyl acetate, washed with aqueous saturated sodium hydrogencarbonate solution and saturated saline water, and the organic layer was dried with anhydrous sodium sulfate. The solvent was evaporated away under reduced pressure, and the crude product was purified through silica gel column chromatography (hexane/ethyl acetate) to obtain 432 mg of the entitled compound as a white solid.

2) Production of 1,1,2-trimethyl-1,2,3,4-tetrahydroisoquinolin-6-amine

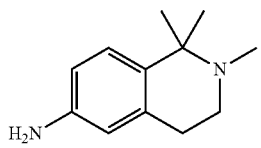

8 mL of trifluoroacetic acid was added to a chloroform (2 mL) solution of 432 mg of the compound obtained in the above 1), and stirred at room temperature for 2 hours. The solvent was evaporated away, the residue was dissolved in ethyl acetate, and made to have a pH of 9 with aqueous 5 N sodium hydroxide solution added thereto. This was extracted with ethyl acetate, the organic layer was washed with saturated saline water/aqueous 1 N sodium hydroxide solution, and dried with anhydrous sodium sulfate. The solvent was evaporated away under reduced pressure to obtain 277 mg of the entitled compound as a yellow-brown oil.

$^1$H-NMR (CDCl$_3$) δ: 7.04 (1H, d, J=8.3 Hz), 6.53 (1H, dd, J=8.3, 2.7 Hz), 6.38 (1H, d, J=2.7 Hz), 3.52 (2H, brs), 2.85 (2H, t, J=5.6 Hz), 2.77 (2H, t, J=5.6 Hz), 2.42 (3H, s), 1.36 (6H, s)

ESI-MS Found: m/z [M+H]$^+$ 191

PRODUCTION EXAMPLE 52

Production of 3-(2,6-dichlorophenyl)-7-(methylthio)pyrimido[4,5-d]pyrimidin-2,4(1H,3H)-dione

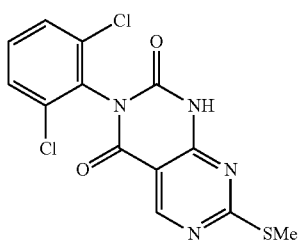 [SMILES: CSc1ncc2c(=O)n(-c3c(Cl)cccc3Cl)c(=O)[nH]c2n1]

315 mg of sodium hydride was added to an N,N-dimethylformamide (15 mL) solution of 1.0 g of ethyl 4-amino-2-(methylthio)pyrimidin-5-carboxylate, and stirred at room temperature for 5 minutes. 970 mg of 2,6-dichlorophenylisocyanate was added to the reaction liquid, and stirred at room temperature for 1 hour. Ethyl acetate and aqueous 1 N hydrochloric acid solution were added to the reaction solution, and the organic layer was separated. This was washed with saturated saline water, dried with anhydrous sodium sulfate, and the solvent was evaporated away. The precipitated solid was solidified with methanol, and the solid was taken out through filtration to obtain 1.43 g of the entitled compound as a white solid.

$^1$H-NMR (400 MHz, DMSO-d$_6$) δ: 12.93 (1H, brs), 9.01 (1H, s), 7.68 (2H, d, J=8.0 Hz), 7.54 (1H, t, J=8.0 Hz), 2.57 (3H, s)

ESI-MS Found: m/z [M+H] 354

PRODUCTION EXAMPLE 53

Production of 3-(2,6-dichlorophenyl)-1-methyl-7-(methylthio)pyrimido[4,5-d]pyrimidin-2,4(1H,3H)-dione

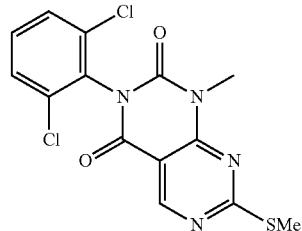 [SMILES: CSc1ncc2c(=O)n(-c3c(Cl)cccc3Cl)c(=O)n(C)c2n1]

211 μL of 1,8-diazabicyclo[5,4,0]undec-7-ene and 105 μL of methyl iodide were added to an N,N-dimethylformamide (5 mL) solution of 500 mg of 3-(2,6-dichlorophenyl)-7-(methylthio)pyrimido[4,5-d]pyrimidin-2,4(1H,3H)-dione obtained in Production Example 52, and stirred at room temperature for 1 hour. The reaction solution was added to ethyl acetate and aqueous 0.5 N hydrochloric acid solution with stirring, and the organic layer was separated. This was washed with saturated saline water, dried with anhydrous sodium sulfate, and the solvent was evaporated away. The crude product was solidified with methanol to obtain 420 mg of the entitled compound as a yellow solid.

$^1$H-NMR (400 MHz, DMSO-d$_6$) δ: 9.11 (1H, s), 7.69 (2H, d, J=8.0 Hz), 7.56 (1H, t, J=8.0 Hz), 3.55 (3H, s), 2.65 (3H, s)

ESI-MS Found: m/z [M+H]$^+$ 368

PRODUCTION EXAMPLE 54

Production of 2'-methyl-2',3'-dihydro-1'H-spiro[cyclopropane-1,4'-isoquinolin]-7'-amine dihydrochloride 1) Production of 2'-methyl-1'H-spiro[cyclopropane-1,4'-isoquinoline]-1',3'(2'H)-dione

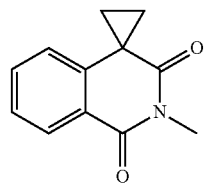

To a solution of N-methylhomophthalimide (4.05 kg), 1,2-dibromoethane (2.39 L), and Bu$_4$NHSO$_4$ (785 g) in N,N-dimethylformamide (32 L) were added K$_2$CO$_3$ (6.39 kg) and N,N-dimethylformamide (8.5 L) at room temperature. Then the solution was heated to 70° C., and was stirred for 2 hours at 68~70° C. After cooling the reaction mixture to 40° C., water (81 L) was added. After the slurry was stirred for 1 hour at 40° C., it was allowed to cool to room temperature and was stirred overnight. The suspension was filtered, and the obtained wet crystal was washed with the mixture of N,N-dimethylformamide and water (N,N-dimethylformamide:water=1:1, 20 L), twice, and water (20 L), sequentially. It was dried at room temperature under $N_2$ flow for several hours and then under the reduced pressure overnight to afford the title compound as pale pink crystal (4.67 kg, 4.30 kg assay, 92% yield).

$^1$H-NMR (400 MHz, CDCl$_3$) δ: 8.26 (1H, dd, J=7.9, 0.9 Hz), 7.59-7.54 (1H, m), 7.41-7.35 (1H, m), 6.81 (1H, d, J=8.1 Hz), 3.41 (3H, s), 2.14 (2H, dd, J=7.9, 4.0 Hz), 1.63 (2H, dd, J=7.9, 4.0 Hz).

2) Production of 2'-methyl-7'-nitro-1'H-spiro[cyclopropane-1,4'-isoquinoline]-1',3'(2'H)-dione

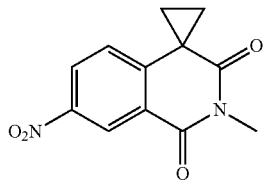 [SMILES: CN1C(=O)c2cc([N+](=O)[O-])ccc2C2(CC2)C1=O]

To the cooled mixture of H$_2$SO$_4$ (9.80 L) and HNO$_3$ (4.90 L) was added the compound prepared by the procedure 1) (4.65 kg) at 0~5° C. over 2 hours. The obtained slurry was stirred for 1 hour at 0~5° C. The mixture was diluted with acetic acid (19 L) below 10° C. Then the obtained solution was poured into cooled water (90 L) over 1 hour. Acetic acid (5.5 L) and water (8 L) was used for rinse. The obtained yellow suspension was stirred overnight at 10° C. After the suspension was filtered, the obtained wet crystal was washed with water (25 L), twice. It was dried at room temperature under N$_2$ flow for 3.5 h, then under reduced pressure overnight to afford the crude compound as pale yellow crystal (6.57 kg, 4.93 kg assay, 94% yield). The crude crystal was suspended in the MTBE (62 L) and it was stirred overnight at room temperature. After it was filtered, the obtained wet crystal was washed with MTBE (24 L, 12 L), twice. It was dried at room temperature under N$_2$ flow for 1 h, then under reduced pressure overnight to afford the title compound as pale yellow crystal (4.76 kg, 4.52 kg assay, 92% recovered).

$^1$H-NMR (400 MHz, CDCl$_3$) δ: 9.11 (1H, d, J=2.4 Hz), 8.39 (1H, dd, J=8.8, 2.4 Hz), 6.98 (1H, d, J=8.8 Hz), 3.44 (3H, s), 2.32 (2H, dd, J=8.2, 4.2 Hz), 1.77 (2H, dd, J=8.2, 4.2 Hz).

3) Production of 2'-methyl-7'-nitro-2',3'-dihydro-1'H-spiro[cyclopropane-1,4'-isoquinoline]hydrochloride

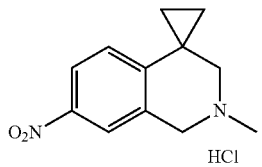 [SMILES: CN1Cc2cc([N+](=O)[O-])ccc2C2(CC2)C1 ; Cl]

The compound prepared by the procedure 2) (4003 g) was suspended in tetrahydrofuran (28 L) and the mixture was warmed to 60° C. BH$_3$-DMS (6.39 L) was dropwisely added at the same temperature over 2 hours. The reaction mixture was stirred at 57-62° C. for 24 h, and then at 60-65° C. for 24 hours under N$_2$ flow. Tetrahydrofuran (2.43 L) was added after 20 h, because of the decrease of the amount of solvent. After the solution was cooled to 10° C., ethanol (24 L) was slowly added. It was further stirred for 1 hour. The solution was then heated to remove tetrahydrofuran with the bath temperature controlled from 80 to 100° C. Temperature of the solution was finally reached to 75° C. After tetrahydrofuran was almost removed, 3 M HCl (40 L) was added and the solution was heated to 78° C. for 2 hours. After the solution was cooled to 10° C., 5M NaOH (32 L) and dichloromethane (40 L) was added with cooling (<15° C.) and the organic phase was separated. After the water phase was extracted with dichloromethane (60 L), it was filtered to remove the insoluble materials and was re-extracted with dichloromethane (20 L). The combined organic phase was concentrated to 30 L. The solvent was switched to toluene and its volume was reduced to 20 L. To the solution, toluene (60 L) and activated charcoal (400 g) were added, and it was stirred overnight. After filtration, it was washed with toluene (12 L), twice. The water phase remained in the toluene solution was separated off and the organic phase was dried through sodium sulfate (2 kg). After filtration, the dring agent was washed with toluene (5 L), twice. 4M HCl-Dioxane (3.75 L) was portionwisely added to the combined solution at room temperature and it was stirred overnight. The suspension was filtered. The obtained crystal was washed twice with toluene (20 L) and was dried under vacuum for one day to afford the title product (3.19 kg, 2.27 kg assay of free aniline, 64.0% yield).

$^1$H-NMR of free base (400 MHz, CDCl$_3$) δ: 7.97 (1H, dd, J=8.8, 2.4 Hz), 7.91 (1H, d, J=2.4 Hz), 6.78 (1H, d, J=8.8 Hz), 3.77 (2H, s), 2.56 (2H, s), 2.48 (3H, s), 1.17-1.11 (2H, m), 1.10-1.05 (2H, m).

4) Production of 2'-methyl-2',3'-dihydro-1'H-spiro[cyclopropane-1,4'-isoquinolin]-7'-amine dihydrochloride

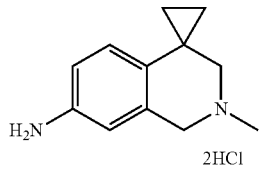

To a solution of the compound prepared by the procedure 3) (5.9 kg, 4.0 kg as free) in ethanol (20 L) was added zinc powder (4.79 kg) at 70° C. over 10 minutes, and then 12M HCl (10.69 L) in ethanol (12 L) over 60 minutes at 70~78° C. The obtained yellow suspension was stirred for 1 hour at 70° C. After cooling to 5° C., dichloromethane (53.24 kg) and 5M NaOH (37.74 kg) was added. It was stirred for 1 hour at room temperature and then filtered through Celite. The wet cake was washed with the mixture of water and dichloromethane (1:1, 20 L), twice. The filtrate and washings were combined and the phases were separated. The aqueous layer was extracted with dichloromethane (53.05 kg, 26.63 kg), twice. The combined organic layer was washed with 1M NaOH (20 L) and water (20 L). The obtained organic layer was evaporated and the solvent was switched to 2-propanol. The volume was adjusted to 40 L. Then the solution was treated with activated carbon (400 g) for 40 minutes at room temperature. The suspension was filtered and the wet carbon was washed with 2-propanol (20 L), twice. To the combined filtrate and washings were added 2M HCl in ethanol (18.3 L) over 60 minutes at room temperature and it was stirred overnight. The suspension was filtered and the wet crystal was washed with 2-propanol (12 L), twice. It was dried at room temperature under $N_2$ flow for several hours, then under reduced pressure overnight to afford the title compound as pale yellow crystal (6.35 kg, 3.83 kg assay of free aniline, quantitative yield).

$^1$H-NMR of free base (400 MHz, CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz).

ESI-MS Found: M/Z [M+H] 189

EXAMPLE 1

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride

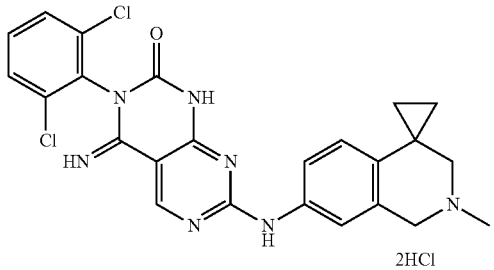 [SMILES: CN1Cc2cc(Nc3ncc4c(=N)n(-c5c(Cl)cccc5Cl)c(=O)[nH]c4n3)ccc2C2(CC2)C1]

A 1-butanol solution of 1.5 g of 7-chloro-3-(2,6-dichlorophenyl)-4-imino-3,4-dihydropyrimido[4,5-d]pyrimidin-2(1H)-one obtained in Production Example 1, 1 g of 2'-methyl-2',3'-dihydro-1'H-spiro[cyclopropane-1,4'-isoquinolin]-7'-amine obtained in Production Example 10, and 0.83 g of p-toluenesulfonic acid monohydrate was stirred at 90° C. for 15 minutes. The reaction liquid was cooled, then diluted with chloroform, and the organic layer was washed with aqueous saturated sodium bicarbonate solution and then saturated saline water, and dried with anhydrous magnesium sulfate, filtered, and the solvent was evaporated away. Thus obtained, the roughly-purified product was purified through basic silica gel column chromatography to obtain 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. This was dissolved in a mixed solvent of chloroform/methanol, and 1.5 equivalents of aqueous hydrochloric acid solution was added thereto, and stirred at room temperature for 5 minutes. Then, the solvent was evaporated away, and the residue was washed with ethyl acetate to obtain 1.5 g (yield, 64%) of the entitled compound as a yellow solid.

$^1$H-NMR (400 MHz, DMSO-d$_6$) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m)

ESI-MS Found: m/z [M+H]$^+$ 494

EXAMPLE 2

Production of 3-(2,6-dichlorophenyl)-4-imino-7-{[2,4,4-trimethyl-1,2,3,4-tetrahydroisoquinolin-7-yl]amino}-3,4-dihydropyrimido[4,5-d]pyrimidin-2(1H)-one

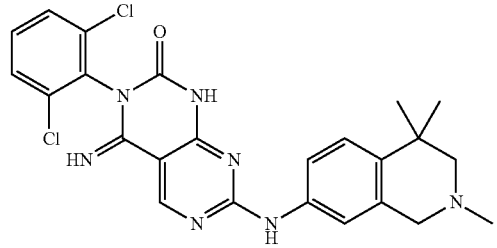 [SMILES: CN1Cc2cc(Nc3ncc4c(=N)n(-c5c(Cl)cccc5Cl)c(=O)[nH]c4n3)ccc2C(C)(C)C1]

A 1-butanol solution (15 mL) of 108 mg of 7-chloro-3-(2,6-dichlorophenyl)-4-imino-3,4-dihydropyrimido[4,5-d]pyrimidin-2(1H)-one obtained in Production Example 1, 60 mg of 2,4,4-trimethyl-1,2,3,4-tetrahydroisoquinolin-7-amine produced according to the method described in WO2005/023807, and 60 mg of p-toluenesulfonic acid monohydrate was stirred at 90° C. for 15 minutes. The roughly-purified product obtained by removing the solvent through evaporation was purified through basic silica gel column chromatography to obtain 102 mg of the entitled compound as a white solid.

$^1$H-NMR (400 MHz, CD$_3$OD) δ: 8.99 (1H, brs), 7.40-7.58 (5H, m), 7.29 (1H, d, J=8.8 Hz), 3.57 (2H, s), 2.48 (2H, s), 2.43 (3H, s), 1.32 (6H, s)

ESI-MS Found: m/z [M+H]$^+$ 496

EXAMPLE 3

Production of 3-(2,6-dichlorophenyl)-7-{[3-(2,2-difluoroethyl)-2,3,4,5-tetrahydro-1H-3-benzazepin-7-yl]amino}-4-imino-3,4-dihydropyrimido[4,5-d]pyrimidin-2(1H)-one

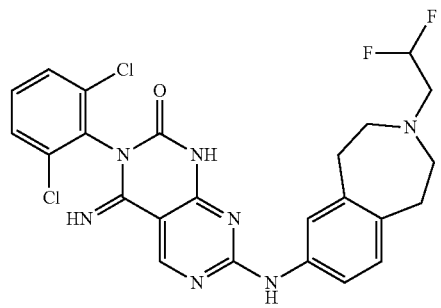 [SMILES: N=c1c2cnc(Nc3ccc4c(c3)CCN(CC(F)F)CC4)nc2[nH]c(=O)n1-c1c(Cl)cccc1Cl]

35 mg of the entitled compound was obtained as a white solid according to the same method as in Example 2, for which, however, 3-(2,2-difluoroethyl)-2,3,4,5-tetrahydro-1H-3-benzazepin-7-amine obtained in Production Example 15 was used in place of 2,4,4-trimethyl-1,2,3,4-tetrahydroisoquinolin-7-amine in Example 2.

¹H-NMR (400 MHz, DMSO-d₆) δ: 11.83 (1H, brs), 10.06 (1H, brs), 9.10 (1H, s), 8.88 (1H, s), 7.79-7.43 (4H, m), 7.03 (1H, d, J=8.3 Hz), 6.15 (1H, tt, J=55.9, 4.3 Hz), 2.96-2.68 (10H, m)

ESI-MS Found: m/z [M+H]⁺ 532

EXAMPLE 4

Production of 3-(2,6-dichlorophenyl)-4-imino-7-[(1,1,2-trimethyl-1,2,3,4-tetrahydroisoquinolin-6-yl)amino]-3,4-dihydropyrimido[4,5-d]pyrimidin-2(1H)-one

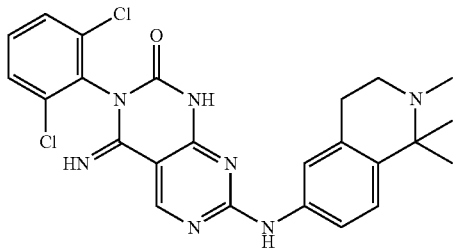 [SMILES: CN1CCc2cc(Nc3ncc4c(=N)n(-c5c(Cl)cccc5Cl)c(=O)[nH]c4n3)ccc2C1(C)C]

450 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2.

¹H-NMR (400 MHz, DMSO-d₆) δ: 11.80 (1H, s), 10.02 (1H, s), 9.10 (1H, s), 8.88 (1H, s), 8.31 (1H, s), 7.76-7.41 (5H, m), 7.22 (1H, d, J=8.8 Hz), 2.73 (3H, s), 2.32 (4H, s), 1.29 (6H, s)

ESI-MS Found: m/z [M+H]⁺ 496

EXAMPLE 5

Production of 3-(2,4-dichloropyridin-3-yl)-4-imino-7-{[1,1,2-trimethyl-1,2,3,4-tetrahydroisoqunolin-6-yl]amino}-3,4-dihydropyrimido[4,5-d]pyrimidin-2(1H)-one

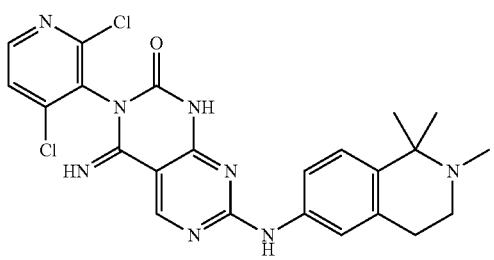 [SMILES: CN1CCc2cc(Nc3ncc4c(=N)n(-c5c(Cl)ccnc5Cl)c(=O)[nH]c4n3)ccc2C1(C)C]

35 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2, and 7-chloro-3-(2,4-dichloropyridin-3-yl)-4-imino-3,4-dihydropyrimido[4,5-d]pyrimidin-2(1H)-one obtained in Production Example 6 was used in place of 7-chloro-3-(2,6-dichlorophenyl)-4-imino-3,4-dihydropyrimido[4,5-d]pyrimidin-2(1H)-one.

¹H-NMR (400 MHz, CD₃OD) δ: 8.93 (1H, s), 8.43 (1H, d, J=5.6 Hz), 7.59 (1H, d, J=5.6 Hz), 7.40-7.46 (2H, m), 7.25 (1H, d, J=8.4 Hz), 2.89-2.95 (4H, m), 2.44 (3H, s), 2.44 (6H, s)

ESI-MS Found: m/z [M+H]⁺ 498

EXAMPLE 6

Production of 3-(2,4-dichloropyridin-3-yl)-4-imino-1-methyl-7-{[1,1,2-trimethyl-1,2,3,4-tetrahydroisoqunolin-6-yl]amino}-3,4-dihydropyrimido[4,5-d]pyrimidin-2(1H)-one

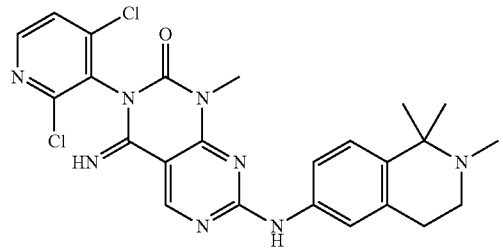 [SMILES: CN1CCc2cc(Nc3ncc4c(=N)n(-c5c(Cl)ccnc5Cl)c(=O)n(C)c4n3)ccc2C1(C)C]

15 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2, and 7-chloro-3-(2,4-dichloropyridin-3-yl)-4-imino-1-methyl-3,4-dihydropyrimido[4,5-d]pyrimidin-2(1H)-one obtained in Production Example 9 was used in place of 7-chloro-3-(2,6-dichlorophenyl)-4-imino-3,4-dihydropyrimido[4,5-d]pyrimidin-2(1H)-one.

¹H-NMR (400 MHz, CD₃OD) δ: 8.99 (1H, s), 7.65-7.40 (5H, m), 7.25 (1H, d, J=8.5 Hz), 3.93-3.71 (3H, m), 3.62 (1H, dd, J=8.4, 4.8 Hz), 2.94-2.76 (4H, m), 2.60-2.44 (3H, m), 2.11-1.99 (1H, m), 1.75-1.63 (1H, m), 1.38 (3H, s), 1.36 (3H, s)

ESI-MS Found: m/z [M+H]⁺ 566

EXAMPLE 7

Production of 3-(2,6-dichlorophenyl)-4-imino-7-[(1,1,2-trimethyl-2,3-dihydro-1H-isoindol-5-yl)amino]-3,4-dihydropyrimido[4,5-d]pyrimidin-2(1H)-one

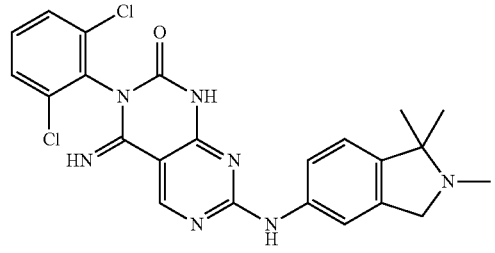 [SMILES: CN1Cc2cc(Nc3ncc4c(=N)n(-c5c(Cl)cccc5Cl)c(=O)[nH]c4n3)ccc2C1(C)C]

85 mg of the entitled compound was obtained as a pale yellow solid according to the same method as in Example 2, for which, however, 5-amino-1,1,2-trimethylisoindoline obtained in Production Example 49 was used in place of 2,4,4-trimethyl-1,2,3,4-tetrahydroisoquinolin-7-amine in Example 2.

$^1$H-NMR (400 MHz, DMSO-d$_6$) δ: 11.78 (1H, brs), 10.08 (1H, brs), 9.10 (1H, s), 8.88 (1H, brs), 7.87-7.40 (5H, m), 7.10 (1H, d, J=8.3 Hz), 3.80 (2H, s), 2.35 (3H, s), 1.16 (6H, s)

ESI-MS Found: m/z [M+H]$^+$ 482

EXAMPLE 8

Production of 3-(2,6-dichlorophenyl)-7-({(2S*)-2-[(2-hydroxyethyl)(methyl)amino]-2,3-dihydro-1H-inden-5-yl}amino)-4-imino-1-methyl-3,4-dihydropyrimido[4,5-d]pyrimidin-2(1H)-one, and 3-(2,6-dichlorophenyl)-7-({(2R*)-2-[(2-hydroxyethyl)(methyl)amino]-2,3-dihydro-1H-inden-5-yl}amino)-4-imino-1-methyl-3,4-dihydropyrimido[4,5-d]pyrimidin-2(1H)-one

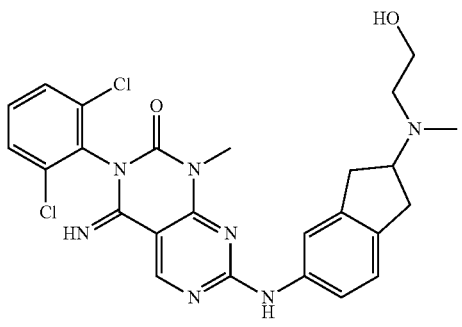 [SMILES: CN(CCO)C1Cc2ccc(Nc3ncc4c(=N)n(-c5c(Cl)cccc5Cl)c(=O)n(C)c4n3)cc2C1]

The entitled compounds, 79 mg and 82 mg, respectively, were obtained both as white solids according to the same method as in Example 2, for which, however, 2-[[(2S*)-5-amino-2,3-dihydro-1H-inden-2-yl](methyl)amino]ethanol or 2-[[(2R*)-5-amino-2,3-dihydro-1H-inden-2-yl](methyl)amino]ethanol obtained in Production Example 18 was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CDCl$_3$) δ: 9.03 (1H, brs), 7.68-7.48 (4H, m), 7.44-7.33 (2H, m), 7.19 (1H, d, J=7.8 Hz), 3.63 (2H, t, J=5.4 Hz), 3.61 (3H, s), 3.57-3.48 (1H, m), 3.14-3.05 (2H, m), 2.91 (2H, td, J=16.5, 8.0 Hz), 2.63 (2H, t, J=5.4 Hz), 2.30 (3H, s)

ESI-MS Found: m/z [M+H]$^+$ 526

EXAMPLE 9

Production of 3-(2,6-dichlorophenyl)-7-{[(2S*)-2-(dimethylamino)-2,3-dihydro-1H-inden-5-yl]amino}-4-imino-1-methyl-3,4-dihydropyrimido[4,5-d]pyrimidin-2(1H)-one, and 3-(2,6-dichlorophenyl)-7-{[(2R*)-2-(dimethylamino)-2,3-dihydro-1H-inden-5-yl]amino}-4-imino-1-methyl-3,4-dihydropyrimido[4,5-d]pyrimidin-2(1H)-one

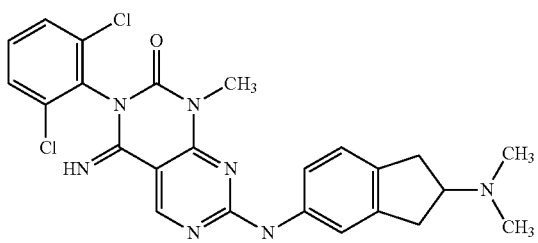 [SMILES: CN(C)C1Cc2ccc(Nc3ncc4c(=N)n(-c5c(Cl)cccc5Cl)c(=O)n(C)c4n3)cc2C1]

The entitled compounds, 67 mg and 91 mg, respectively, were obtained both as white solids according to the same method as in Example 2, for which, however, (2S*)—N$^2$,N$^2$-dimethylindan-2,5-diamine, and (2R*)—N$^2$,N$^2$-dimethylindan-2,5-diamine obtained in Production Example 17 were used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 8.20 (1H, s), 7.09 (1H, s), 6.82-6.63 (4H, m), 6.36 (1H, d, J=8.3 Hz), 2.77 (3H, s), 2.36-2.26 (3H, m), 2.11-2.02 (2H, m), 1.54 (6H, s)

ESI-MS Found: m/z [M+H]$^+$ 497

EXAMPLE 10

Production of 3-(2,6-dichlorophenyl)-7-{[3-(dimethylamino-1,1-dimethyl-2,3-dihydro-1H-inden-5-yl]amino}-4-imino-3,4-dihydropyrimido[4,5-d]pyrimidin-2(1H)-one

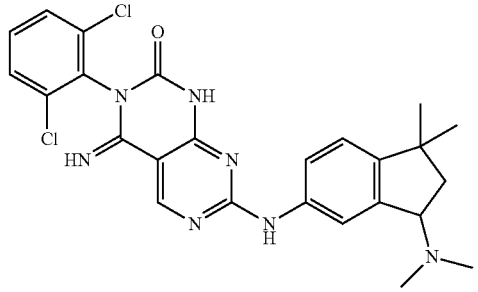 [SMILES: CN(C)C1CC(C)(C)c2ccc(Nc3ncc4c(=N)n(-c5c(Cl)cccc5Cl)c(=O)[nH]c4n3)cc21]

10 mg of the entitled compound was obtained as a white solid according to the same method as in Example 2, for which, however, N$^1$,N$^1$,3,3-tetramethylindan-1,6-diamine was used in place of 2,4,4-trimethyl-1,2,3,4-tetrahydroisoquinolin-7-amine in Example 2.

$^1$H-NMR (400 MHz, CD$_3$OD) δ: 8.97 (1H, s), 7.57 (2H, d, J=8.0 Hz), 7.40-7.50 (1H, m), 7.14-7.20 (1H, brs), 7.12 (1H, d, J=8.0 Hz), 4.59 (1H, m), 2.33 (6H, s), 1.96 (2H, d, J=8.0H), 1.39 (3H, s), 1.21 (3H, s)

ESI-MS Found: m/z [M+H]$^+$ 510

EXAMPLE 11

Production of 3-(2-chloro-6-methylphenyl)-4-imino-7-{[2,4,4-trimethyl-1,2,3,4-tetrahydroisoquinolin-7-yl]amino}-3,4-dihydropyrimido[4,5-d]pyrimidin-2(1H)-one

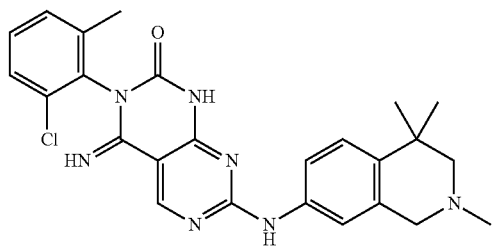 [SMILES: Cc1cccc(Cl)c1-n1c(=O)[nH]c2nc(Nc3ccc4c(c3)CN(C)CC4(C)C)ncc2c1=N]

13 mg of the entitled compound was obtained as a white solid according to the same method as in Example 2, for which, however, 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one in Example 2.

$^1$H-NMR (400 MHz, CD$_3$OD) δ: 9.02 (1H, s), 7.30-7.50 (5H, m), 7.29 (1H, d, J=8.4 Hz), 3.55 (2H, s), 2.48 (2H, s), 2.43 (3H, s), 2.25 (3H, s), 1.32 (6H, s)

ESI-MS Found: m/z [M+H]$^+$ 476

EXAMPLE 12

Production of 3-(2-chloro-6-methylphenyl)-4-imino-7-{[1,1,2-trimethyl-1,2,3,4-tetrahydroisoquinolin-6-yl]amino}-3,4-dihydropyrimido[4,5-d]pyrimidin-2(1H)-one

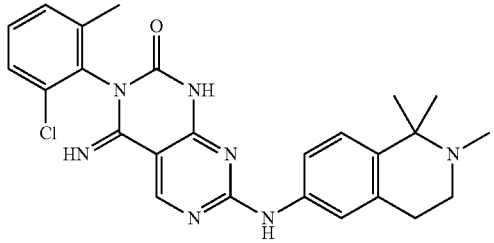 [SMILES: Cc1cccc(Cl)c1-n1c(=O)[nH]c2nc(Nc3ccc4c(c3)CCN(C)C4(C)C)ncc2c1=N]

13 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2, and 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.00 (1H, s), 7.36-7.55 (5H, m), 7.27 (1H, d, J=8.8 Hz), 2.90-2.96 (4H, m), 2.45 (3H, s), 2.23 (3H, s), 1.45 (6H, s)

ESI-MS Found: m/z [M+H]$^+$ 476

EXAMPLE 13

Production of 3-(2-chloro-6-methylphenyl)-7-{[2,5-dimethyl-1,2,3,4-tetrahydroisoquinolin-7-yl]amino}-4-imino-3,4-dihydropyrimido[4,5-d]pyrimidin-2(1H)-one

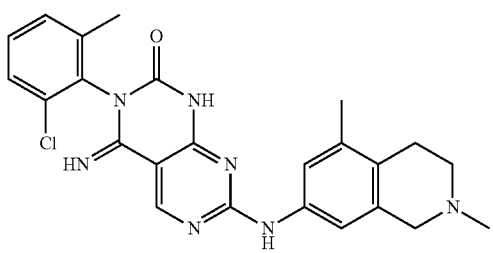 [SMILES: Cc1cc(Nc2ncc3c(=N)n(-c4c(C)cccc4Cl)c(=O)[nH]c3n2)cc2c1CCN(C)C2]

7 mg of the entitled compound was obtained as a white solid according to the same method as in Example 2, for which, however, 2,5-dimethyl-1,2,3,4-tetrahydroisoquinolin-7-amine was used in place of 2,4,4-trimethyl-1,2,3,4-tetrahydroisoquinolin-7-amine in Example 2, and 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 8.99 (1H, s), 7.33-7.50 (6H, m), 3.67 (2H, s), 2.89-2.85 (4H, m), 2.50 (3H, s), 2.27 (3H, s), 2.24 (3H, s)

ESI-MS Found: m/z [M+H]$^+$ 462

EXAMPLE 14

Production of 3-(2-chloro-6-methylphenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one

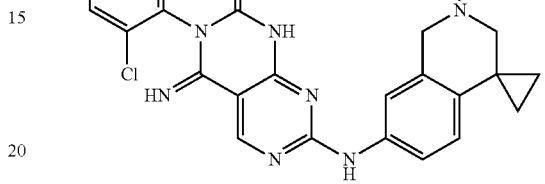

23 mg of the entitled compound was obtained as a white solid according to the same method as in Example 2, for which, however, 2'-methyl-2',3'-dihydro-1'H-spiro[cyclopropane-1,4'-isoquinolin]-7'-amine obtained in Production Example 10 was used in place of 2,4,4-trimethyl-1,2,3,4-tetrahydroisoquinolin-7-amine in Example 2, and 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 11.69 (1H, brs), 9.99 (1H, brs), 9.08 (1H, s), 8.75 (1H, s), 7.56-7.29 (4H, m), 6.62 (1H, d, J=8.5 Hz), 3.57 (2H, s), 2.42 (2H, s), 2.31 (3H, s), 2.13 (4H, s), 0.91-0.86 (2H, m), 0.84-0.79 (2H, m)

ESI-MS Found: m/z [M+H]$^+$ 474

EXAMPLE 15

Production of 3-(2-chloro-6-methylphenyl)-4-imino-1-methyl-7-[(1,1,2-trimethyl-1,2,3,4-tetrahydroisoquinolin-6-yl)amino]-3,4-dihydropyrimido[4,5-d]pyrimidin-2(1H)-one

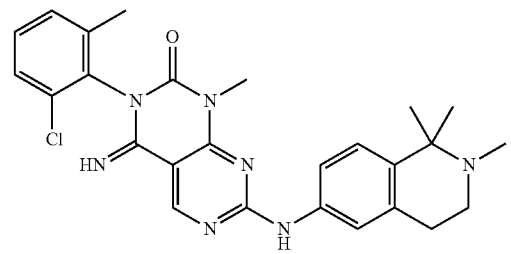 [SMILES: Cc1cccc(Cl)c1-n1c(=N)c2cnc(Nc3ccc4c(c3)CCN(C)C4(C)C)nc2n(C)c1=O]

37 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2, and 7-chloro-3-(2-chloro-6-methylphenyl)-4-imino-1-methyl-3,4-dihydropyrimido[4,5-d]pyrimidin-2(1H)-one obtained in Production Example 8 was used in place of 7-chloro-3-(2,6-dichlorophenyl)-4-imino-3,4-dihydropyrimido[4,5-d]pyrimidin-2(1H)-one.

$^1$H-NMR (400 MHz, CDCl$_3$) δ: 9.09 (1H, S), 7.54-7.22 (6H, M), 3.63 (3H, S), 3.00-2.91 (4H, M), 2.51 (3H, S), 2.22 (3H, S), 1.48 (6H, S)

ESI-MS Found: m/z [M+H]$^+$ 489

EXAMPLE 16

Production of 3-(2-chloro-6-fluorophenyl)-4-imino-7-{[2-methyl-1,2,3,4-tetrahydroisoquinolin-7-yl]amino}-3,4-dihydropyrimido[4,5-d]pyrimidin-2(1H)-one

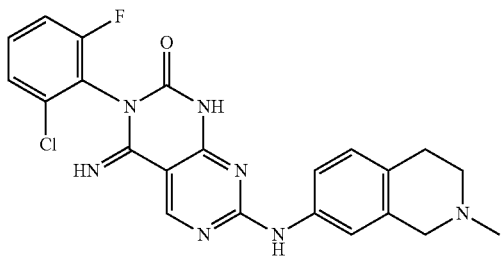 [SMILES: CN1CCc2ccc(Nc3ncc4c(=N)n(-c5c(F)cccc5Cl)c(=O)[nH]c4n3)cc2C1]

32 mg of the entitled compound was obtained as a white solid according to the same method as in Example 2, for which, however, 2-methyl-1,2,3,4-tetrahydroisoquinolin-7-amine was used in place of 2,4,4-trimethyl-1,2,3,4-tetrahydroisoquinolin-7-amine in Example 2, and 7-chloro-3-(2-chloro-6-fluorophenyl)-4-imino-3,4-dihydropyrimido[4,5-d]pyrimidin-2(1H)-one obtained in Production Example 3 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 8.97 (1H, s), 7.25-7.54 (5H, m), 7.10 (1H, d, J=8.0 Hz), 3.63 (2H, s), 2.93 (2H, d, J=6.4 Hz), 2.76 (2H, d, J=6.4 Hz), 2.47 (3H, s)

ESI-MS Found: m/z [M+H]$^+$ 452

EXAMPLE 17

Production of 3-(2-chloro-4,6-difluorophenyl)-4-imino-7-{[2-methyl-1,2,3,4-tetrahydroisoquinolin-7-yl]amino}-3,4-dihydropyrimido[4,5-d]pyrimidin-2(1H)-one

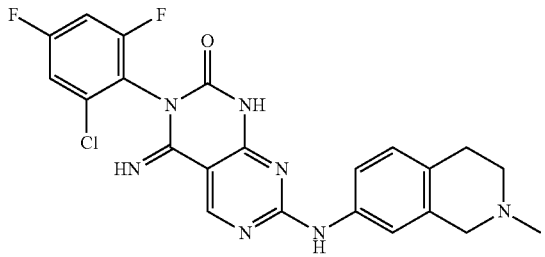 [SMILES: CN1CCc2ccc(Nc3ncc4c(=N)n(-c5c(F)cc(F)cc5Cl)c(=O)[nH]c4n3)cc2C1]

19 mg of the entitled compound was obtained as a white solid according to the same method as in Example 2, for which, however, 2-methyl-1,2,3,4-tetrahydroisoquinolin-7-amine was used in place of 2,4,4-trimethyl-1,2,3,4-tetrahydroisoquinolin-7-amine in Example 2, and 7-chloro-3-(2-chloro-4,6-difluorophenyl)-4-imino-3,4-dihydropyrimido[4,5-d]pyrimidin-2(1H)-one obtained in Production Example 5 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 8.93 (1H, s), 7.43 (1H, brs), 7.38 (2H, d, J=7.6 Hz), 7.24 (1H, d, J=7.6 Hz), 7.10 (1H, d, J=8.4 Hz), 7.04-7.09 (1H, m), 3.63 (2H, s), 2.93 (2H, t, J=6.0 Hz), 2.76 (2H, t, J=6.0 Hz), 2.48 (3H, s)

ESI-MS Found: m/z [M+H]$^+$ 470

EXAMPLE 18

Production of 3-(2,6-dichloro-4-fluorophenyl)-4-imino-7-{[2-methyl-1,2,3,4-tetrahydroisoquinolin-7-yl]amino}-3,4-dihydropyrimido[4,5-d]pyrimidin-2(1H)-one

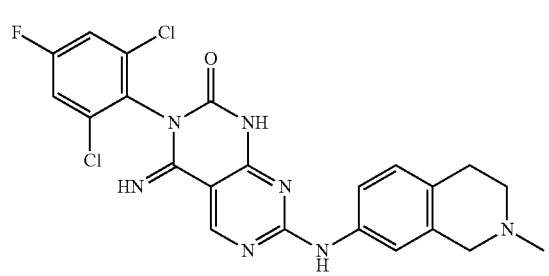 [SMILES: CN1CCc2ccc(Nc3ncc4c(=N)n(-c5c(Cl)cc(F)cc5Cl)c(=O)[nH]c4n3)cc2C1]

15 mg of the entitled compound was obtained as a white solid according to the same method as in Example 2, for which, however, 2-methyl-1,2,3,4-tetrahydroisoquinolin-7-amine was used in place of 2,4,4-trimethyl-1,2,3,4-tetrahydroisoquinolin-7-amine in Example 2, and 7-chloro-3-(2,6-dichloro-4-fluorophenyl)-4-imino-3,4-dihydropyrimido[4,5-d]pyrimidin-2(1H)-one obtained in Production Example 4 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 8.96 (1H, s), 7.30-7.50 (5H, m), 7.12 (1H, d, J=8.0 Hz), 3.64 (2H, s), 2.94 (2H, s), 2.77 (3H, s), 2.48 (3H, s)

ESI-MS Found: m/z [M+H]$^+$ 486

PRODUCTION EXAMPLE 19

Production of 3-(2,6-dichloro-4-fluorophenyl)-4-imino-7-{[1,1,2-trimethyl-1,2,3,4-tetrahydroisoquinolin-6-yl]amino}-3,4-dihydropyrimido[4,5-d]pyrimidin-2(1H)-one

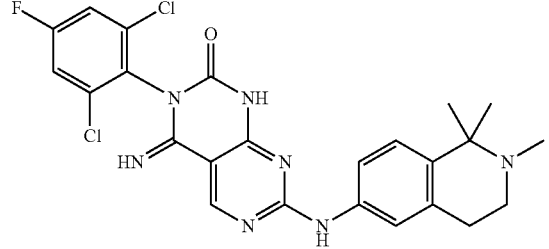 [SMILES: CN1CCc2cc(Nc3ncc4c(=N)n(-c5c(Cl)cc(F)cc5Cl)c(=O)[nH]c4n3)ccc2C1(C)C]

12 mg of the entitled compound was obtained as a white solid according to the same method as in Example 2, for which, however, 1,1,2-trimethyl-1,2,3,4-tetrahydroisoquinolin-6-amine obtained in Production Example 51 was used in place of 2,4,4-trimethyl-1,2,3,4-tetrahydroisoquinolin-7-amine in Example 2, and 7-chloro-3-(2,6-dichloro-4-fluorophenyl)-4-imino-3,4-dihydropyrimido[4,5-d]pyrimidin-2(1H)-one obtained in Production Example 4 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 8.95 (1H, s), 7.44-7.48 (2H, m), 7.35 (2H, d, J=7.6 Hz), 7.25 (1H, d, J=8.0 Hz), 2.91-2.96 (4H, m), 2.44 (3H, s), 1.44 (6H, s)

ESI-MS Found: m/z [M+H]$^+$ 515

EXAMPLE 20

Production of 3-(2,6-dichloro-4-fluorophenyl)-7-{[(2R*)-2-(dimethylamino)-2,3-dihydro-1H-inden-5-yl]amino}-4-imino-3,4-dihydropyrimido[4,5-d]pyrimidin-2(1H)-one, and 3-(2,6-dichloro-4-fluorophenyl)-7-{[(2S*)-2-(dimethylamino)-2,3-dihydro-1H-inden-5-yl]amino}-4-imino-3,4-dihydropyrimido[4,5-d]pyrimidin-2(1H)-one

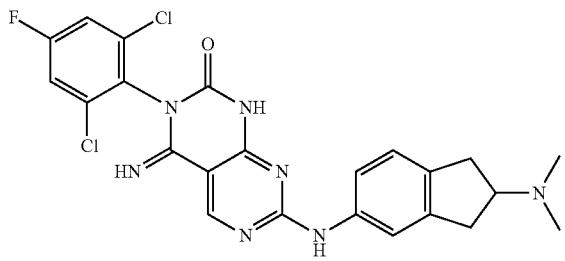 [SMILES: CN(C)C1Cc2ccc(Nc3ncc4c(=N)n(-c5c(Cl)cc(F)cc5Cl)c(=O)[nH]c4n3)cc2C1]

The entitled compounds, 6.0 mg and 5.0 mg, respectively, were obtained both as white solids according to the same method as in Example 2, for which, however, (2S*)—N$^2$,N$^2$-dimethylindan-2,5-diamine, and (2R*)—N$^2$,N$^2$-dimethylindan-2,5-diamine obtained in Production Example 17 were used in place of 2,4,4-trimethyl-1,2,3,4-tetrahydroisoquinolin-7-amine in Example 2, and 7-chloro-3-(2,6-dichloro-4-fluorophenyl)-4-imino-3,4-dihydropyrimido[4,5-d]pyrimidin-2(1H)-one obtained in Production Example 4 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 8.17 (1H, s), 6.85 (1H, s), 6.67 (2H, d, J=8.3 Hz), 6.62 (1H, d, J=7.8 Hz), 6.33 (1H, d, J=8.3 Hz), 2.35-2.25 (3H, m), 2.10-1.99 (2H, m), 1.53 (6H, s)

ESI-MS Found: m/z [M+H]$^+$ 501

EXAMPLE 21

Production of 3-(2,6-dichlorophenyl)-7-{[2,5-dimethyl-1,2,3,4-tetrahydroisoquinolin-7-yl]amino}-4-imino-3,4-dihydropyrimido[4,5-d]pyrimidin-2(1H)-one

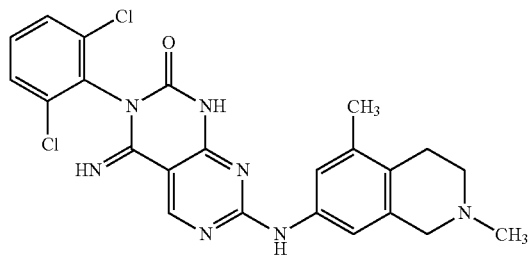 [SMILES: Cc1cc(Nc2ncc3c(=N)n(-c4c(Cl)cccc4Cl)c(=O)[nH]c3n2)cc2c1CCN(C)C2]

36 mg of the entitled compound was obtained as a white solid according to the same method as in Example 2, for which, however, 2,5-dimethyl-1,2,3,4-tetrahydroisoquinolin-7-amine was used in place of 2,4,4-trimethyl-1,2,3,4-tetrahydroisoquinolin-7-amine in Example 2.

$^1$H-NMR (400 MHz, CD$_3$OD) δ: 9.00 (1H, s), 7.46-7.58 (3H, m), 7.32 (1H, br), 7.24 (1H, br), 3.62 (2H, s), 2.78 (4H, brs), 2.47 (3H, s), 2.23 (3H, s)

ESI-MS Found: m/z [M+H]$^+$ 482

EXAMPLE 22

Production of 3-(2,6-dichlorophenyl)-7-{[2-(2-hydroxyethyl)-1,1-dimethyl-1,2,3,4-tetrahydroisoquinolin-6-yl]amino}-4-imino-1-methyl-3,4-dihydropyrimido[4,5-d]pyrimidin-2(1H)-one

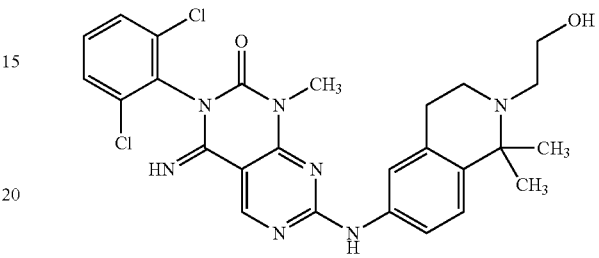

5 mg of the entitled compound was obtained as a colorless amorphous substance according to the same method as in Example 2, for which, however, 2-(6-amino-1,1-dimethyl-3,4-dihydroisoquinolin-2(1H)-yl)ethanol hydrochloride obtained in Production Example 29 was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.01 (1H, s), 7.63-7.44 (5H, m), 7.29 (1H, d, J=8.8 Hz), 3.67 (2H, t, J=6.2 Hz), 3.59 (3H, s), 2.99 (2H, t, J=5.4 Hz), 2.89 (2H, t, J=5.4 Hz), 2.77 (2H, t, J=6.2 Hz), 1.44 (6H, s)

ESI-MS Found: m/z [M+H]$^+$ 540

EXAMPLE 23

Production of 3-(2,6-dichlorophenyl)-4-imino-7-[(1,1,2,3,3-pentamethyl-2,3-dihydro-1H-isoindol-5-yl)amino]-3,4-dihydropyrimido[4,5-d]pyrimidin-2(1H)-one

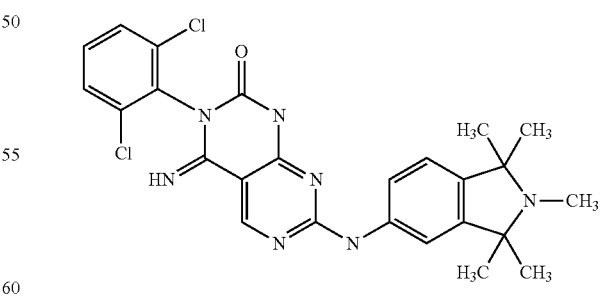

77 mg of the entitled compound was obtained as a colorless solid according to the same method as in Example 2, for which, however, 5-amino-1,1,2,3,3-tetramethylisoindoline obtained in Production Example 48 was used in place of 2,4,4-trimethyl-1,2,3,4-tetrahydroisoquinolin-7-amine in Example 2.

$^1$H-NMR (400 MHz, DMSO-d$_6$) δ: 11.90 (1H, brs), 10.09 (1H, brs), 9.11 (1H, s), 8.88 (1H, s), 8.01-7.37 (5H, m), 7.12 (1H, d, J=8.3 Hz), 2.33 (3H, s), 1.29 (6H, s), 1.24 (6H, s)
ESI-MS Found: m/z [M+H]$^+$ 510

PRODUCTION EXAMPLE 24

Production of 3-(2,6-dichlorophenyl)-7-(3',4'-dihydro-2'H-spiro[cyclobutane-1,1'-isoquinolin]-6'-ylamino)-4-imino-1-methyl-3,4-dihydropyrimido[4,5-d]pyrimidin-2(1H)-one

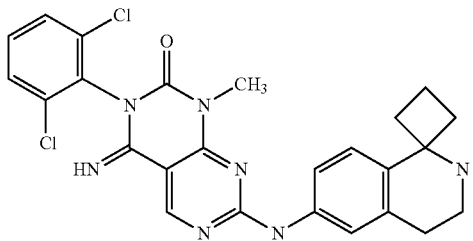 [SMILES: Cn1c(=O)n(-c2c(Cl)cccc2Cl)c(=N)c2cnc(Nc3ccc4c(c3)CCNC43CCC3)nc21]

70 mg of the entitled compound was obtained as a white solid according to the same method as in Example 2, for which, however, 3',4'-dihydro-2'H-spiro[cyclobutane-1,1'-isoquinolin]-6'-amine obtained in Production Example 30 was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 10.19 (1H, s), 9.15 (1H, s), 8.91 (1H, s), 7.63-7.55 (3H, m), 7.49-7.43 (3H, m), 3.48 (3H, s), 2.87 (2H, t, J=5.7 Hz), 2.65 (2H, t, J=5.5 Hz), 2.35-2.30 (2H, m), 2.08-2.01 (3H, m), 1.94-1.89 (1H, m)
ESI-MS Found: m/z [M+H]$^+$ 508

EXAMPLE 25

Production of 3-(2,6-dichlorophenyl)-7-[(1,1-dimethyl-1,2,3,4-tetrahydroisoquinolin-6-yl)amino]-4-imino-1-methyl-3,4-dihydropyrimido[4,5-d]pyrimidin-2(1H)-one

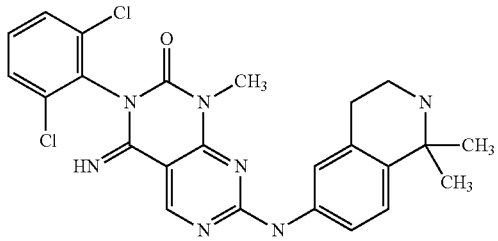 [SMILES: Cn1c(=O)n(-c2c(Cl)cccc2Cl)c(=N)c2cnc(Nc3ccc4c(c3)CCNC4(C)C)nc21]

50 mg of the entitled compound was obtained as a yellow white substance according to the same method as in Example 2, for which, however, 1,1-dimethyl-1,2,3,4-tetrahydroisoquinolin-6-amine obtained in Production Example 29-3) was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.02 (1H, s), 7.66-7.43 (5H, m), 7.29 (1H, d, J=8.5 Hz), 3.59 (3H, s), 3.24 (2H, t, J=6.1 Hz), 2.93 (2H, t, J=6.1 Hz), 1.55 (6H, s)
ESI-MS Found: m/z [M+H]$^+$ 496

EXAMPLE 26

Production of 3-(2,6-dichlorophenyl)-7-{[2'-(2-hydroxyethyl)-3',4'-dihydro-2'H-spiro[cyclobutane-1,1'-isoquinolin]-6'-yl]amino}-4-imino-1-methyl-3,4-dihydropyrimido[4,5-d]pyrimidin-2(1H)-one

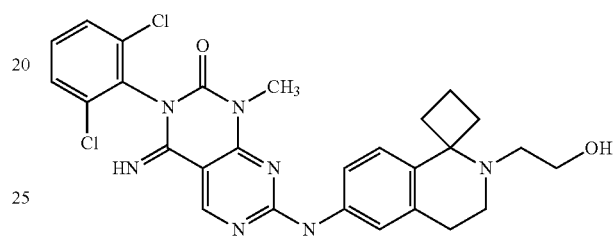

23.4 mg of the entitled compound was obtained as a white solid according to the same method as in Example 2, for which, however, 2-(6'-amino-3',4'-dihydro-2'H-spiro[cyclobutane-1,1'-isoquinolin-2'-yl]ethanol was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 10.22 (1H, s), 9.16 (1H, s), 8.92 (1H, s), 7.64-7.56 (3H, m), 7.52-7.45 (3H, m), 4.34 (1H, s), 3.49 (3H, s), 3.48 (2H, t, J=5.9 Hz), 2.99-2.93 (2H, m), 2.72-2.66 (2H, m), 2.41-2.36 (2H, m), 2.32-2.27 (2H, m), 2.18-2.10 (2H, m), 2.01-1.92 (1H, m), 1.90-1.82 (1H, m)
ESI-MS Found: m/z [M+H]$^+$ 552

EXAMPLE 27

Production of 3-(2,6-dichlorophenyl)-7-{[4,4-dimethyl-1,2,3,4-tetrahydroisoquinolin-7-yl]amino}-4-imino-1-methyl-3,4-dihydropyrimido[4,5-d]pyrimidin-2(1H)-one

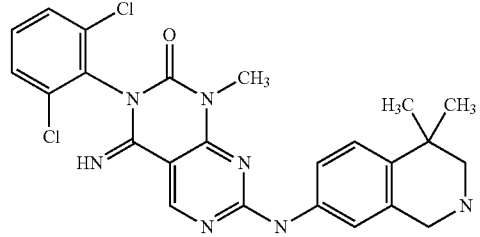 [SMILES: Cn1c(=O)n(-c2c(Cl)cccc2Cl)c(=N)c2cnc(Nc3ccc4c(c3)CNCC4(C)C)nc21]

160 mg of the entitled compound was obtained as a white solid according to the same method as in Example 2, for which, however, 4,4-dimethyl-1,2,3,4-tetrahydroisoquinolin-7-amine was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.00 (1H, s), 7.41-7.60 (5H, m), 7.37 (1H, d, J=8.8 Hz), 4.04 (2H, s), 3.64 (3H, s), 2.91 (2H, s), 1.33 (6H, s)

ESI-MS Found: m/z [M+H]$^+$ 496

EXAMPLE 28

Production of 3-(2,6-dichlorophenyl)-7-(3',4'-dihydro-2'H-spiro[cyclopropane-1,1'-isoquinolin]-6'-ylamino)-4-imino-1-methyl-3,4-dihydropyrimido[4,5-d]pyrimidin-2(1H)-one, and 3-(2,6-dichlorophenyl)-7-[(1-ethyl-1,2,3,4-tetrahydroisoquinolin-6-yl)amino]-4-imino-1-methyl-3,4-dihydropyrimido[4,5-d]pyrimidin-2(1H)-one

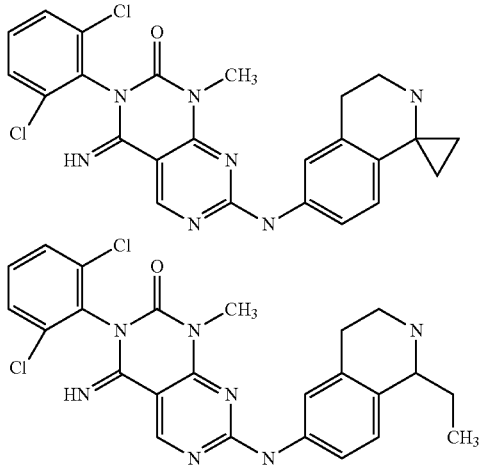

14 mg of 3-(2,6-dichlorophenyl)-7-(3',4'-dihydro-2'H-spiro[cyclopropane-1,1'-isoquinolin]-6'-ylamino)-4-imino-1-methyl-3,4-dihydropyrimido[4,5-d]pyrimidin-2(1H)-one was obtained as a white solid according to the same method as in Example 2, for which, however, tert-butyl 6'-amino-3',4'-dihydro-2'H-spiro[cyclopropane-1,1'-isoquinoline]-2'-carboxylate obtained in the reaction of Production Example 19-5) was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one. In addition, as a by-product, 30 mg of 3-(2,6-dichlorophenyl)-7-[(1-ethyl-1,2,3,4-tetrahydroisoquinolin-6-yl)amino]-4-imino-1-methyl-3,4-dihydropyrimido[4,5-d]pyrimidin-2(1H)-one was obtained as a white solid. 3-(2,6-Dichlorophenyl)-7-(3',4'-dihydro-2'H-spiro[cyclopropane-1,1'-isoquinolin]-6'-ylamino)-4-imino-1-methyl-3,4-dihydropyrimido[4,5-d]pyrimidin-2(1H)-one:

$^1$H-NMR (400 MHz, CDCl$_3$) δ: 9.19-8.89 (1H, m), 7.64-7.53 (1H, m), 7.50 (2H, t, J=4.1 Hz), 7.41-7.32 (3H, m), 6.61 (1H, d, J=9.0 Hz), 3.58 (3H, s), 3.18 (2H, t, J=6.1 Hz), 2.87 (2H, t, J=6.1 Hz), 1.09-1.05 (2H, m), 1.03-0.98 (2H, m)

ESI-MS Found: m/z [M+H]$^+$ 493 3-(2,6-Dichlorophenyl)-7-[(1-ethyl-1,2,3,4-tetrahydroisoquinolin-6-yl)amino]-4-imino-1-methyl-3,4-dihydropyrimido[4,5-d]pyrimidin-2(1H)-one:

$^1$H-NMR (400 MHz, CDCl$_3$) δ: 9.27-9.00 (1H, m), 7.50 (3H, d, J=8.6 Hz), 7.42-7.35 (3H, m), 7.13 (1H, d, J=8.6 Hz), 3.88 (1H, dd, J=9.0, 3.5 Hz), 3.59 (3H, s), 3.24 (1H, dt, J=12.4, 5.3 Hz), 3.01-2.95 (1H, m), 2.89-2.69 (2H, m), 1.95-1.87 (1H, m), 1.76-1.64 (1H, m), 0.99 (3H, t, J=7.4 Hz)

ESI-MS Found: m/z [M+H]$^+$ 495

EXAMPLE 29

Production of 3-(2,6-dichlorophenyl)-4-imino-1-methyl-7-{[2-methyl-1,2,3,4-tetrahydroisoquinolin-6-yl]amino}-3,4-dihydropyrimido[4,5-d]pyrimidin-2(1H)-one

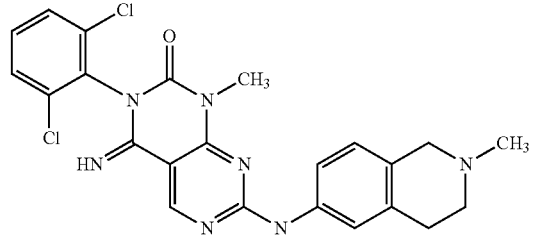 [SMILES: CN1CCc2cc(Nc3ncc4c(=N)n(-c5c(Cl)cccc5Cl)c(=O)n(C)c4n3)ccc2C1]

28 mg of the entitled compound was obtained as a white solid according to the same method as in Example 2, for which, however, 2-methyl-1,2,3,4-tetrahydroisoquinolin-6-amine was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.00 (1H, s), 7.46-7.60 (5H, m), 7.06 (1H, d, J=8.8 Hz), 3.64 (2H, s), 3.62 (3H, s), 2.99 (2H, t, J=6.4 Hz), 2.79 (2H, t, J=6.4 Hz), 2.49 (3H, s)

ESI-MS Found: m/z [M+H]$^+$ 481

EXAMPLE 30

Production of 3-(2,6-dichlorophenyl)-4-imino-7-{[2-ethyl-1,2,3,4-tetrahydroisoquinolin-6-yl]amino}-3,4-dihydropyrimido[4,5-d]pyrimidin-2(1H)-one

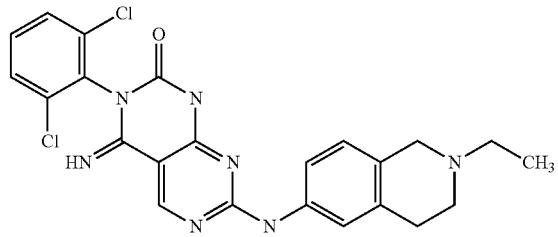 [SMILES: CCN1CCc2cc(Nc3ncc4c(=N)n(-c5c(Cl)cccc5Cl)c(=O)[nH]c4n3)ccc2C1]

111 mg of the entitled compound was obtained as a white solid according to the same method as in Example 2, for which, however, 2-ethyl-1,2,3,4-tetrahydroisoquinolin-6-amine obtained in Production Example 34 was used in place of 2,4,4-trimethyl-1,2,3,4-tetrahydroisoquinolin-7-amine in Example 2.

$^1$H-NMR (400 MHz, DMSO-d$_6$) δ: 11.85 (1H, s), 10.07 (1H, s), 9.14 (1H, s), 8.92 (1H, s), 7.70-7.52 (5H), 7.01 (1H, d, J=8.8 Hz), 3.53 (2H, s), 2.84 (2H, m), 2.67 (2H, m), 2.53-2.52 (2H), 1.20 (3H, d, J=7.6 Hz)

ESI-MS Found: m/z [M+H]$^+$ 482

EXAMPLE 31

Production of 3-(2,6-dichlorophenyl)-4-imino-1-methyl-7-{[2-methyl-1,2,3,4-tetrahydroisoquinolin-7-yl]amino}-3,4-dihydropyrimido[4,5-d]pyrimidin-2(1H)-one

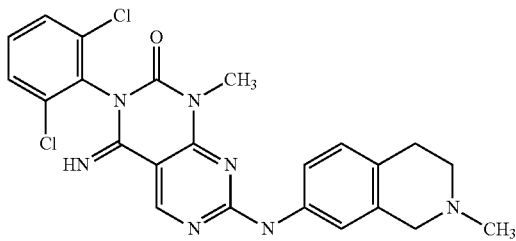 [SMILES: CN1CCc2ccc(Nc3ncc4c(=N)n(-c5c(Cl)cccc5Cl)c(=O)n(C)c4n3)cc2C1]

28 mg of the entitled compound was obtained as a white solid according to the same method as in Example 2, for which, however, 2-methyl-1,2,3,4-tetrahydroisoquinolin-7-amine was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, CD$_3$OD) δ: 9.00 (1H, s), 7.58 (1H, d, J=8.0 Hz), 7.46-7.50 (3H, m), 7.14 (1H, d, J=8.0 Hz), 3.66 (2H, s), 3.63 (3H, s), 2.96 (2H, t, J=6.4 Hz), 2.79 (2H, t, J=6.4 Hz), 2.49 (3H, s)

ESI-MS Found: m/z [M+H]$^+$ 481

EXAMPLE 32

Production of 3-(2,6-dichlorophenyl)-7-({2-[(2S)-2-hydroxypropyl]-1,2,3,4-tetrahydroisoquinolin-6-yl]}amino)-4-imino-1-methyl-3,4-dihydropyrimido[4,5-d]pyrimidin-2(1H)-one Chiral

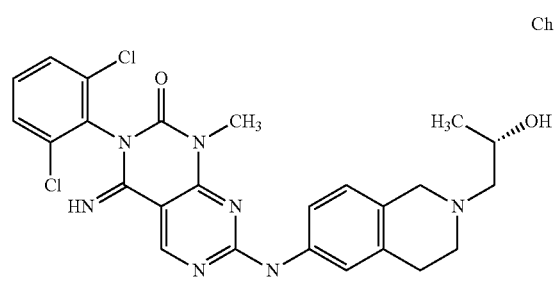

20.9 mg of the entitled compound was obtained as a white solid according to the same method as in Example 2, for which, however, (2S)-1-(6-amino-3,4-dihydroisoquinolin-2(1H)-yl)propan-2-ol obtained in Production Example 35 was used in place of 2,4,4-trimethyl-1,2,3,4-tetrahydroisoquinolin-7-amine in Example 2, and 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one.

$^1$H-NMR (400 MHz, DMSO-d$_6$) δ: 11.84 (1H, s), 10.23 (1H, s), 9.19 (1H, s), 7.65 (2H, d, J=8.4 Hz), 7.57 (1H, s), 7.52-7.48 (2H), 7.03 (1H, d, J=8.4 Hz), 4.40 (1H, d, J=4.0 Hz), 3.88 (1H, m), 3.58 (2H, s), 3.51 (3H, s), 2.82 (2H, m), 2.72 (2H, m), 2.44 (1H, dd, J=12.4, 7.6 Hz), 2.40 (1H, dd, J=12.4, 5.2 Hz), 1.10 (3H, d, J=6.4 Hz)

ESI-MS Found: m/z [M+H]$^+$ 526

EXAMPLE 33

Production of 3-(2,6-dichlorophenyl)-7-(3',4'-dihydro-2'H-spiro[cyclopentane-1,1'-isoquinolin]-6'-ylamino)-4-imino-3,4-dihydropyrimido[4,5-d]pyrimidin-2(1H)-one

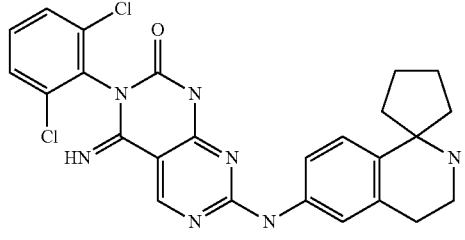 [SMILES: N=c1c2cnc(Nc3ccc4c(c3)CCNC43CCCC3)nc2[nH]c(=O)n1-c1c(Cl)cccc1Cl]

78.4 mg of the entitled compound was obtained as a white solid according to the same method as in Example 2, for which, however, 3',4'-dihydro-2'H-spiro[cyclopentane-1,1'-isoquinolin]-6'-amine obtained in Production Example 31 was used in place of 2,4,4-trimethyl-1,2,3,4-tetrahydroisoquinolin-7-amine in Example 2.

$^1$H-NMR (400 MHz, DMSO-d$_6$) δ: 9.97 (1H, s), 9.07 (1H, s), 8.85 (1H, s), 7.62 (2H, d, J=8.3 Hz), 7.56 (1H, s), 7.52-7.44 (2H, m), 7.10 (1H, d, J=8.8 Hz), 2.88 (2H, t, J=5.9 Hz), 2.66 (2H, t, J=5.4 Hz), 1.83-1.70 (8H, m)

ESI-MS Found: m/z [M+H]$^+$ 508

EXAMPLE 34

Production of 3-(2,6-dichlorophenyl)-4-imino-7-[(2'-methyl-3',4'-dihydro-2'H-spiro[cyclopentane-1,1'-isoquinolin]-6'-yl)amino]-3,4-dihydropyrimido[4,5-d]pyrimidin-2(1H)-one

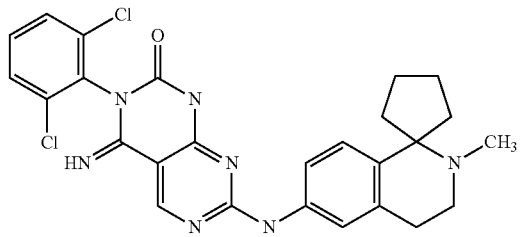 [SMILES: CN1CCc2cc(Nc3ncc4c(=N)n(-c5c(Cl)cccc5Cl)c(=O)[nH]c4n3)ccc2C12CCCC2]

15.7 mg of the entitled compound was obtained as a white solid according to the same method as in Production Example 10-6), for which, however, the compound obtained in Example 33 was used in place of 7'-nitro-1',2'-dihydro-3'H-spiro[cyclopropane-1,4'-isoquinoline] used in Production Example 10-6).

$^1$H-NMR (400 MHz, DMSO-$d_6$) δ: 10.00 (1H, s), 9.10 (1H, s), 8.87 (1H, s), 7.76-7.54 (3H, m), 7.51-7.45 (2H, m), 7.09 (1H, d, J=8.8 Hz), 2.94 (2H, t, J=6.1 Hz), 2.73 (2H, t, J=5.9 Hz), 2.23 (3H, s), 2.05-1.98 (2H, m), 1.79-1.70 (6H, m)
ESI-MS Found: m/z [M+H]$^+$ 522

EXAMPLE 35

Production of 3-(2,6-dichlorophenyl)-4-imino-7-[(2-methyl-1,2,3,4-tetrahydroisoquinolin-6-yl)amino]-3,4-dihydropyrimido[4,5-d]pyrimidin-2(1H)-one

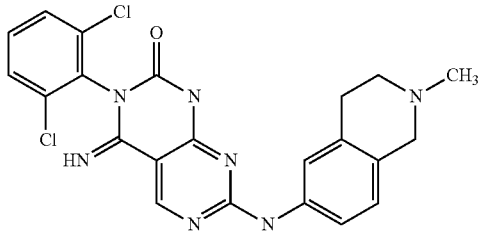 [SMILES: CN1CCc2cc(Nc3ncc4c(=N)n(-c5c(Cl)cccc5Cl)c(=O)[nH]c4n3)ccc2C1]

17 mg of the entitled compound was obtained as a pale yellow solid according to the same method as in Example 2, for which, however, 2-methyl-1,2,3,4-tetrahydroisoquinolin-6-amine was used in place of 2,4,4-trimethyl-1,2,3,4-tetrahydroisoquinolin-7-amine in Example 2.

$^1$H-NMR (400 MHz, DMSO-$d_6$) δ: 11.81 (1H, brs), 10.03 (1H, brs), 9.10 (1H, s), 8.87 (1H, s), 7.74-7.58 (3H, m), 7.51-7.44 (2H, m), 6.96 (1H, d, J=8.3 Hz), 3.42 (2H, s), 2.81 (2H, t, J=5.7 Hz), 2.57 (2H, t, J=5.7 Hz), 2.32 (3H, s)
ESI-MS Found: m/z [M+H]$^+$ 470

EXAMPLE 36

Production of 3-(2,6-dichlorophenyl)-7-(3',4'-dihydro-2'H-spiro[cyclobutane-1,1'-isoquinolin]-6'-ylamino)-4-imino-3,4-dihydropyrimido[4,5-d]pyrimidin-2(1H)-one

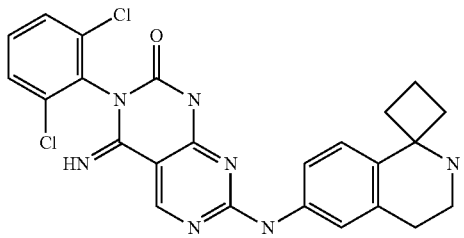 [SMILES: N=c1c2cnc(Nc3ccc4c(c3)CCNC43CCC3)nc2[nH]c(=O)n1-c1c(Cl)cccc1Cl]

95.6 mg of the entitled compound was obtained as a white solid according to the same method as in Example 2, for which, however, 3',4'-dihydro-2'H-spiro[cyclobutane-1,1'-isoquinolin]-6'-amine obtained in Production Example 30 was used in place of 2,4,4-trimethyl-1,2,3,4-tetrahydroisoquinolin-7-amine in Example 2.

$^1$H-NMR (400 MHz, DMSO-$d_6$) δ: 10.00 (1H, s), 9.09 (1H, s), 8.87 (1H, s), 7.66-7.60 (3H, m), 7.54 (2H, d, J=7.3 Hz), 7.49 (1H, s), 7.39 (1H, d, J=8.3 Hz), 2.87 (2H, t, J=5.9 Hz), 2.66 (2H, t, J=5.4 Hz), 2.35-2.26 (2H, m), 2.08-2.03 (3H, m), 1.96-1.88 (1H, m)
ESI-MS Found: m/z [M+H]$^+$ 494

EXAMPLE 37

Production of 3-(2,6-dichlorophenyl)-4-imino-7-[(2'-methyl-3',4'-dihydro-2'H-spiro[cyclobutane-1,1'-isoquinolin]-6'-yl)amino]-3,4-dihydropyrimido[4,5-d]pyrimidin-2(1H)-one

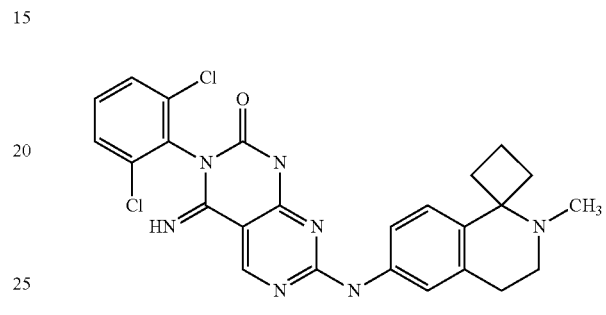

The entitled compound was obtained as a white solid according to the same method as in Production Example 10-6), for which, however, the compound obtained in Example 36 was used in place of 7'-nitro-1',2'-dihydro-3'H-spiro[cyclopropane-1,4'-isoquinoline] used in Production Example 10-6).

$^1$H-NMR (400 MHz, DMSO-$d_6$) δ: 10.03 (1H, s), 9.10 (1H, s), 8.88 (1H, s), 7.73-7.54 (4H, m), 7.51-7.41 (2H, m), 2.87 (2H, t, J=6.2 Hz), 2.70 (2H, t, J=5.9 Hz), 2.33 (2H, dd, J=20.6, 9.4 Hz), 2.20 (3H, s), 2.15-2.07 (2H, m), 1.99-1.83 (2H, m)
ESI-MS Found: m/z [M+H]$^+$ 508

EXAMPLE 38

Production of 3-(2,6-dichlorophenyl)-7-(3',4'-dihydro-2'H-spiro[cyclopropane-1,1'-isoquinolin]-6'-ylamino)-4-imino-3,4-dihydropyrimido[4,5-d]pyrimidin-2(1H)-one

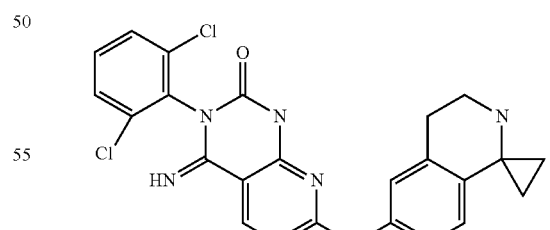

18 mg of the entitled compound was obtained as a pale yellow solid according to the same method as in Example 2, for which, however, tert-butyl 6'-amino-3',4'-dihydro-2'H-spiro[cyclopropane-1,1'-isoquinoline]-2'-carboxylate obtained in Production Example 19 was used in place of 2,4,4-trimethyl-1,2,3,4-tetrahydroisoquinolin-7-amine in Example 2.

¹H-NMR (400 MHz, CDCl₃) δ: 9.18-8.85 (1H, m), 7.64-7.28 (5H, m), 6.59 (1H, d, J=8.6 Hz), 3.17 (2H, t, J=6.1 Hz), 2.89 (2H, t, J=5.9 Hz), 1.13-0.99 (4H, m)
ESI-MS Found: m/z [M+H]⁺ 479

EXAMPLE 39

Production of 3-(2,6-dichlorophenyl)-7-{[(2S*)-2-(dimethylamino)-2,3-dihydro-1H-inden-5-yl]amino}-4-imino-3,4-dihydropyrimido[4,5-d]pyrimidin-2(1H)-one, and 3-(2,6-dichlorophenyl)-7-{[2R*)-2-(dimethylamino)-2,3-dihydro-1H-inden-5-yl]amino}-4-imino-3,4-dihydropyrimido[4,5-d]pyrimidin-2(1H)-one

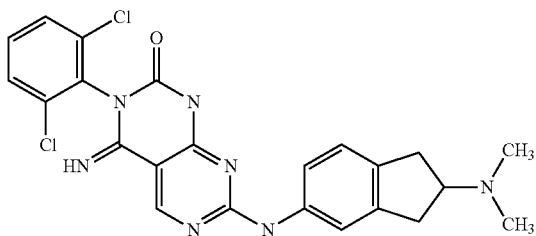 [SMILES: CN(C)C1Cc2ccc(Nc3ncc4c(=N)n(-c5c(Cl)cccc5Cl)c(=O)[nH]c4n3)cc2C1]

The entitled compounds, 350 mg and 280 mg, respectively, were obtained both as white solids according to the same method as in Example 2, for which, however, (2S*)—N²,N²-dimethylindan-2,5-diamine, and (2R*)—N²,N²-dimethylindan-2,5-diamine obtained in Production Example 17 were used in place of 2,4,4-trimethyl-1,2,3,4-tetrahydroisoquinolin-7-amine in Example 2.
¹H-NMR (400 MHz, DMSO-d₆) δ: 11.79 (1H, s), 10.05 (1H, s), 9.10 (1H, s), 8.87 (1H, s), 7.76 (1H, brs), 7.61 (2H, d, J=7.8 Hz), 7.48 (2H, d, J=7.3 Hz), 7.10 (1H, d, J=7.8 Hz), 3.00-2.92 (3H, m), 2.75-2.69 (2H, m), 2.20 (6H, s)
ESI-MS Found: m/z [M+H]⁺ 483

EXAMPLE 40

Production of 3-(2,6-dichlorophenyl)-7-{[2-(2-hydroxyethyl)-1,2,3,4-tetrahydroisoquinolin-7-yl]amino}-4-imino-1-methyl-3,4-dihydropyrimido[4,5-d]pyrimidin-2(1H)-one

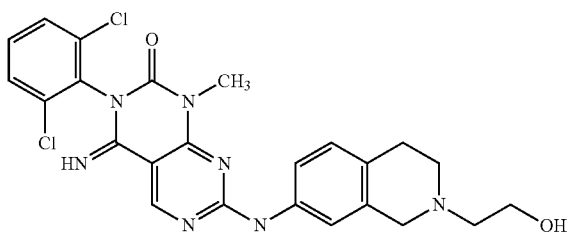 [SMILES: Cn1c(=O)n(-c2c(Cl)cccc2Cl)c(=N)c2cnc(Nc3ccc4c(c3)CN(CCO)CC4)nc21]

170 mg of the entitled compound was obtained as a white solid according to the same method as in Example 2, for which, however, 7-chloro-3-(2,6-dichlorophenyl)-4-imino-1-methyl-3,4-dihydropyrimido[4,5-d]pyrimidin-2(1H)-one obtained in Production Example 7 was used in place of 7-chloro-3-(2,6-dichlorophenyl)-4-imino-3,4-dihydropyrimido[4,5-d]pyrimidin-2(1H)-one used in Example 2, and 2-(7-amino-3,4-dihydroisoquinolin-2(1H)-yl)ethanol was used in place of 2,4,4-trimethyl-1,2,3,4-tetrahydroisoquinolin-7-amine used in Example 2.
¹H-NMR (400 MHz, CD₃OD) δ: 8.99 (1H, s), 7.41-7.58 (5H, m), 7.15 (1H, d, J=8.8 Hz), 3.79 (2H, t, J=5.6 Hz), 3.77 (2H, s), 3.63 (3H, s), 2.89-2.95 (4H, m), 2.78 (2H, t, J=5.6 Hz)
ESI-MS Found: m/z [M+H]⁺ 512

EXAMPLE 41

Production of 3-(2,6-dichlorophenyl)-7-[(2-ethyl-1,1-dimethyl-1,2,3,4-tetrahydroisoquinolin-6-yl)amino]-4-imino-3,4-dihydropyrimido[4,5-d]pyrimidin-2(1H)-one

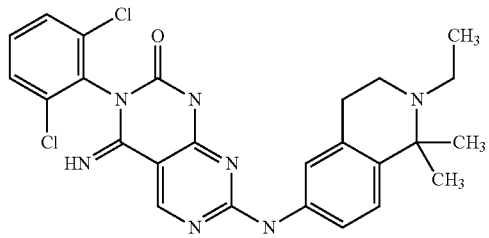 [SMILES: CCN1CCc2cc(Nc3ncc4c(=N)n(-c5c(Cl)cccc5Cl)c(=O)[nH]c4n3)ccc2C1(C)C]

54 mg of the entitled compound was obtained as a pale yellow solid according to the same method as in Example 2, for which, however, 2-ethyl-1,1-dimethyl-1,2,3,4-tetrahydroisoquinolin-6-amine obtained in Production Example 41 was used in place of 2,4,4-trimethyl-1,2,3,4-tetrahydroisoquinolin-7-amine in Example 2.
¹H-NMR (400 MHz, DMSO-d₆) δ: 11.81 (1H, s), 10.01 (1H, s), 9.10 (1H, s), 8.87 (1H, s), 7.81-7.40 (5H, m), 7.20 (1H, d, J=8.8 Hz), 3.36-3.27 (2H, m), 2.72 (4H, s), 1.29 (6H, s), 1.05 (3H, t, J=6.8 Hz)
ESI-MS Found: m/z [M+H]⁺ 510

EXAMPLE 42

Production of 3-(2,6-dichlorophenyl)-7-{[2-(2-hydroxy-2-methylpropyl)-1,1-dimethyl-1,2,3,4-tetrahydroisoquinolin-6-yl]amino}-4-imino-3,4-dihydropyrimido[4,5-d]pyrimidin-2(1H)-one

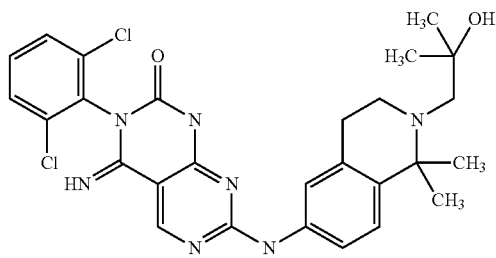 [SMILES: CC(C)(O)CN1CCc2cc(Nc3ncc4c(=N)n(-c5c(Cl)cccc5Cl)c(=O)[nH]c4n3)ccc2C1(C)C]

30 mg of the entitled compound was obtained as a white solid according to the same method as in Example 2, for which, however, 1-(6-amino-1,1-dimethyl-3,4-dihydroisoquinolin-2(1H)-yl)-2-methylpropan-2-ol obtained in Production Example 42 was used in place of 2,4,4-trimethyl-1,2,3,4-tetrahydroisoquinolin-7-amine in Example 2.
¹H-NMR (400 MHz, DMSO-d₆) δ: 11.80 (1H, s), 10.00 (1H, s), 9.10 (1H, s), 8.87 (1H, s), 7.78-7.40 (5H, m), 7.19

(1H, d, J=8.8 Hz), 4.05-3.96 (1H, m), 2.92 (2H, t, J=5.4 Hz), 2.73 (2H, t, J=5.4 Hz), 2.39 (2H, s), 1.26 (6H, s), 1.11 (6H, s)
ESI-MS Found: m/z [M+H]$^+$ 554

EXAMPLE 43

Production of 3-(2,6-dichlorophenyl)-7-{[(7S*)-7-(dimethylamino)-5,6,7,8-tetrahydronaphthalen-2-yl]amino}-4-imino-3,4-dihydropyrimido[4,5-d]pyrimidin-2(1H)-one, and 3-(2,6-dichlorophenyl)-7-{[(7R*)-7-(dimethylamino)-5,6,7,8-tetrahydronaphthalen-2-yl]amino}-4-imino-3,4-dihydropyrimido[4,5-d]pyrimidin-2(1H)-one

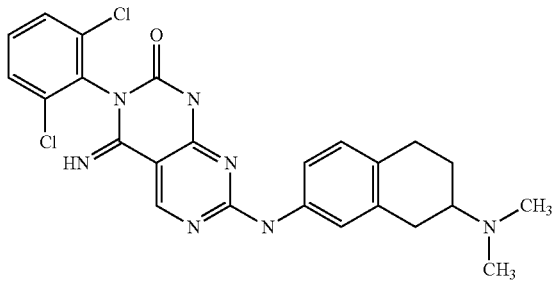 [SMILES: CN(C)C1CCc2ccc(Nc3ncc4c(=N)n(-c5c(Cl)cccc5Cl)c(=O)[nH]c4n3)cc2C1]

The entitled compounds, 51 mg and 60 mg, respectively, were obtained both as yellow solids according to the same method as in Example 2, for which, however, (2S*)—N$^2$,N$^2$-dimethyl-1,2,3,4-tetrahydronaphthalene-2,7-diamine and (2R*)—N$^2$,N$^2$-dimethyl-1,2,3,4-tetrahydronaphthalene-2,7-diamine obtained in Production Example 39 were used in place of 2,4,4-trimethyl-1,2,3,4-tetrahydroisoquinolin-7-amine in Example 2.

$^1$H-NMR (400 MHz, DMSO-d$_6$) δ: 11.80 (1H, s), 10.01 (1H, s), 9.09 (1H, s), 8.87 (1H, s), 7.74-7.57 (3H, m), 7.50-7.39 (2H, m), 6.97 (1H, d, J=8.3 Hz), 2.88-2.75 (3H, m), 2.72-2.63 (2H, m), 2.25 (6H, s), 2.00-1.94 (1H, m), 1.58-1.47 (1H, m)
ESI-MS Found: m/z [M+H]$^+$ 496

EXAMPLE 44

Production of 3-(2,6-dichlorophenyl)-4-imino-7-[(2,3,3-trimethyl-2,3-dihydro-1H-isoindol-5-yl)amino]-3,4-dihydropyrimido[4,5-d]pyrimidin-2(1H)-one

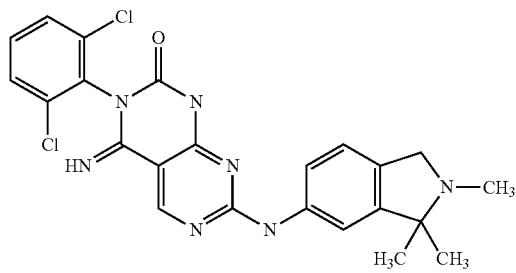 [SMILES: CN1Cc2ccc(Nc3ncc4c(=N)n(-c5c(Cl)cccc5Cl)c(=O)[nH]c4n3)cc2C1(C)C]

83 mg of the entitled compound was obtained as a pale yellow solid according to the same method as in Example 2, for which, however, 5-amino-2,3,3-trimethylisoindoline obtained in Production Example 50 was used in place of 2,4,4-trimethyl-1,2,3,4-tetrahydroisoquinolin-7-amine in Example 2.

$^1$H-NMR (400 MHz, DMSO-d$_6$) δ: 11.89 (1H, brs), 10.10 (1H, brs), 9.12 (1H, s), 8.88 (1H, s), 7.96-7.38 (5H, m), 7.12 (1H, d, J=8.0 Hz), 3.77 (2H, s), 2.35 (3H, s), 1.21 (6H, s)
ESI-MS Found: m/z [M+H]$^+$ 510

EXAMPLE 45

Production of 3-(2,6-dichlorophenyl)-4-imino-7-{[3-(2-methoxyethyl)-2,3,4,5-tetrahydro-1H-3-benzazepin-7-yl]amino}-3,4-dihydropyrimido[4,5-d]pyrimidin-2(1H)-one

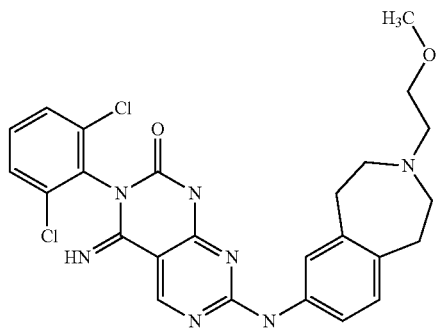 [SMILES: COCCN1CCc2ccc(Nc3ncc4c(=N)n(-c5c(Cl)cccc5Cl)c(=O)[nH]c4n3)cc2CC1]

43 mg of the entitled compound was obtained as a pale yellow solid according to the same method as in Example 2, for which, however, 3-(2-methoxyethyl)-2,3,4,5-tetrahydro-1H-3-benzazepin-7-amine obtained in Production Example 13 was used in place of 2,4,4-trimethyl-1,2,3,4-tetrahydroisoquinolin-7-amine in Example 2.

$^1$H-NMR (400 MHz, DMSO-d$_6$) δ: 11.82 (1H, brs), 10.04 (1H, brs), 9.10 (1H, s), 8.88 (1H, s), 7.75-7.59 (3H, m), 7.50-7.44 (2H, m), 7.02 (1H, d, J=8.3 Hz), 3.44 (2H, t, J=5.9 Hz), 3.23 (3H, s), 2.85-2.76 (4H, m), 2.67-2.54 (6H, m)
ESI-MS Found: m/z [M+H]$^+$ 526

EXAMPLE 46

Production of 3-(2,6-dichlorophenyl)-7-{[2-(2-hydroxyethyl)-4,4-dimethyl-1,2,3,4-tetrahydroisoquinolin-7-yl]amino}-4-imino-3,4-dihydropyrimido[4,5-d]pyrimidin-2(1H)-one

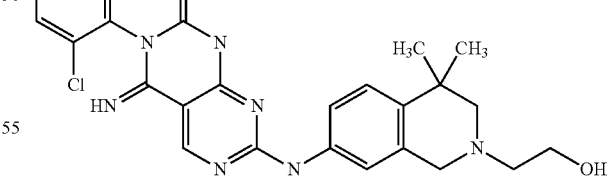

80 mg of the entitled compound was obtained as a white solid according to the same method as in Example 2, for which, however, 2-(7-amino-4,4-dimethyl-3,4-dihydroisoquinolin-2(1H)-yl)ethanol was used in place of 2,4,4-trimethyl-1,2,3,4-tetrahydroisoquinolin-7-amine in Example 2.

$^1$H-NMR (400 MHz, CD$_3$OD) δ: 8.98 (1H, brs), 7.40-7.58 (5H, m), 7.30 (1H, d, J=8.8 Hz), 3.77 (2H, d, J=6.4 Hz), 3.68 (3H, s), 2.68 (2H, d, J=6.4 Hz), 2.54 (2H, s), 1.32 (6H, s)
ESI-MS Found: m/z [M+H]$^+$ 526

EXAMPLE 47

Production of 3-(2,6-dichlorophenyl)-7-({2-[(2S)-2-hydroxypropyl]-1,2,3,4-tetrahydroisoquinolin-6-yl}amino)-4-imino-3,4-dihydropyrimido[4,5-d]pyrimidin-2(1H)-one

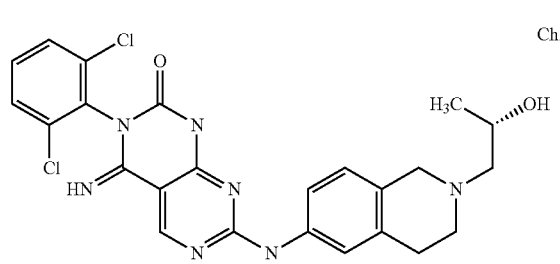

24.2 mg of the entitled compound was obtained as a white solid according to the same method as in Example 2, for which, however, (2S)-1-(6-amino-3,4-dihydroisoquinolin-2 (1H)-yl)propan-2-ol obtained in Production Example 35 was used in place of 2,4,4-trimethyl-1,2,3,4-tetrahydroisoquinolin-7-amine in Example 2.

$^1$H-NMR (400 MHz, DMSO-d$_6$) δ: 11.84 (1H, s), 10.07 (1H, s), 9.14 (1H, s), 8.91 (1H, s), 7.65-7.52 (5H, m), 6.99 (1H, d, J=8.0 Hz), 4.39 (1H, s), 3.88 (1H, s), 3.58 (2H, s), 2.83 (2H, m), 2.72 (2H, m), 2.40 (1H, dd, J=12.4, 7.2 Hz), 2.40 (1H, dd, J=12.4, 5.2 Hz), 1.11 (3H, d, J=6.4 Hz)

ESI-MS Found: m/z [M+H]$^+$ 512

EXAMPLE 48

Production of 3-(2,6-dichlorophenyl)-4-imino-7-[(3-methyl-2,3,4,5-tetrahydro-1H-3-benzazepin-7-yl)amino]-3,4-dihydropyrimido[4,5-d]pyrimidin-2(1H)-one

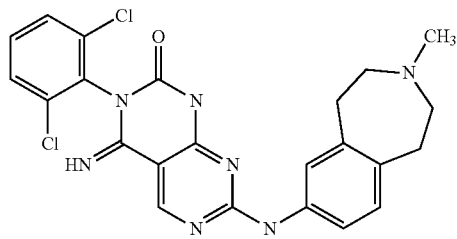 [SMILES: CN1CCc2ccc(Nc3ncc4c(=N)n(-c5c(Cl)cccc5Cl)c(=O)[nH]c4n3)cc2CC1]

24 mg of the entitled compound was obtained as a white solid according to the same method as in Example 2, for which, however, 3-methyl-2,3,4,5-tetrahydro-1H-3-benzazepin-7-amine obtained in Production Example 11 was used in place of 2,4,4-trimethyl-1,2,3,4-tetrahydroisoquinolin-7-amine in Example 2.

$^1$H-NMR (400 MHz, DMSO-d$_6$) δ: 11.82 (1H, brs), 10.04 (1H, brs), 9.10 (1H, brs), 8.87 (1H, brs), 7.76-7.59 (3H, m), 7.50-7.44 (2H, m), 7.02 (1H, d, J=8.3 Hz), 2.87-2.78 (4H, m), 2.47-2.41 (4H, m), 2.25 (3H, s)

ESI-MS Found: m/z [M+H]$^+$ 482

EXAMPLE 49

Production of 3-(2,6-dichlorophenyl)-7-[(1,1-dimethyl-1,2,3,4-tetrahydroisquinolin-6-yl)amino]-4-imino-3,4-dihydropyrimido[4,5-d]pyrimidin-2(1H)-one

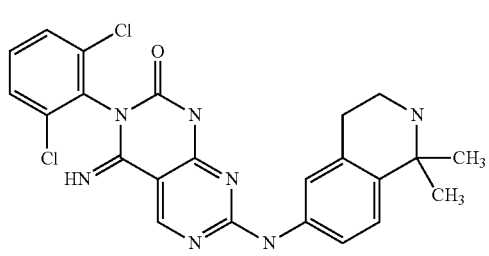 [SMILES: CC1(C)NCCc2cc(Nc3ncc4c(=N)n(-c5c(Cl)cccc5Cl)c(=O)[nH]c4n3)ccc21]

5.4 mg of the entitled compound was obtained as a colorless amorphous substance according to the same method as in Example 2, for which, however, 1,1-dimethyl-1,2,3,4-tetrahydroisoquinolin-6-amine obtained in Production Example 29-3) was used in place of 2,4,4-trimethyl-1,2,3,4-tetrahydroisoquinolin-7-amine in Example 2.

$^1$H-NMR (400 MHz, CD$_3$OD) δ: 8.98 (1H, s), 7.62-7.45 (5H, m), 7.23 (1H, d, J=8.6 Hz), 3.13 (2H, t, J=6.1 Hz), 2.86 (2H, t, J=6.1 Hz), 1.48 (6H, s)

ESI-MS Found: m/z [M+H]$^+$ 482

EXAMPLE 50

Production of 7-[(3-cyclopropyl-2,3,4,5-tetrahydro-1H-3-benzazepin-7-yl)amino]-3-(2,6-dichlorophenyl)-4-imino-3,4-dihydropyrimido[4,5-d]pyrimidin-2(1H)-one

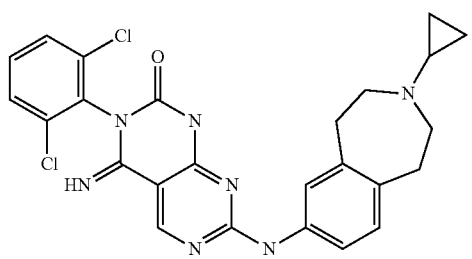 [SMILES: N=c1c2cnc(Nc3ccc4c(c3)CCN(C3CC3)CC4)nc2[nH]c(=O)n1-c1c(Cl)cccc1Cl]

25 mg of the entitled compound was obtained as a white solid according to the same method as in Example 2, for which, however, 3-cyclopropyl-2,3,4,5-tetrahydro-1H-3-benzazepin-7-amine obtained in Production Example 12 was used in place of 2,4,4-trimethyl-1,2,3,4-tetrahydroisoquinolin-7-amine in Example 2.

$^1$H-NMR (400 MHz, DMSO-d$_6$) δ: 11.83 (1H, brs), 10.05 (1H, brs), 9.10 (1H, s), 8.88 (1H, s), 7.76-7.68 (1H, m), 7.63-7.59 (2H, m), 7.49-7.44 (2H, m), 7.03 (1H, d, J=8.6 Hz), 2.84-2.65 (8H, m), 1.83-1.77 (1H, m), 0.49-0.34 (4H, m)

ESI-MS Found: m/z [M+H]$^+$ 508

EXAMPLE 51

Production of 3-(2,6-dichlorophenyl)-4-imino-7-{[2-(2-methoxyethyl)-1,2,3,4-tetrahydroisoquinolin-7-yl]amino}-3,4-dihydropyrimido[4,5-d]pyrimidin-2(1H)-one

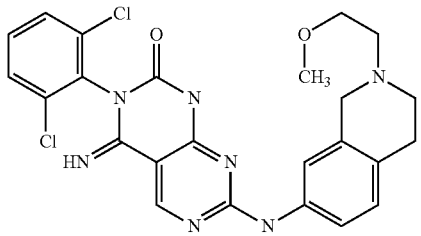 [SMILES: COCCN1CCc2ccc(Nc3ncc4c(=N)n(-c5c(Cl)cccc5Cl)c(=O)[nH]c4n3)cc2C1]

22 mg of the entitled compound was obtained as a pale yellow solid according to the same method as in Example 2, for which, however, 2-(2-methoxyethyl)-1,2,3,4-tetrahydroisoquinolin-7-amine obtained in Production Example 25 was used in place of 2,4,4-trimethyl-1,2,3,4-tetrahydroisoquinolin-7-amine in Example 2.

$^1$H-NMR (400 MHz, DMSO-$d_6$) δ: 11.82 (1H, brs), 10.05 (1H, brs), 9.10 (1H, brs), 8.88 (1H, brs), 7.75-7.57 (3H, m), 7.49-7.41 (2H, m), 7.01 (1H, d, J=8.0 Hz), 3.58 (2H, s), 3.52 (2H, t, J=5.9 Hz), 3.26 (3H, s), 2.75-2.72 (2H, m), 2.71-2.67 (2H, m), 2.64 (2H, t, J=5.9 Hz)

ESI-MS Found: m/z [M+H]$^+$ 512

EXAMPLE 52

Production of 3-(2,6-dichlorophenyl)-4-imino-7-[(2-methyl-1,2,3,4-tetrahydroisoquinolin-7-yl)amino]-3,4-dihydropyrimido[4,5-d]pyrimidin-2(1H)-one

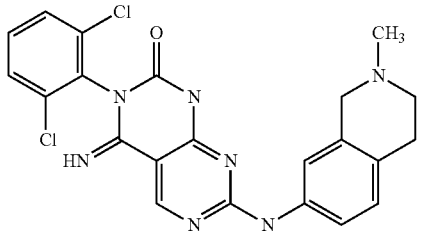 [SMILES: CN1CCc2ccc(Nc3ncc4c(=N)n(-c5c(Cl)cccc5Cl)c(=O)[nH]c4n3)cc2C1]

15 mg of the entitled compound was obtained as a pale yellow solid according to the same method as in Example 2, for which, however, 2-methyl-1,2,3,4-tetrahydroisoquinolin-7-amine obtained in Production Example 22 was used in place of 2,4,4-trimethyl-1,2,3,4-tetrahydroisoquinolin-7-amine in Example 2.

$^1$H-NMR (400 MHz, DMSO-$d_6$) δ: 10.04 (1H, brs), 9.10 (1H, brs), 8.87 (1H, brs), 7.72 (1H, brs), 7.63-7.58 (2H, m), 7.47 (1H, t, J=8.0 Hz), 7.45-7.40 (1H, m), 7.01 (1H, d, J=8.3 Hz), 3.47 (2H, s), 2.76 (2H, t, J=5.9 Hz), 2.57 (2H, t, J=5.9 Hz), 2.33 (3H, s)

ESI-MS Found: m/z [M+H]$^+$ 468

EXAMPLE 53

Production of 3-(2,6-dichlorophenyl)-7-({(6R*)-6-[(dimethylamino)methyl]-5,6,7,8-tetrahydronaphthalen-2-yl}amino)-4-imino-3,4-dihydropyrimido[4,5-d]pyrimidin-2(1H)-one, and 3-(2,6-dichlorophenyl)-7-({(6S*)-6-[(dimethylamino)methyl]-5,6,7,8-tetrahydronaphthalen-2-yl}amino)-4-imino-3,4-dihydropyrimido[4,5-d]pyrimidin-2(1H)-one

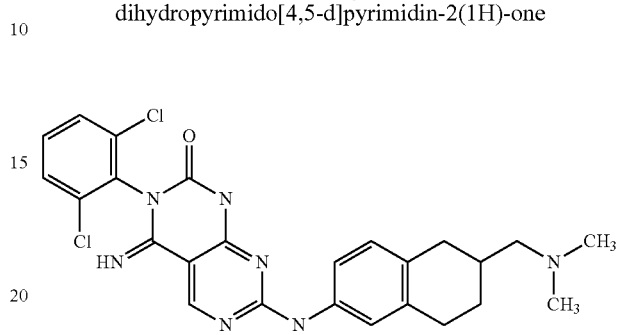

The entitled compounds, 60 mg and 49 mg, respectively, were obtained both as yellow solids according to the same method as in Example 2, for which, however, (6R*)-6-[(dimethylamino)methyl]-5,6,7,8-tetrahydronaphthalen-2-amine and (6S*)-6-[(dimethylamino)methyl]-5,6,7,8-tetrahydronaphthalen-2-amine obtained in Production Example 38 were used in place of 2,4,4-trimethyl-1,2,3,4-tetrahydroisoquinolin-7-amine in Example 2.

$^1$H-NMR (400 MHz, DMSO-$d_6$) δ: 11.78 (1H, s), 9.99 (1H, s), 9.09 (1H, s), 8.86 (1H, s), 7.61 (3H, d, J=7.8 Hz), 7.47 (2H, t, J=8.0 Hz), 6.98 (1H, d, J=8.3 Hz), 2.83-2.70 (3H, m), 2.28 (1H, dd, J=16.1, 9.3 Hz), 2.18-2.14 (2H, m), 2.15 (6H, s), 1.94-1.83 (2H, m), 1.36-1.26 (1H, m)

ESI-MS Found: m/z [M+H]$^+$ 510

EXAMPLE 54

Production of 3-(2,6-dichlorophenyl)-4-imino-7-[(2-isopropyl-1,2,3,4-tetrahydroisoquinolin-7-yl)amino]-3,4-dihydropyrimido[4,5-d]pyrimidin-2(1H)-one 1) Production of 4-amino-2-[(2-isopropyl-1,2,3,4-tetrahydroisoquinolin-7-yl)amino]pyrimidine-5-carbonitrile

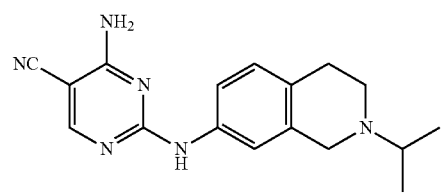 [SMILES: CC(C)N1CCc2ccc(Nc3ncc(C#N)c(N)n3)cc2C1]

1.9 g of 3-chloroperbenzoic acid was added to a toluene (80 mL)-tetrahydrofuran (20 mL) solution of 1.0 g of 4-amino-2-(methylthio)pyrimidine-5-carbonitrile, and stirred at room temperature for 20 minutes. 2.3 g of N,N-diisopropylethylamine and 1.1 g of 2-isopropyl-1,2,3,4-tetrahydroisoquinolin-7-amine obtained in Production Example 23 were added to the reaction liquid, and stirred at 80° C. for 20 hours. The reaction liquid was cooled, then diluted with 10% isopropanol/chloroform mixed solvent, washed with water, dried with anhydrous magnesium sulfate, filtered and the solvent was evaporated away. The resulting roughly-purified product was purified through basic silica gel column chromatography to obtain 0.88 g of the entitled compound as a white solid.

$^1$H-NMR (400 MHz, CDCl$_3$) δ: 8.28 (1H, s), 7.25-7.20 (1H, m), 7.20-7.11 (1H, m), 7.07 (1H, d, J=8.3 Hz), 5.39 (2H, s), 3.73 (2H, s), 2.96-2.88 (1H, m), 2.87 (2H, t, J=5.9 Hz), 2.78 (2H, t, J=5.9 Hz), 1.15 (6H, d, J=6.8 Hz)

ESI-MS Found: m/z [M+H]$^+$ 309

2) Production of 3-(2,6-dichlorophenyl)-4-imino-7-[(2-isopropyl-1,2,3,4-tetrahydroisoquinolin-7-yl)amino]-3,4-dihydropyrimido[4,5-d]pyrimidin-2(1H)-one

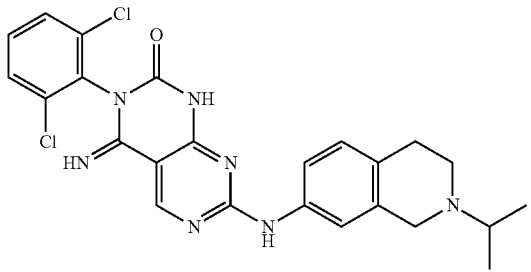 [SMILES: CC(C)N1CCc2ccc(Nc3ncc4c(=N)n(-c5c(Cl)cccc5Cl)c(=O)[nH]c4n3)cc2C1]

172 mg of sodium hydride was added to an N,N-dimethylformamide (20 mL) solution of 884 mg of the compound obtained in the above 1), and stirred at room temperature for 5 minutes. 680 mg of 2,6-dichlorophenyl isocyanate was added to the reaction liquid, and stirred at room temperature for 40 minutes. Water and aqueous 5 N hydrochloric acid solution were added to the reaction solution, and concentrated under reduced pressure. The organic layer was separated. This was washed with saturated saline water, dried with anhydrous magnesium sulfate, and the solvent was evaporated away. The resulting roughly-purified product was purified through basic silica gel column chromatography to obtain 620 mg of the entitled compound as a white solid.

$^1$H-NMR (400 MHz, DMSO-d$_6$) δ: 11.86-11.80 (1H, m), 10.08-10.03 (1H, m), 9.10 (1H, s), 8.88 (1H, s), 7.75-7.69 (1H, m), 7.63-7.59 (2H, m), 7.53-7.38 (2H, m), 7.00 (1H, d, J=8.8 Hz), 3.66-3.60 (2H, m), 2.90-2.81 (1H, m), 2.76-2.63 (4H, m), 1.06 (6H, d, J=5.4 Hz)

ESI-MS Found: m/z [M+H]$^+$ 496

EXAMPLE 55

Production of 7-[(2-cyclopropyl-1,1-dimethyl-1,2,3,4-tetrahydroisoquinolin-6-yl)amino]-3-(2,6-dichlorophenyl)-4-imino-3,4-dihydropyrimido[4,5-d]pyrimidin-2(1H)-one

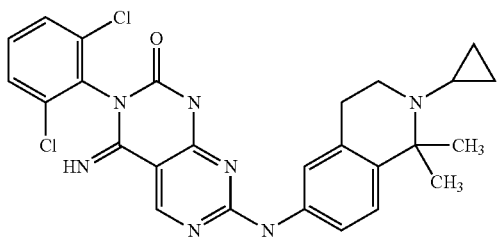 [SMILES: CC1(C)c2ccc(Nc3ncc4c(=N)n(-c5c(Cl)cccc5Cl)c(=O)[nH]c4n3)cc2CCN1C1CC1]

42 mg of the entitled compound was obtained as a yellow solid according to the same method as in Example 2, for which, however, 2-cyclopropyl-1,1-dimethyl-1,2,3,4-tetrahydroisoquinolin-6-amine obtained in Production Example 43 was used in place of 2,4,4-trimethyl-1,2,3,4-tetrahydroisoquinolin-7-amine in Example 2.

$^1$H-NMR (400 MHz, DMSO-d$_6$) δ: 11.80 (1H, s), 10.01 (1H, s), 9.10 (1H, s), 8.88 (1H, s), 7.75-7.42 (5H, m), 7.22 (1H, d, J=8.5 Hz), 2.96 (2H, t, J=5.6 Hz), 2.72 (2H, t, J=5.6 Hz), 1.96-1.89 (1H, m), 1.42 (6H, s), 0.60-0.53 (2H, m), 0.41-0.35 (2H, m)

ESI-MS Found: m/z [M+H]$^+$ 522

EXAMPLE 56

Production of 3-(2,6-dichlorophenyl)-4-imino-7-{[2-(2-methoxyethyl)-1,2,3,4-tetrahydroisoquinolin-6-yl]amino}-3,4-dihydropyrimido[4,5-d]pyrimidin-2(1H)-one

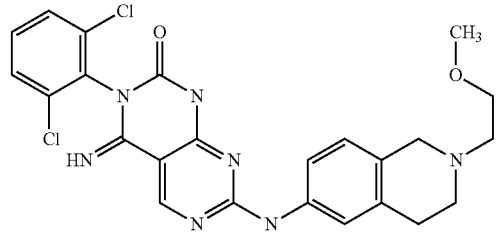 [SMILES: COCCN1CCc2cc(Nc3ncc4c(=N)n(-c5c(Cl)cccc5Cl)c(=O)[nH]c4n3)ccc2C1]

25.5 mg of the entitled compound was obtained as a white solid according to the same method as in Example 2, for which, however, 2-(2-methoxyethyl)-1,2,3,4-tetrahydroisoquinolin-6-amine obtained in Production Example 36 was used in place of 2,4,4-trimethyl-1,2,3,4-tetrahydroisoquinolin-7-amine in Example 2.

$^1$H-NMR (400 MHz, DMSO-d$_6$) δ: 11.85 (1H, s), 10.07 (1H, s), 9.14 (1H, s), 8.91 (1H, s), 7.70-7.52 (5H), 6.99 (1H, d, J=8.0 Hz), 3.58-3.53 (4H, m), 3.29 (3H, s), 2.82 (2H, m), 2.72 (2H, m), 2.66 (2H, m)

ESI-MS Found: m/z [M+H]$^+$ 512

EXAMPLE 57

Production of 3-(2,6-dichlorophenyl)-7-{[(6R*)-6-(dimethylamino)-5,6,7,8-tetrahydronaphthalen-2-yl]amino}-4-imino-3,4-dihydropyrimido[4,5-d]pyrimidin-2(1H)-one, and 3-(2,6-dichlorophenyl)-7-{[(6S*)-6-(dimethylamino)-5,6,7,8-tetrahydronaphthalen-2-yl]amino}-4-imino-3,4-dihydropyrimido[4,5-d]pyrimidin-2(1H)-one

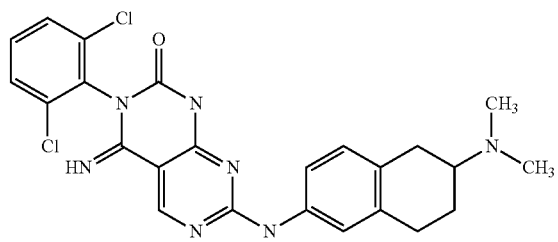 [SMILES: CN(C)C1CCc2cc(Nc3ncc4c(=N)n(-c5c(Cl)cccc5Cl)c(=O)[nH]c4n3)ccc2C1]

The entitled compounds, 71 mg and 62 mg, respectively, were obtained both as yellow solids according to the same method as in Example 2, for which, however, (2S*)—$N^2,N^2$-dimethyl-1,2,3,4-tetrahydronaphthalene-2,6-diamine and (2R*)—$N^2,N^2$-dimethyl-1,2,3,4-tetrahydronaphthalene-2,6-diamine obtained in Production Example 39 were used in place of 2,4,4-trimethyl-1,2,3,4-tetrahydroisoquinolin-7-amine in Example 2.

$^1$H-NMR (400 MHz, DMSO-$d_6$) δ: 11.80 (1H, brs), 9.99 (1H, s), 9.08 (1H, s), 8.86 (1H, s), 7.61 (3H, brs), 7.47 (2H, d, J=7.8 Hz), 7.00 (1H, d, J=8.3 Hz), 2.86-2.68 (4H, m), 2.62 (1H, dd, J=15.9, 10.0 Hz), 2.23 (6H, s), 2.02-1.95 (1H, m), 1.58-1.48 (1H, m)

ESI-MS Found: m/z [M+H]$^+$ 496

EXAMPLE 58

Production of 3-(2,6-dichlorophenyl)-4-imino-7-[(2'-methyl-3',4'-dihydro-2'H-spiro[cyclopropane-1,1'-isoquinolin]-6'-yl)amino]-3,4-dihydropyrimido[4,5-d]pyrimidin-2(1H)-one

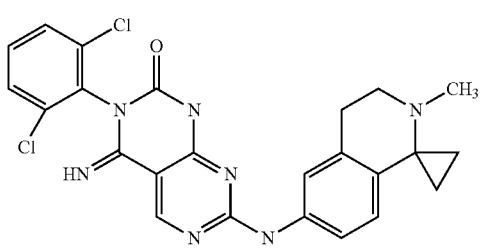 [SMILES: CN1CCc2cc(Nc3ncc4c(=N)n(-c5c(Cl)cccc5Cl)c(=O)[nH]c4n3)ccc2C12CC2]

52 mg of the entitled compound was obtained as a white solid according to the same method as in Example 2, for which, however, 2'-methyl-3',4'-dihydro-2'H-spiro[cyclopropane-1,1'-isoquinolin]-6'-amine obtained in Production Example 20 was used in place of 2,4,4-trimethyl-1,2,3,4-tetrahydroisoquinolin-7-amine in Example 2.

$^1$H-NMR (400 MHz, CDCl$_3$) δ: 9.09 (1H, s), 7.65-7.25 (5H, m), 6.73-6.57 (1H, m), 3.29-3.14 (2H, m), 3.01-2.85 (2H, m), 2.40 (3H, s), 1.17-0.97 (4H, m)

ESI-MS Found: m/z [M+H]$^+$ 494

EXAMPLE 59

Production of 3-(2,6-dichlorophenyl)-4-imino-7-{[2-(2-methoxyethyl)-1,1-dimethyl-1,2,3,4-tetrahydroisoquinolin-6-yl]amino}-3,4-dihydropyrimido[4,5-d]pyrimidin-2(1H)-one

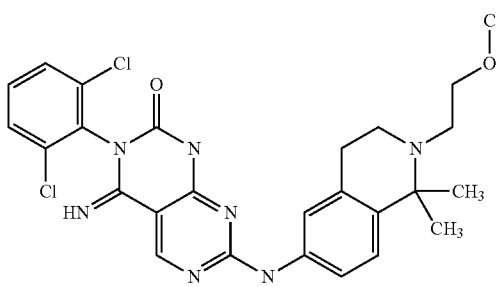

20 mg of the entitled compound was obtained as a white solid according to the same method as in Example 2, for which, however, 2-(2-methoxyethyl)-1,1-dimethyl-1,2,3,4-tetrahydroisoquinolin-6-amine obtained in Production Example 46 was used in place of 2,4,4-trimethyl-1,2,3,4-tetrahydroisoquinolin-7-amine in Example 2.

$^1$H-NMR (400 MHz, DMSO-$d_6$) δ: 11.80 (1H, s), 10.01 (1H, s), 9.10 (1H, s), 8.88 (1H, s), 7.77-7.42 (5H, m), 7.20 (1H, d, J=8.8 Hz), 3.40 (2H, t, J=6.5 Hz), 3.26 (3H, s), 2.79 (2H, t, J=5.4 Hz), 2.72 (2H, t, J=5.4 Hz), 2.63 (2H, t, J=6.5 Hz), 1.28 (6H, s)

ESI-MS Found: m/z [M+H]$^+$ 540

EXAMPLE 60

Production of 3-(2,6-dichloro-7-({7S*)-7-[(dimethylamino)methyl]-5,6,7,8-tetrahydronaphthalen-2-yl}amino)-4-imino-3,4-dihydropyrimido[4,5-d]pyrimidin-2(1H)-one, and 3-(2,6-dichlorophenyl)-7-({(7R*)-7-[(dimethylamino)methyl]-5,6,7,8-tetrahydronaphthalen-2-yl}amino)-4-imino-3,4-dihydropyrimido[4,5-d]pyrimidin-2(1H)-one

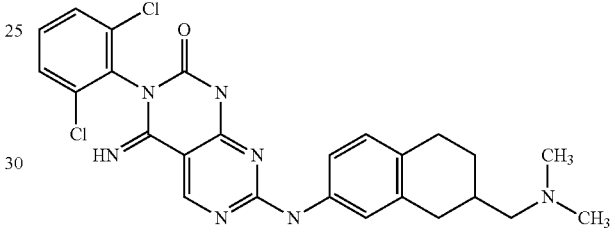

The entitled compounds, 59 mg and 58 mg, respectively, were obtained both as yellow solids according to the same method as in Example 2, for which, however, (7R*)-7-[(dimethylamino)methyl]-5,6,7,8-tetrahydronaphthalen-2-amine and (7S*)-7-[(dimethylamino)methyl]-5,6,7,8-tetrahydronaphthalen-2-amine obtained in Production Example 38 were used in place of 2,4,4-trimethyl-1,2,3,4-tetrahydroisoquinolin-7-amine in Example 2.

$^1$H-NMR (400 MHz, DMSO-$d_6$) δ: 11.85 (1H, s), 10.00 (1H, s), 9.09 (1H, s), 8.86 (1H, s), 7.76-7.57 (3H, m), 7.47 (1H, t, J=8.3 Hz), 7.40 (1H, d, J=7.3 Hz), 6.97 (1H, d, J=8.3 Hz), 2.86 (1H, d, J=17.1 Hz), 2.72-2.65 (2H, m), 2.33 (1H, dd, J=17.3, 10.0 Hz), 2.18-2.13 (2H, m), 2.14 (6H, s), 1.93-1.82 (2H, m), 1.35-1.24 (1H, m)

ESI-MS Found: m/z [M+H]$^+$ 510

EXAMPLE 61

Production of 3-(2,6-dichlorophenyl)-7-{[2-(2-hydroxyethyl)-1,1-dimethyl-1,2,3,4-tetrahydroisoquinolin-6-yl]amino}-4-imino-3,4-dihydropyrimido[4,5-d]pyrimidin-2(1H)-one

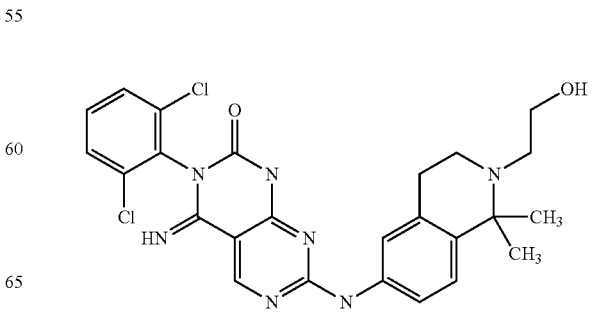

25 mg of the entitled compound was obtained as a white solid according to the same method as in Example 2, for which, however, 2-(6-amino-1,1-dimethyl-3,4-dihydroisoquinolin-2(1H)-yl)ethanol hydrochloride obtained in Production Example 29 was used in place of 2,4,4-trimethyl-1,2,3,4-tetrahydroisoquinolin-7-amine in Example 2.

$^1$H-NMR (400 MHz, DMSO-d$_6$) δ: 11.81 (1H, brs), 10.01 (1H, brs), 9.10 (1H, s), 8.88 (1H, s), 7.78-7.42 (5H, m), 7.20 (1H, d, J=8.8 Hz), 4.30 (1H, brs), 3.50-3.41 (2H, brm), 2.82-2.68 (4H, brm), 2.59-2.46 (2H, m), 1.28 (6H, s)

ESI-MS Found: m/z [M+H]$^+$ 526

EXAMPLE 62

Production of 3-(2,6-dichlorophenyl)-7-{[3-(2-hydroxyethyl)-2,3,4,5-tetrahydro-1H-3-benzazepin-7-yl]amino}-4-imino-3,4-dihydropyrimido[4,5-d]pyrimidin-2(1H)-one

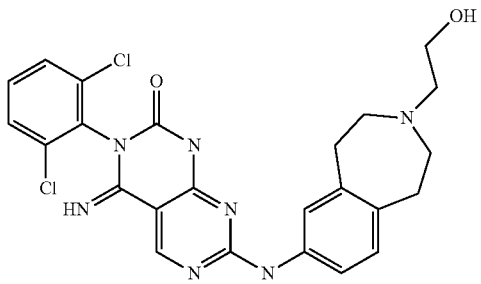 [SMILES: N=c1c2cnc(Nc3ccc4c(c3)CCN(CCO)CC4)nc2[nH]c(=O)n1-c1c(Cl)cccc1Cl]

31 mg of the entitled compound was obtained as a pale yellow solid according to the same method as in Example 2, for which, however, 2-(7-amino-1,2,4,5-tetrahydro-3H-3-benzazepin-3-yl)ethanol obtained in Production Example 14 was used in place of 2,4,4-trimethyl-1,2,3,4-tetrahydroisoquinolin-7-amine in Example 2.

$^1$H-NMR (400 MHz, DMSO-d$_6$) δ: 11.83 (1H, brs), 10.05 (1H, brs), 9.10 (1H, s), 8.88 (1H, s), 7.75-7.58 (3H, m), 7.50-7.44 (2H, m), 7.02 (1H, d, J=8.3 Hz), 4.39 (1H, brs), 3.54-3.48 (2H, m), 2.87-2.77 (4H, m), 2.67-2.46 (6H, m)

ESI-MS Found: m/z [M+H]$^+$ 512

EXAMPLE 63

Production of 3-(2,6-dichlorophenyl)-7-{[2-(N,N-dimethylglycyl)-1,1-dimethyl-1,2,3,4-tetrahydroisoquinolin-6-yl]amino}-4-imino-3,4-dihydropyrimido[4,5-d]pyrimidin-2(1H)-one

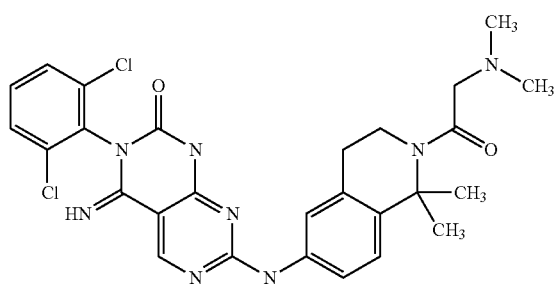 [SMILES: CN(C)CC(=O)N1CCc2cc(Nc3ncc4c(=N)n(-c5c(Cl)cccc5Cl)c(=O)[nH]c4n3)ccc2C1(C)C]

27 mg of the entitled compound was obtained as a white solid according to the same method as in Example 2, for which, however, 2-[(dimethylamino)acetyl]-1,1-dimethyl-1,2,3,4-tetrahydroisoquinolin-6-amine obtained in Production Example 44 was used in place of 2,4,4-trimethyl-1,2,3,4-tetrahydroisoquinolin-7-amine in Example 2.

$^1$H-NMR (400 MHz, CD$_3$OD) δ: 9.00 (1H, s), 7.66-7.55 (4H, m), 7.49 (1H, dd, J=8.8, 7.3 Hz), 7.32 (1H, d, J=8.8 Hz), 3.67 (2H, t, J=5.2 Hz), 3.25 (2H, s), 2.88 (2H, t, J=5.2 Hz), 2.32 (6H, s), 1.80 (6H, s)

ESI-MS Found: m/z [M+H]$^+$ 567

EXAMPLE 64

Production of 3-(2,6-dichlorophenyl)-7-{[2-(2-hydroxyethyl)-1,2,3,4-tetrahydroisoquinolin-6-yl]amino}-4-imino-3,4-dihydropyrimido[4,5-d]pyrimidin-2(1H)-one

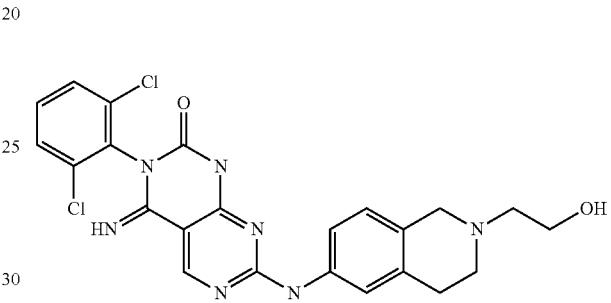

19.8 mg of the entitled compound was obtained as a white solid according to the same method as in Example 2, for which, however, 2-(6-amino-3,4-dihydroisoquinolin-2(1H)-yl)ethanol obtained in Production Example 37 was used in place of 2,4,4-trimethyl-1,2,3,4-tetrahydroisoquinolin-7-amine in Example 2.

$^1$H-NMR (400 MHz, DMSO-d$_6$) δ: 11.84 (1H, s), 10.07 (1H, s), 9.14 (1H, s), 8.91 (1H, s), 7.66-7.52 (5H, m), 6.99 (1H, d, J=8.4 Hz), 4.97 (1H, m), 3.62-3.58 (4H, m), 2.82 (2H, m), 2.72 (2H, m), 2.58 (2H, m)

ESI-MS Found: m/z [M+H]$^+$ 498

EXAMPLE 65

Production of 3-(2,6-dichlorophenyl)-4-imino-7-[(1,1,2-trimethyl-1,2,3,4-tetrahydroisoquinolin-7-yl)amino]-3,4-dihydropyrimido[4,5-d]pyrimidin-2(1H)-one

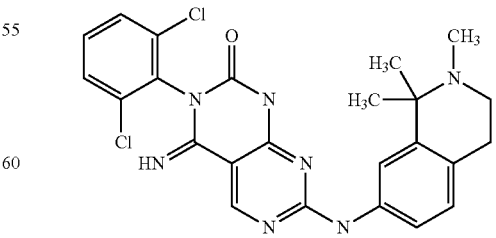

44 mg of the entitled compound was obtained as a yellow solid according to the same method as in Example 2, for which, however, 1,1,2-trimethyl-1,2,3,4-tetrahydroisoquinolin-7-amine obtained in Production Example 33 was used in place of 2,4,4-trimethyl-1,2,3,4-tetrahydroisoquinolin-7-amine in Example 2.

¹H-NMR (400 MHz, DMSO-d₆) δ: 11.81 (1H, s), 9.94 (1H, s), 9.10 (1H, s), 8.87 (1H, s), 7.77-7.42 (5H, m), 6.95 (1H, d, J=8.3 Hz), 2.77-2.68 (4H, m), 2.33 (3H, s), 1.33 (6H, s)

ESI-MS Found: m/z [M+H]⁺ 496

EXAMPLE 66

Production of 3-(2,6-dichlorophenyl)-7-{[2-(2-hydroxy-2-methylpropyl)-1,2,3,4-tetrahydroisoquinolin-7-yl]amino}-4-imino-3,4-dihydropyrimido[4,5-d]pyrimidin-2(1H)-one

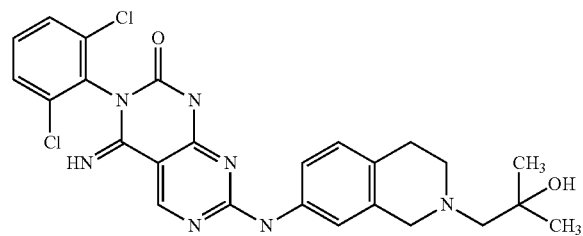 [SMILES: CC(C)(O)CN1CCc2ccc(Nc3ncc4c(=N)n(-c5c(Cl)cccc5Cl)c(=O)[nH]c4n3)cc2C1]

62 mg of the entitled compound was obtained as a pale yellow solid according to the same method as in Example 2, for which, however, 4-(7-amino-3,4-dihydroisoquinolin-2(1H)-yl)-2-methylbutan-2-ol was used in place of 2,4,4-trimethyl-1,2,3,4-tetrahydroisoquinolin-7-amine in Example 2.

¹H-NMR (400 MHz, CD₃OD) δ: 9.00 (1H, s), 7.35-7.58 (5H, m), 7.09 (1H, d, J=8.8 Hz), 3.82 (2H, s), 2.89-2.94 (4H, m), 2.53 (2H, s), 1.24 (6H, s)

ESI-MS Found: m/z [M+H]⁺ 526

EXAMPLE 67

Production of 3-(2,6-dichlorophenyl)-4-imino-7-(1,2,3,4-tetrahydroisoquinolin-7-ylamino)-3,4-dihydropyrimido[4,5-d]pyrimidin-2(1H)-one

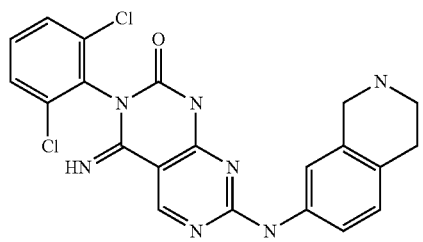 [SMILES: N=c1c2cnc(Nc3ccc4c(c3)CNCC4)nc2[nH]c(=O)n1-c1c(Cl)cccc1Cl]

59 mg of the entitled compound was obtained as a pale yellow solid according to the same method as in Example 2, for which, however, 1,2,3,4-tetrahydroisoquinolin-7-amine obtained in Production Example 27 was used in place of 2,4,4-trimethyl-1,2,3,4-tetrahydroisoquinolin-7-amine in Example 2.

¹H-NMR (400 MHz, DMSO-d₆) δ: 10.01 (1H, s), 9.07 (1H, s), 7.67-7.59 (3H, m), 7.52-7.41 (2H, m), 6.98 (1H, d, J=8.3 Hz), 3.85 (2H, s), 2.94 (2H, t, J=5.6 Hz), 2.64 (2H, t, J=5.9 Hz)

ESI-MS Found: m/z [M+H]⁺ 454

EXAMPLE 68

Production of 3-(2,6-dichlorophenyl)-4-imino-7-[(2-methyl-2,3,4,5-tetrahydro-1H-2-benzazepin-7-yl)amino]-3,4-dihydropyrimido[4,5-d]pyrimidin-2(1H)-one

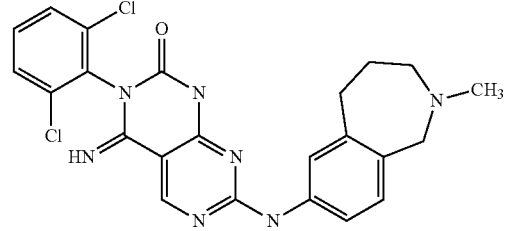 [SMILES: CN1CCCc2cc(Nc3ncc4c(=N)n(-c5c(Cl)cccc5Cl)c(=O)[nH]c4n3)ccc2C1]

1) Production of 3-(2,6-dichlorophenyl)-4-imino-7-[(2,3,4,5-tetrahydro-1H-2-benzazepin-7-yl)amino]-3,4-dihydropyrimido[4,5-d]pyrimidin-2(1H)-one The entitled compound was obtained according to the same method as in Example 2, for which, however, 2,3,4,5-tetrahydro-1H-2-benzazepin-7-amine obtained in Production Example 47 was used in place of 2,4,4-trimethyl-1,2,3,4-tetrahydroisoquinolin-7-amine in Example 2.

2) Production of 3-(2,6-dichlorophenyl)-4-imino-7-[(2-methyl-2,3,4,5-tetrahydro-1H-2-benzazepin-7-yl)amino]-3,4-dihydropyrimido[4,5-d]pyrimidin-2(1H)-one 20 mg of the entitled compound was obtained as a white solid according to the same method as in Production Example 10-6), for which, however, the compound obtained in the above 1) was used in place of (3-tetralone used in Production Example 10-6).

¹H-NMR (400 MHz, DMSO-d₆) δ: 11.82 (1H, brs), 10.06 (1H, brs), 9.11 (1H, s), 8.88 (1H, s), 7.75-7.45 (5H, m), 7.05 (1H, d, J=8.3 Hz), 3.68 (2H, s), 2.92-2.87 (2H, m), 2.85-2.79 (2H, m), 2.16 (3H, s), 1.68-1.61 (2H, m)

ESI-MS Found: m/z [M+H]⁺ 482

EXAMPLE 69

Production of 3-(2,6-dichlorophenyl)-7-({1-[2-(dimethylamino)ethyl]-2,3-dihydro-1H-indol-5-yl}amino)-4-imino-3,4-dihydropyrimido[4,5-d]pyrimidin-2(1H)-one

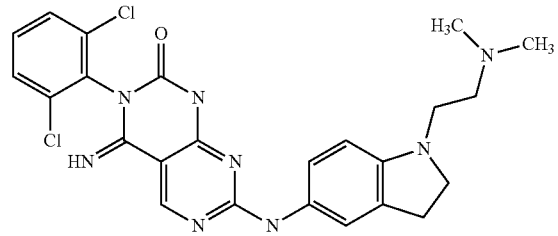 [SMILES: CN(C)CCN1CCc2cc(Nc3ncc4c(=N)n(-c5c(Cl)cccc5Cl)c(=O)[nH]c4n3)ccc21]

The entitled compound was obtained as a yellow solid according to the same method as in Example 2, for which, however, 1-[2-(dimethylamino)ethyl]indolin-5-amine obtained in Production Example 28 was used in place of 2,4,4-trimethyl-1,2,3,4-tetrahydroisoquinolin-7-amine in Example 2.

¹H-NMR (400 MHz, DMSO-d₆) δ: 11.64 (1H, brs), 9.02 (1H, s), 8.76 (1H, s), 7.77-7.21 (5H, m), 6.45 (1H, d, J=8.3 Hz), 3.32 (2H, t, J=8.3 Hz), 3.10 (2H, t, J=7.1 Hz), 2.86 (2H, t, J=8.3 Hz), 2.43 (2H, t, J=7.1 Hz), 2.19 (6H, s)
ESI-MS Found: m/z [M+H]⁺ 511

EXAMPLE 70

Production of 3-(2-chloro-6-methylphenyl)-4-imino-7-{[2-methyl-1,2,3,4-tetrahydroisoquinolin-7-yl]amino}-3,4-dihydropyrimido[4,5-d]pyrimidin-2(1H)-one

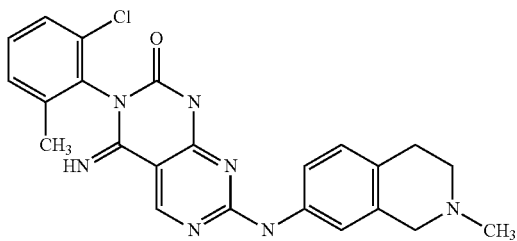 [SMILES: Cc1cccc(Cl)c1-n1c(=O)[nH]c2nc(Nc3ccc4c(c3)CN(C)CC4)ncc2c1=N]

35 mg of the entitled compound was obtained as a white solid according to the same method as in Example 2, for which, however, 2-methyl-1,2,3,4-tetrahydroisoquinolin-7-amine obtained in Production Example 22 was used in place of 2,4,4-trimethyl-1,2,3,4-tetrahydroisoquinolin-7-amine in Example 2, and 7-chloro-3-(2-chloro-6-methylphenyl)-4-imino-3,4-dihydropyrimido[4,5-d]pyrimidin-2(1H)-one obtained in Production Example 2 was used in place of 7-chloro-3-(2,6-dichlorophenyl)-4-imino-3,4-dihydropyrimido[4,5-d]pyrimidin-2(1H)-one.
¹H-NMR (400 MHz, CD₃OD) δ: 9.00 (1H, s), 7.35-7.49 (5H, m), 7.11 (1H, d, J=8.8 Hz), 3.68 (2H, s), 2.95 (2H, t, J=6.4 Hz), 2.81 (2H, t, J=6.4 Hz), 2.25 (3H, s)
ESI-MS Found: m/z [M+H]⁺ 448

EXAMPLE 71

Production of 3-(2,6-dichlorophenyl)-7-{[2-(2-hydroxyethyl)-1,2,3,4-tetrahydroisoquinolin-7-yl]amino}-4-imino-3,4-dihydropyrimido[4,5-d]pyrimidin-2(1H)-one

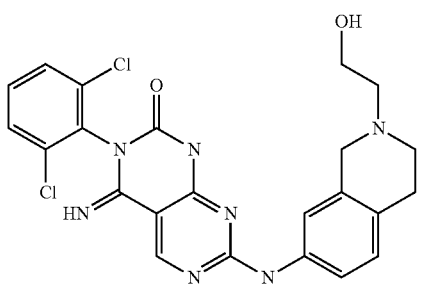 [SMILES: N=c1c2cnc(Nc3ccc4c(c3)CN(CCO)CC4)nc2[nH]c(=O)n1-c1c(Cl)cccc1Cl]

20 mg of the entitled compound was obtained as a white solid according to the same method as in Example 2, for which, however, 2-(7-amino-3,4-dihydroisoquinolin-2(1H)-yl)ethanol obtained in Production Example 26 was used in place of 2,4,4-trimethyl-1,2,3,4-tetrahydroisoquinolin-7-amine in Example 2.

¹H-NMR (400 MHz, DMSO-d₆) δ: 11.84-11.80 (1H, m), 10.08-10.03 (1H, m), 9.10 (1H, s), 8.88 (1H, s), 7.75-7.67 (1H, m), 7.63-7.60 (2H, m), 7.49-7.42 (2H, m), 7.01 (1H, d, J=8.3 Hz), 4.52-4.44 (1H, m), 3.63-3.56 (4H, m), 2.78-2.68 (4H, m), 2.59-2.53 (2H, m)
ESI-MS Found: m/z [M+H]⁺ 498

EXAMPLE 72

Production of 3-(2,6-dichlorophenyl)-1-(2-hydroxyethyl)-4-imino-7-{[2-methyl-1,2,3,4-tetrahydroisoquinolin-7-yl]amino}-3,4-dihydropyrimido[4,5-d]pyrimidin-2(1H)-one

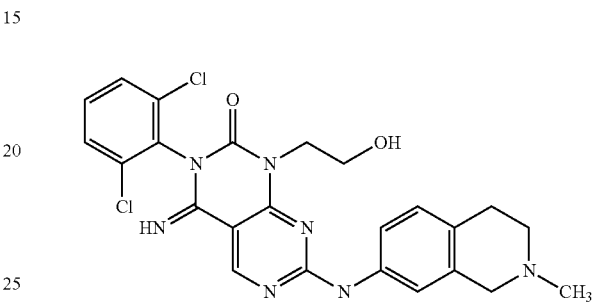

11 mg of the entitled compound was obtained as a pale yellow solid according to the same method as in Example 2, for which, however, 7-chloro-3-(2,6-dichlorophenyl)-4-imino-1-[2-(tetrahydro-2H-pyran-2-yloxy)ethyl]-3,4-dihydropyrimido[4,5-d]pyrimidin-2(1H)-one, which has been obtained according to the same method as in Production Example 7 but using 2-(2-bromoethoxy)tetrahydro-2H-pyran in place of methyl iodide used in Production Example 7, was used as the starting compound and 2-methyl-1,2,3,4-tetrahydroisoquinolin-7-amine obtained according to Production Example 22 was used in place of 2,4,4-trimethyl-1,2,3,4-tetrahydroisoquinolin-7-amine in Example 2.
¹H-NMR (400 MHz, CD₃OD) δ: 8.99 (1H, s), 7.38-7.60 (5H, m), 7.15 (1H, d, J=8.4 Hz), 4.39 (2H, t, J=6.4 Hz), 3.88 (2H, t, J=6.4 Hz), 3.70 (2H, s), 2.96 (2H, t, J=6.4 Hz), 2.82 (2H, t, J=6.4 Hz), 2.51 (3H, s)
ESI-MS Found: m/z [M+H]⁺ 513

EXAMPLE 73

Production of 3-(2,6-dichlorophenyl)-7-{[8-(dimethylamino)-5,6,7,8-tetrahydronaphthalen-2-yl]amino}-4-imino-3,4-dihydropyrimido[4,5-d]pyrimidin-2(1H)-one

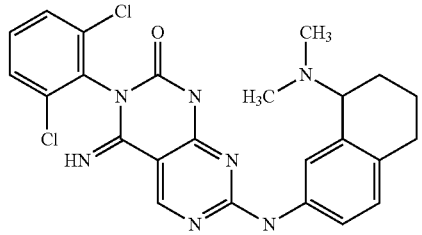 [SMILES: CN(C)C1CCCc2ccc(Nc3ncc4c(=N)n(-c5c(Cl)cccc5Cl)c(=O)[nH]c4n3)cc21]

21 mg of the entitled compound was obtained as a yellow solid according to the same method as in Example 2, for which, however, N',N'-dimethyl-1,2,3,4-tetrahydronaphthalene-1,7-diamine obtained in Production Example 45 was used in place of 2,4,4-trimethyl-1,2,3,4-tetrahydroisoquinolin-7-amine in Example 2.

¹H-NMR (400 MHz, DMSO-d₆) δ: 9.94 (1H, s), 9.08 (1H, s), 8.86 (1H, s), 7.79-7.57 (4H, m), 7.46 (1H, t, J=8.2 Hz), 6.99 (1H, d, J=7.8 Hz), 3.76-3.65 (1H, m), 2.70-2.60 (2H, m), 2.20 (6H, s), 1.98-1.81 (2H, m), 1.65-1.51 (2H, m)

ESI-MS Found: m/z [M+H]⁺ 496

EXAMPLE 74

Production of 2-(7-{[6-(2,6-dichlorophenyl)-5-imino-7-oxo-5,6,7,8-tetrahydropyrimido[4,5-d]pyrimidin-2-yl]amino}-1,2,4,5-tetrahydro-3H-3-benzazepin-3-yl)-N,N-dimethylacetamide

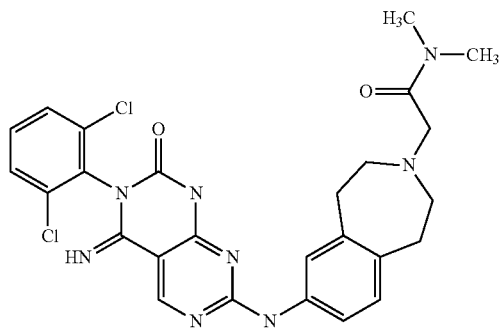 [SMILES: CN(C)C(=O)CN1CCc2ccc(Nc3ncc4c(=N)n(-c5c(Cl)cccc5Cl)c(=O)[nH]c4n3)cc2CC1]

19.9 mg of the entitled compound was obtained as a yellow solid according to the same method as in Example 2, for which, however, 2-(7-amino-1,2,4,5-tetrahydro-3H-3-benzazepin-3-yl)-N,N-dimethylacetamide obtained in Production Example 16 was used in place of 2,4,4-trimethyl-1,2,3,4-tetrahydroisoquinolin-7-amine in Example 2.

¹H-NMR (400 MHz, DMSO-d₆) δ: 11.81 (1H, brs), 10.05 (1H, brs), 9.10 (1H, s), 8.88 (1H, s), 7.74-7.67 (1H, m), 7.63-7.59 (2H, m), 7.49-7.45 (2H, m), 7.02 (1H, d, J=7.8 Hz), 3.28 (2H, brs), 3.04 (3H, s), 2.86-2.77 (7H, m), 2.67-2.58 (4H, m)

ESI-MS Found: m/z [M+H]⁺ 553

EXAMPLE 75

Production of 3-(2,6-dichlorophenyl)-4-imino-7-(1,2,3,4-tetrahydroisoquinolin-6-ylamino)-3,4-dihydropyrimido[4,5-d]pyrimidin-2(1H)-one

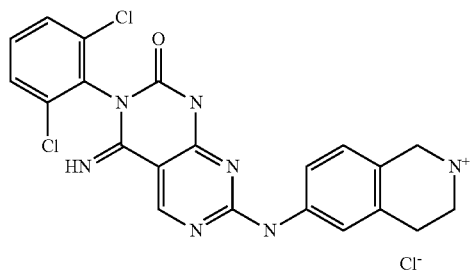 [SMILES: N=c1c2cnc(Nc3ccc4c(c3)CC[NH2+]C4)nc2[nH]c(=O)n1-c1c(Cl)cccc1Cl ; [Cl-]]

19.9 mg of the entitled compound was obtained as a yellow solid according to the same method as in Example 2, for which, however, 1,2,3,4-tetrahydroisoquinolin-6-amine was used in place of 2,4,4-trimethyl-1,2,3,4-tetrahydroisoquinolin-7-amine in Example 2.

¹H-NMR (400 MHz, DMSO-d₆) δ: 11.49 (½H, s), 11.06 (½H, s), 9.85 (1H, s), 9.75-9.62 (3H), 7.93 (1H, s), 7.84 (1H, d, J=0.8 Hz), 7.82 (1H, s), 7.84 (1H, dd, J=8.8, 7.6 Hz), 7.68 (1H, d, J=7.6 Hz), 7.24 (1H, d, J=8.8 Hz), 4.24 (2H, m), 3.37 (2H, m), 3.06 (2H, m)

ESI-MS Found: m/z [M+H]⁺ 454

EXAMPLE 76

Production of 3-(2,6-dichlorophenyl)-4-imino-7-[(2-methyl-2,3,4,5-tetrahydro-1H-2-benzazepin-8-yl)amino]-3,4-dihydropyrimido[4,5-d]pyrimidin-2(1H)-one

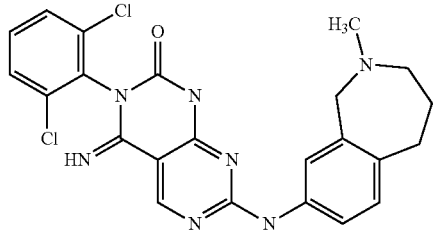 [SMILES: CN1CCCc2ccc(Nc3ncc4c(=N)n(-c5c(Cl)cccc5Cl)c(=O)[nH]c4n3)cc2C1]

5 mg of the entitled compound was obtained as a pale yellow solid according to the same method as in Example 2, for which, however, 2-methyl-2,3,4,5-tetrahydro-1H-2-benzazepin-8-amine obtained in Production Example 21 was used in place of 2,4,4-trimethyl-1,2,3,4-tetrahydroisoquinolin-7-amine in Example 2.

¹H-NMR (400 MHz, DMSO-d₆) δ: 11.84 (1H, brs), 10.06 (1H, brs), 9.11 (1H, brs), 8.88 (1H, brs), 7.88-7.67 (1H, m), 7.63-7.59 (2H, m), 7.49-7.42 (2H, m), 7.04 (1H, d, J=8.3 Hz), 3.74 (2H, s), 2.93-2.89 (2H, m), 2.80-2.76 (2H, m), 2.19 (3H, s), 1.65-1.58 (2H, m)

ESI-MS Found: m/z [M+H]⁺ 482

EXAMPLE 77

Production of 3-(2,6-dichlorophenyl)-4-imino-7-{[4-methyl-2,3,4,5-tetrahydro-1,4-benzoxazepin-7-yl]amino}-3,4-dihydropyrimido[4,5-d]pyrimidin-2(1H)-one

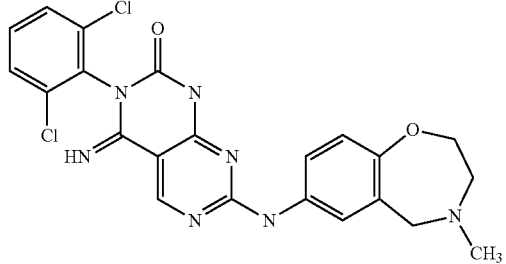 [SMILES: CN1CCOc2ccc(Nc3ncc4c(=N)n(-c5c(Cl)cccc5Cl)c(=O)[nH]c4n3)cc2C1]

10 mg of the entitled compound was obtained as a yellow solid according to the same method as in Example 2, for which, however, 4-methyl-2,3,4,5-tetrahydro-1,4-benzoxazepine-7-amine was used in place of 2,4,4-trimethyl-1,2,3,4-tetrahydroisoquinolin-7-amine in Example 2.

¹H-NMR (400 MHz, CD₃OD) δ: 8.98 (1H, s), 7.48-7.70 (5H, m), 6.97 (1H, d, J=8.8 Hz), 4.05-4.07 (2H, m), 3.77 (2H, s), 2.98-3.00 (2H, m), 2.44 (3H, s)

ESI-MS Found: m/z [M+H]⁺ 484

EXAMPLE 78

Production of 3-(2,6-dichlorophenyl)-4-imino-7-[(2-pyridin-2-yl-1,2,3,4-tetrahydroisoquinolin-6-yl)amino]-3,4-dihydropyrimido[4,5-d]pyrimidin-2(1H)-one

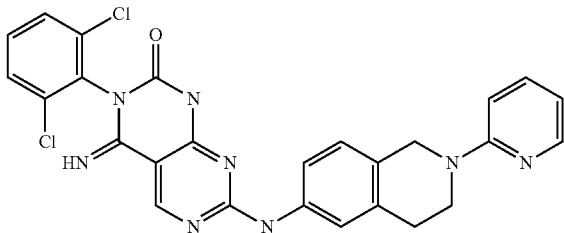 [SMILES: N=c1c2cnc(Nc3ccc4c(c3)CCN(c3ccccn3)C4)nc2[nH]c(=O)n1-c1c(Cl)cccc1Cl]

61 mg of the entitled compound was obtained as a yellow solid according to the same method as in Example 2, for which, however, 2-pyridin-2-yl-1,2,3,4-tetrahydroisoquinolin-6-amine obtained in Production Example 40 was used in place of 2,4,4-trimethyl-1,2,3,4-tetrahydroisoquinolin-7-amine in Example 2.

¹H-NMR (400 MHz, DMSO-d₆) δ: 11.85 (1H, brs), 10.12 (1H, s), 9.11 (1H, s), 8.90 (1H, brs), 8.12 (1H, dd, J=4.9, 1.5 Hz), 7.79 (1H, brs), 7.65-7.46 (5H, m), 7.17 (1H, d, J=8.8 Hz), 6.85 (1H, d, J=8.3 Hz), 6.61 (1H, dd, J=6.8, 5.4 Hz), 4.62 (2H, s), 3.80 (2H, t, J=5.9 Hz), 2.89 (2H, t, J=5.6 Hz)

ESI-MS Found: m/z [M+H]⁺ 531

EXAMPLE 79

Production of 7-[(2-acetyl-1,1-dimethyl-1,2,3,4-tetrahydroisoquinolin-6-yl)amino]-3-(2,6-dichlorophenyl)-4-imino-3,4-dihydropyrimido[4,5-d]pyrimidin-2(1H)-one

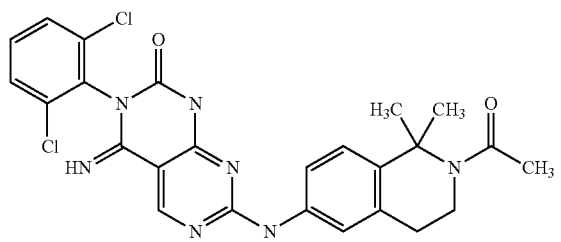 [SMILES: CC(=O)N1CCc2cc(Nc3ncc4c(=N)n(-c5c(Cl)cccc5Cl)c(=O)[nH]c4n3)ccc2C1(C)C]

61.5 mg of the entitled compound was obtained as a white solid according to the same method as in Example 2, for which, however, 2-acetyl-1,1-dimethyl-1,2,3,4-tetrahydroisoquinolin-6-amine obtained in Production Example 32 was used in place of 2,4,4-trimethyl-1,2,3,4-tetrahydroisoquinolin-7-amine in Example 2.

¹H-NMR (400 MHz, DMSO-d₆) δ: 11.84 (1H, s), 10.11 (1H, s), 9.12 (1H, s), 8.90 (1H, s), 7.79-7.68 (1H, m), 7.61 (2H, d, J=7.8 Hz), 7.53 (1H, d, J=9.3 Hz), 7.47 (1H, t, J=8.0 Hz), 7.28 (1H, d, J=8.8 Hz), 3.51 (2H, t, J=5.4 Hz), 2.81 (2H, t, J=4.9 Hz), 2.11 (3H, s), 1.71 (6H, s)

ESI-MS Found: m/z [M+H]⁺ 524

EXAMPLE 80

Production of 3-(2,6-dichlorophenyl)-7-[(2-methyl-1,2,3,4-tetrahydroisoquinolin-7-yl)amino]pyrimido[4,5-d]pyrimidin-2,4(1H,3H)-dione

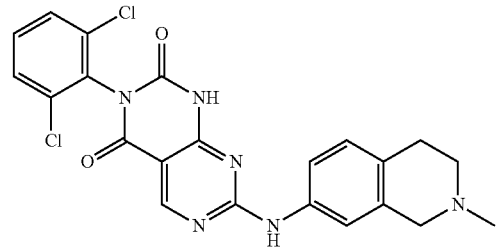 [SMILES: CN1CCc2ccc(Nc3ncc4c(=O)n(-c5c(Cl)cccc5Cl)c(=O)[nH]c4n3)cc2C1]

49 mg of m-chloroperbenzoic acid was added to a chloroform solution of 50 mg of 3-(2,6-dichlorophenyl)-7-(methylthio)pyrimido[4,5-d]pyrimidin-2,4(1H,3H)-dione obtained in Production Example 52, and stirred at room temperature for 15 minutes. Then the solvent was evaporated away. The resulting crude product was dissolved in 10 mL of toluene, and 23 mg of 2-methyl-1,2,3,4-tetrahydroisoquinolin-7-amine obtained in Production Example 22 and 48 μL of N,N-diisopropylethylamine were added thereto, and stirred at 90° C. for 12 hours. The solvent was evaporated away, then the resulting crude product was purified through basic silica gel column chromatography to obtain 26 mg (yield: 39%) of the entitled compound as a yellow solid.

¹H-NMR (400 MHz, DMSO-d₆) δ: 8.95 (1H, brs), 7.55-7.51 (4H, m), 7.43 (1H, t, J=8.0 Hz), 7.13 (1H, d, J=8.8 Hz), 3.66 (2H, s), 2.95 (2H, t, J=5.6 Hz), 2.77 (2H, t, J=5.6 Hz), 2.49 (3H, s).

ESI-MS Found: m/z [M+H] 468

EXAMPLE 81

Production of 3-(2,6-dichlorophenyl)-1-methyl-7-[(2-methyl-1,2,3,4-tetrahydroisoquinolin-7-yl)amino]pyrimido[4,5-d]pyrimidin-2,4(1H,3H)-dione

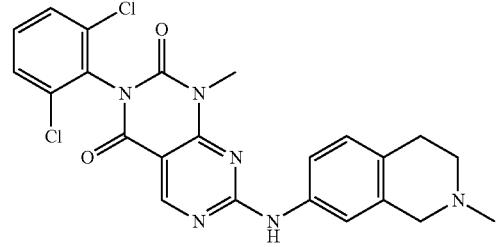 [SMILES: CN1CCc2ccc(Nc3ncc4c(=O)n(-c5c(Cl)cccc5Cl)c(=O)n(C)c4n3)cc2C1]

47 mg of m-chloroperbenzoic acid was added to a chloroform solution of 50 mg of 3-(2,6-dichlorophenyl)-1-methyl-7-(methylthio)pyrimido[4,5-d]pyrimidin-2,4(1H,3H)-dione obtained in Production Example 53, and stirred at room temperature for 15 minutes. Then the solvent was evaporated away. The resulting crude product was dissolved in 10 mL of toluene, and 23 mg of 2-methyl-1,2,3,4-tetrahydroisoquinolin-7-amine obtained in Production Example 22 and 47 μL of N,N-diisopropylethylamine were added thereto, and stirred at 90° C. for 12 hours. The solvent was evaporated away, then the resulting crude product was purified through basic silica gel column chromatography to obtain 19 mg (yield: 23%) of the entitled compound as a yellow solid.

$^1$H-NMR (400 MHz, CD$_3$OD-d$_6$) δ: 8.99 (1H, brs), 7.55-7.51 (4H, m), 7.41 (1H, t, J=8.0 Hz), 7.08 (1H, d, J=8.8 Hz), 3.67 (2H, s), 3.64 (3H, s), 2.95 (2H, t, J=5.6 Hz), 2.78 (2H, t, J=5.6 Hz), 2.49 (3H,$).

ESI-MS Found: m/z [M+H] 484

EXAMPLE 82

Production of 3-(2,6-dichlorophenyl)-7-[(2'-methyl-2',3'-dihydro-1'H-spiro[cyclopropane-1,4'-isoquinolin]-7'-yl)amino]pyrimido[4,5-d]pyrimidin-2,4(1H,3H)-dione

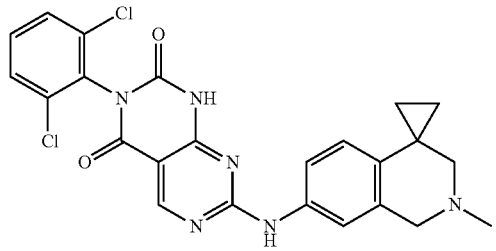 [SMILES: CN1Cc2cc(Nc3ncc4c(=O)n(-c5c(Cl)cccc5Cl)c(=O)[nH]c4n3)ccc2C2(CC2)C1]

76 mg of m-chloroperbenzoic acid was added to a chloroform solution of 100 mg of 3-(2,6-dichlorophenyl)-7-(methylthio)pyrimido[4,5-d]pyrimidin-2,4(1H,3H)-dione obtained in Production Example 52, and stirred at room temperature for 15 minutes. Then the solvent was evaporated away. The resulting crude product was dissolved in 15 mL of toluene, and 65 mg of 2'-methyl-2',3'-dihydro-1'H-spiro[cyclopropane-1,4'-isoquinolin]-7'-amine obtained in Production Example 10 and 200 μL of N,N-diisopropylethylamine were added thereto, and stirred at 90° C. for 12 hours. The solvent was evaporated away, then the resulting crude product was purified through basic silica gel column chromatography to obtain 8 mg (yield: 5.7%) of the entitled compound as a yellow solid.

$^1$H-NMR (400 MHz, CD$_3$OD-d$_6$) δ: 8.89 (1H, brs), 7.34-7.48 (5H, m), 6.65 (1H, d, J=8.8 Hz), 3.71 (2H,$), 2.56 (2H, s), 2.41 (3H, s), 0.98 (2H, brs), 0.91 (2H, brs).

ESI-MS Found: m/z [M+H] 495

EXAMPLE 83

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate To a stirred suspension of 2'-methyl-2',3'-dihydro-1'H-spiro[cyclopropane-1,4'-isoquinolin]-7'-amine dihydrochloride (1.90 kg, 7.27 mol, 1.09 eq.) in chloroform (19 L) at room temperature was added 5 N NaOH (3.8 L), and the mixture was stirred for 5 minutes. The chloroform layer was separated and the aqueous layer was extracted with chloroform (9.5 L). Combined chloroform layers were washed with 5% aqueous NaCl (9.5 L), then dried over anhydrous sodium sulfate (3.8 kg) for 1 hour. Sodium sulfate was filtered and washed with chloroform (3.8 L). Combined filtrate and washing were evaporated to give crude oil. Methanol (4.6 L) was added and the solution was evaporated to give 2'-methyl-2',3'-dihydro-1'H-spiro[cyclopropane-1,4'-isoquinolin]-7'-amine (1.40 kg) as brownish crystals in crude 102% recovery.

To a stirred solution of the compound obtained above (1.40 kg, 7.27 mol, 1.09 eq.) in methanol (10 L) were added 4 N HCl-ethyl acetate (1.92 L) below 15° C. and then Hf(OTf)$_4$ (103 g) was added. After cooled to 14° C., 7-chloro-3-(2,6-dichlorophenyl)-4-imino-3,4-dihydropyrimido[4,5-d]pyrimidin-2(1H)-one (2.28 kg, 6.66 mol) and methanol (1.5 L) were added and the slurry was stirred at room temperature for 5 hours. Methanol (6.9 L) and ethyl acetate (9.2 L) were added and the slurry was stirred at room temperature for 1 hour. Ethyl acetate (4.6 L) was added and the slurry was stirred for 1 hour. Then, ethyl acetate (4.6 L) was added and the slurry was stirred at room temperature overnight. The slurry was filtered, washed with methanol-ethyl acetate (1:1, 6.9 L) and then methanol-ethyl acetate (1:2, 6.9 L), and dried at room temperature by sucking under N$_2$ flow for 6 hours. then under reduced pressure with N$_2$ flow overnight to give the crude 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride (3.883 kg, 3.324 kg assay of free base) as yellow crystals in 101% yield.

To a stirred suspension of the crude compound obtained above (3.862 kg, 3.306 kg assay of free base, 6.687 mol) in chloroform (79 L) and methanol (33 L) at room temperature was added 5% aqueous NaHCO$_3$ (33 L), and the mixture was stirred for a few minutes. Organic layer was separated and dried over anhydrous sodium sulfate (6.62 kg). Sodium sulfate was removed by filtration and washed with chloroform-methanol (12:5, 14.1 L). The filtrate and washing were concentrated to 6 L and ethanol (33 L) was added and the solution was concentrated to 10 L. Ethanol (33 L) was added again and the solution was concentrated to 10 L. Ethanol (16.5 L) and N,N-dimethylformamide (6.6 L) were added to the slurry and heated to 55° C. 2N HCl-ethanol (3.34 L) was added at 55° C., then 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate (17 g) was added and 2N HCl-ethanol (3.68 L) was added dropwise over 1 hour at 55° C. and aged for 1 hour at the same temperature. Then the slurry was cooled gradually to room temperature and aged for overnight at room temperature. The slurry was filtered, washed with ethanol (9.9 L×2 times), and dried at the room temperature under N$_2$ flow for several hours then under reduced pressure overnight. The dried crystal was treated with wet N$_2$ to control water content in the crystal. 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one dihydrochloride 3.5 hydrate (3.401 kg, 2.600 kg assay of free base) was obtained as pale yellow crystals in 79% yield.

$^1$H-NMR (400 MHz, DMSO-d$_6$) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m).

ESI-MS Found: m/z [M+H] 494

XRPD Patterns:

(2 theta (degrees), Intensity (cps)): (8.4°, 26.4), (12.7°, 20.4), (15.3°, 18.8), (16.3°, 18.1), (22.32°, 30.9), (24.5°, 24.5), (24.9°, 31.2), (26.5°, 24.6), (28.6°, 16.6).

Water Content:

When water content of the crystalline was measured by Karl Fischer test using a Kyoto electronics manufacturing MKC-510, the water content of the crystalline was 10.3%, theoretically 10.0%.

Using the corresponding starting materials and according to the same method as in the above-mentioned Examples, Compounds Nos. 1a to 74a shown in the following Tables were obtained. (In the above-mentioned and the following structural formulae, the expression of the hydrogen atom in the group of —NH— or —NH$_2$ may be omitted for convenience's sake, and the group may be expressed as —N— or —N.)

| Compound No. | Structure |
|---|---|
| 1a | 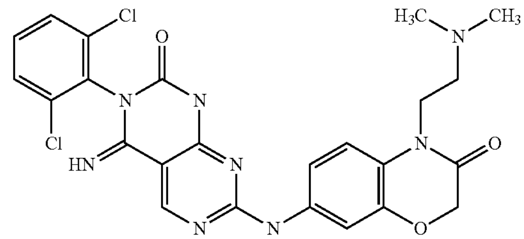 [SMILES: CN(C)CCN1C(=O)COc2cc(Nc3ncc4c(=N)n(-c5c(Cl)cccc5Cl)c(=O)[nH]c4n3)ccc21] |
| 2a | 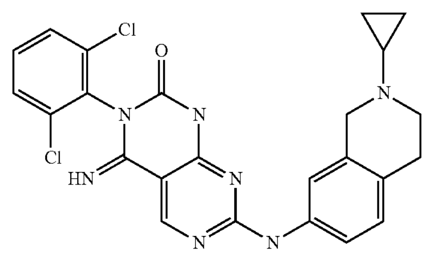 [SMILES: N=c1c2cnc(Nc3ccc4c(c3)CN(C3CC3)CC4)nc2[nH]c(=O)n1-c1c(Cl)cccc1Cl] |
| 3a | 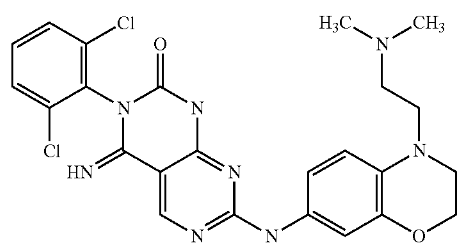 [SMILES: CN(C)CCN1CCOc2cc(Nc3ncc4c(=N)n(-c5c(Cl)cccc5Cl)c(=O)[nH]c4n3)ccc21] |
| 4a | 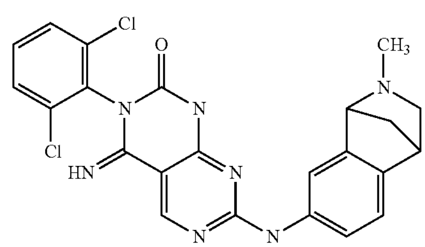 [SMILES: CN1CC2CC1c1cc(Nc3ncc4c(=N)n(-c5c(Cl)cccc5Cl)c(=O)[nH]c4n3)ccc12] |
| 5a | 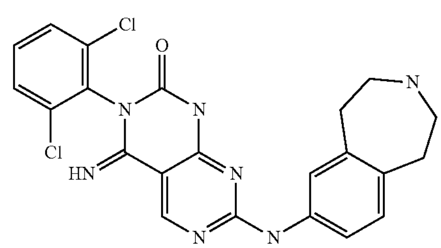 [SMILES: N=c1c2cnc(Nc3ccc4c(c3)CCNCC4)nc2[nH]c(=O)n1-c1c(Cl)cccc1Cl] |

-continued

| Compound No. | Structure |
|---|---|
| 6a | 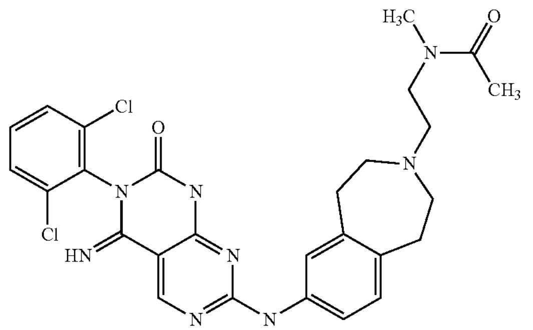 [SMILES: CC(=O)N(C)CCN1CCc2ccc(Nc3ncc4c(=N)n(-c5c(Cl)cccc5Cl)c(=O)[nH]c4n3)cc2CC1] |
| 7a | 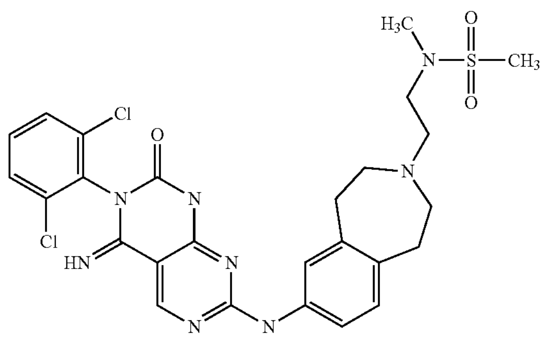 [SMILES: CN(CCN1CCc2ccc(Nc3ncc4c(=N)n(-c5c(Cl)cccc5Cl)c(=O)[nH]c4n3)cc2CC1)S(C)(=O)=O] |
| 8a | 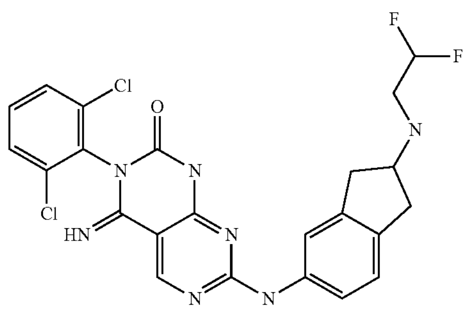 [SMILES: N=c1c2cnc(Nc3ccc4c(c3)CC(NCC(F)F)C4)nc2[nH]c(=O)n1-c1c(Cl)cccc1Cl] |
| 9a | 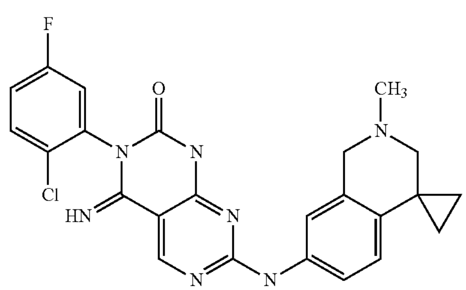 [SMILES: CN1Cc2cc(Nc3ncc4c(=N)n(-c5cc(F)ccc5Cl)c(=O)[nH]c4n3)ccc2C2(CC2)C1] |
| 10a | 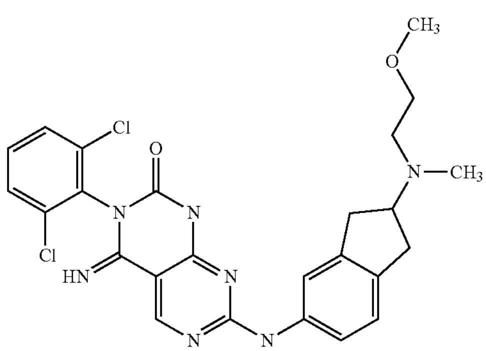 [SMILES: COCCN(C)C1Cc2ccc(Nc3ncc4c(=N)n(-c5c(Cl)cccc5Cl)c(=O)[nH]c4n3)cc2C1] |

-continued
| Compound No. | Structure |
|---|---|
| 11a | 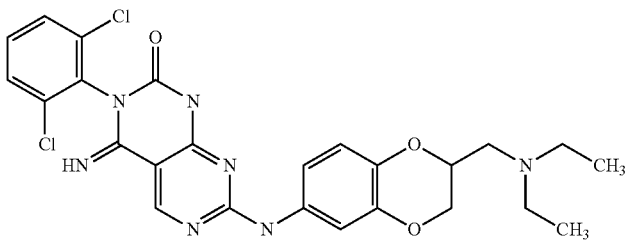 [SMILES: CCN(CC)CC1COc2cc(Nc3ncc4c(=N)n(-c5c(Cl)cccc5Cl)c(=O)[nH]c4n3)ccc2O1] |
| 12a | 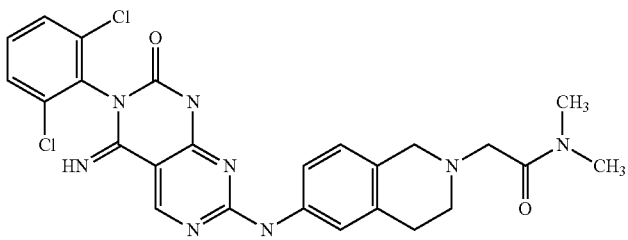 [SMILES: CN(C)C(=O)CN1CCc2cc(Nc3ncc4c(=N)n(-c5c(Cl)cccc5Cl)c(=O)[nH]c4n3)ccc2C1] |
| 13a | 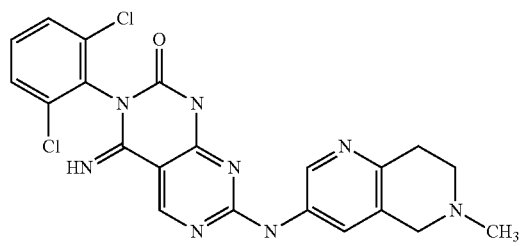 [SMILES: CN1CCc2ncc(Nc3ncc4c(=N)n(-c5c(Cl)cccc5Cl)c(=O)[nH]c4n3)cc2C1] |
| 14a | 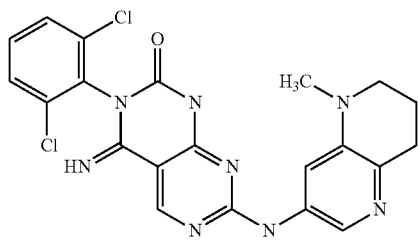 [SMILES: CN1CCCc2ncc(Nc3ncc4c(=N)n(-c5c(Cl)cccc5Cl)c(=O)[nH]c4n3)cc21] |
| 15a | 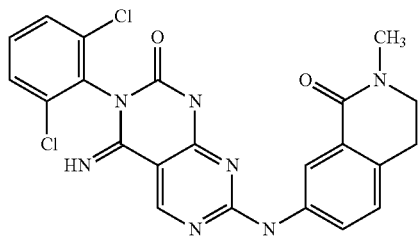 [SMILES: CN1CCc2ccc(Nc3ncc4c(=N)n(-c5c(Cl)cccc5Cl)c(=O)[nH]c4n3)cc2C1=O] |
| 16a | 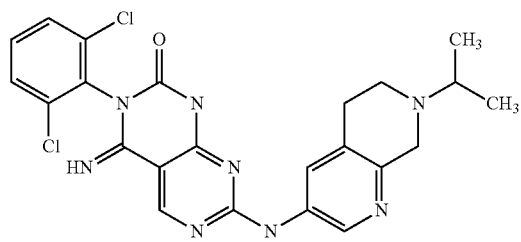 [SMILES: CC(C)N1CCc2cc(Nc3ncc4c(=N)n(-c5c(Cl)cccc5Cl)c(=O)[nH]c4n3)cnc2C1] |

-continued
| Compound No. | Structure |
|---|---|
| 17a | 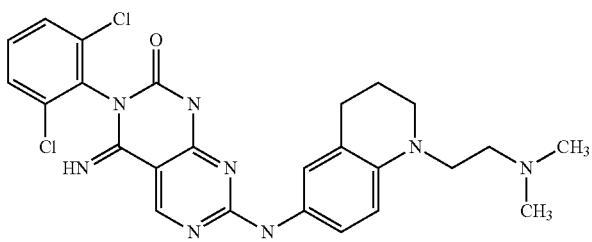 [SMILES: CN(C)CCN1CCCc2cc(Nc3ncc4c(=N)n(-c5c(Cl)cccc5Cl)c(=O)[nH]c4n3)ccc21] |
| 18a | 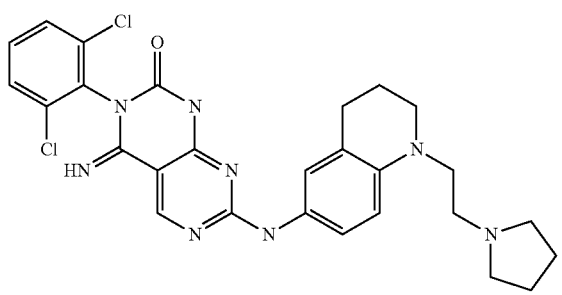 [SMILES: N=c1c2cnc(Nc3ccc4c(c3)CCCN4CCN3CCCC3)nc2[nH]c(=O)n1-c1c(Cl)cccc1Cl] |
| 19a | Chiral 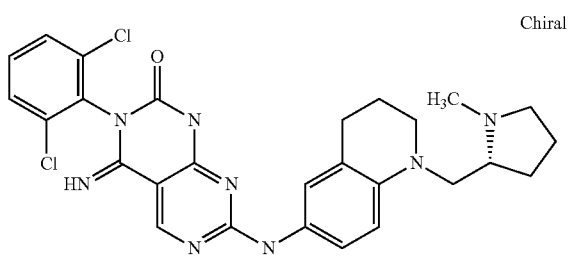 [SMILES: CN1CCC[C@@H]1CN1CCCc2cc(Nc3ncc4c(=N)n(-c5c(Cl)cccc5Cl)c(=O)[nH]c4n3)ccc21] |
| 20a | 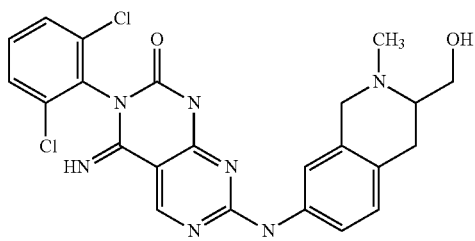 [SMILES: CN1Cc2cc(Nc3ncc4c(=N)n(-c5c(Cl)cccc5Cl)c(=O)[nH]c4n3)ccc2CC1CO] |
| 21a | 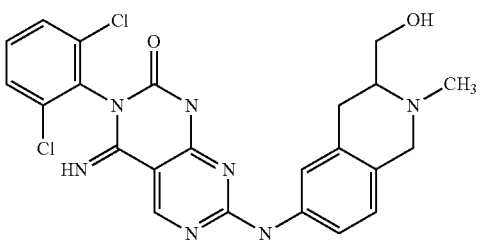 [SMILES: CN1Cc2ccc(Nc3ncc4c(=N)n(-c5c(Cl)cccc5Cl)c(=O)[nH]c4n3)cc2CC1CO] |
| 22a | 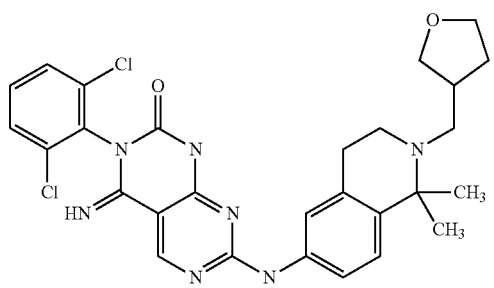 [SMILES: CC1(C)c2ccc(Nc3ncc4c(=N)n(-c5c(Cl)cccc5Cl)c(=O)[nH]c4n3)cc2CCN1CC1CCOC1] |

-continued

| Compound No. | Structure |
|---|---|
| 23a | 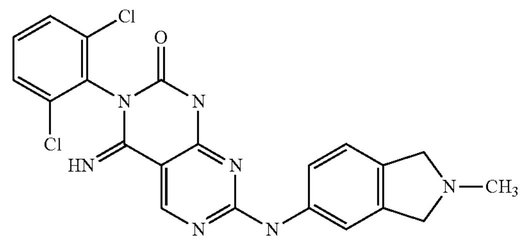 [SMILES: CN1Cc2ccc(Nc3ncc4c(=N)n(-c5c(Cl)cccc5Cl)c(=O)[nH]c4n3)cc2C1] |
| 24a | 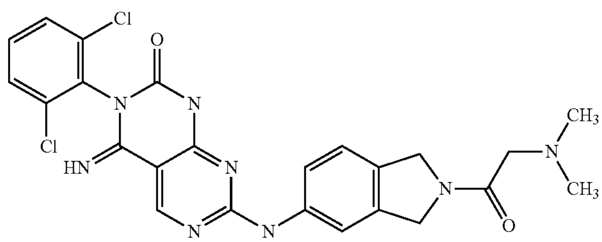 [SMILES: CN(C)CC(=O)N1Cc2ccc(Nc3ncc4c(=N)n(-c5c(Cl)cccc5Cl)c(=O)[nH]c4n3)cc2C1] |
| 25a | 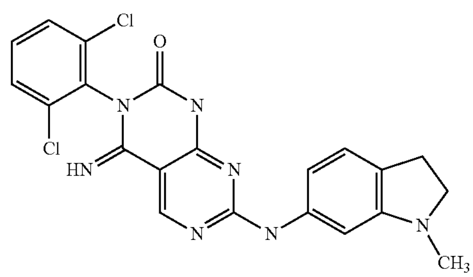 [SMILES: CN1CCc2ccc(Nc3ncc4c(=N)n(-c5c(Cl)cccc5Cl)c(=O)[nH]c4n3)cc21] |
| 26a | 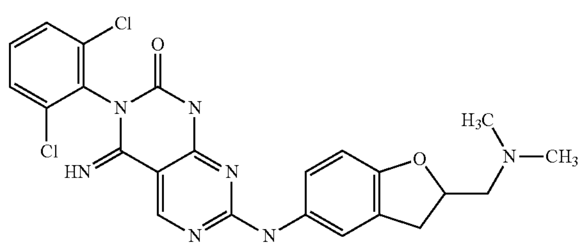 [SMILES: CN(C)CC1Cc2cc(Nc3ncc4c(=N)n(-c5c(Cl)cccc5Cl)c(=O)[nH]c4n3)ccc2O1] |
| 27a | 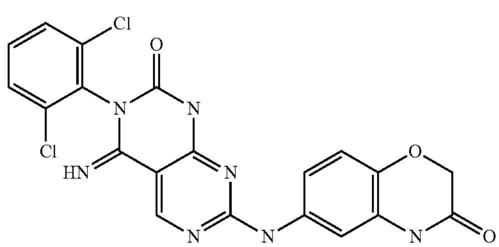 [SMILES: N=c1c2cnc(Nc3ccc4c(c3)NC(=O)CO4)nc2[nH]c(=O)n1-c1c(Cl)cccc1Cl] |
| 28a | 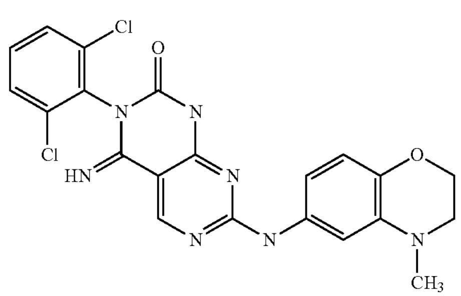 [SMILES: CN1CCOc2ccc(Nc3ncc4c(=N)n(-c5c(Cl)cccc5Cl)c(=O)[nH]c4n3)cc21] |

-continued

| Compound No. | Structure |
| --- | --- |
| 29a | (structure) |
| 30a | (structure) |
| 31a | (structure) |
| 32a | (structure) |
| 33a | (structure) |

| Compound No. | Structure |
|---|---|
| 34a | 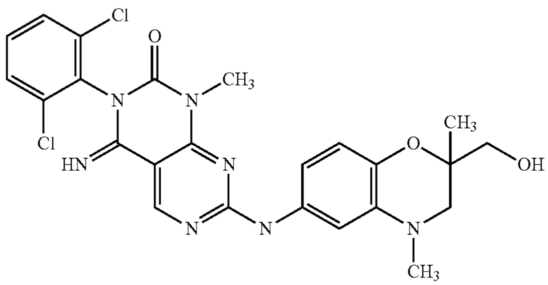 [SMILES: CN1CC(C)(CO)Oc2ccc(Nc3ncc4c(=N)n(-c5c(Cl)cccc5Cl)c(=O)n(C)c4n3)cc21] |
| 35a | 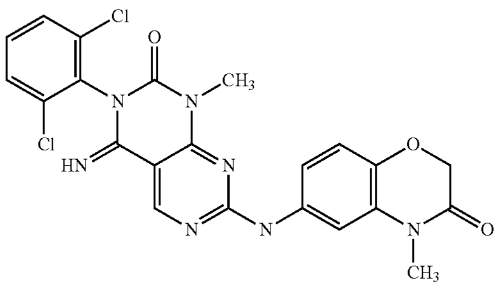 [SMILES: CN1C(=O)COc2ccc(Nc3ncc4c(=N)n(-c5c(Cl)cccc5Cl)c(=O)n(C)c4n3)cc21] |
| 36a | 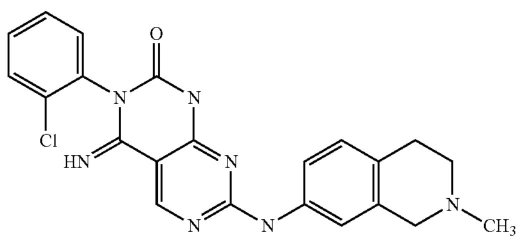 [SMILES: CN1CCc2ccc(Nc3ncc4c(=N)n(-c5ccccc5Cl)c(=O)[nH]c4n3)cc2C1] |
| 37a | 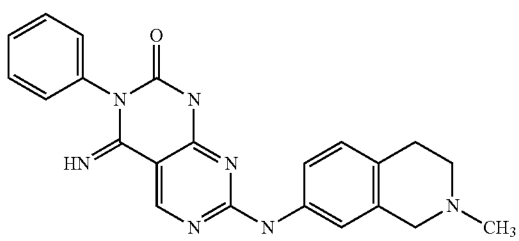 [SMILES: CN1CCc2ccc(Nc3ncc4c(=N)n(-c5ccccc5)c(=O)[nH]c4n3)cc2C1] |
| 38a | 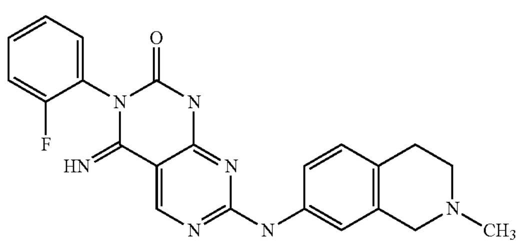 [SMILES: CN1CCc2ccc(Nc3ncc4c(=N)n(-c5ccccc5F)c(=O)[nH]c4n3)cc2C1] |
| 39a | 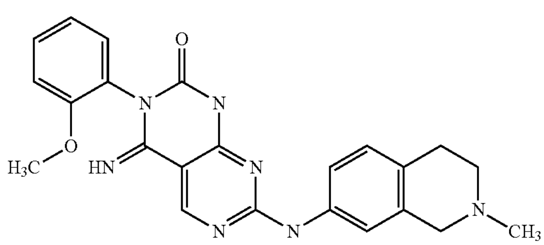 [SMILES: COc1ccccc1-n1c(=O)[nH]c2nc(Nc3ccc4c(c3)CN(C)CC4)ncc2c1=N] |

| Compound No. | Structure |
|---|---|
| 40a | 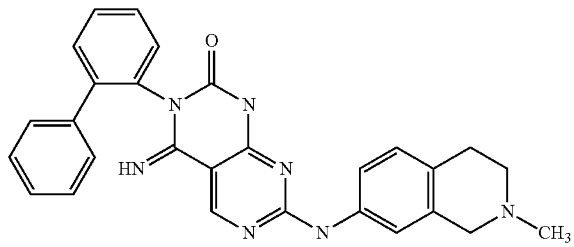 [SMILES: CN1CCc2ccc(Nc3ncc4c(=N)n(-c5ccccc5-c5ccccc5)c(=O)[nH]c4n3)cc2C1] |
| 41a | 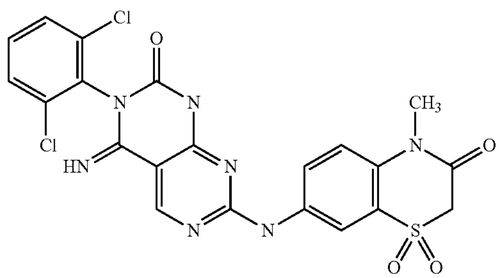 [SMILES: CN1C(=O)CS(=O)(=O)c2cc(Nc3ncc4c(=N)n(-c5c(Cl)cccc5Cl)c(=O)[nH]c4n3)ccc21] |
| 42a | 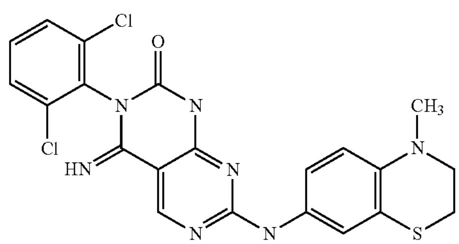 [SMILES: CN1CCSc2cc(Nc3ncc4c(=N)n(-c5c(Cl)cccc5Cl)c(=O)[nH]c4n3)ccc21] |
| 43a | 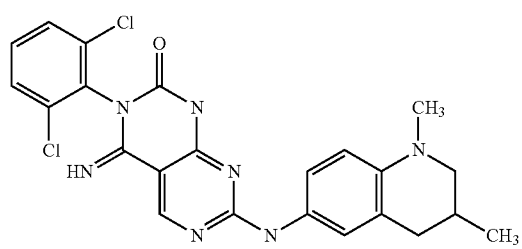 [SMILES: CC1Cc2cc(Nc3ncc4c(=N)n(-c5c(Cl)cccc5Cl)c(=O)[nH]c4n3)ccc2N(C)C1] |
| 44a | 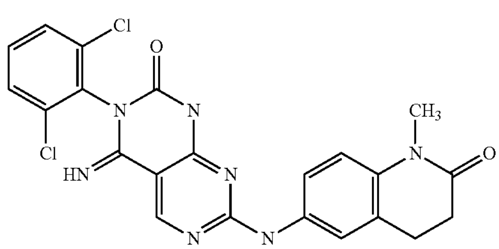 [SMILES: CN1C(=O)CCc2cc(Nc3ncc4c(=N)n(-c5c(Cl)cccc5Cl)c(=O)[nH]c4n3)ccc21] |
| 45a | 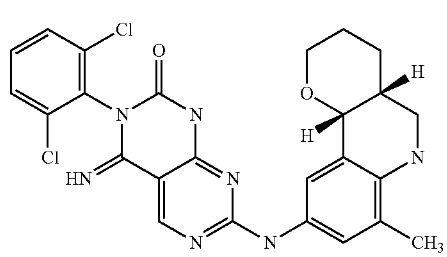 [SMILES: Cc1cc(Nc2ncc3c(=N)n(-c4c(Cl)cccc4Cl)c(=O)[nH]c3n2)cc2c1NC[C@H]1CCCO[C@@H]21] |

-continued

| Compound No. | Structure |
|---|---|
| 46a | 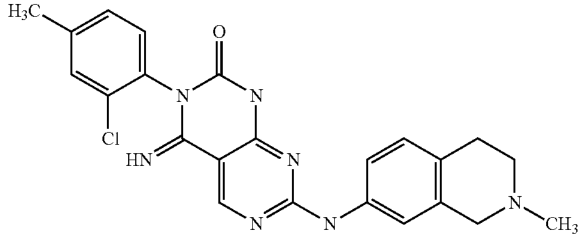 |
| 47a | 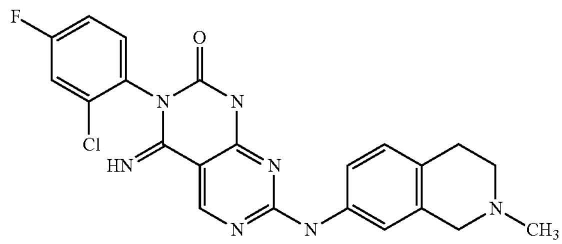 [SMILES: CN1CCc2ccc(Nc3ncc4c(=N)n(-c5ccc(F)cc5Cl)c(=O)[nH]c4n3)cc2C1] |
| 48a | 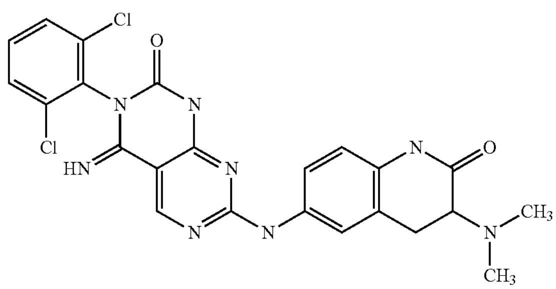 [SMILES: CN(C)C1Cc2cc(Nc3ncc4c(=N)n(-c5c(Cl)cccc5Cl)c(=O)[nH]c4n3)ccc2NC1=O] |
| 49a | 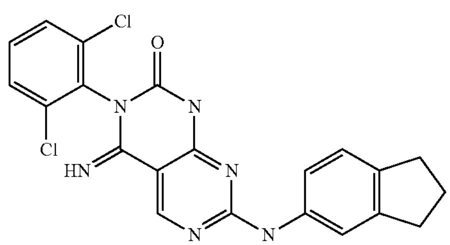 [SMILES: N=c1c2cnc(Nc3ccc4c(c3)CCC4)nc2[nH]c(=O)n1-c1c(Cl)cccc1Cl] |
| 50a | 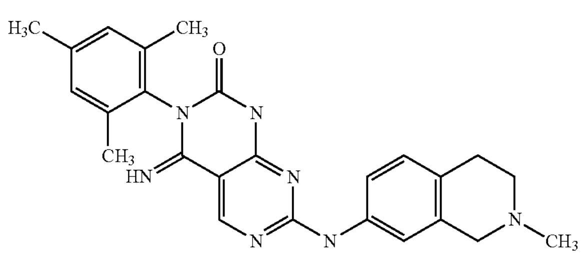 |
| 51a | 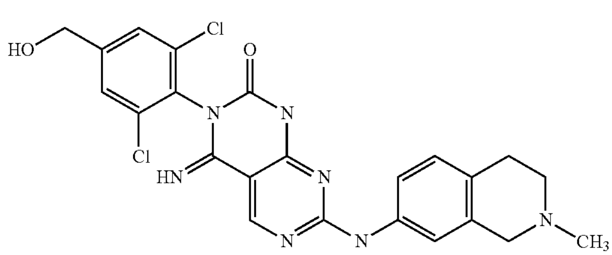 [SMILES: CN1CCc2ccc(Nc3ncc4c(=N)n(-c5c(Cl)cc(CO)cc5Cl)c(=O)[nH]c4n3)cc2C1] |

| Compound No. | Structure |
|---|---|
| 52a | (chemical structure) |
| 53a | (chemical structure) |
| 54a | (chemical structure) |
| 55a | (chemical structure) |
| 56a | (chemical structure) |

| Compound No. | Structure |
|---|---|
| 57a | 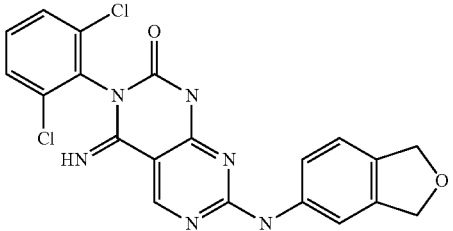 [SMILES: N=c1c2cnc(Nc3ccc4c(c3)COC4)nc2[nH]c(=O)n1-c1c(Cl)cccc1Cl] |
| 58a | 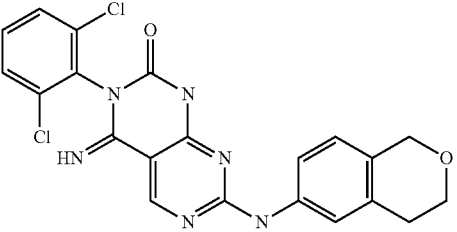 [SMILES: N=c1c2cnc(Nc3ccc4c(c3)COCC4)nc2[nH]c(=O)n1-c1c(Cl)cccc1Cl] |
| 59a | 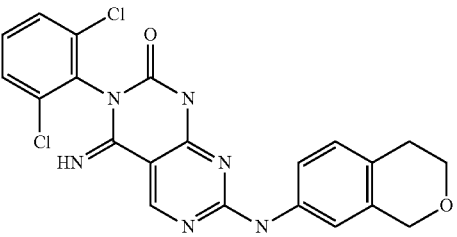 |
| 60a | 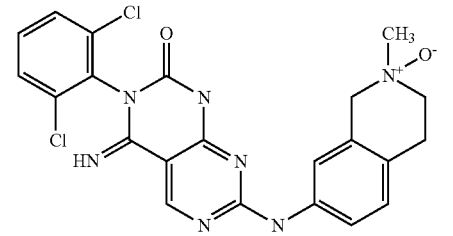 [SMILES: C[N+]1([O-])CCc2ccc(Nc3ncc4c(=N)n(-c5c(Cl)cccc5Cl)c(=O)[nH]c4n3)cc2C1] |
| 61a | Chiral<br>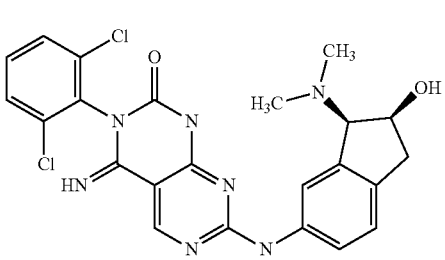 |
| 62a | 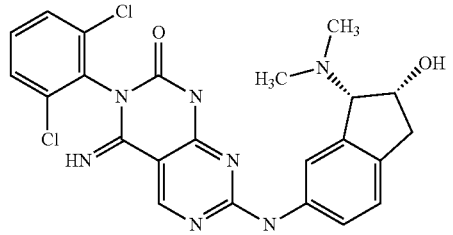 [SMILES: CN(C)[C@H]1c2cc(Nc3ncc4c(=N)n(-c5c(Cl)cccc5Cl)c(=O)[nH]c4n3)ccc2C[C@H]1O] |

-continued

| Compound No. | Structure |
|---|---|
| 63a | 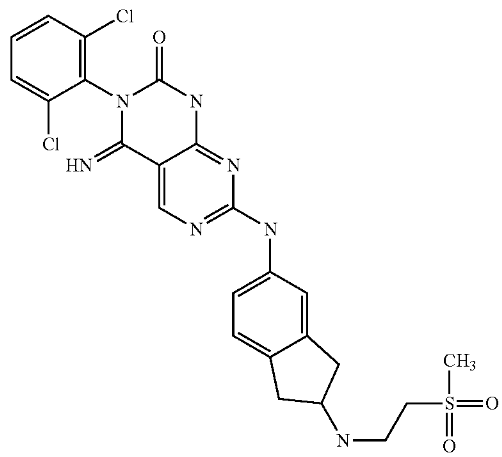 [SMILES: CS(=O)(=O)CCNC1Cc2ccc(Nc3ncc4c(=N)n(-c5c(Cl)cccc5Cl)c(=O)[nH]c4n3)cc2C1] |
| 64a | 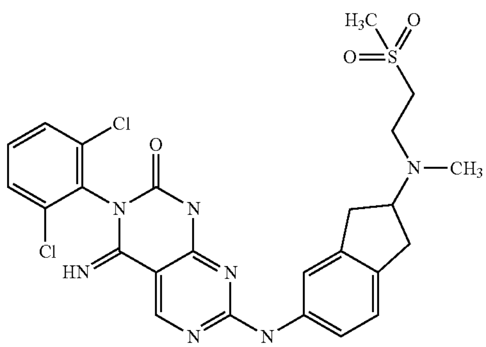 [SMILES: CN(CCS(C)(=O)=O)C1Cc2ccc(Nc3ncc4c(=N)n(-c5c(Cl)cccc5Cl)c(=O)[nH]c4n3)cc2C1] |
| 65a | 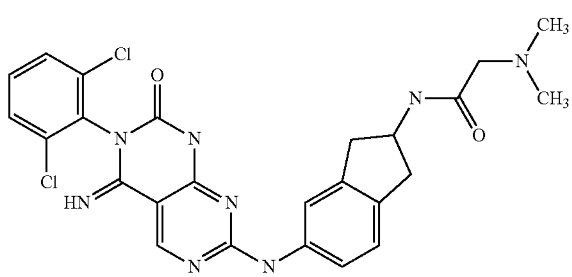 [SMILES: CN(C)CC(=O)NC1Cc2ccc(Nc3ncc4c(=N)n(-c5c(Cl)cccc5Cl)c(=O)[nH]c4n3)cc2C1] |
| 66a | 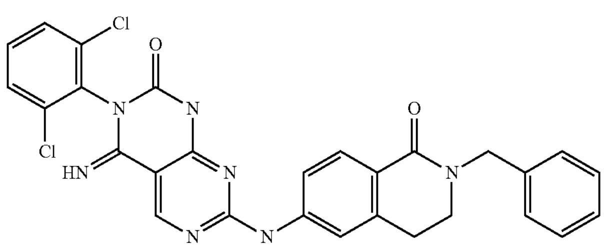 [SMILES: N=c1c2cnc(Nc3ccc4c(c3)CCN(Cc3ccccc3)C4=O)nc2[nH]c(=O)n1-c1c(Cl)cccc1Cl] |
| 67a | 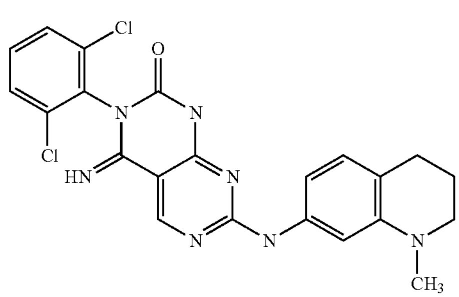 |

-continued

| Compound No. | Structure |
|---|---|
| 68a | 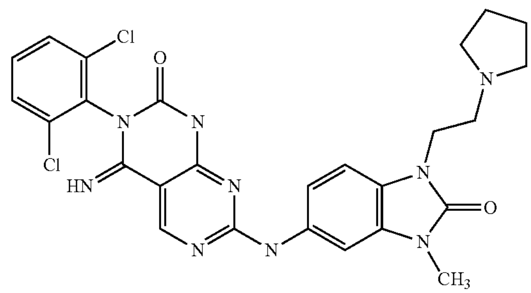 [SMILES: Cn1c(=O)n(CCN2CCCC2)c2ccc(Nc3ncc4c(=N)n(-c5c(Cl)cccc5Cl)c(=O)[nH]c4n3)cc21] |
| 69a | 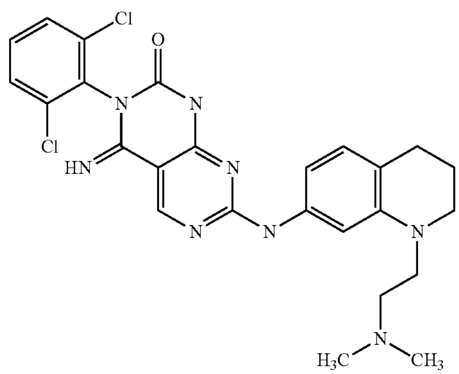 [SMILES: CN(C)CCN1CCCc2ccc(Nc3ncc4c(=N)n(-c5c(Cl)cccc5Cl)c(=O)[nH]c4n3)cc21] |
| 70a | 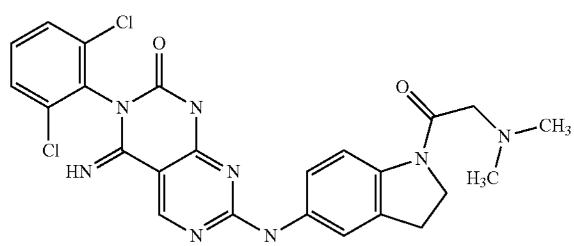 [SMILES: CN(C)CC(=O)N1CCc2cc(Nc3ncc4c(=N)n(-c5c(Cl)cccc5Cl)c(=O)[nH]c4n3)ccc21] |
| 71a | 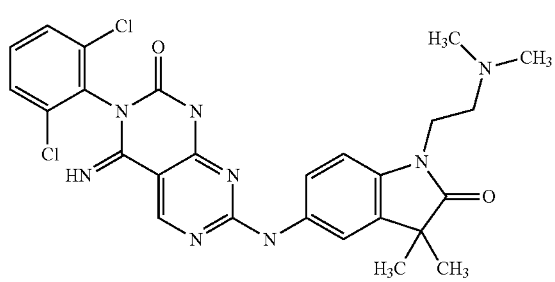 [SMILES: CN(C)CCN1C(=O)C(C)(C)c2cc(Nc3ncc4c(=N)n(-c5c(Cl)cccc5Cl)c(=O)[nH]c4n3)ccc21] |
| 72a | 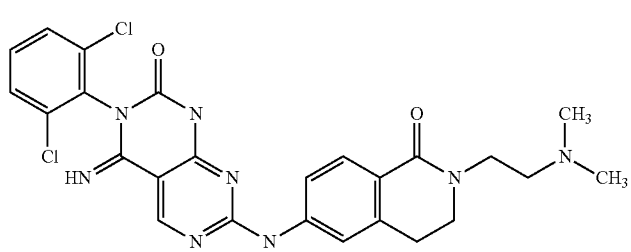 [SMILES: CN(C)CCN1CCc2cc(Nc3ncc4c(=N)n(-c5c(Cl)cccc5Cl)c(=O)[nH]c4n3)ccc2C1=O] |

| Compound No. | Structure |
|---|---|
| 73a | [Structure: 3-(2,6-dichlorophenyl)-imino-pyrimido-pyrimidinone linked via NH to tetrahydroisoquinolinone N-substituted with 2-pyridyl] |
| 74a | [Structure: 3-(4-methoxybenzothiazol-2-yl)-imino-pyrimido-pyrimidinone linked via NH to 2-methyl-1,2,3,4-tetrahydroisoquinoline] |

The data of $^1$H-NMR and MS spectrum on the above compounds are shown in the below tables.

| Compound No. | $^1$H NMR (400 MHz) | ESI-MS (M + H)+ |
|---|---|---|
| 1a | (DMSO-d6) δ: 11.88 (1H, brs), 10.17 (1H, brs), 9.12 (1H, s), 8.91 (1H, s), 7.76-7.58 (3H, m), 7.50-7.44 (2H, m), 7.13 (1H, d, J = 8.8 Hz), 4.61 (2H, s), 3.98 (2H, t, J = 6.6 Hz), 2.4 (2H, t, J = 6.6 Hz), 2.18 (6H, s). | 541 |
| 2a | (DMSO-d6) δ: 11.86-11.82 (1H, m), 10.11-10.03 (1H, m), 9.10 (1H, s), 8.88 (1H, s), 7.63-7.59 (2H, m), 7.52-7.44 (2H, m), 7.40-7.36 (1H, m), 7.02-6.97 (1H, m), 3.73-3.69 (2H, m), 2.85-2.69 (4H, m), 1.81-1.74 (1H, m), 0.53-0.44 (2H, m), 0.42-0.36 (2H, m). | 494 |
| 3a | (DMSO-d6) δ: 11.76-11.67 (1H, m), 9.86-9.73 (1H, m), 9.03 (1H, t, J = 6.0 Hz), 8.78 (1H, s), 7.62-7.58 (2H, m), 7.48-7.43 (1H, m), 7.26-7.13 (2H, m), 6.61 (1H, d, J = 8.5 Hz), 4.14 (2H, t, J = 4.3 Hz), 3.34-3.29 (4H, m), 2.40 (2H, t, J = 6.8 Hz), 2.18 (6H, s). | 527 |
| 4a | (DMSO-d6) δ: 10.07 (1H, brs), 9.09 (1H, brs), 8.86 (1H, brs), 7.84-7.76 (1H, m), 7.68-7.57 (2H, m), 7.55-7.44 (2H, m), 7.20 (1H, d, J = 8.0 Hz), 3.98 (1H, brs), 3.37-3.27 (2H, m), 1.88 (1H, d, J = 8.8 Hz), 1.86 (3H, s), 1.65 (1H, d, J = 8.2 Hz), 1.30 (1H, d, J = 8.2 Hz). | 480 |
| 5a | (DMSO-d6) δ: 9.99 (1H, brs), 9.06 (1H, s), 7.70-7.59 (3H, m), 7.51-7.45 (2H, m), 7.01 (1H, d, J = 8.3 Hz), 2.85-2.74 (8H, m). | 470 |
| 6a | (DMSO-d6) δ: 11.82 (1H, brs), 10.05 (1H, brs), 9.10 (1H, s), 8.88 (1H, s), 7.76-7.57 (3H, m), 7.50-7.43 (2H, m), 7.04-7.00 (1H, m), 3.38 (2H, t, J = 7.1 Hz), 2.97 (1.6H, s), 2.86-2.76 (4H, m), 2.81 (1.4H, s), 2.67-2.52 (6H, m), 2.02 (1.4H, s), 1.95 (1.6H, s). | 567 |
| 7a | (DMSO-d6) δ: 11.82 (1H, brs), 10.05 (1H, brs), 9.10 (1H, s), 8.88 (1H, s), 7.77-7.68 (1H, m), 7.63-7.59 (2H, m), 7.49-7.44 (2H, m), 7.03 (1H, d, J = 8.3 Hz), 3.20 (2H, t, J = 6.6 Hz), 2.91 (3H, s), 2.86-2.77 (4H, m), 2.80 (3H, s), 2.67-2.57 (6H, m). | 603 |
| 8a | (DMSO-d6) δ: 11.78 (1H, brs), 10.04 (1H, brs), 9.10 (1H, s), 8.86 (1H, s), 7.79-7.70 (1H, m), 7.63-7.59 (2H, m), 7.50-7.44 (2H, m), 7.09 (1H, d, J = 8.3 Hz), 5.99 (1H, tt, J = 56.3, 4.3 Hz), 3.58-3.50 (1H, m), 3.04 (2H, td, J = 15.0, 7.0 Hz), 2.93 (2H, td, J = 15.9, 4.3 Hz), 2.69-2.58 (2H, m). | 518 |
| 9a | (DMSO-d6) δ: 11.73-11.71 (1H, brm), 10.00-9.97 (1H, brm), 9.07 (1H, s), 8.83 (1H, s), 7.78-7.28 (5H, m), 6.62 (1H, d, J = 8.5 Hz), 3.57 (2H, s), 2.42 (2H, s), 2.31 (3H, s), 0.90-0.85 (2H, m), 0.84-0.79 (2H, m). | 478 |

-continued

| Compound No. | $^1$H NMR (400 MHz) | ESI-MS (M + H)+ |
|---|---|---|
| 10a | (DMSO-d6) δ: 11.77 (1H, brs), 10.04 (1H, brs), 9.09 (1H, s), 8.87 (1H, s), 7.81-7.71 (1H, m), 7.63-7.58 (2H, m), 7.51-7.43 (2H, m), 7.09 (1H, d, J = 8.0 Hz), 3.43 (2H, t, J = 6.0 Hz), 3.34-3.27 (1H, m), 3.23 (3H, s), 2.97 (2H, td, J = 15.5, 7.6 Hz), 2.79-2.66 (2H, m), 2.56 (2H, t, J = 5.9 Hz), 2.20 (3H, s). | 526 |
| 11a | (DMSO-d6) δ: 9.11 (1H, s), 8.88 (1H, s), 7.64-7.47 (5H), 4.33-3.95 (7H), 2.59-2.52 (2H), 0.99 (6H, t, J = 7.6 Hz) | 542 |
| 12a | (DMSO-d6) δ: 11.85 (1H, s), 10.09 (1H, s), 9.14 (1H, s), 8.92 (1H, s), 7.71-7.50 (5H), 6.99 (1H, d, J = 8.0 Hz), 3.61 (2H, s), 3.34 (2H, m), 3.06 (3H, s), 2.86-2.84 (5H), 2.76 (2H, m) | 539 |
| 13a | (CD3OD) δ: 9.25 (1H, s), 8.70 (1H, dd, J = 1.8, 0.9 Hz), 8.24 (1H, dd, J = 3.5, 0.9 Hz), 8.12 (1H, t, J = 8.0 Hz), 7.89-7.83 (2H, m), 7.64 (1H, dq, J = 8.3, 1.1 Hz), 7.46 (1H, dd, J = 3.5, 1.8 Hz), 4.24 (3H, s), 4.19-4.11 (6H, m). | 469 |
| 14a | (CD3OD) δ: 9.02 (1H, s), 8.15 (1H, s), 7.59 (2H, d, J = 7.8 Hz), 7.49 (1H, t, J = 7.8 Hz), 7.34 (1H, s), 3.27 (2H, t, J = 5.7 Hz), 2.94 (3H, s), 2.85 (2H, t, J = 6.7 Hz), 2.05 (2H, tt, J = 6.7, 5.7 Hz). | 469 |
| 15a | (CD3OD) δ: 9.02 (1H, s), 8.92-8.49 (1H, brm), 7.79-7.37 (4H, m), 7.24 (1H, d, J = 8.3 Hz), 3.63 (2H, t, J = 6.8 Hz), 3.18 (3H, s), 3.01 (2H, t, J = 6.8 Hz). | 482 |
| 16a | (CD3OD) δ: 9.05 (1H, s), 8.61 (1H, d, J = 1.6 Hz), 8.26 (1H, brs), 7.66-7.44 (3H, m), 3.85 (2H, s), 3.04-2.92 (5H, m), 1.21 (6H, d, J = 6.7 Hz). | 497 |
| 17a | (CD3OD) δ: 8.92 (1H, s), 7.62-7.55 (2H, m), 7.52-7.45 (1H, m), 7.38-7.14 (2H, m), 6.61 (1H, d, J = 9.0 Hz), 3.44 (2H, t, J = 7.6 Hz), 3.36-3.21 (2H, m), 2.76 (2H, t, J = 6.3 Hz), 2.59 (2H, t, J = 7.6 Hz), 2.36 (6H, s), 1.97-1.92 (2H, m) | 525 |
| 18a | (CD3OD) δ: 8.98 (1H, s), 7.64-7.58 (2H, m), 7.54-7.47 (1H, m), 6.86 (1H, d, J = 8.2 Hz), 6.72 (1H, d, J = 7.8 Hz), 3.62-3.53 (2H, m), 3.35-3.30 (2H, m), 3.09-2.92 (6H, m), 2.70 (2H, t, J = 6.5 Hz), 1.99-1.87 (6H, m). | 551 |
| 19a | (CD3OD) δ: 8.92 (1H, s), 7.63-7.55 (2H, m), 7.49 (1H, t, J = 8.2 Hz), 7.40-7.15 (2H, m), 6.63 (1H, d, J = 9.0 Hz), 3.56 (1H, dd, J = 14.8, 5.5 Hz), 3.37-3.31 (2H, m), 3.22-3.15 (2H, m), 2.86-2.73 (3H, m), 2.54 (3H, s), 2.47-2.37 (1H, m), 2.17-2.05 (1H, m), 1.98-1.79 (4H, m), 1.74-1.62 (1H, m). | 551 |
| 20a | (DMSO-d6) δ: 11.82 (1H, brs), 10.05 (1H, brs), 9.10 (1H, s), 8.88 (1H, brs), 7.76-7.38 (5H, m), 7.02 (1H, d, J = 8.6 Hz), 4.59-4.50 (1H, m), 3.79-3.34 (5H, m), 2.79-2.59 (2H, m), 2.37 (3H, s). | 498 |
| 21a | (DMSO-d6) δ: 11.83 (1H, brs), 10.07 (1H, brs), 9.11 (1H, s), 8.89 (1H, s), 7.84-7.37 (5H, m), 7.06-6.96 (1H, m), 4.75-4.57 (1H, m), 3.86-3.70 (1H, m), 3.64-3.37 (4H, m), 2.85-2.55 (2H, m), 2.40 (3H, s). | 498 |
| 22a | (CD3OD) δ: 8.99 (1H, s), 7.65-7.40 (5H, m), 7.25 (1H, d, J = 8.5 Hz), 3.93-3.71 (3H, m), 3.62 (1H, dd, J = 8.4, 4.8 Hz), 2.94-2.76 (4H, m), 2.60-2.44 (3H, m), 2.11-1.99 (1H, m), 1.75-1.63 (1H, m), 1.38 (3H, s), 1.36 (3H, s). | 566 |
| 23a | (DMSO-d6) δ: 11.79 (1H, brs), 10.11 (1H, brs), 9.10 (1H, brs), 8.88 (1H, brs), 7.91-7.40 (5H, m), 7.13 (1H, d, J = 8.0 Hz), 3.79 (2H, s), 3.75 (2H, s), 2.47 (3H, s). | 455 |
| 24a | (DMSO-d6) δ: 11.82 (1H, brs), 10.23 (1H, brs), 9.12 (1H, brs), 8.92 (1H, brs), 8.05 (1H, brs), 7.72-7.40 (4H, m), 7.26 (1H, dd, J = 8.0, 6.3 Hz), 4.90 (1H, s), 4.85 (1H, s), 4.64 (1H, s), 4.59 (1H, s), 3.14 (2H, d, J = 2.7 Hz), 2.24 (6H, s). | 526 |
| 25a | (DMSO-d6) δ: 11.84 (1H, brs), 9.94 (1H, brs), 9.09 (1H, s), 8.85 (1H, s), 7.77-7.55 (1H, m), 7.61 (1H, d, J = 7.8 Hz), 7.47 (1H, t, J = 7.8 Hz), 7.21 (1H, brs), 6.97-6.85 (2H, m), 3.24 (2H, t, J = 8.1 Hz), 2.81 (2H, t, J = 8.1 Hz), 2.73 (3H, s). | 455 |
| 26a | (DMSO-d6) δ: 9.94 (1H, brs), 11.71 (1H, brs), 8.82 (1H, brs), 7.88-7.25 (5H, m), 6.67 (1H, d, J = 8.5 Hz), 4.94-4.84 (1H, m), 3.24 (1H, dd, J = 16.0, 9.0 Hz), 2.93 (1H, dd, J = 16.0, 7.4 Hz), 2.54 (1H, dd, J = 12.9, 6.8 Hz), 2.45 (1H, dd, J = 12.9, 5.4 Hz), 2.45 (1H, s), 2.21 (6H, s). | 499 |
| 27a | (DMSO) δ: 8.93 (1H, s), 7.65 (2H, br), 7.29-7.52 (4H, m), 6.91 (1H, d, J = 8.0 Hz), 4.55 (2H, s). | 469 |
| 28a | (DMSO) δ: 8.84 (1H, s), 7.63 (2H, d, J = 8.4 Hz), 7.47-7.51 (1H, m), 7.19 (1H, m), 6.98 (1H, m), 6.61 (1H, d, J = 8.4 Hz), 4.21-4.23 (2H, m), 3.24-3.26 (2H, m), 2.87 (3H, s). | 469 |
| 29a | (DMSO) δ: 8.93 (1H, s), 7.77 (1H, br), 7.64 (2H, d, J = 8.0 Hz) 7.48-7.52 (1H, m), 7.33 (1H, d, J = 8.0 Hz), 6.98 (1H, d, J = 8.0 Hz), 4.64 (2H, s), 3.35 (3H, s). | 483 |
| 30a | (CD3OD) δ: 9.04 (1H, s), 7.63 (2H, d, J = 8.0 Hz) 7.46-7.55 (2H, m), 7.22 (1H, br-s), 6.92 (1H, d, J = 8.0 Hz), 1.56 (6H, s). | 497 |
| 31a | (CD3OD) δ: 8.96 (1H, s), 7.49-7.59 (4H, m), 7.15 (1H, br-s), 6.94 (1H, d, J = 8.0 Hz), 4.63-4.65 (1H, m), 1.55 (3H, d, J = 7.2 Hz). | 483 |

-continued

| Compound No. | ¹H NMR (400 MHz) | ESI-MS (M + H)+ |
|---|---|---|
| 32a | (CD3OD) δ: 9.00 (1H, s), 7.62 (2H, d, J = 8.4 Hz), 7.51-7.55 (2H, m), 7.23 (1H, dd, J = 8.0, 2.2 Hz), 6.97 (1H, d, J = 8.4 Hz), 4.71-4.73 (1H, m), 3.79-3.85 (2H, m), 2.02-2.16 (2H, m). | 513 |
| 33a | (CD3OD) δ: 8.94 (1H, br), 7.25-7.78 (5H, m) 6.87 (1H, d, J = 8.0 Hz), 3.66-3.81 (2H, br), 2.42 (3H, s), 1.36 (6H, s). | 527 |
| 34a | (CD3OD) δ: 9.00 (1H, s), 7.45-7.65 (3H, m), 7.20 (1H, br-s), 6.93 (1H, d, J = 8.0 Hz), 6.73 (1H, d, J = 8.0 Hz), 3.61 (3H, s), 3.59 (2H, AB-q, J = 11.0 Hz), 3.10 (2H, AB-q, J = 11.0 Hz), 3.63 (3H, s), 2.96 (3H, s), 1.33 (3H, s). | 528 |
| 35a | (CD3OD) δ: 9.03 (1H, s), 7.50-7.61 (4H, m), 7.32 (1H, d, J = 8.4 Hz), 7.00 (1H, d, J = 8.4 Hz), 4.63 (2H, s), 3.64 (3H, s), 3.42 (3H, s). | 499 |
| 36a | (CD3OD) δ: 9.00 (1H, s), 7.39-7.68 (5H, m), 7.10 (1H, d, J = 8.4 Hz), 3.64 (2H, s), 2.93 (2H, t, J = 5.4 Hz), 2.76 (2H, t, J = 5.4 Hz), 2.47 (3H, s). | 434 |
| 37a | (CD3OD) δ: 8.98 (1H, s), 7.44-7.65 (5H, m), 7.30 (7H, d, J = 8.0 Hz), 7.12 (1H, d, J = 8.4 Hz), 3.67 (2H, s), 2.95 (2H, t, J = 5.4 Hz), 2.79 (2H, t, J = 5.4 Hz), 2.50 (3H, s). | 400 |
| 38a | (CD3OD) δ: 8.98 (1H, s), 7.33-7.59 (6H, m), 7.12 (1H, d, J = 8.0 Hz), 3.70 (2H, s), 2.98 (2H, t, J = 5.4 Hz), 2.83 (2H, t, J = 5.4 Hz), 2.52 (3H, s). | 418 |
| 39a | (CD3OD) δ: 8.99 (1H, s), 7.43-7.57 (3H, m), 7.25 (1H, d, J = 7.6 Hz), 7.16 (2H, d, J = 7.2 Hz), 7.12 (1H, d, J = 8.4 Hz), 3.83 (3H, s), 3.70 (2H, s), 2.94 (2H, t, J = 5.4 Hz), 2.82 (2H, t, J = 5.4 Hz), 2.56 (3H, s). | 430 |
| 40a | (CD3OD) δ: 8.89 (1H, s), 7.56-7.64 (3H, m), 7.27-7.41 (7H, m), 7.08 (1H, d, J = 8.4 Hz), 3.61 (2H, s), 2.91 (2H, t, J = 5.4 Hz), 2.75 (2H, t, J = 5.4 Hz), 2.46 (3H, s). | 476 |
| 41a | (CD3OD) δ: 9.07 (1H, s), 7.86 (1H, br), 7.45-7.60 (4H, m), 7.38 (1H, d, J = 8.8 Hz), 4.32 (2H, s), 3.55 (3H, s). | 532 |
| 42a | (CD3OD) δ: 8.92 (1H, s), 7.56 (2H, d, J = 8.0 Hz), 7.22-7.40 (3H, m), 6.70 (1H, d, J = 8.0 Hz), 3.53-3.56 (2H, m), 3.11-3.14 (2H, m), 2.97 (3H, s). | 486 |
| 43a | (CD3OD) δ: 8.91 (1H, s), 7.55 (2H, d, J = 8.0 Hz), 7.40-7.48 (1H, m), 7.25-7.29 (1H, br-s), 7.13 (1H, s), 6.60 (1H, d, J = 8.4 Hz), 3.15-3.19 (1H, m), 2.89 (3H, s), 2.77-2.86 (2H, m),, 2.42-2.49 (1H, m), 2.10-2.15 (1H, m), 1.06 (3H, d, J = 6.4 Hz). | 482 |
| 44a | (CD3OD) δ: 9.03 (1H, s), 7.48-7.59 (5H, m), 7.00 (1H, d, J = 8.4 Hz), 4.03 (3H, s), 2.93 (2H, t, J = 5.4 Hz), 2.66 (2H, t, J = 5.4 Hz). | 482 |
| 45a | (CD3OD) δ: 8.90 (1H, s), 7.40-7.60 (4H, m), 7.18 (1H, br), 4.54 (1H, br), 3.94-3.97 (1H, m), 3.70-3.76 (1H, m), 3.50-3.62 (1H, m), 3.15-3.19 (1H, m), 2.13 (3H, s), 1.80-2.10 (4H, m), 1.49-1.55 (1H, m). | 524 |
| 46a | (CD3OD) δ: 9.02 (1H, s), 7.30-7.48 (4H, m), 7.25 (1H, d, J = 8.0 Hz), 7.09 (1H, d, J = 8.0 Hz), 3.62 (2H, s), 2.92 (2H, t, J = 5.4 Hz), 2.75 (2H, t, J = 5.4 Hz), 2.47 (3H, s), 2.46 (3H, s). | 448 |
| 47a | (CD3OD) δ: 8.97 (1H, s), 7.42-7.50 (4H, m), 7.24-7.28 (1H, m), 7.11 (1H, d, J = 8.0 Hz), 3.65 (2H, s), 2.94 (2H, t, J = 5.4 Hz), 2.78 (2H, t, J = 5.4 Hz), 2.49 (3H, s). | 452 |
| 48a | (CD3OD) δ: 8.99 (1H, s), 7.45-7.80 (5H, m), 6.80 (1H, d, J = 8.4 Hz), 3.40-3.42 (1H, m), 3.05-3.15 (2H, m), 2.47 (6H, s). | 511 |
| 49a | (DMSO) δ: 8.89 (1H, br-s), 7.81 (1H, br), 7.65 (2H, d, J = 8.0 Hz), 7.50-7.54 (2H, m), 7.17 (1H, d, J = 8.0 Hz), 2.82-2.90 (4H, m), 2.00-2.08 (2H, m). | 439 |
| 50a | (CD3OD) δ: 9.03 (1H, s), 7.44 (1H, br), 7.38 (1H, d, J = 7.2 Hz), 7.29 (1H, br), 7.16 (1H, br), 7.10 (1H, d, J = 8.8 Hz), 3.63 (2H, s), 2.93 (2H, t, J = 5.4 Hz), 2.76 (2H, t, J = 5.4 Hz), 2.48 (3H, s), 2.40 (3H, s), 2.19 (3H, s). | 462 |
| 51a | (CD3OD) δ: 8.97 (1H, s), 7.45-7.56 (4H, m), 7.11 (1H, d, J = 8.0 Hz), 4.68 (2H, s), 3.66 (2H, s), 2.94 (2H, t, J = 5.4 Hz), 2.76 (2H, t, J = 5.4 Hz), 2.48 (3H, s). | 498 |
| 52a | (CD3OD) δ: 8.97 (1H, s), 7.61-7.65 (1H, m), 7.37-7.44 (2H, m), 7.25-7.29 (1H, m), 7.17 (1H, dd, J = 8.8, 2.0 Hz), 7.10 (1H, d, J = 8.8 Hz), 3.63 (2H, s), 2.93 (2H, t, J = 5.4 Hz), 2.76 (2H, t, J = 5.4 Hz), 2.48 (3H, s). | 452 |
| 53a | (CD3OD) δ: 8.95 (1H, s), 7.65 (1H, t, J = 8.8 Hz), 7.42-7.53 (2H, m), 7.21 (1H, dd, J = 8.8, 2.0 Hz), 7.09-7.12 (2H, m), 3.64 (2H, s), 2.94 (2H, t, J = 5.4 Hz), 2.77 (2H, t, J = 5.4 Hz), 2.48 (3H, s). | 452 |
| 54a | (CD3OD) δ: 8.70 (1H, br-s), 7.73 (2H, br-s), 7.27-7.33 (2H, m), 7.02 (1H, d, J = 8.4 Hz), 3.52 (2H, s), 2.85 (2H, t, J = 6.0 Hz), 2.67 (2H, t, J = 6.0 Hz), 2.39 (3H, s). | 536 |
| 55a | (CD3OD) δ: 8.97 (1H, s), 7.70-7.90 (2H, m), 7.70 (1H, s), 7.40-7.43 (2H, m), 7.10 (1H, d, J = 8.4 Hz), 3.63 (2H, s), 2.93 (2H, t, J = 5.4 Hz), 2.77 (2H, t, J = 5.4 Hz), 2.47 (3H, s). | 502 |

-continued

| Compound No. | ¹H NMR (400 MHz) | ESI-MS (M + H)+ |
|---|---|---|
| 56a | (DMSO-d6) δ: 11.93-11.74 (1H, m), 10.07-9.91 (1H, m), 9.08 (1H, s), 8.85 (1H, s), 7.75-7.62 (1H, m), 7.59 (2H, d, J = 8.2 Hz), 7.46 (2H, d, J = 7.8 Hz), 6.97 (1H, d, J = 8.4 Hz), 3.50 (1H, q, J = 6.2 Hz), 2.92-2.86 (1H, m), 2.68 (2H, t, J = 5.7 Hz), 2.50-2.43 (1H, m), 2.34 (3H, s), 1.27 (3H, d, J = 6.4 Hz). | 481 |
| 57a | (DMSO-d6) δ: 10.21 (1H, s), 9.12 (1H, s), 8.91 (1H, s), 7.95 (1H, s), 7.63-7.60 (4H, m), 7.49-7.47 (1H, m), 7.23 (1H, d, J = 8.3 Hz), 4.98 (2H, s). | 442 |
| 58a | (DMSO-d6) δ: 10.08 (1H, s), 9.11 (1H, s), 8.89 (1H, s), 7.72-7.47 (5H, m), 6.95 (1H, d, J = 8.3 Hz), 4.64 (2H, s), 3.86 (2H, t, J = 5.6 Hz), 2.78 (2H, t, J = 5.4 Hz). | 456 |
| 59a | (DMSO-d6) δ: 11.83 (1H, s), 10.10 (1H, s), 9.11 (1H, s), 8.88 (1H, s), 7.68-7.50 (5H, m), 7.05 (1H, d, J = 4.6 Hz), 4.67 (2H, s), 3.86 (2H, t, J = 5.6 Hz), 2.73 (2H, t, J = 5.4 Hz). | 456 |
| 60a | (DMSO-d6) δ: 10.11 (1H, s), 9.06 (1H, s), 8.72-8.30 (2H, br), 7.70-7.41 (4H, m), 7.32-7.21 (1H, m), 7.12 (1H, d, J = 8.3 Hz), 4.84-4.73 (1H, m), 4.68-4.42 (1H, br), 4.12-3.88 (1H, m), 3.69-3.53 (1H, m), 3.30-3.12 (3H, m), 3.03-2.88 (2H, m) | 485 |
| 61a | (CDCl3) δ: 10.13 (1H, brs), 9.23 (1H, s), 7.77-7.75 (1H, brm), 7.55-7.40 (5H, m), 7.17 (1H, d, J = 8.3 Hz), 6.53 (1H, brs), 4.42-4.40 (1H, m), 4.00 (1H, d, J = 7.8 Hz), 3.20 (1H, dd, J = 16.1, 7.8 Hz), 2.75 (1H, dd, J = 16.3, 7.6 Hz), 2.22 (6H, d, J = 20.0 Hz). | 499 |
| 62a | (CDCl3) δ: 10.13 (1H, brs), 9.23 (1H, s), 7.77-7.75 (1H, brm), 7.55-7.40 (5H, m), 7.17 (1H, d, J = 8.3 Hz), 6.53 (1H, brs), 4.42-4.40 (1H, m), 4.00 (1H, d, J = 7.8 Hz), 3.20 (1H, dd, J = 16.1, 7.8 Hz), 2.75 (1H, dd, J = 16.3, 7.6 Hz), 2.22 (6H, d, J = 20.0 Hz). | 499 |
| 63a | (DMSO-d6) δ: 10.04 (1H, s), 9.10 (1H, s), 8.87 (1H, s), 7.76 (1H, brs), 7.61 (2H, d, J = 8.3 Hz), 7.49-7.47 (2H, m), 7.10 (1H, d, J = 8.3 Hz), 3.54-3.52 (1H, m), 3.32 (3H, s), 3.22 (2H, t, J = 6.6 Hz), 3.05-2.99 (2H, m), 3.02 (2H, t, J = 10.0 Hz), 2.68-2.58 (2H, m). | 561 |
| 64a | (DMSO-d6) δ: 11.79 (1H, s), 10.06 (1H, s), 9.10 (1H, s), 8.87 (1H, s), 7.72-7.56 (5H, m), 7.11 (1H, d, J = 8.3 Hz), 3.31 (2H, t, J = 7.7 Hz), 3.05-2.96 (3H, m), 3.03 (3H, s), 2.84 (2H, t, J = 7.7 Hz), 2.81-2.76 (2H, m), 2.23 (3H, s). | 575 |
| 65a | (DMSO-d6) δ: 10.08 (1H, brs), 8.88 (1H, brs), 7.92 (1H, d, J = 6.8 Hz), 7.81-7.78 (1H, m), 7.61 (2H, d, J = 6.8 Hz), 7.53-7.45 (1H, m), 7.12 (1H, d, J = 8.3 Hz), 3.39-3.31 (1H, m), 3.15-3.05 (2H, m), 2.84-2.74 (2H, m), 2.84 (2H, s), 2.17 (6H, s). | 540 |
| 66a | (DMSO-d6) δ: 11.97 (1H, s), 10.46 (1H, s), 9.18 (1H, s), 9.01 (1H, s), 8.00 (1H, s), 7.84 (1H, d, J = 8.5 Hz), 7.67 (3H, dd, J = 37.6, 7.8 Hz), 7.48 (1H, m), 7.37-7.24 (6H, m), 4.69 (2H, s), 3.48 (2H, t, J = 6.6 Hz), 2.95 (2H, t, J = 6.5 Hz). | 558 |
| 67a | (DMSO-d6) δ: 9.78 (1H, s), 9.04 (1H, s), 8.80 (1H, s), 7.59 (2H, s), 7.45 (1H, s), 7.01 (1H, s), 6.98 (1H, d, J = 8.2 Hz), 6.77 (1H, d, J = 8.0 Hz), 3.14 (2H, t, J = 5.6 Hz), 2.82 (3H, s), 2.62 (2H, t, J = 6.4 Hz), 1.84 (2H, td, J = 8.9, 5.6 Hz). | 486 |
| 68a | (DMSO-d6) δ: 10.16 (1H, s), 9.11 (1H, s), 8.87 (1H, s), 7.61 (2H, d, J = 8.3 Hz), 7.47 (1H, t, J = 8.0 Hz), 7.18 (1H, s), 7.11 (1H, d, J = 8.8 Hz), 3.91 (2H, t, J = 6.6 Hz), 3.36 (3H, s), 3.32 (4H, s), 2.68 (2H, t, J = 6.6 Hz), 1.63 (4H, s). | 566 |
| 69a | (DMSO-d6) δ: 9.94 (1H, s), 9.08 (1H, s), 8.85 (1H, s), 7.76-7.42 (4H, m), 6.83-6.75 (2H, m), 3.37 (2H, t, J = 7.0 Hz), 3.26 (2H, t, J = 5.4 Hz), 2.61 (2H, t, J = 6.2 Hz), 2.21 (6H, s), 1.82 (2H, t, J = 5.4 Hz). | 525 |
| 70a | (DMSO-d6) δ: 9.18 (1H, s), 8.60 (1H, s), 7.91 (2H, d, J = 8.3 Hz), 7.60 (1H, s), 7.48 (3H, dd, J = 15.6, 9.8 Hz), 7.30 (1H, d, J = 8.3 Hz), 4.13 (2H, t, J = 8.5 Hz), 3.17 (2H, s), 3.12 (2H, t, J = 8.5 Hz), 2.26 (6H, s). | 525 |
| 71a | (DMSO-d6) δ: 11.85 (1H, s), 10.09 (1H, s), 9.08 (1H, s), 8.85 (1H, s), 8.12 (1H, s), 7.59 (2H, d, J = 8.0 Hz), 7.47-7.39 (2H, m), 6.96 (1H, d, J = 8.6 Hz), 3.71 (2H, t, J = 6.6 Hz), 3.29 (3H, s), 2.43 (2H, t, J = 6.8 Hz), 2.15 (6H, s), 1.27 (6H, s). | 553 |
| 72a | (DMSO-d6) δ: 11.94 (1H, s), 10.42 (1H, s), 9.18 (1H, s), 9.00 (1H, s), 7.98 (1H, s), 7.76 (1H, d, J = 8.3 Hz), 7.65 (3H, dd, J = 24.1, 8.0 Hz), 7.49 (1H, d, J = 7.3 Hz), 3.55 (4H, dd, J = 11.0, 6.6 Hz), 2.94 (2H, t, J = 6.6 Hz), 2.43 (2H, t, J = 6.6 Hz), 2.18 (6H, s). | 539 |
| 73a | (DMSO-d6) δ: 12.00 (1H, s), 10.55 (1H, s), 9.21 (1H, s), 9.04 (1H, s), 8.45 (1H, dd, J = 4.9, 1.5 Hz), 8.14 (1H, s), 7.91 (2H, t, J = 8.8 Hz), 7.81 (1H, td, J = 7.8, 2.0 Hz), 7.74 (1H, d, J = 8.8 Hz), 7.62 (2H, d, J = 8.3 Hz), 7.48 (1H, t, J = 8.0 Hz), 7.19 (1H, ddd, J = 7.1, 4.9, 1.2 Hz), 4.20 (2H, t, J = 6.3 Hz), 3.11 (2H, t, J = 6.1 Hz). | 545 |

-continued

| Compound No. | ¹H NMR (400 MHz) | ESI-MS (M + H)+ |
|---|---|---|
| 74a | (CDCl3) δ: 8.52 (1H, s), 7.50-7.44 (2H, m), 7.42 (1H, d, J = 7.8 Hz), 7.31 (1H, d, J = 8.3 Hz), 7.07 (1H, d, J = 7.3 Hz), 6.93 (1H, d, J = 8.3 Hz), 4.04 (3H, s), 3.65-3.63 (2H, m), 3.03-2.98 (2H, m), 2.79-2.74 (2H, m), 2.50 (3H, s). | 487 |

INDUSTRIAL APPLICABILITY

The compounds of the invention have an excellent Wee1 kinase-inhibitory effect, and are therefore useful in the field of medicine, especially in the field of treatment of various cancers.

The invention claimed is:

1. A compound of a general formula (I):

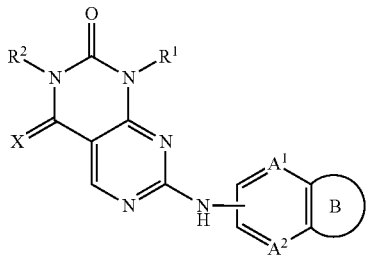

wherein, $A^1$ and $A^2$ each independently mean a nitrogen atom, or mean a methine group optionally substituted with a halogen atom, a hydroxyl group, a cyano group, a C1-C6 alkyl group, a C1-C6 alkoxy group or a hydroxy-C1-C6 alkyl group;

Ring B means a 5-membered to 7-membered aliphatic ring condensed with a ring of formula (a):

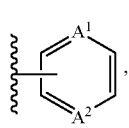

or means a spiro or bicyclo ring formed from the 5-membered to 7-membered aliphatic ring with any other 3-membered to 7-membered aliphatic ring, which is condensed with the ring of formula (a), in which one or two or more methylene groups constituting said Ring B may be independently replaced by an oxygen atom, a sulfur atom, a sulfinyl group, a sulfonyl group, a carbonyl group or a group of —N($R^{1a}$)—, and one or two or more methylene groups constituting said Ring B may be independently substituted with a halogen atom, a hydroxyl group, a C1-C6 alkyl group, a hydroxy-C1-C6 alkyl group or a group of -$Q^{1a}$-N($R^{1b}$)$R^{1c}$;

Cy means an aryl or heterocyclic group optionally substituted with a halogen atom or a C1-C6 alkyl group;

$Q^{1a}$, $Q^{1b}$, $Q^{1d}$ and $Q^{1e}$ each independently mean a single bond or a C1-C6 alkylene group, in which one or two or more methylene groups constituting the C1-C6 alkylene group may be independently replaced by a sulfinyl group, a sulfonyl group or a carbonyl group;

$R^1$ means a hydrogen atom, or means a C1-C6 alkyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

$R^2$ means an aryl, aralkyl or heteroaryl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group;

$R^{1a}$ means a hydrogen atom, or means a C1-C6 alkyl, C3-C6 cycloalkyl or C2-C7 alkanoyl group optionally having a substituent selected from a group consisting of a halogen atom, a hydroxyl group, a cyano group, a C1-C6 alkoxy group, a C3-C6 cycloalkyl group and a C2-C7 alkanoyl group, or means a group of -$Q^{1b}$-Cy or -$Q^{1d}$—N($R^{1f}$)$R^{1g}$;

$R^{1b}$ and $R^{1c}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group, or mean a group of -$Q^{1e}$-N($R^{1h}$)$R^{1i}$;

$R^{1f}$ and $R^{1g}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group;

$R^{1h}$ and $R^{1i}$ each independently mean a hydrogen atom, or mean a C1-C6 alkyl, C2-C7 alkanoyl or C1-C6 alkylsulfonyl group optionally having a substituent selected from a group consisting of a halogen atom, a hydroxyl group, a cyano group, a C1-C6 alkoxy group, a C3-C6 cycloalkyl group, a C2-C7 alkanoyl group and a C1-C6 alkylsulfonyl group; and X means a group of =NH or =O, or a pharmaceutically acceptable salt thereof.

2. The compound, or a pharmaceutically acceptable salt thereof as claimed in claim 1, wherein X is =NH.

3. The compound, or a pharmaceutically acceptable salt thereof as claimed in claim 2, wherein $R^1$ is a hydrogen atom, or a C1-C6 alkyl group optionally substituted with a halogen atom or a hydroxyl group.

4. The compound, or a pharmaceutically acceptable salt thereof as claimed in claim 3, wherein $R^2$ is a phenyl or pyridyl group optionally having a substituent selected from a group consisting of a halogen atom, a hydroxyl group, a cyano group, an amino group, a C1-C6 alkyl group, a C1-C6 alkoxy group, a halo-C1-C6 alkyl group and a hydroxy-C1-C6 alkyl group.

5. The compound, or a pharmaceutically acceptable salt thereof as claimed in claim 2, wherein $A^1$ and $A^2$ are both unsubstituted methine groups.

6. The compound, or a pharmaceutically acceptable salt thereof as claimed in claim 5, wherein the 5-membered to 7-membered aliphatic ring condensed with the ring of formula (a) of Ring B is a ring selected from a group consisting of a formula (b-1):

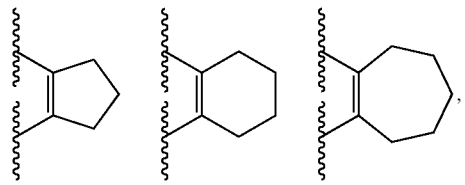

(b-1)

the spiro ring condensed with the ring of formula (a) is a ring selected from a group consisting of a formula (b-2):

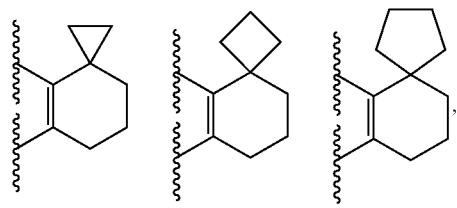

(b-2)

and the bicyclo ring condensed with the ring of formula (a) is a ring selected from a group consisting of a formula (b-3):

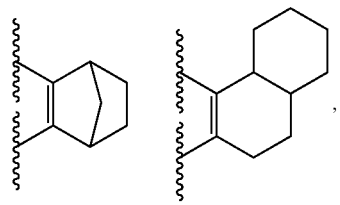

(b-3)

in which one or two or more methylene groups constituting said Ring B may be independently replaced by a an oxygen atom, a sulfur atom, a sulfinyl group, a sulfonyl group, a carbonyl group or a group of —$N(R^{1a})$—, and one or two or more methylene groups constituting said Ring B may be independently substituted with a halogen atom, a hydroxyl group, a C1-C6 alkyl group, a hydroxy-C1-C6 alkyl group or a group of -$Q^{1a}$—$N(R^{1b})R^{1c}$.

7. The compound, or a pharmaceutically acceptable salt thereof as claimed in claim 6, wherein a group of formula (ab-1):

(ab-1)

is a group selected from a group consisting of a formula (b-10):

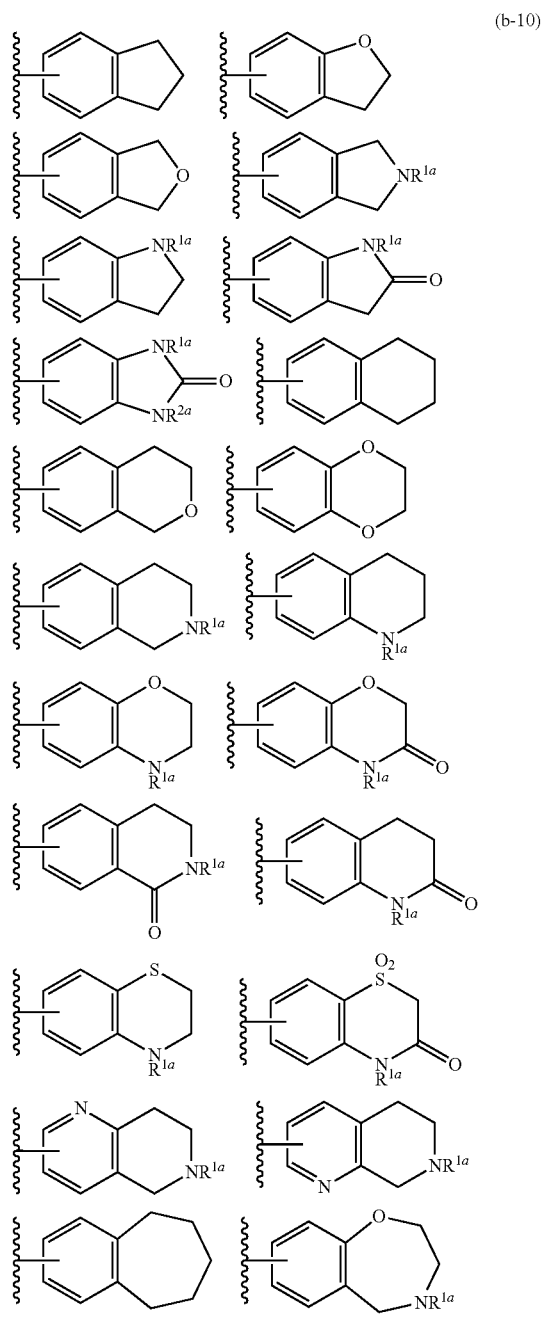

(b-10)

-continued

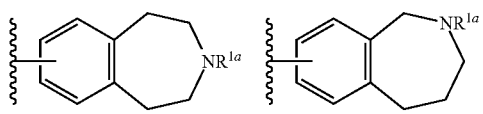

wherein, $R^{2a}$ means a hydrogen atom, or means a C1-C6 alkyl, C3-C6 cycloalkyl or C2-C7 alkanoyl group optionally having a substituent selected from a group consisting of a halogen atom, a hydroxyl group, a cyano group, a C1-C6 alkoxy group, a C3-C6cycloalkyl group and a C2-C7 alkanoyl group, or means a group of or $-Q^{1b}$-Cy or $-Q^{1d}$-N($R^{1f}$)$R^{1g}$; Cy, $Q^{1b}$, $Q^{1d}$, $R^{1f}$ and $R^{1g}$ have the same meanings as in claim 1, in which one or two or more methylene groups constituting the aliphatic ring of the group may be independently substituted with a halogen atom, a hydroxyl group, a C1-C6 alkyl group, a hydroxy-C1-C6 alkyl group or a group of $-Q^{1a}$-N($R^{1b}$)$R^{1c}$.

8. The compound, or a pharmaceutically acceptable salt thereof as claimed in claim 7, wherein the group of formula (ab-1):

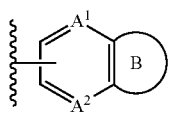
(ab-1)

is a group selected from a group consisting of a formula (b-11):

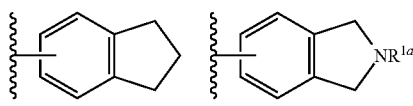
(b-11)

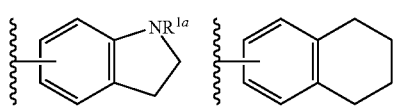

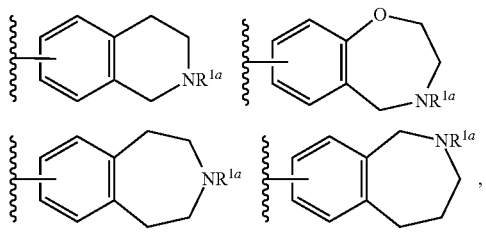

in which one or two or more methylene groups constituting the aliphatic ring of the group may be independently substituted with a halogen atom, a hydroxyl group, a C1-C6 alkyl group, a hydroxy-C1-C6 alkyl group or a group of $-Q^{1a}$-N($R^{1b}$)$R^{1c}$.

9. The compound, or a pharmaceutically acceptable salt or thereof as claimed in claim 8, wherein the group of formula (ab-1):

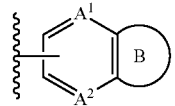
(ab-1)

is a group selected from a group consisting of a formula (b-12):

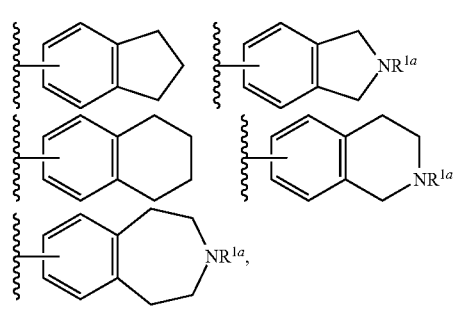
(b-12)

in which one or two or more methylene groups constituting the aliphatic ring of the group may be independently substituted with a halogen atom, a hydroxyl group, a C1-C6 alkyl group, a hydroxy-C1-C6 alkyl group or a group of $-Q^{1a}$-N($R^{1b}$)$R^{1c}$.

10. The compound, or a pharmaceutically acceptable salt thereof as claimed in claim 6, wherein the group of formula (ab-1):

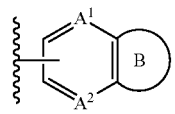
(ab-1)

is a group selected from a group consisting of a formula (b-20):

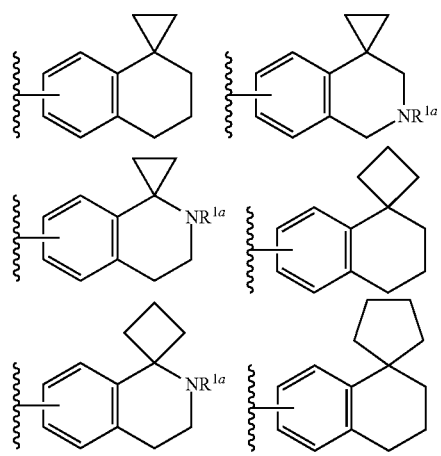
(b-20)

-continued

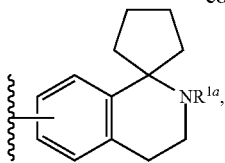

in which one or two or more methylene groups constituting the aliphatic ring of the group may be independently substituted with a halogen atom, a hydroxyl group, a C1-C6 alkyl group, a hydroxy-C1-C6 alkyl group or a group of -$Q^{1a}$-N($R^{1b}$)$R^{1c}$.

11. The compound, or a pharmaceutically acceptable salt thereof as claimed in claim 10, wherein the group of formula (ab-1):

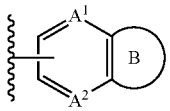
(ab-1)

is a group selected from a group consisting of a formula (b-21):

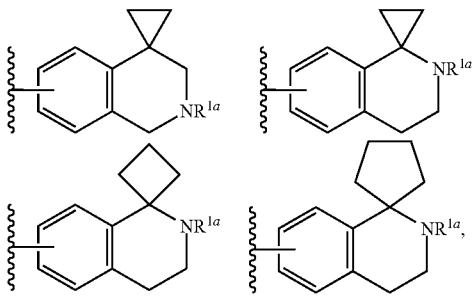
(b-21)

in which one or two or more methylene groups constituting the aliphatic ring of the group may be independently substituted with a halogen atom, a hydroxyl group, a C1-C6 alkyl group, a hydroxy-C1-C6 alkyl group or a group of -$Q^{1a}$-N($R^{1b}$)$R^{1c}$.

12. The compound, or a pharmaceutically acceptable salt thereof as claimed in claim 11, wherein the group of formula (ab-1):

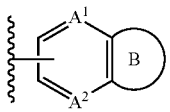
(ab-1)

is a group of a formula (b-22):

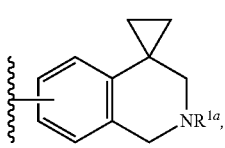
(b-22)

in which one or two or more methylene groups constituting the aliphatic ring of the group may be independently substituted with a halogen atom, a hydroxyl group, a C1-C6 alkyl group, a hydroxy-C1-C6 alkyl group or a group of -$Q^{1a}$-N($R^{1b}$)$R^{1c}$.

13. The compound, or a pharmaceutically acceptable salt thereof as claimed in claim 6, wherein the group of formula (ab-1):

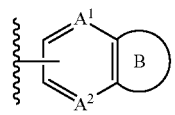
(ab-1)

is a group selected from a group consisting of a formula (b-30):

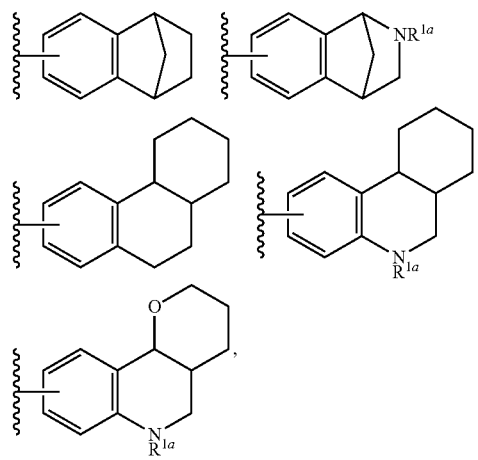
(b-30)

in which one or two or more methylene groups constituting the aliphatic ring of the group may be independently substituted with a halogen atom, a hydroxyl group, a C1-C6 alkyl group, a hydroxy-C1-C6 alkyl group or a group of -$Q^{1a}$-N($R^{1b}$)$R^{1c}$.

14. The compound as claimed in claim 1, which is selected from the following compounds:
(1) 3-(2,6-dichlorophenyl)-4-imino-7-[(2'-methyl-2',3'-dihydro spiro[cyclopropane-1,4'-isoquinolin]-7'-yl)amino]-3,4-dihydropyrimido [4,5-d]pyrimidin-2(1H)-one;
(2) 3-(2,6-dichlorophenyl)-4-imino-7-{[2,4,4-trimethyl-1,2,3,4-tetrahydroisoquinolin-7-yl]amino}-3,4-dihydropyrimido [4,5-d]pyrimidin-2(1H)-one;
(3) 3-(2,6-dichlorophenyl)-4-imino-7-[(1,1,2-trimethyl-1,2,3,4-tetrahydroisoquinolin-6-yl)amino]-3,4-dihydropyrimido [4,5-d]pyrimidin-2(1H)-one;
(4) 3-(2,4-dichloropyridin-3-yl)-4-imino-7-{[1,1,2-trimethyl-1,2,3,4-tetrahydroisoqunolin-6-yl]amino}-3,4-dihydropyrimido [4,5-d]pyrimidin-2(1H)-one;
(5) 3-(2,6-dichlorophenyl)-4-imino-7-[(1,1,2-trimethyl-2,3-dihydro-1H-isoindol-5-yl)amino]-3,4-dihydropyrimido [4,5-d]pyrimidin-2(1H)-one;
(6) 3-(2,6-dichlorophenyl)-7-{[2-(dimethylamino)-2,3-dihydro-1H-inden-5-yl]amino}-4-imino-1-methyl-3,4-dihydropyrimido [4,5-d]pyrimidin-2(1H)-one;

(7) 3-(2,6-dichlorophenyl)-7-{[3-(dimethylamino)-1,1-dimethyl-2,3-dihydro-1H-inden-5-yl]amino}-4-imino-3,4-dihydropyrimido [4,5-d]pyrimidin-2(1H)-one;
(8) 3-(2-chloro-6-methylphenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one;
(9) 3-(2-chloro-6-fluorophenyl)-4-imino-7-[2-methyl-1,2,3,4-tetrahydroisoquinolin-7-yl]amino-3,4-dihydropyrimido[4,5-d]pyrimidin-2(1H)-one;
(10) 3-(2-chloro-4,6-difluorophenyl)-4-imino-7-{[2-methyl-1,2,3,4-tetrahydroisoquinolin-7-yl]amino}-3,4-dihydropyrimido [4,5-d]pyrimidin-2(1H)-one;
(11) 3-(2,6-dichloro-4-fluorophenyl)-4-imino-7-{[2-methyl-1,2,3,4-tetrahydroisoquinolin-7-yl]amino}-3,4-dihydropyrimido [4,5-d]pyrimidin-2(1H)-one;
(12) 3-(2,6-dichlorophenyl)-7-{[2,5-dimethyl-1,2,3,4-tetrahydroisoquinolin-7-yl]amino}-4-imino-3,4-dihydropyrimido[4,5-d]pyrimidin-2(1H)-one;
(13) 3-(2,6-dichlorophenyl)-7-[2-(2-hydroxyethyl)-1,1-dimethyl-1,2,3,4-tetrahydroisoquinolin-6-yl]amino-4-imino-1-methyl-3,4-dihydropyrimido[4,5-d]pyrimidin-2(1H)-one;
(14) 3-(2,6-dichlorophenyl)-4-imino-7-{[2-ethyl-1,2,3,4-tetrahydroisoquinolin-6-yl]amino}-3,4-dihydropyrimido[4,5-d]pyrimidin-2(1H)-one;
(15) 3-(2,6-dichlorophenyl)-4-imino-7-[(2-methyl-1,2,3,4-tetrahydroisoquinolin-6-yl)amino]-3,4-dihydropyrimido [4,5-d]pyrimidin-2(1H)-one;
(16) 3-(2,6-dichlorophenyl)-7-{[2-(dimethylamino)-2,3-dihydro-1H-inden-5-yl]amino}-4-imino-3,4-dihydropyrimido[4,5-d]pyrimidin-2(1H)-one;
(17) 3-(2,6-dichlorophenyl)-7-{[7-(dimethylamino)-5,6,7,8-tetrahydronaphthalen-2-yl]amino}-4-imino-3,4-dihydropyrimido [4,5-d]pyrimidin-2(1H)-one;
(18) 3-(2,6-dichlorophenyl)-4-imino-7-[(3-methyl-2,3,4,5-tetrahydro-1H-3-benzazepin-7-yl)amino]-3,4-dihydropyrimido [4,5-d]pyrimidin-2(1H)-one;
(19) 3-(2,6-dichlorophenyl)-7-{6-[(dimethylamino)methyl]-5,6,7,8-tetrahydronaphthalen-2-yl}amino)-4-imino-3,4-dihydropyrimido [4,5-d]pyrimidin-2(1H)-one; or
(20) 7-[(2-acetyl-1,1-dimethyl-1,2,3,4-tetrahydroisoquinolin-6-yl)amino]-3-(2,6-dichlorophenyl)-4-imino-3,4-dihydropyrimido [4,5-d]pyrimidin-2(1H)-one;
or a pharmaceutically acceptable salt thereof.

15. A pharmaceutical composition comprising a therapeutically effective amount of the compound of claim 1 or a pharmaceutically acceptable salt thereof, and a pharmaceutically acceptable carrier or diluent.

* * * * *

UNITED STATES PATENT AND TRADEMARK OFFICE
CERTIFICATE OF CORRECTION

| | | |
|---|---|---|
| PATENT NO. | : 8,436,004 B2 | Page 1 of 1 |
| APPLICATION NO. | : 12/663729 | |
| DATED | : May 7, 2013 | |
| INVENTOR(S) | : Bamba et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 447 days.

Signed and Sealed this
Twentieth Day of August, 2013

Teresa Stanek Rea
*Acting Director of the United States Patent and Trademark Office*